United States Patent [19]

Karanewsky et al.

[11] Patent Number: 5,276,021
[45] Date of Patent: Jan. 4, 1994

[54] PHOSPHORUS-CONTAINING HMG-COA REDUCTASE INHIBITORS, NEW INTERMEDIATES AND METHOD

[75] Inventors: Donald S. Karanewsky, East Windsor; Michael C. Badia, Lawrenceville; Scott A. Biller, Ewing; Eric M. Gordon, Pennington; Michael J. Sofia, Lawrenceville, all of N.J.

[73] Assignee: E. R. Squibb & Sons, Inc., Princeton, N.J.

[21] Appl. No.: 810,099

[22] Filed: Dec. 19, 1991

Related U.S. Application Data

[60] Division of Ser. No. 182,710, Apr. 18, 1988, Pat. No. 5,091,378, which is a continuation-in-part of Ser. No. 109,681, Oct. 19, 1987, abandoned, which is a continuation-in-part of Ser. No. 53,238, May 22, 1987, abandoned.

[51] Int. Cl.$^5$ .................. C07F 9/02; C07C 69/73; A61K 31/66
[52] U.S. Cl. ................... 514/120; 558/197; 558/198; 560/183
[58] Field of Search ............... 558/197, 198; 560/183; 514/120

[56] References Cited

U.S. PATENT DOCUMENTS

| | | | |
|---|---|---|---|
| 4,613,610 | 9/1986 | Wareing | 514/422 |
| 4,647,576 | 3/1987 | Hoefle | 514/422 |

FOREIGN PATENT DOCUMENTS

| | | | |
|---|---|---|---|
| 0221025A1 | 5/1987 | European Pat. Off. | 548/562 |
| 2596393A1 | 4/1986 | France | 558/197 |
| WO86/03488 | 6/1986 | PCT Int'l Appl. | 514/422 |
| WO86/07054 | 12/1986 | PCT Int'l Appl. | 514/422 |

OTHER PUBLICATIONS

Tetrahedron Letter, vol. 29, No. 8, 929–930, 1988, Synthesis of a novel HMG-COA reductase inhibitor.

Primary Examiner—Mary C. Lee
Assistant Examiner—Joseph K. McKane
Attorney, Agent, or Firm—Burton Rodney

[57] ABSTRACT

Compounds which are useful as inhibitors of cholesterol biosynthesis and thus as hypocholesterolemic agents are provided which have the structure

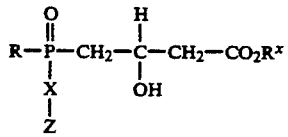

wherein
R is OH, or salts thereof or lower alkoxy;
$R^x$ is H or alkyl;
X is —CH$_2$—, —CH$_2$—CH$_2$—, —CH=CH—, —C≡C—, —CH$_2$CH$_2$CH$_2$— or —CH$_2$O— (where O is linked to Z);
Z is a hydrophobic anchor, such as

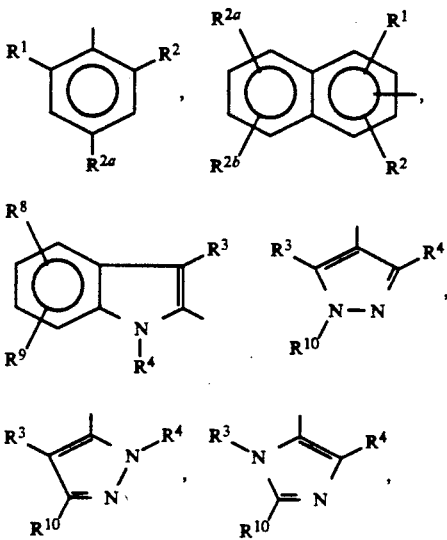

(Abstract continued on next page.)

-continued
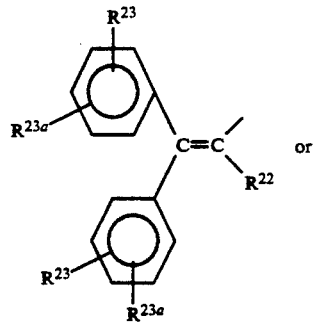
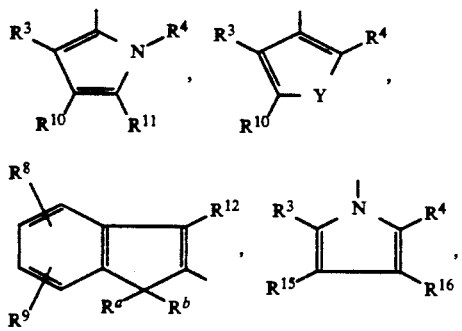
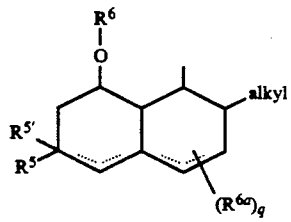
wherein the dotted lines represent optional double bonds.
19 Claims, No Drawings

PHOSPHORUS-CONTAINING HMG-COA REDUCTASE INHIBITORS, NEW INTERMEDIATES AND METHOD

REFERENCE TO OTHER APPLICATIONS

This is a division of application Ser. No. 182,710, filed Apr. 18, 1988, U.S. Pat. No. 5,091,378, which is a continuation-in-part of application Ser. No. 109,681, filed Oct. 19, 1987, now abandoned, which is a continuation-in-part of application Ser. No. 053,238, filed May 22, 1987, now abandoned.

FIELD OF THE INVENTION

The present invention relates to new phosphorus-containing compounds which inhibit the activity of 3-hydroxy-3-methylglutaryl-coenzyme A reductase and thus are useful in inhibiting cholesterol biosynthesis, to hypocholesterolemic compositions containing such compounds, to new intermediates formed in the preparation of such compounds and to a method of using such compounds for such purposes.

BACKGROUND OF THE INVENTION

F. M. Singer et al., *Proc. Soc. Exper. Biol. Med.*, 102, 370 (1959) and F. H. Hulcher, *Arch. Biochem. Biophys.*, 146, 422 (1971) disclose that certain mevalonate derivatives inhibit the biosynthesis of cholesterol.

Endo et al in U.S. Pat. Nos. 4,049,495, 4,137,322 and 3,983,140 disclose a fermentation product which is active in the inhibition of cholesterol biosynthesis. This product is called compactin and was reported by Brown et al., (*J. Chem. Soc. Perkin I.* 1165 (1976)) to have a complex mevalonolactone structure.

GB 1,586,152 discloses a group of synthetic compounds of the formula

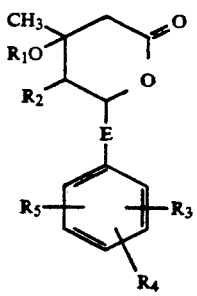

in which E represents a direct bond, a $C_{1-3}$ alkylene bridge or a vinylene bridge and the various R's represent a variety of substituents.

The activity reported in the U.K. patent is less than 1% that of compactin.

U.S. Pat. No. 4,375,475 to Willard et al discloses hypocholesterolemic and hypolipemic compounds having the structure

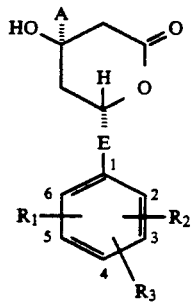

wherein A is H or methyl; E is a direct bond, $-CH_2-$, $-CH_2-CH_2-$, $-CH_2-CH_2-CH_2-$ or $-CH=CH-$; $R_1$, $R_2$ and $R_3$ are each selected from H, halogen, $C_{1-4}$ alkyl, $C_{1-4}$ haloalkyl, phenyl, phenyl substituted by halogen, $C_{1-4}$ alkoxy, $C_{2-8}$ alkanoyloxy, $C_{1-4}$ alkyl, or $C_{1-4}$ haloalkyl, and $OR_4$ in which $R_4$ is H, $C_{2-8}$ alkanoyl, benzoyl, phenyl, halophenyl, phenyl $C_{1-3}$ alkyl, $C_{1-9}$ alkyl, cinnamyl, $C_{1-4}$ haloalkyl, allyl, cycloalkyl-$C_{1-3}$-alkyl, adamantyl-$C_{1-3}$-alkyl, or substituted phenyl $C_{1-3}$-alkyl in each of which the substituents are selected from halogen, $C_{1-4}$ alkoxy, $C_{1-4}$ alkyl, or $C_{1-4}$ haloalkyl; and the corresponding dihydroxy acids resulting from the hydrolytic opening of the lactone ring, and the pharmaceutically acceptable salts of said acids, and the $C_{1-3}$ alkyl and phenyl, dimethylamino or acetylamino substituted $C_{1-3}$-alkyl esters of the dihydroxy acids; all of the compounds being the enantiomers having a 4 R configuration in the tetrahydropyran moiety of the trans racemate shown in the above formula.

WO 84/02131 (PCT/EP83/00308) (based on U.S. application Ser. No. 443,668, filed Nov. 22, 1982, and U.S. application Ser. No. 548,850, filed Nov. 4, 1983), filed in the name of Sandoz A. G. discloses heterocyclic analogs of mevalono lactone and derivatives thereof having the structure

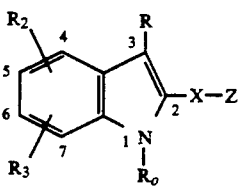

wherein one of R and $R_o$ is

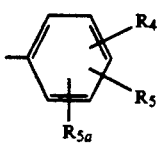

and the other is primary or secondary $C_{1-6}$ alkyl, $C_{3-6}$ cycloalkyl or phenyl-$(CH_2)_m-$, wherein $R_4$ is hydrogen, $C_{1-4}$ alkyl, $C_{1-4}$ alkoxy, (except t-butoxy), trifluoromethyl, fluoro, chloro, phenoxy or benzyloxy, $R_5$ is hydrogen, $C_{1-3}$ alkyl, $C_{1-3}$ alkoxy, trifluoromethyl, fluoro, chloro, phenoxy or benzyloxy, $R_{5a}$ is hydrogen, $C_{1-2}$ alkyl, $C_{1-2}$ alkoxy, fluoro or chloro, and m is 1, 2 or 3, with the provisos that both $R_5$ and $R_{5a}$ must be hydrogen when $R_4$ is hydrogen, $R_{5a}$ must be hydrogen when $R_5$ is hydrogen, not more than one of $R_4$ and $R_5$ is trifluoromethyl, not more than one of $R_4$ and $R_5$ is phenoxy and not more than one of $R_4$ and $R_5$ is benzyloxy, $R_2$ is hydrogen, $C_{1-4}$ alkyl, $C_{3-6}$ cycloalkyl, $C_{1-4}$ alkoxy (except t-butoxy), trifluoromethyl, fluoro, chloro, phenoxy or benzyloxy, $R_3$ is hydrogen, $C_{1-3}$ alkyl, $C_{1-3}$ alkoxy, trifluoromethyl, fluoro, chloro, phenoxy or benzyloxy, with the provisos that $R_3$ must be hydrogen when $R_2$ is hydrogen, not more than one of $R_2$ and $R_3$ is trifluoromethyl, not more than one of $R_2$ and $R_3$ is phenoxy, and not more than one of $R_2$ and $R_3$ is benzyloxy.

X is $-(CH_2)_n-$ or $-CH=CH-$ (n=0, 1, 2 or 3), Z is $$-\overset{5}{C}H-\overset{4}{C}H_2-\overset{3}{\underset{OH}{C}}\overset{R_6}{\underset{|}{-}}\overset{2}{C}H_2-\overset{1}{C}OOH \qquad II$$
$$\qquad\ \ \, |\qquad\quad\ \, |$$
$$\quad\ \ OH\quad\ \ OH$$

wherein $R_6$ is hydrogen or $C_{1-3}$ alkyl in free acid form or in the form of a physiologically-hydrolysable and -acceptable ester or a δ lactone thereof or in salt form.

GB 2162-179-A discloses naphthyl analogues of mevalolactone useful as cholesterol biosynthesis inhibitors having the structure wherein $R_1 = 1-3C$ alkyl;
Z is a gp. of formula $Z_1$ or $Z_2$:

$$-CHCH_2CHCH_2COOR_7 \qquad (Z_1)$$
$$\ \ \uparrow\qquad\ \ \uparrow$$
$$\ \ OH\quad\ OH$$

(Z_2)

$R_7 =$ H, a hydrolysable ester gp. or a cation.

European Patent No. 164-698-A discloses preparation of lactones useful as anti-hypercholesterolemic agents by treating an amide with an organic sulphonyl halide $R^5SO_2X$, then removing the protecting group Pr.

wherein
X=halo;
Pr=a carbinol-protecting group;
$R^1$=H or $CH_3$;
$R^3$, $R^4$=H, 1-3C alkyl or phenyl-(1-3C alkyl), the phenyl being optionally substituted by 1-3C alkyl, 1-3C alkoxy or halo;
$R^2$=a group of formula (A) or (B):

(A)

(B)

Q=

$$R^6-\underset{CH_3}{\overset{|}{\underset{|}{C}}}- \quad \text{or} \quad R^6-\overset{|}{\underset{|}{C}}H;$$

$R^6$=H or OH;
R=H or $CH_3$;
a, b, c and d=optional double bonds;
$R^7$=phenyl or benzyloxy, the ring in each case being optionally substituted by 1-3C alkyl or halo;
$R^8$, $R^9$=1-3C alkyl or halo;
$R^5$=1-3C alkyl, phenyl or mono- or di-(1-3C alkyl)-phenyl.

Anderson, Paul Leroy, Ger. Offen. DE 3,525,256 discloses naphthyl analogs of mevalonolactones of the structure

I

-continued

 Q

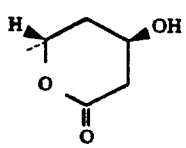 Q' wherein $R^1$ is alkyl, $Z=Q$, $Q^1$; $R^7=H$, or a hydrolyzable ester group useful as inhibitors of cholesterol biosynthesis and in treatment of atherosclerosis.

WO 8402-903 (based on U.S. application Ser. No. 460,600, filed Jan. 24, 1983) filed in the name of Sandoz A. G. discloses mevalono-lactone analogues useful as hypolipoproteinaemic agents having the structure

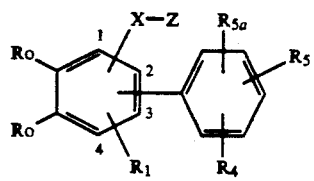 I wherein the two groups Ro together form a radical of formula

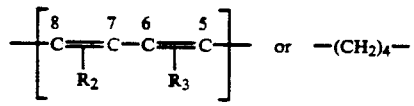

wherein $R_2$ is hydrogen, $C_{1-4}$ alkyl, $C_{1-4}$ alkoxy, (except t-butoxy), trifluoromethyl, fluoro, chloro, phenoxy or benzyloxy, $R_3$ is hydrogen, $C_{1-3}$ alkyl, $C_{1-3}$ alkoxy, trifluoromethyl, fluoro, chloro, phenoxy or benzyloxy, with the provisos that not more than one of $R_2$ and $R_3$ is trifluoromethyl, not more than one of $R_2$ and $R_3$ is phenoxy, and not more than one of $R_2$ and $R_3$ is benzyloxy, $R_1$ is hydrogen, $C_{1-6}$ alkyl, fluoro, chloro or benzyloxy, $R_4$ is hydrogen, $C_{1-4}$ alkyl, $C_{1-4}$ alkoxy, (except t-butoxy), trifluoromethyl, fluoro, chloro, phenoxy or benzyloxy, $R_5$ is hydrogen, $C_{1-3}$ alkyl, $C_{1-3}$ alkoxy, trifluoromethyl, fluoro, chloro, phenoxy or benzyloxy, $R_{5a}$ is hydrogen, $C_{1-2}$ alkyl, $C_{1-2}$ alkoxy, fluoro or chloro, and with the provisos that not more than one of $R_4$ and $R_5$ is trifluoromethyl, not more than one of $R_4$ and $R_5$ is phenoxy and not more than one of $R_4$ and $R_5$ is benzyloxy, X is $-(CH_2)_n-$, 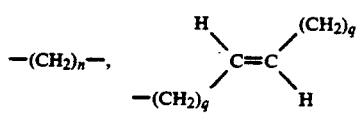

wherein n is 0, 1, 2 or 3 and both q's are 0 or one is 0 and the other is 1,

Z is

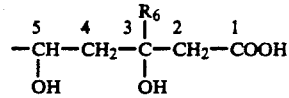 II wherein $R_6$ is hydrogen or $C_{1-3}$ alkyl, with the general proviso that $-X-Z$ and the $R_4$ bearing phenyl group are ortho to each other;

in free acid form or in the form of a physiologically-hydrolysable and acceptable ester or a δ lactone thereof or in salt form.

U.S. Pat. No. 4,613,610 to Wareing (assigned to Sandoz) discloses a series of 7-pyrazolo-3,5-dihydrohept-6-enoic acid HMG-CoA reductase inhibitors of the structure

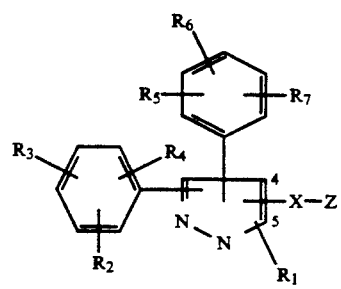

wherein $R_1$ is $C_{1-6}$alkyl not containing an asymmetric carbon atom, each of $R_2$ and $R_5$ is independently hydrogen, $C_{1-3}$alkyl, n-butyl, i-butyl, t-butyl, $C_{1-3}$alkoxy, n-butoxy, i-butoxy, trifluoromethyl, fluoro, chloro, phenyl, phenoxy or benzyloxy, each of $R_3$ and $R_6$ is independently hydrogen, $C_{1-3}$alkyl, $C_{1-3}$alkoxy, trifluoromethyl, fluoro, chloro, phenoxy or benzyloxy, each of $R_4$ and $R_7$ is independently hydrogen, $C_{1-2}$alkyl, $C_{1-2}$alkoxy, fluoro or chloro, with the provisos that not more than one of $R_2$ and $R_3$ is trifluoromethyl, not more than one of $R_2$ and $R_3$ is phenoxy, not more than one of $R_2$ and $R_3$ is benzyloxy, not more than one of $R_5$ and $R_6$ is trifluoromethyl, not more than one of $R_5$ and $R_6$ is phenoxy, and not more than one of $R_5$ and $R_6$ is benzyloxy, X is $-(CH_2)_m-$, $-CH=CH-$, $-CH=CH-CH_2-$ or $-CH_2-CH=CH-$, wherein m is 0, 1, 2 or 3, and Z is

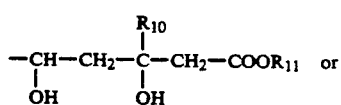

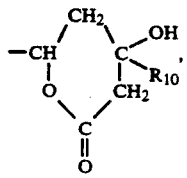

wherein $R_{10}$ is hydrogen or $C_{1-3}$alkyl, and $R_{11}$ is hydrogen, $R_{12}$ or M, wherein $R_{12}$ is a physiologically acceptable and hydrolyzable ester group, and M is a cation, with the provisos that (i) the —X—Z group is in the 4- or 5-position of the pyrazole ring, and (ii) the $R_1$ group and the —X—Z group are ortho to each other.

WO 8607-054A (Sandoz-Erfindungen) discloses imidazole analogues of mevalonolactone, useful for treating hyperlipoproteinaemia and atherosclerosis, which have the formula

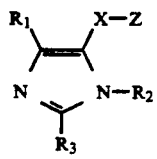

(I)

$R_1$ = alkyl, cycloalkyl, adamantyl-1 or $R_4$, $R_5$, $R_6$-substituted phenyl (gp. A);

$R_2$ = alkyl, cycloalkyl, adamantyl-1 or $R_7$, $R_8$, $R_9$-substituted phenyl (gp. B);

$R_3$ = H, alkyl, cycloalkyl, adamantyl-1, styryl or $R_{10}$, $R_{11}$, $R_{12}$-substituted phenyl (gp, C);

X = —(CH$_2$)$_m$—, —CH=CH—, —CH=CH—CH$_2$— or —CH$_2$—CH=CH—;

m = 0–3;

Z = —CH(OH)—CH$_2$—C($R_{13}$)(OH)—CH$_2$—COOR$_{14}$ (gp. a), —Q—CH$_2$C($R_{13}$)(OH)—CH$_2$—COOR$_{14}$ (gp. c) or a gp. of formula (b):

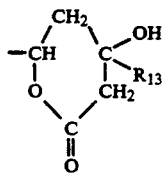

Q = CO or —C(OR$_{15}$)$_2$—;

$R_{15}$ = primary or sec. alkyl; each $R_{15}$ being the same; or $R_{15}$+$R_{15}$ = (CH$_2$)$_2$ or (CH$_2$)$_3$;

$R_{13}$ = H or 1-3C alkyl;

$R_{14}$ = H, $R_{16}$ or M;

$R_{16}$ = ester gp;

M = cation;

provided that Z may be gp. (c) only when X is CH=CH or CH$_2$—CH=CH and/or when $R_{13}$ = 1-3C alkyl;

$R_4$, $R_7$ and $R_{10}$ = 1-3C alkyl, n-, i- or t-butyl, 1-3C alkoxy, n- or i-butoxy, CF$_3$, F, Cl, Br, phenyl, phenoxy or benzyloxy;

$R_5$, $R_8$ and $R_{11}$ = H, 1-3C alkyl, 1-3C alkoxy, CF$_3$, F, Cl, Br, COOR$_{17}$, N($R_{19}$)$_2$, phenoxy or benzyloxy;

$R_{17}$ = H, $R_{18}$ or M;

$R_{18}$ = 1-3C alkyl, n, i- or t-butyl or benzyl;

$R_{19}$ = alkyl;

$R_6$, $R_9$ and $R_{12}$ = H, 1-2C alkyl, 1-2C alkoxy, F or Cl; provided that (1) not more than one substituent of each of gps. A, B and C is CF$_3$, not more than one substituent of each of gps. A, B and C is phenoxy, and not more than one substituent of each of gps, A, B and C is benzyloxy;

(2) when Z is gp. (c; Q=C(OR$_{15}$)$_2$), the compound is in free base form and either (i) $R_{14}$ is $R_{16}$ and each $R_{17}$ is independently $R_{18}$ or (ii) $R_{14}$ is M and each $R_{17}$ is independently $R_{18}$ or M; and (3) when $R_{14}$ and/or at least one $R_{17}$ is M, the compound is in free base form.

Unless otherwise stated, all "alkyl" gps. are 1-6C and do not contain an asymmetric C; and "cycloalkyl" has 3-7C.

WO 8603-488-A (Sandoz AG) discloses indene analogues of mevalolactone, useful as hypolipoproteinaemia and anti-atherosclerotic agents, in free acid form or in the form of an ester or delta-lactone or in salt form which have the formula

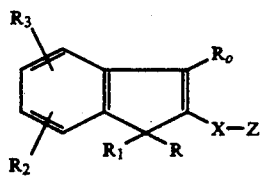

(I)

R = H or primary or secondary 1-6C alkyl;

$R_1$ = primary or secondary 1-6C alkyl;

or R+$R_1$ = (CH$_2$)$_m$ or (Z)—CH$_2$—CH=CH—CH$_2$;

m = 2–6;

$R_o$ = 1-6C alkyl, 3-7C cycloalkyl or $R_4$, $R_5$, $R_6$-substituted phenyl;

$R_2$, $R_4$ = H, 1-4C alkyl, 1-4C alkoxy (except t-butoxy), CF$_3$, F, Cl, phenoxy or benzyloxy;

$R_3$ and $R_5$ = H, 1-3C alkyl, 1-3C alkoxy, CF$_3$, F, Cl, phenoxy or benzyloxy;

$R_6$ = H, 1-2C alkyl, 1-2C alkoxy, F or Cl;

provided that there may only be one each of CF$_3$, phenoxy or benzyloxy on each of the phenyl and indene rings;

X = (CH$_2$)$_n$ or —(CH$_2$)$_q$—CH=CH(CH$_2$)$_q$—;

n = 1–3;

both q's = 0, or one is 0 and the other is 1;

Z = —Q—CH$_2$—C($R_{10}$)(OH)—CH$_2$COOH, in free acid form or in the form of an ester or delta-lactone or salt;

Q = CO, —C(OR$_7$)$_2$— or CHOH;

R'$_{7s}$ = the same primary or secondary 1-6C alkyl, or together are (CH$_2$)$_2$ or (CH$_2$)$_3$;

$R_{10}$ = H or 1-3C alkyl;

provided that Q may be other than CHOH only when X is CH=CH or CH$_2$—CH=CH and/or $R_{10}$ is 1-3C alkyl.

U.S. Pat. No. 4,647,576 to Hoefle et al (Warner Lambert) discloses new C- and N-substituted pyrrole(s), useful as hypolipidaemic and hypocholesterolaemic agents, which have the formula

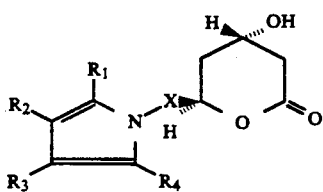

(I)

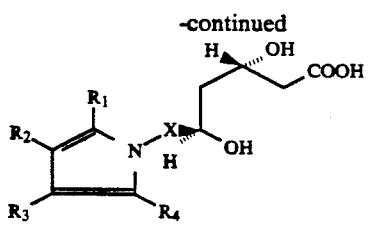

(II)

$X = -CH_2-$, $-CH_2CH_2-$ or $-CH(CH_3)CH_2-$;

$R_1 = $ 1- or 2-naphthyl; cyclohexyl; norbornenyl; phenyl optionally substituted by F, Cl, OH, CF$_3$, 1-4C alkyl, 1-4C alkoxy or 2-8C alkanoyloxy; 2-, 3- or 4-pyridinyl or their N-oxides; or

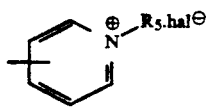

$R_5 = $ 1-4C alkyl;

hal = chloride, bromide or iodide;

$R_2$ and $R_3 = $ H, Cl, Br, CN, CF$_3$, phenyl, 1-4C alkyl, 2-8C carboalkoxy, $-CH_2OR_6$ or $-CH_2OCONHR_7$;

$R_6 = $ H or 1-6C alkanoyl;

$R_7 = $ alkyl or phenyl optionally substituted by Cl, Br or 1-4C alkyl;

or $R_2$ and $R_3$ together $= -(CH_2)_n-$, $-CH_2OCH_2-$, $-CON(R_8)CO-$ or $-CON(R_9)N(R_{10})CO-$;

n = 3 or 4;

$R_8 = $ H, 1-6C alkyl, phenyl or benzyl;

$R_9$ and $R_{10} = $ H, 1-4C alkyl or benzyl;

$R_4 = $ 1-4C alkyl, cyclopropyl, cyclobutyl or CF$_3$.

European patent application 0 221 025 A1 (Sandoz AG) discloses heterocyclic analogs of mevalonolactone and derivatives thereof having the formula

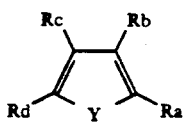

wherein

Ra is a group $-X-Z$, Rb is $R_2$, Rc is $R_3$, Rd is $R_4$ and Y is a group

or

Ra is $R_1$, Rb is a group $-X-Z$, Rc is $R_2$, Rd is $R_3$ and Y is O, S or a group

$R_1$, $R_2$, $R_3$ and $R_4$ independently are $C_{1-4}$ alkyl not containing an asymmetric carbon atom, $C_{3-7}$cycloalkyl or a ring

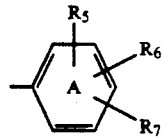

or in the case of $R_3$ and $R_4$ additionally hydrogen or for $R_3$ when Y is O or S

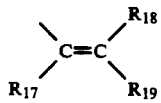

whereby $R_{17}$ is hydrogen or $C_{1-3}$alkyl and $R_{18}$ and $R_{19}$ are independently hydrogen, $C_{1-3}$alkyl or phenyl; each $R_5$ is independently hydrogen, $C_{1-3}$alkyl, n-butyl, i-butyl, t-butyl, $C_{1-3}$alkoxy, n-butoxy, i-butoxy, trifluoromethyl, fluoro, chloro, bromo, phenyl, phenoxy or benzyloxy; each $R_4$ is independently hydrogen, $C_{1-3}$alkyl, $C_{1-3}$alkoxy, trifluoromethyl, fluoro, chloro, bromo, phenoxy or benzyloxy and each $R_7$ is independently hydrogen, $C_{1-2}$alkyl, $C_{1-2}$alkoxy, fluoro or chloro with the proviso that there may only be one each of trifluoromethyl, phenoxy or benzyloxy in each ring A present. X is $(CH_2)_m$ or $(CH_2)_q CH=CH(CH_2)_q$, m is 0, 1, 2 or 3 and both q's are 0 or one is 0 and the other is 1.

Z is

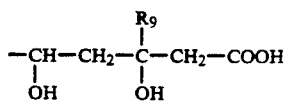

wherein $R_9$ is hydrogen or $C_{1-3}$alkyl, in free acid form or in the form of an ester of $\beta$-lactone thereof or in salt form as appropriate which compounds are indicated for use as hypolipoproteinemic and antiatherosclerotic agents.

Tetrahedron Letters, 29, 929, 1988, discloses the synthesis of a 3-hydroxy-3-methylglutaryl coenzyme A reductase inhibitor of the structure

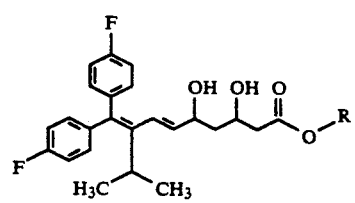

where R is Na or $C_2H_5$.

European patent application 127,848-A (Merck & Co, Inc.) discloses derivatives of 3-hydroxy-5-thia-$\omega$-arylalkanoic acids having the structural formula:

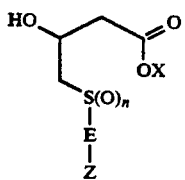

wherein Z is:

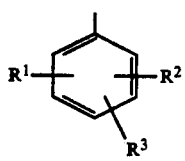

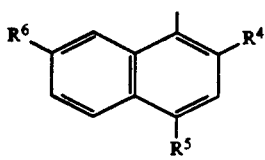

n is 0, 1 or 2;

E is —CH$_2$—, —CH$_2$—CH$_2$—, —CH$_2$—CH$_2$—CH$_2$—, —CH=CH—CH$_2$—; or —CH$_2$—CH=CH—;

R$_1$, R$_2$ and R$_3$ are, e.g., hydrogen, chloro, bromo, fluoro, C$_1$-alkyl, phenyl, substituted phenyl or OR$_7$ in which R$_7$ is, e.g., hydrogen, C$_{2-8}$alkanoyl, benzoyl, phenyl, substituted phenyl, C$_{1-9}$alkyl, cinnamyl, C$_{1-4}$haloalkyl, allyl, cycloalkyl-C$_{1-3}$alkyl, adamantyl-C$_{1-3}$-alkyl, or phenyl C$_{1-3}$ alkyl;

R$^4$, R$^5$ and R$^6$ are hydrogen, chloro, bromo, fluoro or C$_{1-3}$ alkyl; and X is, e.g., hydrogen, C$_{1-3}$ alkyl, a cation derived from an alkali metal or is ammonium.

Those compounds have antihypercholesterolemic activity by virtue of their ability to inhibit 3-hydroxy-3-methylglutaryl-coenzyme A (HMG-CoA) reductase and antifungal activity.

French patent application 2,596,393 A filed on Apr. 1, 1986 (Sanofi SA) discloses 3-carboxy-2-hydroxy-propane-phosphonic acid derivatives including salts thereof which are useful as hypolipaemic agents and have the formula:

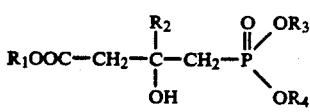

wherein R$_1$ and R$_2$=H, lower alkyl or optionally substituted aralkyl;

R$_3$ and R$_4$=H, lower alkyl or optionally substituted aryl or aralkyl.

These comounds are disclosed as giving greater reductions in cholesterol, triglyceride and phospholipid levels than meglutol.

European patent application 142, 146-A (Merck & Co., Inc) discloses mevinolin-like compounds of the structural formula:

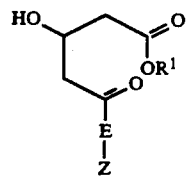

wherein:
R$^1$ is, e.g., hydrogen or C$_{1-4}$alkyl;
E is —CH$_2$CH$_2$—, —CH=CH—, or —(CH$_2$)$_r$—; and
Z is
1)

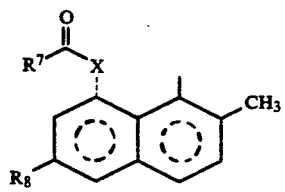

wherein X is —O— or —NR$^9$ wherein R$^9$ is hydrogen or C$_{1-3}$alkyl;
R$^7$ is C$_{2-8}$ alkyl; and
R$^8$ is hydrogen or CH$_3$;

2)

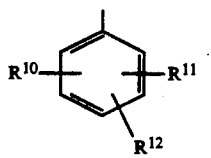

wherein R$^{10}$, R$^{11}$ and R$^{12}$ are independently, e.g., hydrogen, halogen or C$_{1-4}$ alkyl;

3)

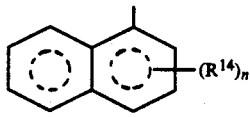

wherein n is 0–2 and R$^{14}$ is halo or C$_{1-4}$alkyl; or

4)

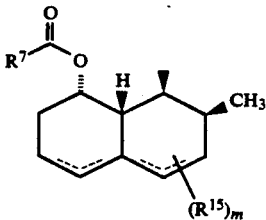

These compounds are HMG-CoA reductase inhibitors.

DESCRIPTION OF THE INVENTION

In accordance with the present invention, there is provided phosphorus-containing compounds which inhibit the enzyme 3-hydroxy-3-methylglutarylcoenzyme A reductase (HMG-CoA Reductase) and thus are useful as hypocholesterolemic agents and include the following moiety

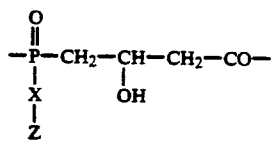

wherein X is —$(CH_2)_a$—, —CH=CH—, —C≡C—, or —$CH_2O$— (where O is linked to Z), "a" is 1, 2 or 3, and Z is an "hydrophobic anchor".

The term hydrophobic anchor as employed herein refers to a lipophilic group which when linked to the HMG-like upper side chain of the molecule by the appropriate linker ("X"), binds to a hydrophobic pocket of the enzyme not utilized in binding the substrate HMG CoA, resulting in enhancing potency relative to compounds whree Z=H.

In preferred embodiments, the compounds of the invention have the formula I

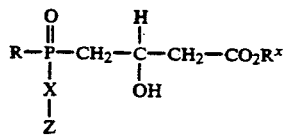

I wherein R is OH or lower alkoxy;

$R^x$ is H or lower alkyl;

X is $CH_2$, —$CH_2CH_2$—, —$CH_2CH_2CH_2$—, —CH=CH—, —C≡C— or —$CH_2O$— (where O is linked to Z);

Z is a hydrophobic anchor;

and including pharmaceutically acceptable salts thereof.

The terms "salt" and "salts" refer to basic salts formed with inorganic and organic bases. Such salts include ammonium salts, alkali metal salts like, lithium, sodium and potassium salts (which are preferred), alkaline earth metal salts like the calcium and magnesium salts, salts with organic bases, such as amine like salts, e.g., dicyclohexylamine salt, benzathine, N-methyl-D-glucamine, hydrabamine salts, salts with amino acids like arginine, lysine and the like. The nontoxic, pharmaceutically acceptable salts are preferred, although other salts are also useful, e.g., in isolating or purifying the product.

Examples of hydrophobic anchors which may be included in accordance with the present invention include, but are not limited to

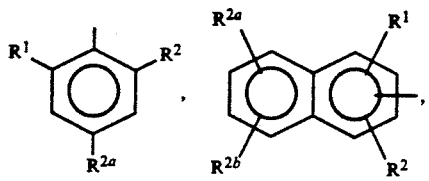

-continued

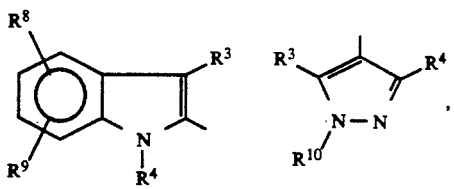

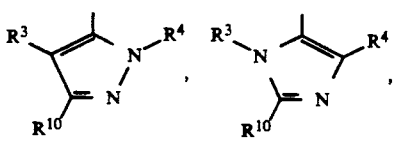

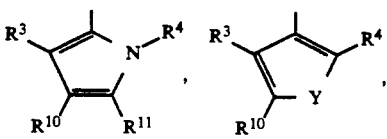

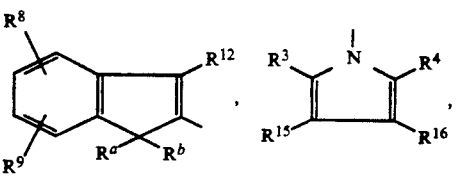

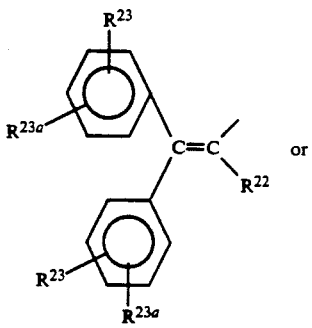

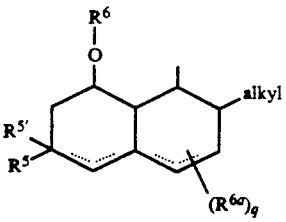

wherein the dotted lines represent optional double bonds, for example,

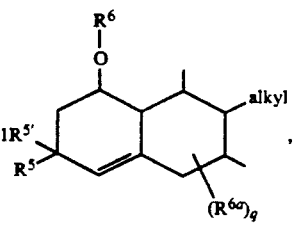

-continued

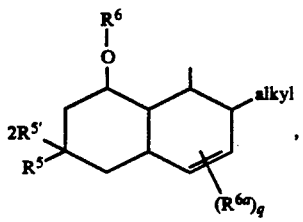

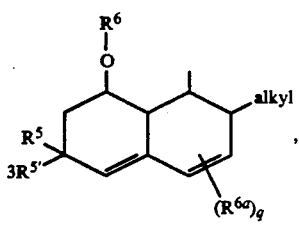

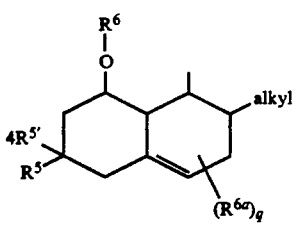

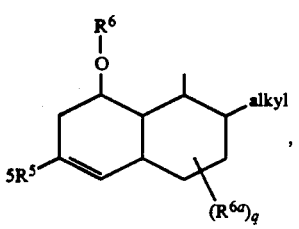

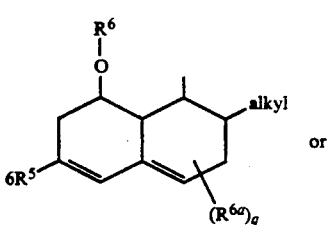

or

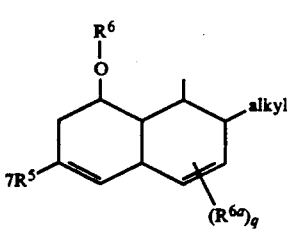

wherein $R^1$, $R^2$, $R^{2a}$ and $R^{2b}$ may be the same or different and are each independently selected from H, halogen, lower alkyl, haloalkyl, phenyl, substituted phenyl or $OR^y$ wherein $R^y$ is H, alkanoyl, benzoyl, phenyl, halophenyl, phenyl-lower alkyl, lower alkyl, cinnamyl, haloalkyl, allyl, cycloalkyl-lower alkyl, adamantyl-lower alkyl or substituted phenyl-lower alkyl. Where Z is

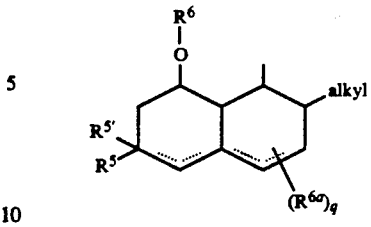

$R^5$ and $R^{5'}$ are the same or different and are H, lower alkyl or OH;
$R^6$ is lower alkyl

such as

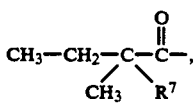

or arylCH$_2$—;
$R^{6a}$ is lower alkyl, hydroxy, oxo or halogen; q is 0, 1, 2 or 3, and
$R^7$ is H or lower alkyl.
Where Z is

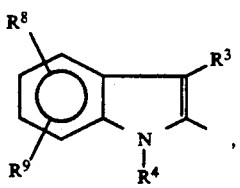

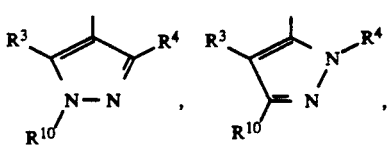

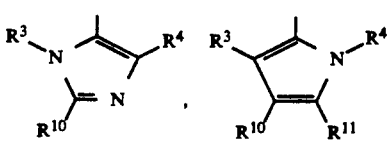

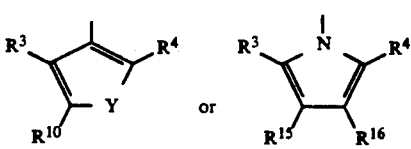

one of $R^3$ and $R^4$ is

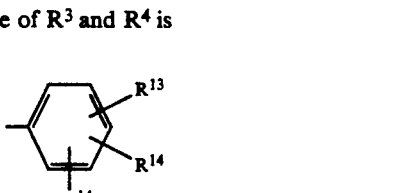

and the other is lower alkyl, cycloalkyl or phenyl—$(CH_2)_p$—, p is 0, 1, 2, 3 or 4;

wherein $R^{13}$ is hydrogen, lower alkyl, lower alkoxy, (except t-butoxy), halogen, phenoxy or benzyloxy;

$R^{14}$ is hydrogen, lower alkyl, lower alkoxy, halogen, phenoxy or benzyloxy;

$R^{14a}$ is hydrogen, lower alkyl, lower alkoxy, or halogen; and with the provisos that both $R^{14}$ and $R^{14a}$ must be hydrogen when $R^{13}$ is hydrogen, $R^{14a}$ must be hydrogen when $R^{14}$ is hydrogen, not more than one of $R^{13}$ and $R^{14}$ is trifluoromethyl, not more than one of $R^{13}$ and $R^{14}$ is phenoxy and not more than one of $R^{13}$ and $R^{14}$ is benzyloxy;

$R^8$ is hydrogen, $C_{1-4}$ alkyl, $C_{3-6}$ cycloalkyl, $C_{1-4}$ alkoxy (except t-butoxy), trifluoromethyl, fluoro, chloro, phenoxy or benzyloxy;

$R^9$ is hydrogen, $C_{1-3}$ alkyl, $C_{1-3}$ alkoxy, trifluoromethyl, fluoro, chloro, phenoxy or benzyloxy, with the provisos that $R^9$ must be hydrogen when $R^8$ is hydrogen, not more than one of $R^8$ and $R^9$ is trifluoromethyl, not more than one of $R^8$ and $R^9$ is phenoxy, and not more than one of $R^8$ and $R^9$ is benzyloxy.

$R^{10}$ and $R^{11}$ are independently selected from hydrogen, alkyl, cycloalkyl, adamantyl-1 or

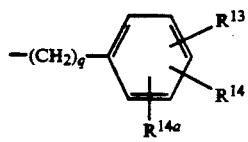

where $R^{13}$, $R^{14}$ and $R^{14a}$ are as defined above and q=0, 1, 2, 3 or 4.

Y is O, S or N—$R^{10}$.

Where Z is

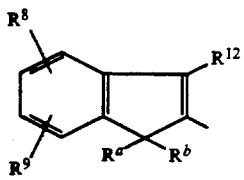

$R^a$ is H or primary or secondary 1-6C alkyl;
$R^b$ is primary or secondary 1-6C alkyl;
or $R^a+R^b$ is $(CH_2)_r$ or (cis)—$CH_2$—$CH=CH$—$CH_2$;
$R^{12}$ is lower alkyl, cycloalkyl or

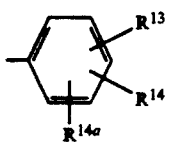

wherein $R^8$, $R^9$, $R^{13}$, $R^{14}$ and $R^{14a}$ are as defined above.

When Z is

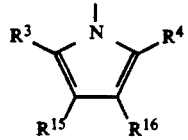

$R^{15}$ and $R^{16}$ are both H, Cl, Br, CN, $CF_3$, phenyl, 1-4C alkyl, 2-8C alkoxycarbonyl, —$CH_2OR^{17}$ or —$CH_2OCONHR^{18}$;

$R^{17}$ is H or 1-6C alkanoyl;

$R^{18}$ is alkyl or phenyl optionally substituted by F, Cl, Br or 1-4C alkyl;

or $R^{15}$ and $R^{16}$ taken together are —$(CH_2)_s$—, —$CH_2OCH_2$—, —$CON(R^{19})CO$—, or —$CON(R^{20})N(R^{21})CO$—;

S=3 or 4;

$R^{19}$=H, 1-6C alkyl, phenyl, or benzyl;

$R^{20}$ and $R^{21}$ are H, 1-4C alkyl or benzyl;

with the added proviso that when Z is

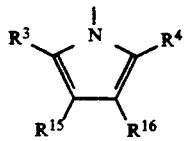

X can only be —$CH_2$—, —$CH_2CH_2$— or —$CH_2CH_2CH_2$.

Where Z is

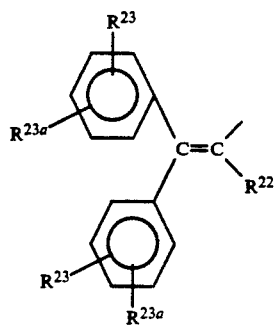

$R^{22}$ is lower alkyl, cycloalkyl, adamantyl-1 or

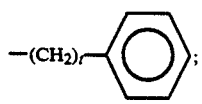

t=1, 2, 3 or 4;

$R^{23}$ and $R^{23a}$ are the same or different and are each independently selected from hydrogen, lower alkyl, lower alkoxyl (except t-butoxy), halogen, phenoxy or benzyloxy; and with the provisos that $R^{23a}$ must be hydrogen when $R^{23}$ is hydrogen, not more than one of $R^{23}$ and $R^{23a}$ is trifluoromethyl, not more than one of $R^{23}$ and $R^{23a}$ is phenoxy, and not more than one of $R^{23}$ and $R^{23a}$ is benzyloxy.

Where X is —$CH_2O$— (carbon attached to P and O attached to Z), the hydrophobic anchor Z will be a phenyl or naphthalene type anchor such as

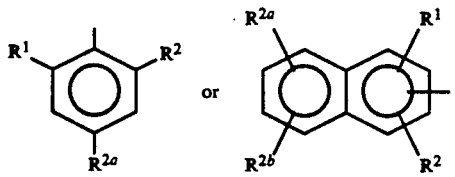

Thus, the compounds of formula I encompass

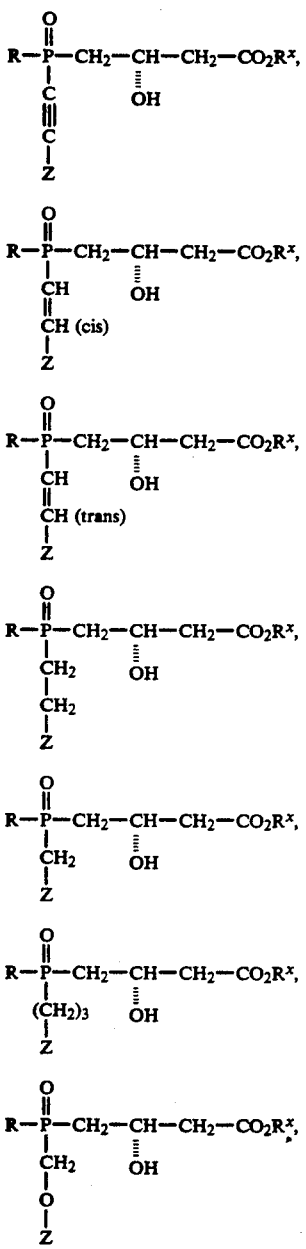

The term "lower alkyl" or "alkyl" as employed herein alone or as part of another group includes both straight and branched chain hydrocarbons, containing 1 to 12 carbons in the normal chain, preferably 1 to 7 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent, such as F, Br, Cl or I or $CF_3$, an alkoxy substituent, an aryl substituent, an alkylaryl substituent, a haloaryl substituent, a cycloalkyl substituent, an alkylcycloalkyl substituent, hydroxy, and alkylamino substituent, an alkanoylamino substituent, an arylcarbonylamino substituent, a nitro substituent, a cyano substituent, a thiol substituent or an alkylthio substituent.

The term "cycloalkyl" as employed herein alone or as part of another group includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups, 1 or 2 lower alkoxy groups, 1 or 2 hydroxy groups, 1 or 2 alkylamino groups, 1 or 2 alkanoylamino groups, 1 or 2 arylcarbonylamino groups, 1 or 2 amino groups, 1 or 2 nitro groups, 1 or 2 cyano groups, 1 or 2 thiol groups, and/or 1 or 2 alkylthio groups.

The term "aryl" or "Ar" as employed herein refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be 1, 2 or 3 lower alkyl groups, halogens (Cl, Br or F), 1, 2 or 3 lower alkoxy groups, 1, 2 or 3 hydroxy groups, 1, 2 or 3 phenyl groups, 1, 2 or 3 alkanoyloxy group, 1, 2 or 3 benzoyloxy groups, 1, 2 or 3 haloalkyl groups, 1, 2 or 3 halophenyl groups, 1, 2 or 3 allyl groups, 1, 2 or 3 cycloalkylalkyl groups, 1, 2 or 3 adamantylalkyl groups, 1, 2 or 3 alkylamino groups, 1, 2 or 3 alkanoylamino groups, 1, 2 or 3 arylcarbonylamino groups, 1, 2 or 3 amino groups, 1, 2 or 3 nitro groups, 1, 2 or 3 cyano groups, 1, 2 or 3 thiol groups, and/or 1, 2 or 3 alkylthio groups with the aryl group preferably containing 3 substituents.

The term "aralkyl", "aryl-alkyl" or "aryl-lower alkyl" as used herein alone or as part of another group refers to lower alkyl groups as discussed above having an aryl substituent, such as benzyl.

The term "lower alkoxy", "alkoxy", or "aryloxy" or "aralkoxy" as employed herein alone or as part of another group includes any of the above lower alkyl, alkyl, aralkyl or aryl groups linked to an oxygen atom.

The term "lower alkylthio", "alkylthio", "arylthio" or "aralkylthio" as employed herein alone or as part of another group includes any of the above lower alkyl, alkyl, aralkyl or aryl groups linked to a sulfur atom.

The term "lower alkylamino", "alkylamino", "arylamino", "arylalkylamino" as employed herein alone or as part of another group includes any of the above lower alkyl, alkyl, aryl or arylalkyl groups linked to a nitrogen atom.

The term "alkanoyl" as used herein as part of another group refers to lower alkyl linked to a carbonyl group.

The term "halogen" or "halo" as used herein refers to chlorine, bromine, fluorine, iodine and $CF_3$, with chlorine or fluorine being preferred.

Preferred are those compounds of formula I which have the following structure

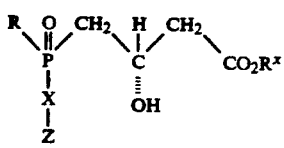   II wherein R is OH, OLi or CH$_3$O; R$^x$ is Li or H;
X is —CH$_2$—, —CH$_2$CH$_2$—, —CH$_2$CH$_2$CH$_2$, —CH=CH—, —C≡C— or —CH$_2$O—; and
Z is

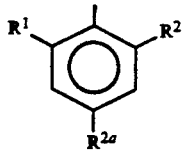

wherein R$^1$ is phenyl or phenyl which includes an alkyl and/or halo substitutent,
R$^1$ is cycloalkylalkyl such as cyclohexylmethyl,
or R$^1$ is benzyloxy which includes a halo substituent;
D$^2$ and D$^{2a}$ are the same and are hydrogen, halogen or lower alkyl;
Z may also preferably be

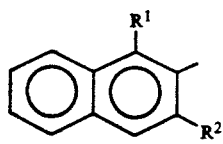

wherein R$^1$ and R$^2$ are as defined immediately above with respect to the compound of formula II;
Z may be also preferably be

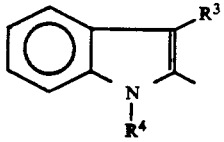

wherein R$^3$ is substituted phenyl, lower alkyl, cycloalkyl or phenylalkyl and R$^4$ is substituted phenyl, lower alkyl, such as isopropyl, cycloalkyl or phenylalkyl; or
Z may also preferably be

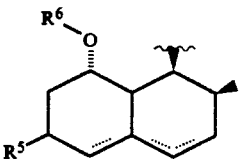

wherein R$^5$ is H, CH$_3$ or OH and R$^6$ is

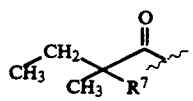

or (substituted)phenylmethyl wherein R is H or CH$_3$.
Z may also preferably be

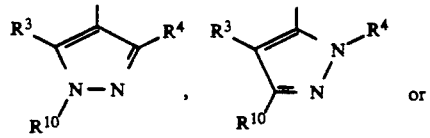

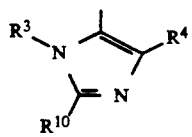

wherein at least one of R$^3$ and R$^4$ are phenyl or substituted phenyl and the remaining R$^3$ or R$^4$ is lower alkyl.

The compounds of formula I of the invention may be prepared according to the following reaction sequence and description thereof.

Reaction Sequence A.
Preparation of Compounds of Formula I where X is —CH=CH—

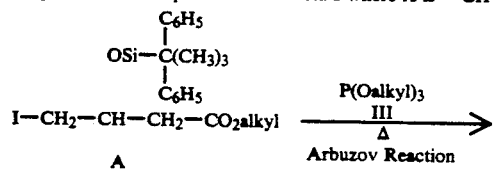

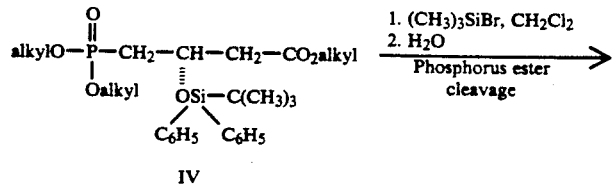

IV

-continued
Reaction Sequence A.
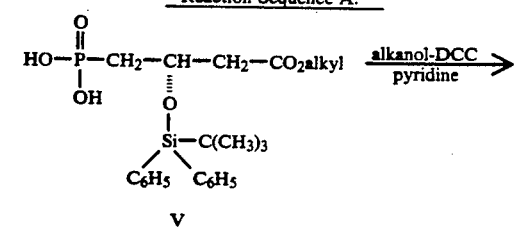
V
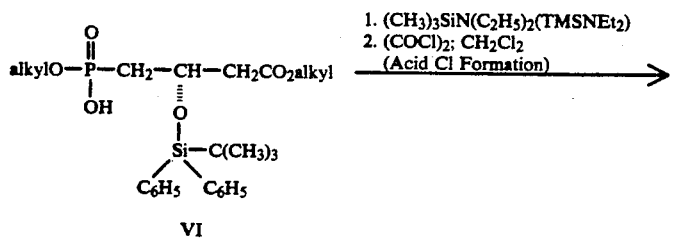
VI
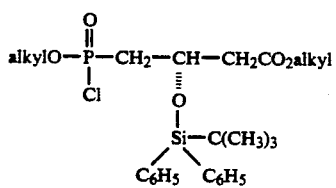
VII
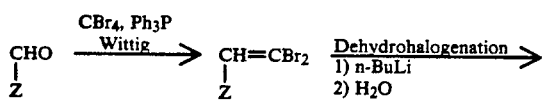
VIII    IX
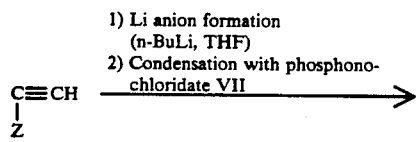
X
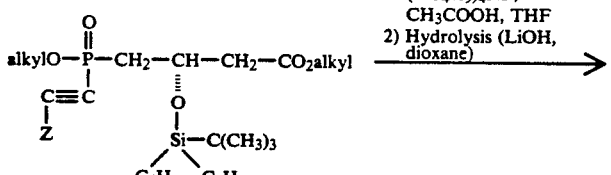
XI
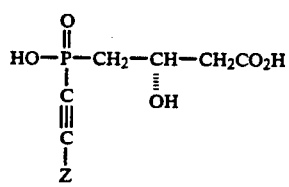
IA
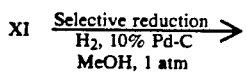

Reaction Sequence A.
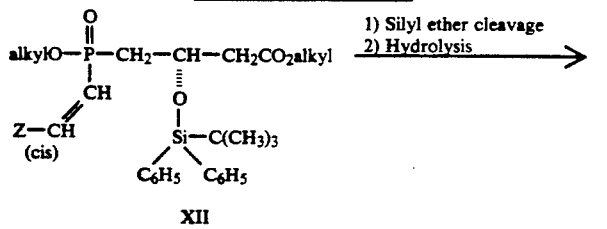
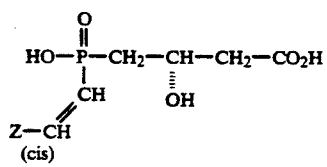
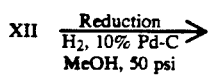
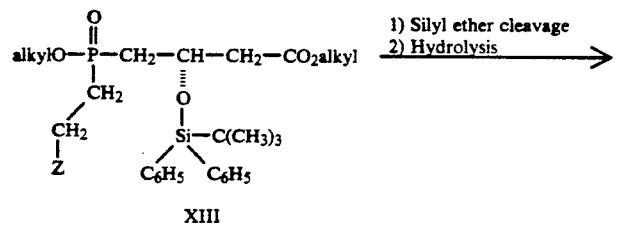
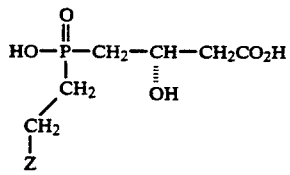
Reaction Sequence B
Preparation of compounds I where X linkage (—CH=CH—)
is trans, that is
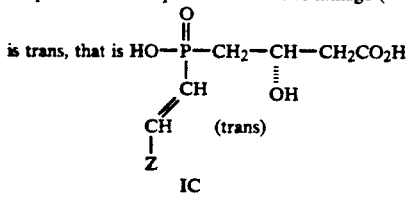
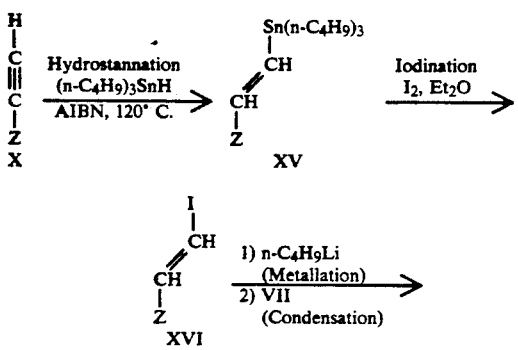
-continued
Reaction Sequence B
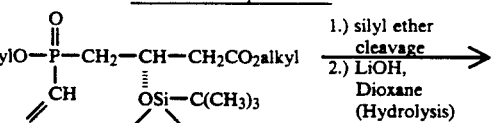
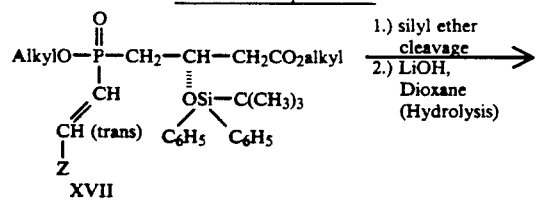
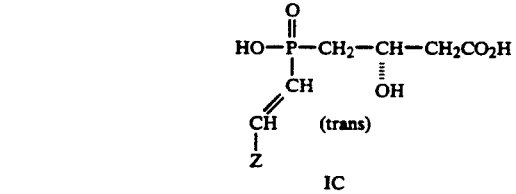
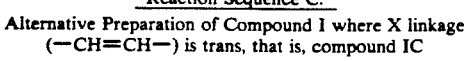
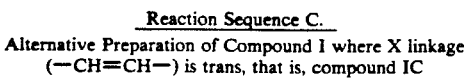
Reaction Sequence C.
Alternative Preparation of Compound I where X linkage
(—CH=CH—) is trans, that is, compound IC

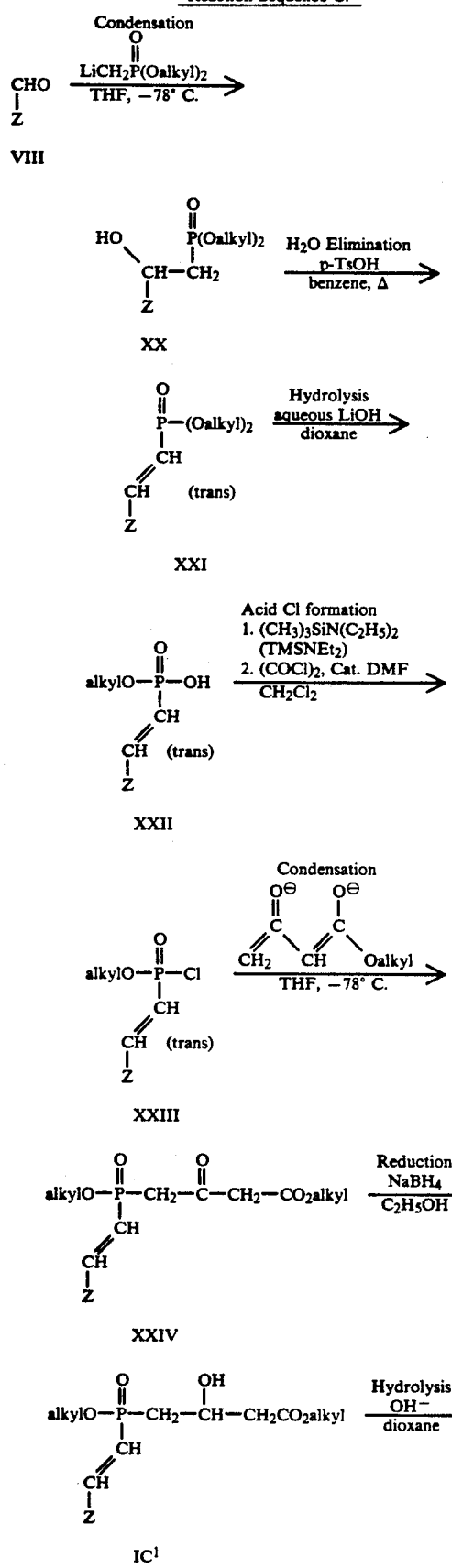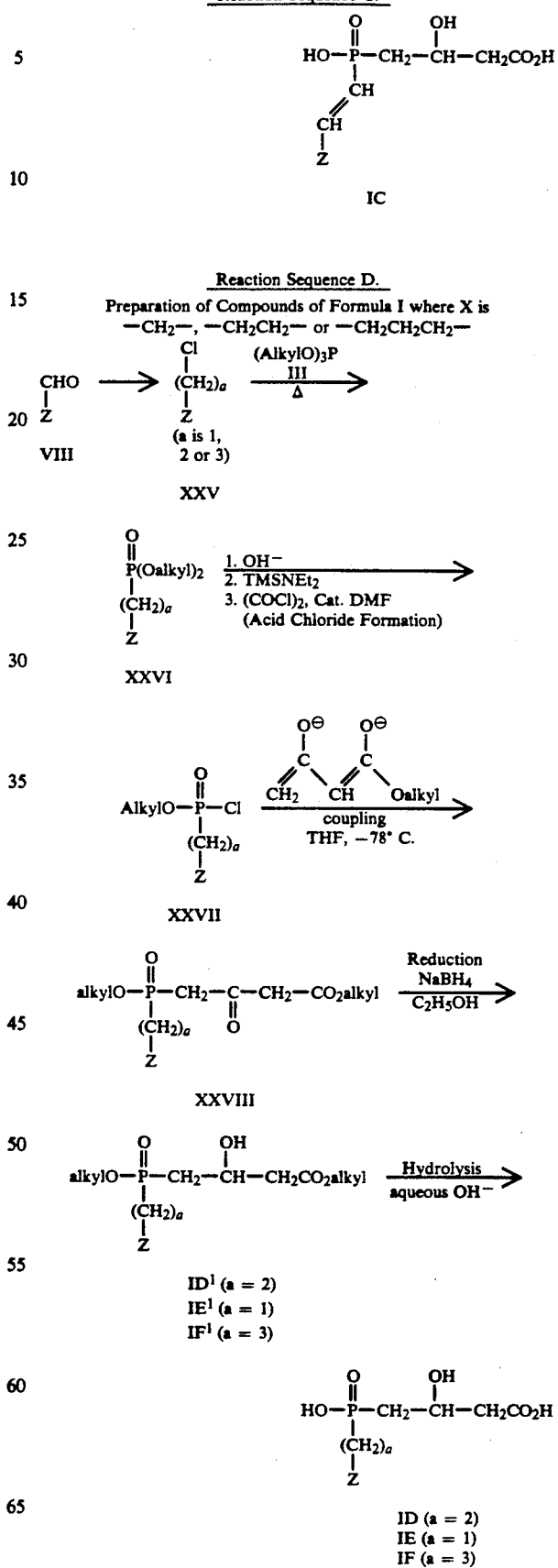

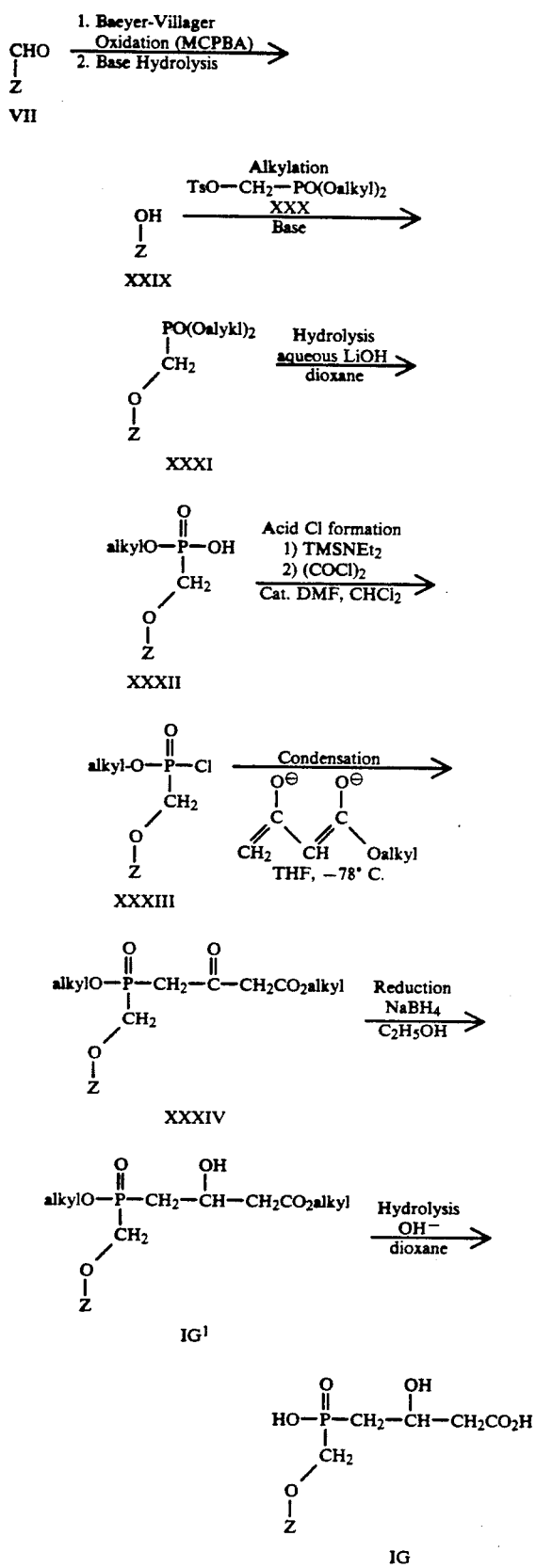

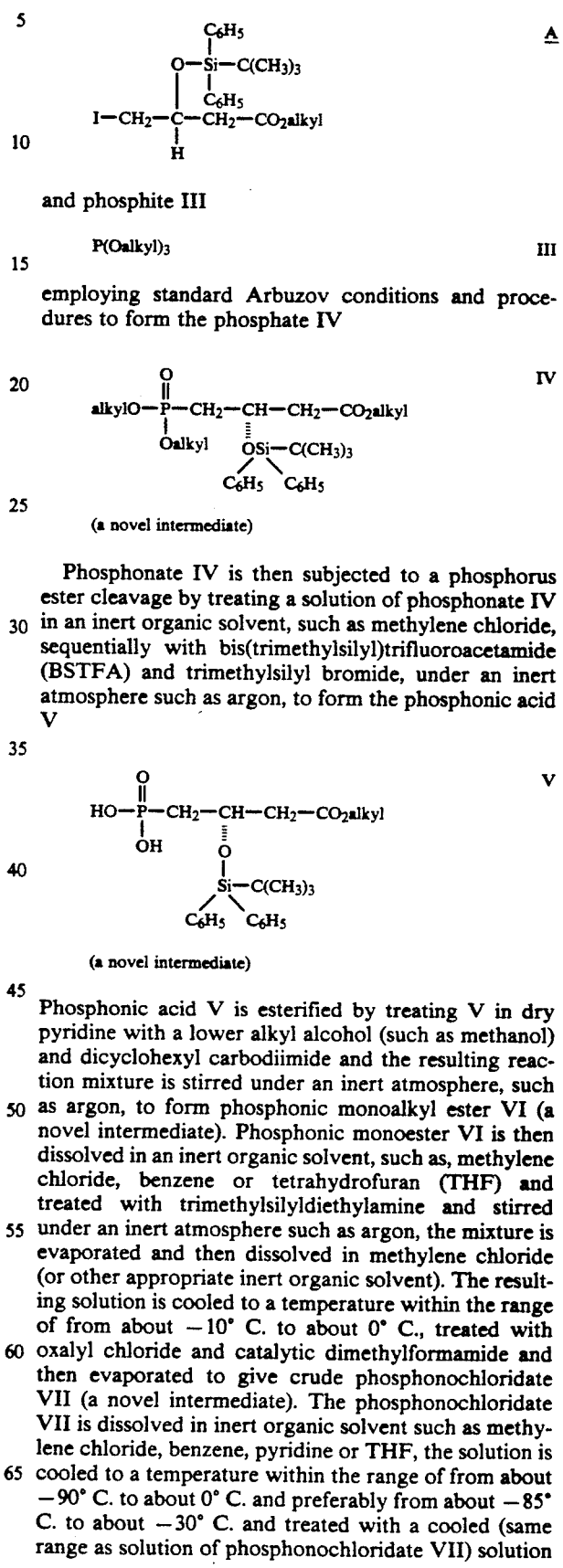

As seen in the above Reaction Sequence "A", compounds of Formula I may be prepared by subjecting iodide A to an Arbuzov reaction by heating iodide A and phosphite III employing standard Arbuzov conditions and procedures to form the phosphate IV (a novel intermediate)

Phosphonate IV is then subjected to a phosphorus ester cleavage by treating a solution of phosphonate IV in an inert organic solvent, such as methylene chloride, sequentially with bis(trimethylsilyl)trifluoroacetamide (BSTFA) and trimethylsilyl bromide, under an inert atmosphere such as argon, to form the phosphonic acid V (a novel intermediate)

Phosphonic acid V is esterified by treating V in dry pyridine with a lower alkyl alcohol (such as methanol) and dicyclohexyl carbodiimide and the resulting reaction mixture is stirred under an inert atmosphere, such as argon, to form phosphonic monoalkyl ester VI (a novel intermediate). Phosphonic monoester VI is then dissolved in an inert organic solvent, such as, methylene chloride, benzene or tetrahydrofuran (THF) and treated with trimethylsilyldiethylamine and stirred under an inert atmosphere such as argon, the mixture is evaporated and then dissolved in methylene chloride (or other appropriate inert organic solvent). The resulting solution is cooled to a temperature within the range of from about $-10°$ C. to about $0°$ C., treated with oxalyl chloride and catalytic dimethylformamide and then evaporated to give crude phosphonochloridate VII (a novel intermediate). The phosphonochloridate VII is dissolved in inert organic solvent such as methylene chloride, benzene, pyridine or THF, the solution is cooled to a temperature within the range of from about $-90°$ C. to about $0°$ C. and preferably from about $-85°$ C. to about $-30°$ C. and treated with a cooled (same range as solution of phosphonochloridate VII) solution of the lithium anion of acetylene X formed by treating with a lithium source such as n-butyllithium in hexane or other inert solvent,

X employing a molar ratio of VII:X of within the range of from about 3:1 to about 1:1 and preferably from about 1.5:1 to about 2:1 to form the acetylenic phosphinate XI

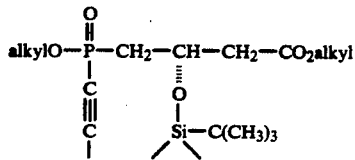

XI (a novel intermediate)

Acetylenic phosphinate XI may then be employed to prepare the various compounds of the present invention as follows. Acetylenic phosphinate XI is converted to acetylenic phosphinate IA¹ by subjecting XI to silyl ether cleavage by treating XI in an inert organic solvent such as tetrahydrofuran, with glacial acetic acid and tetrabutylammonium fluoride to form ester IA¹

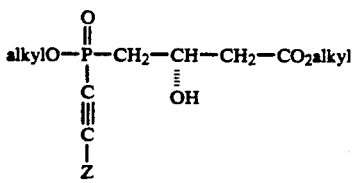

IA¹ which may then be hydrolyzed to the corresponding basic salt or acid, that is, where $R^x$ is $R^{xa}$ which is ammonium, alkali metal, alkaline earth metal, an amine and the like, by treatment with strong base such as lithium hydroxide in the presence of dioxane, tetrahydrofuran or other inert organic solvent under an inert atmosphere such as argon, at 25° C., employing a molar ratio of base:ester IA¹ of within the range of from about 1:1 to about 1.1:1 to form the corresponding basic salt

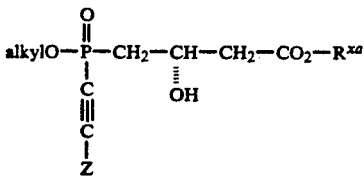

IA²

Compound IA² may then be treated with strong acid such as HCl to form the corresponding acid IA³

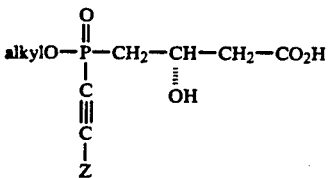

IA³

The ester IA¹ may be converted to the corresponding di-basic salt by treating ester IA¹ with strong base at 50°-60° C. employing a molar ratio of base:ester IA¹ of within the range of from about 2:1 to about 4:1 to form IA⁴

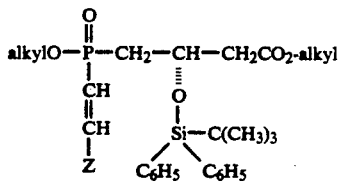

IA⁴

The dibasic salt IA⁴ may be converted to the corresponding acid by treatment with strong acid such as HCl to form acid IA.

Phosphinate compounds of the invention where X is (cis) —CH=CH—, that is, IB are formed by subjecting acetylenic phosphinate XI to selective reduction, for example by treating XI with H₂ in the presence of a reduction catalyst such as palladium on carbon, palladium on barium carbonate and an inert organic solvent such as methanol to form the silyl ether XII

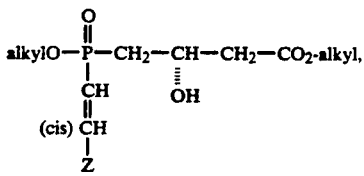

XII (a novel intermediate)

Silyl ether XII may then be subjected to silyl ether cleavage and hydrolysis as described above to form the ester IB¹

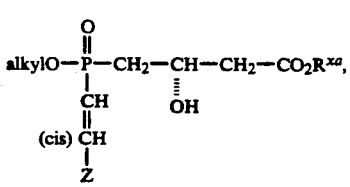

IB¹ the basic salt IB²

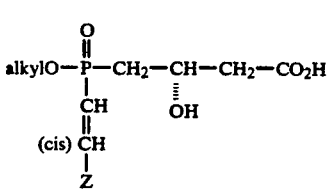

IB² the acid IB³

IB³ the dibasic metal salt IB⁴

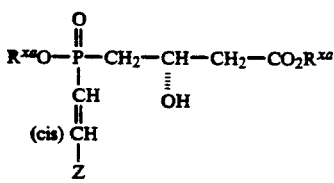

IB⁴ and the corresponding diacid IB.

Phosphinate compounds of the invention where X is —CH₂—CH₂—, that is, ID are formed by subjecting acetylenic phosphinate XII to catalytic reduction, for example by treating XII with H₂ in the presence of a reduction catalyst such as palladium on carbon and an inert organic solvent such as methanol at 50 psi to form the silyl ether XIII

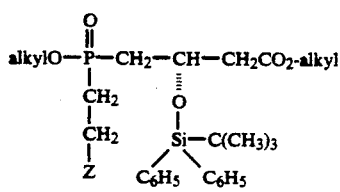

XIII (a novel intermediate)

Silyl ether XIII may then be subjected to silyl ether cleavage and hydrolysis as described above to form the ester ID¹

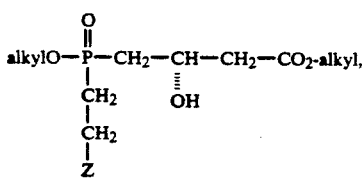

ID¹ the basic salt ID²

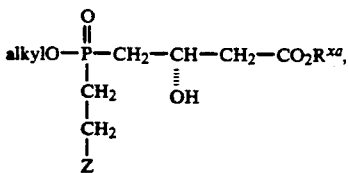

ID² the acid ID³

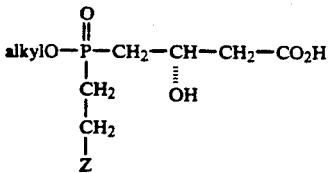

ID³ the dibasic salt ID⁴

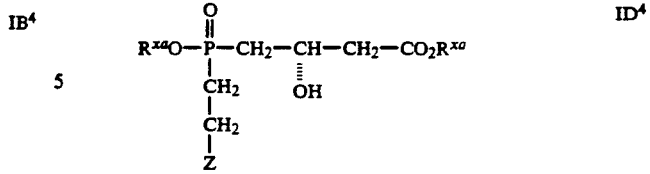

ID⁴ and the corresponding diacid ID.

Referring now to Reaction Sequence "B", compounds of Formula I wherein the X linking group between the phosphorus atom and the hydrophobic anchor Z is (trans) —CH=CH— may be prepared by treating a mixture of acetylene X and n—C₄H₉SnH with a radical initiator such as azobisisobutyrylnitrile (AIBN), hydrogen peroxide, benzoyl peroxide and the like, and heating the resulting solution to a temperature of within the range of from about 100° to about 140° C. under an inert atmosphere such as argon to form the vinyl stannane XV

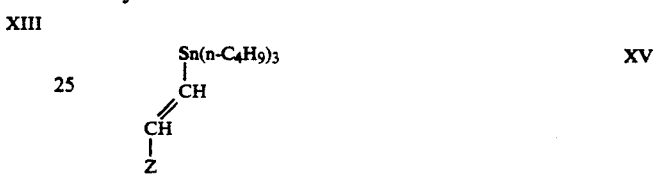

XV

Vinyl stannane XV dissolved in an organic solvent such as ethyl ether, methylene chloride or chloroform is treated with iodine and stirred under an inert atmosphere such as argon to form vinyl iodide XVI

XVI

A cooled solution of vinyl iodide XVI (−78° to 40° C.) in dry organic solvent such as tetrahydrofuran, or ethyl ether is treated with a metallating agent such as n-butyllithium in an inert organic solvent such as hexane and the mixture is cooled at a temperature of from −78° to −40° C. under an inert atmosphere such as argon. The anion is added to a cooled (−78° to −40° C.) solution of phosphonochloridate VII at a molar ratio of XVI:VII of within the range of from about 1:1 to about 2:1 and preferably from about 1:1 to about 1.5:1 in dry inert organic solvent such as tetrahydrofuran, or ethyl ether to form the silyl ether XVII

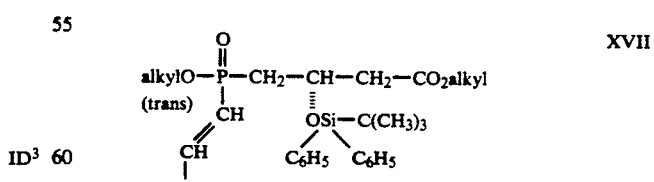

XVII (a novel intermediate)

The silyl ether XVII is subjected to silyl ether cleavage by treating a solution of XVII in an inert organic solvent such as tetrahydrofuran, or acetonitrile with glacial acetic acid and a solution of (n—C₄H₉)₄NF in an inert organic solvent such as tetrahydrofuran to form the hydroxy diester IC¹

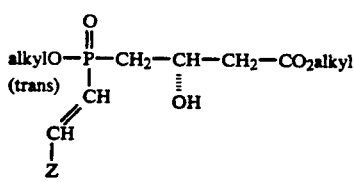

Diester IC¹ may then be hydrolyzed as described above to form the basic salt IC²,

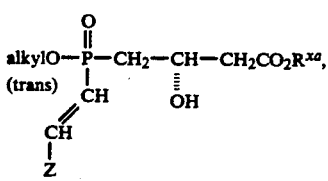

the acid IC³

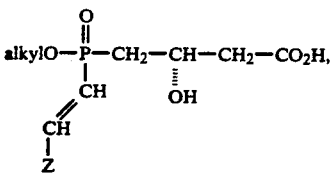

the basic salt IC⁴

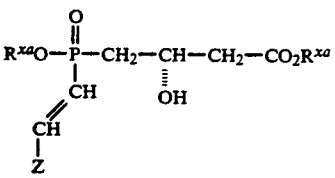

and the corresponding diacid IC

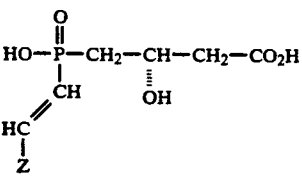

In an alternative process, as shown in Reaction Sequence "C", compounds of Formula I wherein the X linking group between the phosphorus atom and the hydrophobic anchor Z is (trans)—CH=CH— may be prepared by subjecting aldehyde VIII CHO  VIII
|
Z to a condensation reaction with a cooled (−90° to 0° C.) solution of dialkyl methylposhonate and butyl lithium (LiCH₂PO(alkyl)₂) in the presence of an organic solvent such as tetrahydrofuran or ethyl ether to form the β-hydroxyphosphonate XX

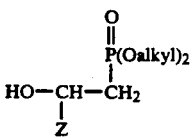

The β-hydroxyphosphonate XX is then treated with p-toluenesulfonic acid in the presence of benzene or toluene while heating to a temperature within the range of from about 50° to about 120° C., preferably at reflux, to eliminate water and from the trans-olefin XXI

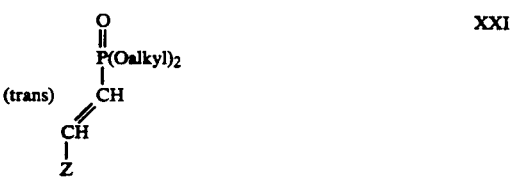

which is hydrolyzed by treating with aqueous alkali metal hydroxide, such as LiOH, in the presence of dioxane or other inert organic solvent and then with acid such as hydrochloric acid to form the monoacid ester XXII

A solution of the monoacid ester XXII in dry methylene chloride is treated with trimethylsilyldiethylamine. The mixture is evaporated and the resulting oil is taken up in dry methylene chloride cooled to 0° C. and treated with oxalyl chloride and a catalytic amount of dimethyl formamide under an inert atmosphere such as argon to form phosphonochloridate XXIII

Phosphonochloridate XXIII is condensed with an alkyl acetoacetate dianion such as methyl acetoacetate dianion in the presence of an inert organic solvent such as tetrahydrofuran at reduced temperature of −90° to −40° C. employing a molar ratio of phosphonochloridate:dianion of within the range of from about 1:1 to about 0.75:1 to form the ketophosphonate XXIV

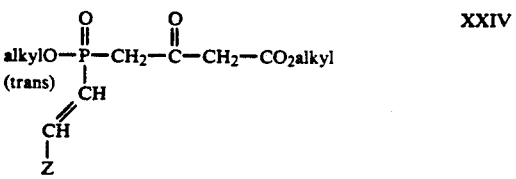

-continued
(a novel intermediate)

which is reduced by treatment with a reducing agent such as sodium borohydride in the presence of an alkanol such as ethanol to form the phosphinate IC¹

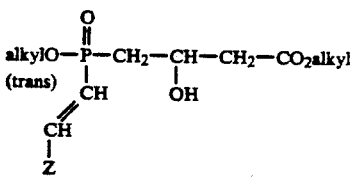
IC¹

Diester IC¹ may then be hydrolyzed as described above to form the basic salt IC²,

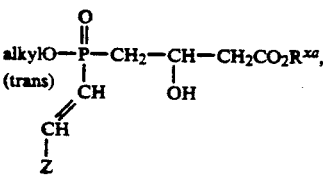
IC² the acid IC³

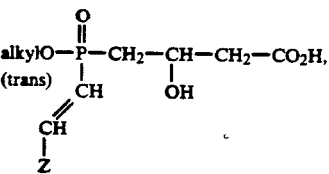
IC³ the basic salt IC⁴

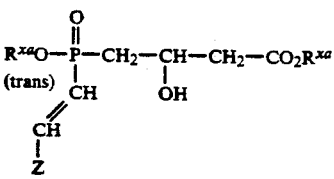
IC⁴ and the corresponding diacid IC.

Referring to Reaction Sequence D, compounds of Formula I wherein X is —(CH₂)$_a$— and a is 1,2 or 3, that is —CH₂—, —CH₂CH₂— or —CH₂CH₂CH₂— may be prepared starting with aldehyde VIII which is converted to halide VIIIa using conventional procedures. For example, the aldehyde VIII may be reduced with NaBH₄ in the presence of ethanol and ether to form the corresponding alcohol CH₂OH  VIIIa
|
Z which is treated with mesyl chloride in the presence of an organic base such as triethylamine and a solvent such as methylene chloride to form the chloride XXV (a=1).

The chloride XXV is subjected to a condensation reaction where XXV is treated with phosphite III employing a molar ratio of III:XXV of within the range of from about 1:1 to about 10:1 and a temperature within the range of from about 100 to about 150° C. to form phosphonate diester XXVI. A solution of the phosphonate diester XXVI in a solvent such as dioxane is treated with a strong base such as an alkali metal hydroxide, for example, LiOH, to form a corresponding monoester which is treated with oxalyl chloride in the presence of an inert organic solvent such as dimethylformamide to form the corresponding phosphonochloridate XXVII. XXVII is condensed with an alkyl acetoacetate dianion such as methylacetoacetate dianion in the presence of an inert organic solvent such as tetrahydrofuran at reduced temperatures of from about −90° to about −40° C. employing a molar ratio of phosphonochloridate XXVII:dianion of within the range of from about 1:1 to 0.75:1 to form the ketophosphinate XXVII which is a novel intermediate. Ketophosphinate XXVII may then be reduced to the corresponding phosphinate ID¹, IE¹ and IF¹ which may be hydrolyzed to form the corresponding diacids ID, IE and IF following procedures as described with respect to Reaction Sequence C.

Referring to Reaction Sequence E, compounds of formula I wherein X is —CH₂O— may be prepared starting with aldehyde VIII which is subjected to a Baeyer-Villiger oxidation by reacting VIII with meta-chloroperbenzoic acid (MCPBA) in the presence of an inert organic solvent such as methylene chloride and followed by a strong base such as an alkali metal hydroxide like KOH or NaOH and a solvent such as tetrahydrofuran to form the corresponding alcohol XXIX. The alcohol XXIX is alkylated by treating XXIX with sodium hydride in the presence of an inert organic solvent such as dimethylformamide under an inert atmosphere such as argon and a solution of a dialkyl tosyloxymethylphosphonate XXX employing a molar ratio of XXX:XXIX of within the range of from about 1:1 to about 3:1 to form the corresponding dialkyl ester XXXI. The remainder of the synthesis described in Reaction Sequence E that is forming the monoester XXXII, chloride XXXIII, ketophosphinate XXXIV (a new intermediate), diester IG¹ and diacid IG is similar to that set out hereinbefore with respect to in Reaction Sequence D.

The acetylene starting material X may be prepared from the corresponding aldehyde VIII

CHO  VIII
|
Z by subjecting VIII to a Wittig reaction, for example, by treating a cooled solution of VIII (−25° C. to 0° C.) in triphenylphosphine, and an inert organic solvent such as methylene chloride, with a solution of tetrabromomethane (CBr₄) in an inert organic solvent such as methylene chloride to form vinyl dibromide IX CH═CBr₂  IX
|
Z Compound IX is subjected to dehydrohalogenation by treatment with n-butyllithium in an inert organic solvent such as hexane under an inert atmosphere to give X.

Alternatively, aldehyde VIII may be converted directly to acetylene X by treatment with dimethyl diazomethylphosphonate in the presence of potassium t-butoxide in an inert solvent such as tetrahydrofuran (−78° C. to 25° C.) under an inert atmosphere.

The iodide starting material A may be prepared starting with the bromide C

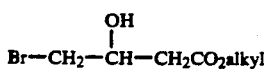

(which is prepared by employing procedures as described in Tetrahedron Lett. 26, 2951 (1985)) which is dissolved in solution in dimethylformamide (DMF) with imidazole and 4-dimethylamino pyridine and the resulting solution is treated with t-butyldiphenyl silyl chloride under an inert atmosphere such as argon to form the silyl ether D

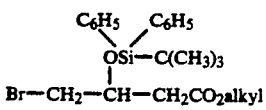

A solution of silyl ether D in an inert organic solvent such as methyl ethyl ketone or DMF is treated with sodium iodide under an inert atmosphere such as argon, to form iodide A.

The starting aldehyde compounds VIII, that

are known compounds.

The various intermediates IV, V, VI, VII, XI, XII, XIII, XVII and XXIV also are part of the present invention. These novel intermediates may be represented by the following generic formulae:

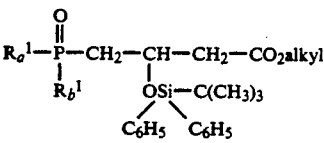

including all stereoisomers thereof, wherein $R_a^1$ is alkoxy or hydroxy and $R_b^1$ is alkoxy, hydroxy, Cl, —CH$_2$—Z, —CH$_2$CH$_2$CH$_2$—Z, —CH$_2$O—Z, —C≡C—Z, —CH=CH—Z, —CH$_2$CH$_2$—Z, wherein Z is a hydrophobic anchor as defined above; provided that where $R_b^1$ is hydroxy, $R_a^1$ is preferably hydroxy or alkoxy; and

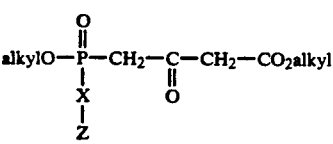

wherein Z is as defined above, including all stereoisomers thereof.

The compounds of the invention may be prepared as racemic mixtures and may later be resolved to obtain the S-isomer which is preferred. However, the compounds of the invention may be prepared directly in the form of their S-isomers as described herein and in the working examples set out hereinafter.

The compounds of the invention are inhibitors of 3-hydroxy-3-methyl-glutaryl coenzyme A (HMG-CoA) reductase and thus are useful in inhibiting cholesterol biosynthesis as demonstrated by the following tests.

1) Rat Hepatic HMG-CoA Reductase

Rat hepatic HMG-CoA reductase activity is measured using a modification of the method described by Edwards (Edwards, P. A., et al., J. Lipid Res. 20:40, 1979). Rat hepatic microsomes are used as a source of enzyme, and the enzyme activity is determined by measuring the conversion of the $^{14}$C-HMG-CoA substrate to $^{14}$C-mevalonic acid.

a. Preparation of Microsomes

Livers are removed from 2-4 cholestyramine-fed, decapitated, Sprague Dawley rats, and homogenized in phosphate buffer A (potassium phosphate, 0.04M, pH 7.2; KCl, 0.05M; sucrose, 0.1M; EDTA, 0.03M; aprotinin, 500 KI units/ml). The homogenate is spun at 16,000×g for 15 minutes at 4° C. The supernatant is removed and recentrifuged under the same conditions a second time. The second 16,000×g supernatant is spun at 100,000×g for 70 minutes at 4° C. Pelleted microsomes are resuspended in a minimum volume of buffer A (3-5 ml per liver), and homogenized in a glass/glass homogenizer. Dithiothreitol is added (10 mM), and the preparation is aliquoted, quick frozen in acetone/dry ice, and stored at −80° C. The specific activity of the first microsomal preparation was 0.68 nmole mevalonic acid/mg protein/minute.

b. Enzyme Assay

The reductase is assayed in 0.25 ml which contains the following components at the indicated final concentrations:

0.04M: Potassium phosphate, pH 7.0
0.05M: KCl
0.10M: Sucrose
0.03M: EDTA
0.01M: Dithiothreitol
3.5 mM: NaCl
1%: Dimethylsulfoxide
50-200 μg: Microsomal protein
100 μM: $^{14}$C-[DL]HMG-CoA (0.05 μCi, 30-60 mCi/mmole)
2.7 mM: NADPH (nicotinamide adenine dinucleotide phosphate).

Reaction mixtures are incubated at 37° C. Under conditions described, enzyme activity increases linearly up to 300 μg microsomal protein per reaction mixture, and is linear with respect to incubation time up to 30 minutes. The standard incubation time chosen for drug studies is 20 minutes, which results in 12-15% conversion of HMG-CoA substrate to the mevalonic acid product. [DL-]HMG-CoA substrate is used at 100 μM, twice the concentration needed to saturate the enzyme under the conditions described. NADPH is used in excess at a level 2.7 times the concentration required to achieve maximum enzyme velocity.

Standardized assays for the evaluation of inhibitors are conducted according to the following procedure. Microsomal enzyme is incubated in the presence of NADPH at 37° C. for 15 minutes. DMSO vehicle with or without test compound is added, and the mixture further incubated for 15 minutes at 37° C. The enzyme assay is initiated by adding $^{14}$C-HMG-CoA substrate. After 20 minutes incubation at 37° C. the reaction is stopped by the addition of 25 μl of 33% KOH. $^3$H-mevalonic acid (0.05 μCi) is added, and the reaction mixture allowed to stand at room temperature for 30 minutes. Fifty μl 5N HCl is added to lactonize the mevalonic acid. Bromophenol blue is added as a pH indicator to monitor an adequate drop in pH. Lactonization is allowed to proceed for 30 minutes at room temperature. Reaction mixtures are centrifuged for 15 minutes at 2800 rpm. The supernatants are layered onto 2 grams AG 1-X8 anion exchange resin (Biorad, formate form) poured in 0.7 cm (id) glass columns, and eluted with 2.0 ml $H_2O$. The first 0.5 ml is discarded, and the next 1.5 ml is collected and counted for both tritium and carbon 14 in 10.0 ml Opti-fluor scintillation fluid. Results are calculated as nmoles mevalonic acid produced per 20 minutes, and are corrected to 100% recovery of tritium. Drug effects are expressed as $I_{50}$ values (concentration of drug producing 50% inhibition of enzyme activity) derived from composite dose response data with the 95% confidence interval indicated.

Conversion of drugs in lactone form to their sodium salts is accomplished by solubilizing the lactone in DMSO, adding a 10-fold molar excess of NaOH, and allowing the mixture to stand at room temperature for 15 minutes. The mixture is then partially neutralized (pH 7.5–8.0) using 1N HCl, and diluted into the enzyme reaction mixture.

2) Cholesterol Synthesis in Freshly Isolated Rat Hepatocytes

Compounds which demonstrate activity as inhibitors of HMG-CoA reductase are evaluated for their ability to inhibit $^{14}C$-acetate incorporation into cholesterol in freshly isolated rat hepatocyte suspensions using methods originally described by Capuzzi et al. (Capuzzi, D. M. and Margolis, S., Lipids, 6:602, 1971).

a. Isolation of Rat Hepatocytes

Sprague Dawley rats (180–220 grams) are anesthetized with Nembutol (50 mg/kg). The abdomen is opened and the first branch of the portal vein is tied closed. Heparin (100–200 units) is injected directly into the abdominal vena cava. A single closing suture is placed on the distal section of the portal vein, and the portal vein is canulated between the suture and the first branching vein. The liver is perfused at a rate of 20 ml/minute with prewarmed (37° C.), oxygenated buffer A (HBSS without calcium or magnesium containing 0.5 mM EDTA) after severing the vena cava to allow drainage of the effluent. The liver is additionally perfused with 200 ml of prewarmed buffer B (HBSS containing 0.05% bacterial collagenase). Following perfusion with buffer B, the liver is excised and decapsulated in 60 ml Waymouth's medium allowing free cells to disperse into the medium, Hepatocytes are isolated by low speed centrifugation for 3 minutes at $50 \times g$ at room temperature. Pelleted hepatocytes are washed once in Waymouth's medium, counted and assayed for viability by trypan blue exclusion. These hepatocyte enriched cell suspensions routinely show 70–90% viability.

b. $^{14}C$-Acetate Incorporation into Cholesterol

Hepatocytes are resuspended at $5 \times 10^6$ cells per 2.0 ml in incubation medium (IM) [0.22M Tris-HCl (pH 7.4), 0.1M KCl, 3.3 mM sodium citrate, 6.7 mM nicotinamide, 0.23 mM NADP, 1.7 mM glucose-6-phosphate].

Test compounds are routinely dissolved in DMSO or DMSO:$H_2O$ (1:3) and added to the IM. Final DMSO concentration in the IM is $\leq 1.0\%$, and has no significant effect on cholesterol synthesis.

Incubation is initiated by adding $^{14}C$-acetate 958 mCi/mmol, 2 $\mu$Ci/ml), and placing the cell suspensions (2.0 ml) in 35 mm tissue culture dishes, at 37° C. for 2.0 hours. Following incubation, cell suspensions are transferred to glass centrifuge tubes and spun at $50 \times g$ for 3 minutes at room temperature. Cell pellets are resuspended and lysed in 1.0 ml $H_2O$, and placed in an ice bath.

Lipids are extracted essentially as described by Bligh, E. G and W. J. Dyer, Can. J. Biochem. and Physiol., 37:911, 1959. The lower organic phase is removed and dried under a stream of nitrogen, and the residue resuspended in (100 $\mu$l) chloroform:methanol (2:1). The total sample is spotted on silica gel (LK6D) thin-layer plates and developed in hexane:ethyl ether:acetic acid (75:25:1). Plates are scanned and counted using a BioScan automated scanning system. Radiolabel in the cholesterol peak (RF 0.28) is determined and expressed at total counts per peak and as a percent of the label in the total lipid extract. Cholesterol peaks in control cultures routinely contain 800–1000 cpm, and are 9–20% of the label present in the total lipid extract; results compatable with Capuzzi, et al., indicating 9% of extracted label in cholesterol.

Drug effects (% inhibition of cholesterol synthesis) are determined by comparing % of label in cholesterol for control and drug treated cultures. Dose response curves are constructed from composite data from two or more studies, and results are expressed as $I_{50}$ values with a 95% confidence interval.

3) Cholesterol Synthesis in Human Skin Fibroblasts

Compound selectivity favoring greater inhibitory activity in hepatic tissue would be an attribute for a cholesterol synthesis inhibitor. Therefore, in addition to evaluating cholesterol synthesis inhibitors in hepatocytes, these compounds are also tested for their activity as inhibitors of cholesterol synthesis in cultured fibroblasts.

a. Human Skin Fibroblast Cultures

Human skin fibroblasts (passage 7–27) are grown in Eagles' minimal essential medium (EM) containing 10% fetal calf serum. For each experiment, stock cultures are trypsonized to disperse the cell monolayer, counted, and plated in 35 mm tissue culture wells ($5 \times 10^5$ cells/2.0 ml). Cultures are incubated for 18 hours at 37° C. in 5% $CO_2$/95% humidified room air. Cholesterol biosynthetic enzymes are induced by removing the serum containing medium, washing the cell monolayers, and adding 1.0 ml of EM containing 1.0% fatty acid free bovine serum albumin, and incubating the cultures an additional 24 hours.

b. $^{14}C$-Acetate Incorporation into Cholesterol

Induced fibroblast cultures are washed with $EMEM_{100}$ (Earle's minimal essential medium). Test compounds are dissolved in DMSO or DMSO:EM (1:3) (final DMSO concentration in cell cultures $\leq 1.0\%$), added to the cultures, and the cultures preincubated for 30 minutes at 37° C. in 5% $CO_2$/95% humidified room air. Following preincubation with drugs, [1-$^{14}C$]Na acetate (2.0 $\mu$Ci/ml, 58 mCi/mmole) is added, and the cultures reincubated for 4 hours. After incubation, the culture medium is removed, and the cell monolayer (200 $\mu$g cell protein per culture) is scraped into 1.0 ml of $H_2O$. Lipids in the lysed cell suspension are extracted into chloroform:methanol as described for hepatocyte suspensions. The organic phase is dried under nitrogen, and the residue resuspended in chloroform:methanol (2:1) (100 $\mu$l), and the total sample spotted on silica gel (LK6D) thin-layer plates, and analyzed as described for hepatocytes.

Inhibition of cholesterol synthesis is determined by comparing the percent of label in the cholesterol peak from control and drug-treated cultures. Results are expressed as $I_{50}$ values, and are derived from composite dose response curves from two or more experiments. A 95% confidence interval for the $I_{50}$ value is also calculated from the composite dose response curves.

A further aspect of the present invention is a pharmaceutical composition consisting of at least one of the compounds of formula I in association with a pharmaceutical vehicle or diluent. The pharmaceutical composition can be formulated employing conventional solid or liquid vehicles of diluents and pharmaceutical additives of a type appropriate to the mode of desired administration. The compounds can be administered by an oral route, for example, in the form of tablets, capsules, granules or powders, or they can be administered by a parenteral route in the form of injectable preparations, such dosage forms containing from 1 to 2000 mg of active compound per dosage, for use in the treatment. The dose to be administered depends on the unitary dose, the symptoms, and the age and the body weight of the patient.

The compounds of formula I may be administered in a similar manner as known compounds suggested for use in inhibiting cholesterol biosynthesis, such as lovastatin, in mammalian species such as humans, dogs, cats and the like. Thus, the compounds of the invention may be administered in an amount from about 4 to 2000 mg in a single dose or in the form of individual doses from 1 to 4 times per day, preferably 4 to 200 mg in divided dosages of 1 to 100 mg, suitably 0.5 to 50 mg 2 to 4 times daily or in sustained release form.

The following working Examples represent preferred embodiments of the present invention. Unless otherwise indicated, all temperatures are expressed in degrees Centigrade. Flash chromatography was performed on either Merck 60 or Whatmann LPS-I silica gel. Reverse phase chromatography was performed on CHP-20 MCI gel resin supplied by Mitsubishi, Ltd.

As used in the following Examples, the abbreviations "Et₂O", "EtOAc", "MeOH" and "EtOH" refer to ethyl ether, ethyl acetate, methanol and ethanol, respectively.

EXAMPLE 1

(S)-4-[[[4'-Fluoro-3,3',5-trimethyl[1,1'-biphenyl]-2-yl]methoxy]methoxyphosphinyl]-3-hydroxy-butanoic acid, monolithium salt A. N-(2,4-Dimethylbenzylidene)benzeneamine Ref. Merck U.S. Pat. No. 4,375,475, pg. 39.

A solution of freshly distilled 2,4-dimethylbenzaldehyde (Aldrich, 6.97 ml, 50 mmole) and distilled aniline (Aldrich, 4.56 ml, 50 mmole) in dry toluene (80.0 ml) was refluxed for 3.0 hours under argon in a flask equipped with a Dean-Stark apparatus. The mixture was cooled, then evaporated in vacuo to a yellow oil. The crude oil was purified by Kugelrohr distillation (0.5 mm Hg; 160°-180° C.) to give 8.172 g (78.1%) of desired title benzeneimine as a light yellow oil which crystallized on standing to a low melting solid. TLC (4:1) Hex-acetone, Rf=0.67 and 0.77 (geometric isomers), U.V. and I₂.

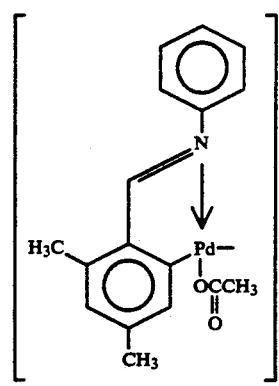

Ref. Merck U.S. Pat. No. 4,375,475, pg. 39.

A mixture of Part A benzeneimine (6.0 g, 28.7 mmol) in glacial HOAc (144 ml) was treated with palladium (II) acetate (6.44 g, 28.7 mmole) and the clear, red homogeneous solution refluxed under argon for one hour. The resulting turbid mixture was filtered warm through a packed ½" bed of Celite into 900 ml of H₂O. Precipitated orange solid was collected by filtration and dried in vacuo at 65° C. over P₂O₅ for 16 hours to give 10.6 g (85.5%) of desired title palladium complex as an orange solid with m.p.=194°-196° C. (Literature m.p. of a recrystallized analytical sample=203°-205° C.).

C. 4'-Fluoro-3,3',5-trimethyl[1,1'-biphenyl]-2-carboxaldehyde (1) Bromo[4-fluoro-3-methylphenyl]magnesium Ref. Merck U.S. Pat. No. 4,375,475, pp. 37 and 38.

The title Part C(1) Grignard reagent was prepared by adding 5-bromo-2-fluorotoluene (22.5 g, 60.9 mmole, Fairfield Chemical Co.) dropwise at a rate sufficient to maintain the reaction at reflux to stirred magnesium turnings (1.35 g, 55.4 mmole, 8.0 eq.) in dry Et₂O (70.0 ml). The reaction was initiated in an ultrasound device. After bromide addition was complete, the mixture was stirred for one hour under argon at room temperature, refluxed for 15 minutes and then allowed to cool to room temperature.

(2) 4'-Fluoro-3,3',5-trimethyl[1,1'-biphenyl]-2-carboxaldehyde

In a second flask, a mixture of the Part B dipalladium complex (3.0 g, 6.92 mmole) and triphenylphosphine (14.52 g, 55.4 mmole, 8.0 eq.) in dry benzene (100 ml) was stirred at room temperature under argon for 30 minutes. Freshly prepared and filtered (glass wool plug) Part C (1) Grignard reagent was then added in one portion by means of a cannula to this solution and the mixture was stirred for 1.5 hours at room temperature under argon. 6.0N HCl (35 ml) was added, the mixture stirred an additional hour at room temperature, then filtered through packed Celite (½" bed). The filtrate was extracted with Et₂O (250 ml), the extract washed with brine (2×100 ml), dried over anhydrous MgSO₄ and evaporated in vacuo to give 13.35 g of a viscous orange oil which crystallized on standing. The crude orange solid was purified by flash chromatography on silica gel (700 g) eluting with hexane, followed by (95:5) hexane-Et₂O. Product fractions were combined and evaporated to give 1.507 g (89.9%) of desired title aldehyde as a light yellow solid with m.p.=72°-75° C.) (Literature reports m.p.=73°-74° C.).

TLC: (95:5) Hex-Et$_2$O, Rf=0.40, U.V. and PMA.

D. 2-(2,2-Dibromoethenyl)-4'-fluoro-3,3',5-trimethyl[1,1'-biphenyl]

A cooled (−10° C., salt/ice bath) solution of the Part C biphenyl aldehyde (242 mg, 1.0 mmole) and triphenylphosphine (787 mg, 3.0 mmole, 3.0 eq) in dry CH$_2$Cl$_2$ (10 ml) was treated dropwise with a solution of CBr$_4$ (497 mg, 1.5 mmole, 1.5 eq) in CH$_2$Cl$_2$ (5.0 ml) over a 5 minute period. After 30 minutes at 0° C. the red-orange solution was partitioned between CH$_2$Cl$_2$ and saturated NaHCO$_3$. The organic phase was washed with saturated NaHCO$_3$ and brine, then dried over anhydrous Na$_2$SO$_4$ and evaporated to give 1.478 g of a light brown solid. The crude solid was purified by flash chromatography on silica gel (50:1) eluting with (9:1) Hex-CH$_2$Cl$_2$. Product fractions were combined and evaporated to give 392 mg (99%) of pure title vinyl dibromide as a pale yellow oil. TLC (95:5) Hex-EtOAc, Rf=0.51, UV and PMA.

E. 2-Ethynyl-4'-fluoro-3,3',5-trimethyl[1,1'-biphenyl]

A −78° C. (dry ice/acetone) solution of the Part D vinyl dibromide (336 mg, 0.844 mmole) in dry THF (5 ml) was treated dropwise via syringe with a 1.6M solution of n-BuLi in hexanes (1.06 ml, 1.7 mole, 2.0 eq) and the mixture stirred at −78° C. under argon for one hour. During the n-BuLi addition color changes from colorless to deep yellow to pale yellow to deep blue-purple were evident. The mixture was quenched at −78° C. by the dropwise addition of saturated NH$_4$Cl (4 ml), allowed to warm to room temperature, extracted with Et$_2$O, the ethereal layer washed with brine, dried over anhydrous MgSO$_4$ and evaporated to give 191 mg of a green oil. The crude oil was purified by flash chromatography on LPS-1 silica gel (60:1) eluting with hexanes. Product fractions were combined and evaporated to give 185 mg (92%) of desired title acetylene as a colorless oil which eventually turned deep blue on standing at −20° C. under argon. TLC hexane, Rf=0.18 UV and PMA.

E. (S)-3-[[(1,1-Dimethylethyl)diphenylsilyl]oxy]-4-(chloromethyloxyphosphinyl)butanoic acid, methyl ester (1) (S)-4-Bromo-3-hydroxybutanoic acid, methyl ester (1)(a) [R-(R*,R*)]-2,3,4-trihydroxybutanoic acid, calcium salt, hydrate Ref. Carbohydrate Research 72, pp. 301–304 (1979).

Calcium carbonate (50 g) was added to solution of D-isoascorbic acid (44.0 g, 250 mmol) in H$_2$O (625 ml), the suspension cooled to 0° C. (ice bath) and treated portionwise with 30% H$_2$O$_2$ (100 ml). The mixture was stirred at 30°–40° C. (oil bath) for 30 minutes. Darco (10 g) was added and the black suspension heated on a steam bath until evolution of O$_2$ ceased. The suspension was filtered through Celite, evaporated in vacuo (bath temperature 40° C.). The residue was taken up in H$_2$O (50 ml), warmed on a steam bath and CH$_3$OH was added until the solution was turbid. The gummy precipitated solid was collected by filtration and air dried to give 30.836 g (75.2%) of desired calcium salt as a powdery white solid. TLC (7:2:1) iPrOH—NH$_4$OH—H$_2$O, Rf=0.19, PMA.

(1)(b) [S-(R*,S*)]-2,4-Dibromo-3-hydroxybutanoic acid, methyl ester

Ref. Bock, K. et al., Acta Scandinavica (B) 37, pp. 341–344 (1983)

Part (1)(a) calcium salt (30 g) was dissolved in 30–32% HBr in acetic acid (210 ml) and stirred at room temperature for 24 hours. Methanol (990 ml) was then added to the brown solution and it was stirred overnight. The mixture was evaporated to an orange oil, taken up in CH$_3$OH (75 ml), refluxed for 2.0 hours and evaporated. The residue was partitioned between EtOAc (100 ml) and H$_2$O, the organic phase washed with H$_2$O (2x) and brine then dried over anhydrous Na$_2$SO$_4$ and evaporated to give 22.83 g (90.5%) of crude dibromide as a light orange oil. TLC (1:1) EtOAc-Hex, Rf=0.69, UV & PMA.

(1)(c) (S)-4-Bromo-3-hydroxybutanoic acid, methyl ester

Ref. the same as for preparation of (1)(b).

An argon purged solution of the dibromide (20.80 g, 75.4 mmol) and anhydrous NaOAc (21.0 g) in EtOAc (370 ml) and glacial HOAc (37 ml) was treated with 5% Pd/C (1.30 g) and the black suspension stirred under of H$_2$ (1 atm) while monitoring H$_2$ uptake. After 2.0 hours H$_2$ uptake was complete, the mixture was filtered through Celite, the filtrate washed with saturated NaHCO$_3$ and brine then dried over anhydrous MgSO$_4$ and evaporated to give crude dibromoester as a brown oil. The crude oil was combined with another batch (starting from 36.77 g of the dibromide) and vacuum distilled to give 25.77 g (61.3%) of desired title bromoester as a colorless oil with b.p.=79°–80° C. (1.0 mm Hg). TLC (1:1) EtOAc-Hex, Rf=0.44, PMA.

Anal Calcd for C$_5$H$_9$O$_3$Br: C, 30.48; H, 4.60; Br, 40.56. Found: C, 29.76; H, 4.50; Br, 39.86.

(2) (S)-4-Bromo-3-[[(1,1-dimethylethyl)diphenylsilyl]oxy]butanoic acid, methyl ester A solution of part F(1) bromohydrin (4.0 g, 20.4 mmol), imidazole (6.94 g, 5.0 eq.), and 4-dimethylamino pyridine (4-DMAP) (12 mg, 0.005 eq.) in dry DMF (40 ml) was treated with t-butyldiphenylsilyl chloride (5.84 ml, 1.1 eq.) and the homogeneous mixture stirred overnight under argon at room temperature. The mixture was partitioned between 5% KHSO$_4$ and EtOAc, the organic phase washed with H$_2$O and brine, dried over anhydrous Na$_2$SO$_4$ and evaporated to give 9.32 g (100%) of crude silyl ether as a colorless, viscous oil. TLC (3:1) Hex-EtOAc, Rf silyl ether=0.75, U.V. and PMA.

(3) (S)-4-Iodo-3-[[(1,1-dimethylethyl)diphenylsilyl]oxy]butanoic acid, methyl ester A solution of the crude Part F(2) bromide (9.32 g, 201 mmole) in methyl ethyl ketone (60 ml, dried over 4 Å sieves) was treated with sodium iodide (15.06 g, 100.5 mmole, 5.0 eq.) and the yellow suspension refluxed for 5.0 hours under argon. The mixture was cooled, diluted with EtOAc, filtered, the filtrate washed with dilute NaHSO$_3$ (until colorless) and brine then dried over anhydrous Na$_2$SO$_4$ and evaporated in vacuo to give 10.17 g of a yellow oil. The crude oil was purified by flash chromatography on silica gel (600 g) eluting with (3:1) Hexane-CH$_2$Cl$_2$. Product fractions were combined and evaporated to give 7.691 g (74.2%, overall yield for both steps) of desired title iodide as a clear, colorless, viscous oil. TLC (3:1) Hex-EtOAc, product. Rf=0.75, U.V. and PMA. (Note: Product iodide co-spots with starting bromide).

(4) (S)-4-(Diethoxyphosphinyl)-3-[[(1,1-dimethylethyl)diphenylsilyl]oxy]butanoic acid, methyl ester A solution of the iodide (7.691 g) in triethyl phosphite (20 ml) was heated at 155° C. (oil bath) for 3.5 hours under argon. The mixture was cooled and excess phosphite distilled off in vacuo (0.5 mm Hg, 75° C.) to leave a yellow oil (~8.0 g). The crude oil was purified by flash chromatography on silica gel (400 g) eluting with (4:1) Hexane-acetone. Product fractions were evaporated to give 3.222 g (41.1%) of desired title phosphonate as a clear, colorless, viscous oil. TLC (1:1) Hex-acetone, Rf=0.51, U.V. and PMA. Additionally 2.519 g (61.1% corrected yield) of starting Part (3) iodide was recovered.

(5) (S)-3-[[(1,1-Dimethylethyl)diphenylsilyl]oxy]-4-phosphonobutanoic acid, methyl ester A solution of the Part F(4) phosphonate (9.85 g, 20.0 mmole) in dry $CH_2Cl_2$ (20 ml) was treated sequentially with bistrimethylsilyltrifluoroacetamide (BSTFA) (5.31 ml, 32.0 mmole, 1.6 eq.) and trimethylsilyl bromide (TMSBr) (6.60 ml 50.0 mmole, 2.5 eq.) and the clear mixture stirred overnight under argon at room temperature. 5% $KHSO_4$ (80 ml) was added and the mixture was extracted with EtOAc. The aqueous phase was saturated with NaCl and re-extracted with EtOAc. The combined organic layers were washed with brine, dried over anhydrous $Na_2SO_4$ and evaporated in vacuo to give crude title phosphonic acid as a viscous oil. TLC (7:2:1) $iPrOH$—$NH_4OH$—$H_2O$, Rf=0.30, U.V. and PMA.

(6) (S)-3-[[(1,1-Dimethylethyl)diphenylsilyl]oxy]-4-(hydroxymethoxyphosphinyl)butanoic acid, methyl ester Part F(5) crude phosphonic acid (~20.0 mmole) in dry pyridine (25 ml) was treated with dried $CH_3OH$ (over 3 Å sieves, 1.62 ml, 40.0 mmole, 2.0 eq.) and dicyclohexyl carbodiimide (DCC) (4.54 gm, 22.0 mmole, 1.10 eq.) and the resulting white suspension stirred under argon at room temperature overnight. Pyridine was removed in vacuo, then azeotroped with benzene (2×15 ml). The residual oil was dissolved in EtOAc, filtered and washed with 1.0 N HCl and brine, dried over anhydrous $Na_2SO_4$ and evaporated in vacuo to give 8.272 g of crude title ester as an oil containing a small amount of precipitated dicyclohexyl urea (DCU). TLC (7:2:1) $iPrOH$—$NH_4$—$OH$ $H_2O$, Rf=0.60, U.V. and PMA.

(7) (S)-3-[[(1-Dimethylethyl)diphenylsilyl]oxy]-4-(chloromethoxyphosphinyl)butanoic acid, methyl ester Part F(6) crude phosphonic acid mono methyl ester (6.595 gm, ~14.7 mmole) was dissolved in dry $CH_2Cl_2$ (30 ml), treated with distilled trimethylsilyldiethylamine (5.60 ml, 29.4 mmole, 2.0 eq.) and stirred under argon at room temperature for 1 hour. The mixture was evaporated in vacuo, chased with benzene (1×30 ml) and dried in vacuo. The light yellow viscous oil was dissolved in dry $CH_2Cl_2$ (30 ml) and DMF (dried over 4 Å sieves, 2 drops), the clear solution cooled to −10° C. (salt/ice bath) and treated dropwise via syringe with distilled oxalyl chloride (1.41 ml, 16.2 mmole, 1.1 eq.). Vigorous gas evolution was evident and the solution become deeper yellow in color. The mixture was stirred under argon at −10° C. for 15 minutes then allowed to stir at room temperature for 1 hour. The mixture was evaporated in vacuo, chased with benzene (1×30 ml) and dried in vacuo to give crude phosphonochloridate as a yellow oil.

G. (S)-4-[[2-[4'-Fluoro-3,3',5-trimethyl[1,1'-biphenyl]-2-yl]ethynyl]methoxyphosphinyl]-3-t-butyldiphenylsilyloxybutanoic acid, methyl ester A −78° C. ($CO_2$/acetone) solution of the Part E acetylene (2.678 g, 11.2 mmole) in dry THF (20 ml) was treated dropwise with a 1.6 M solution of n-BuLi in hexanes (7 ml, 11.2 mmole, 1.0 eq). The purple mixture was stirred under argon at −78° C. for one hour, briefly warmed to 0° C., recooled to −78° C., transferred by cannula into an addition funnel and added dropwise to a −78° C. ($CO_2$/acetone) solution of the Part F phosphonochloridate (8.27 g, 18.4 mmole, 1.6 eq) in dry THF (20 ml). After one hour at −78° C. the mixture was quenched with saturated $NH_4Cl$, then allowed to warm to room temperature and extracted with $Et_2O$. The ethereal layer was washed with saturated $NaHCO_3$ and brine then dried over anhydrous $MgSO_4$ and evaporated to give 11.705 g of a brown oil. The crude oil was purified by flash chromatography on silica gel eluting with (7:3) Hex-EtOAc. Product fractions were combined and evaporated to give 4.246 g (56%) of desired title acetylenic phosphinate as a light brown oil. Additionally, 457 mg (68% corrected yield) of Part E biphenyl acetylene was recovered. TLC (7:3) Hex-Acetone, Rf=0.20, UV and PMA.

H. (S)-4-[(2-[4'-Fluoro-3,3',5-trimethyl[1,1'-biphenyl]-2-yl]ethyl]methoxyphosphinyl]-3-t-butyldiphenylsilyloxybutanoic acid, methyl ester An argon purged solution of the Part G acetylenic phosphinate (333 mg) in $CH_3OH$ (5 ml) was treated with 10% Pd/C (121 mg, 36% by weight) and shaken on a Parr apparatus under $H_2$ (40 psi) for 30 hours. Catalyst was removed by filtration through packed Celite and the filtrate evaporated to a pale yellow oil. The crude oil was purified by flash chromatography on silica gel eluting with (1:1) EtOAc-Hex. Product fractions were evaporated to give 250 mg (75%) of the title saturated phosphinate as a clear oil. TLC (4:1) EtOAc-Hex, Rf=0.33, UV and PMA.

J. (S)-4-[[2-(4'-Fluoro-3,3',5-trimethyl[1,1'-biphenyl]-2-yl]ethyl]methoxyphosphinyl]-3-hydroxybutanoic acid, methyl ester A solution of the Part H silyl ether (330 mg, 0.489 mmole) in dry THF (6 ml) was treated with glacial HOAc (115 μl, 1.96 mmole, 4.0 eq) followed by a 1.0 M tetrabutylammonium fluoride solution in THF (1.47 ml, 1.47 mmole, 3.0 eq) and the resulting mixture stirred overnight at room temperature under argon. The mixture was diluted with 10 ml of ice water and extracted with EtOAc (2×). The organic phase was washed with saturated $NaHCO_3$ and brine then dried over anhydrous $Na_2SO_4$ and evaporated to give 364 mg of a pale yellow oil. The crude oil was purified by flash chromatography on silica gel eluting with (6:4) Acetone-Hexane. Product fractions were evaporated to give 205 mg (96%) of desired title free alcohol as a clear oil which slowly crystallized on standing. TLC (7:3) Acetone-hexane, Rf=0.28, UV and PMA.

EXAMPLE 2

(S)-4-[[2-[4'-Fluoro-3,3',5-trimethyl]1,1'-biphenyl]-2-yl]ethyl]hydroxyphosphinyl]-3-hydroxybutanoic acid, dilithium salt A solution of the Example 1 diester (187 mg, 0.429 mmole) in dioxane (5 ml) was treated with a 1.0N LiOH solution (1.29 ml, 1.29 mmole, 3.0 eq) and the mixture heated at 55° C. (oil bath) under argon for 2.5 hours. The mixture was cooled, diluted with $H_2O$, filtered and evaporated in vacuo. The residue was dissolved in a minimum amount of $H_2O$ and chromatographed on HP-20 resin (25 mm column diameter, ~15 cm bed) eluting with $H_2O$ followed by a (1:1) $CH_3OH$-$H_2O$ mixture. Collected product fractions were evaporated, dissolved in $H_2O$ (50 ml), filtered, and lyophilized to give 175 mg (91%, based on hydrate weight) of desired title dilithium salt as a white, electrostatic solid. TLC (8:1:1) $CH_2Cl_2$—$CH_3OH$—HOAc, Rf=0.1, UV and PMA and (7:2:1) iPrOH—$NH_4OH$—$H_2O$, Rf=0.45, UV and PMA.

Microanalysis for $C_{21}H_{24}O_5FPLi_2$ and 1.7 moles $H_2O$ (MW 450.90): Calcd: C, 55.93; H, 6.13; F, 4.21; P, 6.87. Found: C, 55.91; H, 5.84; F, 3.92; P, 6.89.

$^1$H-NMR (400 MHz, $CD_3OD$) $\delta$1.34–1.56 ppm (4H, multiplet); 2.22–2.31 ppm (2H, multiplet); 2.25–2.37 ppm (6H, two singlets); 2.29 ppm (3H, doublet, $J_{H-F}$=1.4 Hz); 2.75 ppm (2H, multiplet); 4.13 ppm (1H, multiplet); 6.73–7.10 ppm (5H, multiplet).

EXAMPLE 3

(S)-4-[[2-[4'-Fluoro-3,3',5-trimethyl[1,1'-biphenyl]-2-yl]ethynyl]methoxyphosphinyl]-3-hydroxybutanoic acid, methyl ester A mixture of the Example 1 Part G silyl ether (455 mg, 0.678 mmole) and glacial acetic acid (155 µl, 2.71 mmole, 4.0 eq.) in dry THF (7 ml) was treated with a 1.0M tetrabutylammonium fluoride solution in THF (2.0 ml, 2.0 mmole, 3.0 eq.) and the resulting solution stirred overnight under argon at room temperature. The mixture was poured into ice cold $H_2O$ (10 ml) and extracted with EtOAc (2×). The organic phase was washed with saturated $NaHCO_3$ and brine, then dried over anhydrous $Na_2SO_4$ and evaporated to give 498 mg of a yellow oil. The crude product was purified by flash chromatography on silica gel eluting with (3:2) Hexane-Acetone. Product fractions were evaporated to give 217 mg (74%) of title alcohol as a colorless oil. TLC (7:3) Hexane-Acetone, Rf=0.10, U.V. and PMA.

EXAMPLE 4

(S)-4-[[2-[4'-Fluoro-3,3',5-trimethyl[1,1'-biphenyl]-2-yl]ethynyl]hydroxyphosphinyl]-3-hydroxybutanoic acid, dilithium salt A mixture of the Example 3 diester (203 mg, 0.469 mmole) in dioxane (6 ml) was treated with a 1.0N LiOH (1.6 ml, 1.6 mmole, 3.5 eq.) and the solution heated at 55° (oil bath) under argon for 30 minutes. The mixture was cooled, diluted with $H_2O$, filtered, evaporated, taken up in $H_2O$ (30 ml) and lyophilized. The white lyophilate was dissolved in a minimum amount of $H_2O$ and chromatographed on HP-20 resin (25 mm diameter column, 10 cm resin bed), eluting with $H_2O$ followed by (50:50) $H_2O$—$CH_3OH$. Product fractions were combined and evaporated, the residue taken up in $H_2O$ (30 ml) and lyophilized to give 199 mg (97%, based on hydrate, MW=435.36) of the title di-lithium salt as a white solid. TLC (8:1:1) $CH_2Cl_2$—$CH_3OH$—HOAc, Rf=0.13, U.V. and PMA.

Microanalysis for $C_{21}H_{20}O_5FPLi_2$+1.06 moles $H_2O$ (MW 435.36): Calcd: C, 57.93; H, 5.12; F, 4.36; P, 7.11. Found: C, 57.91; H, 4.89; F, 4.22; P. 6.89.

$^1$H NMR (400 MHz $CD_3OD$): $\delta$1.76–1.82 ppm (2H, multiplet); 2.32 (3H, doublet, $J_{HF}$=1.8 Hz); 2.34 (3H, singlet); 2.37 (1H, dd, J=8.4 Hz); 2.41 (1H, dd, J=4.1 Hz); 2.49 (3H, singlet); 4.27 (1H, multiplet); 6.98–7.37 (5H, m).

EXAMPLE 5

(S,Z)-4-[[2-[4'-Fluoro-3,3',5-trimethyl[1,1'-biphenyl]-2-yl]ethenyl]methoxyphosphinyl]-3-hydroxybutanoic acid, methyl ester A. (S,Z)-4-[[2-[4'-Fluoro-3,3',5-trimethyl[1,1'-biphenyl]-2-yl]ethenyl]methoxyphosphinyl]-3-t-butyldiphenylsilyloxy-butanoic acid, methyl ester A degassed solution of the Example 1 Part G acetylenic phosphinate (498 mg, 0.742 mmole) in $CH_3OH$ (10 ml) was treated with 10% Pd/C (50 mg, 10% by weight) and the black suspension stirred under an $H_2$ atmosphere (1 atm) for 2 hours. Catalyst was removed by filtration through Celite and the filtrate evaporated to give 500 mg of a yellow oil. The crude product was purified by flash chromatography on silica gel eluting with (3:2) Hexane-EtOAc. Product fractions were combined and evaporated to give 498 mg (100%) of desired olefin as a colorless oil.

TLC (4:1) EtOAc-Hexane, Rf diastereomers=0.44 and 0.51, U.V. and PMA.

B. (S,Z)-4-[[2-[4'-Fluoro-3,3',5-trimethyl[1,1'-biphenyl]-2-yl]ethenyl]methoxyphosphinyl]-3-hydroxybutanoic acid, methyl ester A solution of the Part A silyl ether (498 mg, 0.74 mmole) in dry THF (6 ml) was treated with glacial acetic acid (170 µl, 2.96 mmole, 4.0 eq.) followed by a 1.0M tetrabutylammonium fluoride solution in THF (2.2 ml, 2.2 mmole, 3.0 eq.) and the clear, colorless mixture stirred at room temperature under argon for 16 hours. TLC indicated a small amount of remaining starting material. Additional HOAc (40 µl, 1.0 eq.) and n-$Bu_4NF$ (0.74 ml, 1.0 eq.) were added and stirring continued for 6 more hours. The mixture was diluted with ice cold $H_2O$ (10 ml) and extracted with EtOAc (2×). The combined extracts were washed with saturated $NaHCO_3$ and brine, dried over anhydrous $Na_2SO_4$ and evaporated to give 468 mg of a pale yellow oil. The crude product was purified by flash chromatography on silica gel eluting with (7:3) Hexane-Acetone. Product fractions were combined and evaporated to give 243 mg (76%) of title alcohol as a colorless oil. TLC (7:3) Hexane-Acetone, Rf=0.19, U.V. and PMA.

EXAMPLE 6

(S,Z)-4-[[2-[4'-Fluoro-3,3',5-trimethyl[1,1'-biphenyl]-2-yl]ethenyl]hydroxyphosphinyl]-3-hydroxybutanoic acid, dilithium salt A solution of the Example 5 diester (240 mg, 0.552 mmole) in dioxane (7 ml) was treated with a 1.0N LiOH solution (1.9 ml, 1.9 mmole, 3.5 eq.) and the stirred mixture heated under argon at 50° (oil bath) for 3 hours. A white precipitate was evident. The mixture was cooled, diluted with $H_2O$, filtered and evaporated in vacuo to a white solid. The crude solid was dissolved in a minimum amount of $H_2O$ and chromatographed on HP-20 resin, eluting with $H_2O$ followed by (50:50) $H_2O$:$CH_3OH$. Product fractions were combined and evaporated, taken up in $H_2O$ (50 ml), filtered, and lyophilized to give 255 mg (100%, based on hydrate weight, MW 457.58) of title di-lithium salt as a white electrostatic solid. TLC (8:1:1) $CH_2Cl_2$—$CH_3OH$—HOAc, Rf=0.26, U.V. and PMA.

Microanalysis for $C_{21}H_{22}O_5FPLi_2$+2.18 moles $H_2O$ (457.58): Calcd: C, 55.12; H, 5.81; F, 4.15; P, 6.77. Found: C, 55.35; H, 5.68; F. 4.27; P, 7.09.

$^1$H NMR (400 MHz, CD$_3$OD): δ1.24 ppm (2H, multiplet); 2.09 (2H, doublet, J=6.2 Hz); 2.27 (3H, doublet, J$_{HF}$=1.8 Hz); 2.30 (3H, singlet); 2.38 (3H, singlet); 4.06 (1H, multiplet); 5.87 (1H, d doublet, J$_{HH}$=12,4 Hz, J$_{HP}$=14.3 Hz); 6.87 (1H, s); 6.91 (1H, d doublet, J$_{HP}$=43.4 Hz); 6.98 (2H, triplet); 7.22 (2H, multiplet).

EXAMPLE 7

(S)-4-[[2-[3-(4-Fluorophenyl)-1-(1-methylethyl)-1H-indol-2-yl]ethyl]methoxyphosphinyl]-3-hydroxybutanoic acid, methyl ester A. 2-[(4-Fluorophenyl)methyl]-3-oxobutanoic acid, ethyl ester Sodium pellets (8.31 g, 362 mmole) were dissolved with mechanical stirring in absolute EtOH (1 liter) and distilled ethyl acetoacetate (47 g, 362 mmole, 1 eq.) was added to the clear solution under argon. The pale yellow mixture was refluxed for 1 hour, cooled to room temperature, treated with 4-fluorobenzyl bromide (75 g, 398 mmole, 1.1 eq.) and the light orange mixture stirred under argon at room temperature for 2.5 hours. The mixture was concentrated in vacuo. The residue was partitioned between EtOAc-H$_2$O, the organic phase washed with H$_2$O (2×) and brine, dried over anhydrous Na$_2$SO$_4$ and evaporated to give an orange oil. The crude product was purified by vacuum distillation (5 mm Hg) to give 46.47 g (54%) of alkylated product as a clear, colorless liquid with b.p. 142°-144° C. TLC (7:3) Hex-Et$_2$O, Rf product=0.31.

$^1$H NMR (CDCl$_3$): δ1.20 (3H, t), 2.19 (3H, s), 3.13 (2H, d), 3.73 (1H, t), 4.14 (2H, q), 6.95 (2H, t), 7.13 (2H, m) ppm.

$^{13}$C NMR (CD$_3$CN): δ14.4, 29.7, 33.7, 62.1, 62.3, 115.3, 116.8, 131.4, 131.9, 145.1 (J$_{C-F}$=284 Hz), 170.1, 203.5 ppm.

B. 3-(4-Fluorophenyl)-1H-indole-2-carboxylic acid, ethyl ester

Ref. *Chemical Abstracts* Vol. 33, p, 587.

Ref. Helmuth R. et al. *J. Chem. Society* pp. 6–7, (1927).

Ref. *Preparative Organic Chemistry* 4th Ed. p. 582 (1972).

A solution of the Part A ester (46.4 g, 195 mmole) in absolute EtOH (290 ml) at 0° C. (ice bath) was treated with an aqueous NaOH solution (23.4 g, in 58 ml H$_2$O), then treated inmediately with a benzenediazonium chloride solution (Prep. Org. Chem, 4th Ed. p. 582 (1972) prepared from aniline (17.8 ml), conc HCl (88 ml), H$_2$O (98 ml) and NaNO$_2$ (13.5 g)) to give a deep orange-red biphasic solution. The mixture was stirred for 1 hour at room temperature, poured into ice cold H$_2$O (500 ml) and extracted with EtOAc (3×300 ml). The organic phase was washed with brine, (500 ml), dried over anhydrous Na$_2$SO$_4$ and evaporated in vacuo to give 55.62 g of crude hydrazone intermediate as an orange oil. TLC (7:3) Hex-Et$_2$O, Rf hydrazone=0.22, UV and PMA. Crude material was used as is for subsequent Fischer cyclization.

A solution of the hydrazone in absolute EtOH (200 ml) was treated with gaseous, bubbling HCl for 30 minutes with intermittent ice bath cooling. The brownish mixture was poured into ice cold H$_2$O (600 ml) and extracted with EtOAc (3×). The organic phase was washed with H$_2$O (2×) and brine, dried over anhydrous Na$_2$SO$_4$ and evaporated in vacuo to a brownish-tan solid. Trituration with ice cold hexane and filtration afforded 26.74 g (49%) of desired title indole as tan, granular crystals with m.p.=129°-130° C. TLC (7:3) Hex-Et$_2$O, Rf=0.26, U.V. and PMA.

Microanalysis for C$_{17}$H$_{14}$FNO$_2$: Calcd: C, 72.07; H, 4.98; F, 6.71; N, 4.94. Found: C, 72.38; H, 5.05; F, 6.87; N, 5.01.

$^1$H NMR (CDCl$_3$): δ1.22 ppm (3H, t), 4.29 (2H, q), 7.10–7.62 (8H, m), 9.21 (1H, bs) ppm.

$^{13}$C NMR (CDCl$_3$): δ14.1, 60.9, 111.8, 114.5, 114.8, 120.9, 121.4, 122.9, 123.1, 125.9, 127.9, 129.5, 132.2 (J$_{C-F}$=7.6 Hz), 135.7, 162.0, 162.2 (J$_{C-F}$=244 Hz) ppm.

C. 3-(4-Fluorophenyl)-1-(1-methylethyl)-1H-indole-2-carboxylic acid, ethyl ester Ref. Sandoz International Patent #158675 p. 35 (1984).

A solution of the Part B indole (26.74 g, 94.4 mmole) in dry, distilled dimethyl acetamide (100 ml) at 0° C. (ice bath) was treated portionwise (vigorous gas evolution) with 60% NaH dispersion in mineral oil (4.53 g, 113.3 mmole, 1.2 eq.) and the mixture stirred under argon at 0° C. for 1 hour. 2-Iodopropane (85 g, 500 mmole, 5.3 eq.) was added and the mixture allowed to warm to room temperature under argon and stirred for 1 hour. The mixture was re-cooled to 0° C., treated with another 1.2 eq. of NaH, allowed to stir at room terperature for 1 hour. This procedure was repeated two more times. The final mixture was cooled to 0° C. (ice bath) and excess NaH quenched by careful dropwise addition of absolute EtOH (30 ml). The mixture was diluted with EtOAc, washed with 5% KHSO$_4$, the aqueous phase back extracted once with EtOAc, the combined EtOAc layers washed with H$_2$O, and brine (2×), dried over anhydrous Na$_2$SO$_4$ and evaporated to give 38.54 g of a brown solid. The solid was taken up in hot CH$_2$Cl$_2$ and starting indole crystallized out with the addition of hexane. 13.88 g of the starting indole was recovered. The mother liquor was evaporated in vacuo to give 22.32 g of a brown oil. The crude product was purified by flash chromatography on silica gel eluting with hexane followed by (95:5) Hex-Acetone. Product fractions were evaporated to give 6.55 g (21%) (62% corrected yield) of desired title N-isopropyl indole as a yellow oil.

TLC (4:1) Hexane-Acetone, Rf=0.57, U.V. and PMA.

$^1$H NMR (CDCl$_3$): δ1.04 (3H, t), 1.20 (6H, d), 4.17 (2H, q), 5.40 (1H, m), 7.10–7.7 (8H, m) ppm.

$^{13}$C NMR (CDCl$_3$): δ13.6, 21.5, 48.7, 53.3, 60.8, 112.7, 114.5, 114.8, 120.3, 121.4, 122.4, 124.3, 125.9, 127.6, 130.8, 131.7 (J$_{C-F}$=7.5 Hz), 136.2, 162.3 (J$_{C-F}$=144 Hz), 163.0 ppm.

D. 3-(4-Fluorophenyl)-1-(1-methylethyl)1H-indole-2-Methanol

Lithium aluminum hydride (1.12 g, 29.6 mmole, 1.5 eq.) was carefully added to a 0° C. (ice bath) solution of dry, distilled Et$_2$O (30 ml). The resulting suspension was treated dropwise over 10 minutes with an ethereal solution of the Part C indole ester (6.42 g, 19.7 mmole in 20 ml of Et$_2$O). After stirring for 30 minutes at 0° C. under argon, the mixture was quenched by sequential dropwise addition of H$_2$O (1.1 ml), 15% NaOH (1.1 ml) and H$_2$O (3.4 ml). The resulting suspension was filtered through packed Celite, dried over anhydrous MgSO$_4$ and evaporated in vacuo to give 5.1 g of a yellow foam. The crude product was purified by flash chromatography on silica gel eluting with (85:15) Hex-Acetone to give 5.08 g (91%) of pure title alcohol as a pale yellow foam.

TLC (7:3) Hex-Acetone, Rf=0.38, U.V. and PMA. A small sample was crystallized from hexanes to give the title alcohol as white crystals with m.p.=101°–103° C.

Microanalysis for $C_{18}H_{17}NOF$: Calcd: C, 76.30; H, 6.40; F, 6.71; N, 4.94. Found: C, 76.49; H, 6.46; F, 6.84; N, 4.88.

$^1H$ NMR (CDCl$_3$): δ1.60 (1H, t), 1.69 (6H, d), 4.76 (2H, d), 4.93 (1H, m), 7.05–7.62 (8H, m) ppm.

$^{13}C$ NMR (CDCl$_3$): δ20.9, 47.3, 54.8, 113.0, 115.9, 116.3, 116.6, 120.2, 120.6, 122.9, 128.5, 131.6, 132.4, 135.1, 135.7, 163.0 ($J_{C-F}$=245 Hz) ppm.

E. 3-(4-Fluorophenyl)-1-(1-methylethyl)-1H-indole-2-carboxaldehyde

A solution of Dess-Martin periodinane (5.9 g, 13.9 mmole, 1.2 eq.) in dry, CH$_2$Cl$_2$ (30 ml) was treated with dry t-butanol (1.3 ml, 13.9 mmole, 1.2 eq.) and the mixture stirred at room temperature under argon for 15 minutes. Part D indole alcohol (3.28 g, 11.6 mmole, 1 eq) in dry CH$_2$Cl$_2$ (12 ml) was added dropwise over 5 minutes and the yellow mixture stirred under argon at room temperature for 1 hour. The reaction mixture was added to a stirred solution of sodium thiosulfate (15.3 g, 97 mmol, 7 eq.) in freshly prepared 1.0N NaHCO$_3$ (40 ml) and the resulting mixture stirred vigorously for 5 minutes. The organic phase was separated, washed with 1.0N NaHCO$_3$, H$_2$O and brine, dried over anhydrous Na$_2$SO$_4$ and evaporated to give 3.69 g of a yellow oil. The crude product was purified by flash chromatography on silica gel eluting with (40:1) Hexane-Et$_2$O to give 2.7 g (83%) of pure title aldehyde as a white crystalline solid with m.p.=88°–89° C.

TLC (7:3) Hex-Acetone, Rf=0.56, U.V. and PMA.

Microanalysis for $C_{18}H_{16}FNO$: Calcd: C, 76.85; H, 5.73; N, 4.98; F. 6.75. Found: C, 76.91; H, 5.71; N, 4.95; F, 6.76.

$^1H$ NMR (CDCl$_3$): δ1.69 (6H, d), 5.92 (1H, m), 7.10–7.70 (8H, m), 9.80 (1H, s) ppm.

$^{13}C$ NMR (CDCl$_3$): δ21.4, 48.0, 112.5, 113.2, 115.4, 115.7, 120.8, 122.1, 126.9, 127.0, 132.0, 132.6 ($J_{C-F}$=7.5 Hz), 183.6 ppm.

F. 3-(4-Fluorophenyl)-1-(1-methylethyl)-2-(2,2-dibromoethenyl)-1H-indole

A cooled (−15° C., ice/salt bath) solution of the Part E indole aldehyde (1.84 g, 6.54 mmole) and triphenylphosphine (5.14 g, 19.6 mmole, 3 eq.) in dry CH$_2$Cl$_2$ (30 ml) was treated dropwise over 5 minutes with a dry CH$_2$Cl$_2$ (10 ml) solution of CBr$_4$ (3.25 g, 9.8 mmole, 1.5 eq.) and the yellow mixture stirred at 15° C. under argon for 15 minutes. The mixture was partitioned between saturated NaHCO$_3$ and CH$_2$Cl$_2$, the organic phase washed with saturated NaHCO$_3$ and brine, dried over anhydrous Na$_2$SO$_4$ and evaporated to give 9.44 g of a brown oil. The crude product was purified by flash chromatography on silica gel eluting with (95:5) Hexane-CH$_2$Cl$_2$. Product fractions were evaporated to give 2.87 g (100%) of desired title vinyl dibromide as a yellow oil which crystallized on standing. One recrystallization from ethyl ether gave 2.46 g (86%) of purified product as pale yellow, granular crystals with m.p. 135°–137° C.

TLC (7:3) Hex-CH$_2$Cl$_2$, Rf=0.45, U.V. and PMA.

Microanalysis for $C_{19}H_{16}NF$ Br$_2$: Calcd: C, 52.20; H, 3.69; N, 3.20; Br, 36.56. Found: C, 52.25; H, 3.68; N, 3.20; Br, 36.58.

$^1H$ NMR (CDCl$_3$): δ1.15 (6H, d), 4.67 (1H, m), 7.10–7.70 (9H, m) ppm.

$^{13}C$ NMR (CDCl$_3$): δ21.9, 48.6, 98.6, 111.6, 115.3, 115.6, 115.9, 119.9 ($J_{C-F}$=7.6 Hz), 122.4, 127.5, 129.3, 130.5, 130.7, 130.9, 135.2, 161.5 ($J_{C-F}$=246 Hz) ppm.

G. 3-(4-Fluorophenyl)-1-(1-methylethyl)-2-ethynyl-1H-indole

A −78° C. solution (dry ice/acetone) of the Part F vinyl dibromide (2.395 g, 5.48 mmole) in dry THF (10 ml) under argon was treated dropwise with a 1.6M solution of n-BuLi in hexanes (6.9 ml, 10.96 mmole, 2 eq.). The resulting mixture was stirred at −78° C. for 1 hour then quenched by dropwise addition of saturated NH$_4$Cl (5 ml). The mixture was allowed to warm to room temperature then extracted with Et$_2$O (2×). The ethereal layers were washed with brine, dried over anhydrous MgSO$_4$ and evaporated in vacuo to give 1.893 of a dark brown oil. The crude product was purified by flash chromatography on silica gel (80:1) eluting with (200:1) Hexane-Et$_2$O to give 1.12 g of purified product as a (3.3:1) mixture of acetylene to terminal olefin. This mixture was separated by chromatography on alumina (neutral, activity=II) column eluting with (200:1) Hexane-Et$_2$O. Evaporation of product fractions gave 900 mg of off-white crystals. One recrystallization from hot hexane gave 700 mg (46%) of purified title acetylene as white needles with m.p.=105°–106° C.

TLC (95:5) Hex-Et$_2$O, Rf acetylene=0.44, Rf olefin=0.49, U.V. and PMA.

Microanalysis for $C_{19}H_{16}NF$: Calcd: C, 82.28; H, 5.81; N, 5.05; F, 6.85. Found: C, 82.70; H, 5.85; N, 5.10; F, 6.62.

$^1H$ NMR (CDCl$_3$): δ1.70 (6H, d), 3.5 (1H, s), 5.06 (1H, m), 7.10–7.75 (8H, m) ppm.

H. (S)-4-[[2-[3-(4-Fluorophenyl)-1-(1-methylethyl)-1H-indol-2-yl]ethynyl]methoxyphosphinyl]-3-(t-butyldiphenylsilyloxy)butanoic acid, methyl ester A −78° C. (dry ice/acetone) solution of the Part G acetylene (678 mg, 244 mmole, 1.0 eq.) in dry THF (6 ml) under argon was treated dropwise with a 1.6M solution of n-BuLi in hexanes (1.53 ml, 2.44 mmole, 1.0 eq.). After 30 minutes at −78° C., the mixture was transferred by cannula to a −78° C. solution of Example 1 Part F phosphonochloridate (~4.3 mmole, 1.75 eq.) in dry THF (5 ml). The dark brown mixture was stirred at −78° C. for 30 minutes then quenched by dropwise addition of saturated NH$_4$Cl (5 ml) and allowed to warm to room temperature. The mixture was extracted with Et$_2$O (2×), washed with saturated NH$_4$Cl and brine, dried over anhydrous MgSO$_4$ and evaporated in vacuo to give 2.567 g of a brown-red oil. The crude oil was purified by flash chromatography on silica gel eluting with (3:2) Hexane-EtOAc to give 756 mg (44%) of desired title acetylenic phosphinate as a dark yellow oil.

TLC (7:3) Hex-Acetone, Rf=0.27, U.V. and PMA.

$^1H$ NMR (CDCl$_3$): δ1.0 (9H, s), 1.64 (6H, d), 2.10–2.90 (4H, m), 3.56 (3H, s), 3.58 (3H, dd), 4.6 (1H, bm), 4.90 (1H, m), 7.05–7.55 (18H, m) ppm.

$^{13}C$ NMR (CDCl$_3$): δ14.2, 19.1, 21.0, 26.7, 27.8, 37.5, 39.2, 42.2, 45.1, 49.2, 51.4, 51.9, 60.3, 65.5 ($J_{C-P}$=15.1 Hz), 88.1, 91.2, 98.3, 111.3, 115.3, 115.6, 120.8 (J=5.7 Hz), 122.3, 124.9, 125.9, 126.4, 127.6, 129.2, 130.7, 133.0, 135.7, 136.1, 170.9 ppm.

J. (S)-4-[[2-[3-(4-Fluorophenyl)-1-(1-methylethyl)-1H-indol-2-yl]ethyl]methoxyphosphinyl]-3-(t-butyldiphenylsilyloxy)butanoic acid, methyl ester An argon purged solution of the Part H acetylenic phosphinate (422 mg) in CH$_3$OH (9 ml) was treated with 10% Pt/C (420 mg) and the resulting mixture shaken on a Parr apparatus for 2 hours under 40 psi of hydrogen. Catalyst was removed by filtration through Celite and the filtrate evaporated to give 380 (90%) of title indole phosphinate as a yellow foam. TLC (4:1) EtOAc-Hex, Rf=0.27 U.V. and PMA.

$^1$H NMR (CDCl$_3$): δ1.00 (9H, s), 1.63 (6H, d), 1.5-2.0 (2H, m), 2.20 (1H, m), 2.58-3.00 (5H, m), 3.44 (3H, dd, $J_{H-P}$=10.6 Hz), 3.61 (3H, s), 4.52 (2H, m), 7.07-7.66 (18H, m) ppm.

$^{13}$C NMR (CDCl$_3$): δ12.6, 16.8, 17.2, 19.1, 21.5, 26.7, 36.0, 42.1, 47.2, 50.9, 51.4, 65.8; 111.8, 115.3, 119.1, 121.1, 127.7, 128.3, 129.9, 131.2, 131.3, 132.8, 133.4, 134.3, 134.8, 135.7, 171.3 ppm.

K. (S)-4-[[2-[3-(4-Fluorophenyl)-1-(1-methylethyl)-1H-indol-2-yl]ethyl]methoxyphosphinyl]-3-hydroxybutanoic acid, methyl ester A solution of the Part J silyl ether (379 mg, 0.531 mmole) in dry THF (5 ml) was treated successively with glacial HOAc (120 μl, 2.12 mmole, 4 eq.) and a 1.0M tetrabutylammonium fluoride solution in THF (1.6 ml, 1.6 mmole, 3 eq.) and the resulting solution stirred overnight under argon at room temperature. The mixture was diluted with ice cold H$_2$O (10 ml), extracted with EtOAc (2×), the organic phase washed with saturated NaHCO$_3$ and brine then dried over anhydrous Na$_2$SO$_4$ and evaporated to give 408 mg of a yellow oil. The crude product was purified by flash chromatography on silica gel eluting with (7:3) Acetone-Hexane. Product fractions were evaporated to give 197 mg (78%) of desired title alcohol as a white foam.

TLC (1:1) Hexane-Acetone, Rf=0.09 U.V. and PMA.

$^1$H NMR (CDCl$_3$): δ1.68 (6H, d), 1.80-2.0 (2H, m), 2.10 (2H, m), 2.58 (2H, m), 3.08 (2H, m), 3.63 (3H, dd, $J_{H-P}$=10.1 Hz), 3.70 (3H, d), 3.96 (1H, t), 4.35+4.49 (1H, 2 broad multiplets), 4.67 (1H, m), 7.0-7.6 (8H, m) ppm.

$^{13}$C NMR (CDCl$_3$): δ17.6, 17.7, 21.4, 29.2, 29.4, 33.2, 33.3, 34.6, 41.6, 41.8, 42.0, 42.2, 47.3, 50.9, 51.7, 63.4, 111.8, 113.5, 115.2, 115.5, 119.0, 119.4, 121.1, 128.3, 131.3, 131.5, 134.2, 134.8, 161.5 $J_{C-F}$=244.1 Hz), 172.1 ppm.

EXAMPLE 8

(S)-4-[[2-[3-(4-Fluorophenyl)-1-(1-methylphenyl)-1H-indol-2-yl]ethyl]hydroxyphosphinyl]-3-hydroxybutanoic acid, dilithium salt A stirred solution of the Example 7 diester (197 mg, 0.414 mmole) in dioxane (5 ml) was treated with 1.0N LiOH (1.45 ml, 3.5 eq.) and the resulting white suspension was heated at 55° C. (oil bath) under argon for 40 minutes. The mixture was cooled, diluted with H$_2$O, filtered, evaporated in vacuo. The residue was taken up in a minimum amount of H$_2$O and chromatographed on HP-20 resin, eluting with H$_2$O followed by (50:50) H$_2$O-CH$_3$OH. Product fractions were combined and evaporated. The glassy residue was taken up in H$_2$O (50 ml), filtered and lyophilized to give 178 mg (85%, based on hydrate weight) of pure title di-lithium salt as a white solid.

Microanalysis for C$_{23}$H$_{25}$NFP.2Li+2.52 moles H$_2$O (MW 504.71): Calcd: C, 54.73; H, 6.00; N, 2.78; F, 3.76; P, 6.14. Found: C, 54.62; H, 5.67; N, 2.90; F, 3.61; P, 6.06.

$^1$H NMR (400 MHz, CDCl$_3$): δ1.69 ppm (6H, dd, J=5.8 Hz); 1.71 (2H, multiplet); 1.93 (2H, multiplet); 2.38 (2H, multiplet); 3.06 (2H, quartet); 4.32 (1H, multiplet); 4.87 (1H, multiplet); 6.97 (1H, dt, J=0.7 Hz); 7.07 (1H, dt, J=1.1 Hz); 7.16 (2H, t); 7.41 (3H, m); 7.57 (1H, ½ AB quartet).

EXAMPLE 9

(S)-4-[[2-[[1,1'-Biphenyl]-2-yl]ethyl]methoxyphosphinyl]-3-hydroxybutanoic acid, methyl ester A. Biphenyl-2-carboxaldehyde Dess-Martin periodinane (27.64 g, 65.2 mmol) was stirred under argon atmosphere with 150 ml of CH$_2$Cl$_2$. Dry t-BuOH (8.0 ml) was added to the stirring solution, and this mixture was stirred for 10 minutes at room temperature. A CH$_2$Cl$_2$ solution (20 ml) of biphenyl-2-methanol (10 g, 54.3 mmol) was added dropwise over 15 minutes. After the addition was complete, the reaction was allowed to stir at room temperature. After stirring for 1 hour at room temperature, 600 ml of Et$_2$O (anhydrous) was added to the reaction followed by 1N NaOH (225 ml). After 10 minutes, the resulting slurry was filtered, and the filter cake was washed with Et$_2$O. The filtrate was washed 2× with 250 ml portions of 1N NaOH. The organic layer was dried over MgSO$_4$ and filtered to give a yellow oil (10 g) after solvent removal. Purification by flash (silica gel, 1:10/Et$_2$O:Hexane) provided title aldehyde (9.58 g, 97%) as a colorless oil.

TLC (1/9 EtOAc/Hexane, silica gel) Rf=0.29.

IR (film) 3065, 3025, 2850, 2760, 1685, 1700, 1600, 1470, 1450, 1395 cm$^{-1}$.

$^1$H NMR (270 MHz) (CDCl$_3$): δ8.00 (d, 1, J=70. Hz), 7.60 (m, 1), 7.40 (m, 7).

Mass Spec m/e 183 (M$^+$+H).

B. 2-(2,2-Dibromoethenyl)-[1,1'-biphenyl]

A solution of Part A aldehyde (2.0 g, 11 mmol) in CH$_2$Cl$_2$ (60 ml) was placed under argon atmosphere and cooled to −10° C. Triphenylphosphine (9.21 g, 35 mmol) was added, and this mixture was stirred until all of the solid dissolved. To the resulting solution at −10° C. was added over 15 minutes a CH$_2$Cl$_2$ (40 ml) solution of CBr$_4$ (5.5 g, 16.5 mmol). The reaction was stirred at −10° C. for 1 hour 15 minutes, and then it was quenched at −10° C. with 50 ml of saturated aqueous NaHCO$_3$ solution. The CH$_2$Cl$_2$ and aqueous layers were separated and the aqueous layer was extracted 1× with CH$_2$Cl$_2$. The combined CH$_2$Cl$_2$ extracts were washed 1× with saturated aqueous NaHCO$_3$ solution and 1× with saturated aqueous NaCl solution. The CH$_2$Cl$_2$ extract was dried over Na$_2$SO$_4$ and evaporated to dryness. The crude product was purified by flash chromatography eluting with hexane to give the title dibromide as an off white solid (2.45 g, 65%).

TLC (5:95/EtOAc:Hexane silica gel) Rf=0.47.

IR (CHCl$_3$) 3064, 3011, 1596, 1473, 1450, 1435, 889, 860, 702 cm$^{-1}$.

$^1$H NMR (270 MHz) (CDCl$_3$): δ7.75 (m, 1), 7.35 (m, 8), 7.20 (s, 1).

$^{13}$C NMR (67.0 MHz) (CDCl$_3$): δ141.06, 140.08, 137.49, 133.83, 129.81, 129.45, 129.17, 128.61, 128.22, 127.50, 127.08, 90.78.

Mass Spec m/e 337/339/341 (M$^+$+H).

C. 2-Ethynyl-[1,1'-biphenyl]

A THF (35 ml) solution of Part B vinyl dibromide (2.31 g, 6.9 mmol) was cooled to −78° C. under an argon atmosphere. With stirring at −78° C., n-BuLi (5.52 ml of 2.5M solution in hexane) was added over 10 minutes to the vinyl dibromide. On completion of the n-BuLi addition, the reaction mixture became deep purple. After stirring at −78° C. for 2 hours 45 minutes, the reaction was quenched with saturated aqueous NH4Cl solution. After the quenched reaction was warmed to room temperature, the THF was removed from the reaction mixture and the resulting material was diluted with H2O and extracted 3× with 1: Et2O/hexane. The organic extract was dried over MgSO4 and filtered to give 1.3 g of a yellow oil. Purification by flash chromatography eluting with 1% Et2O/hexane provided the desired title acetylene (1.04 g, 88%).

TLC (100% Hexane, silica gel) Rf=0.16.

IR (film) 3287, 3061, 3026, 1474, 1449, 1432, 1008, 775, 758, 738 cm$^{-1}$.

$^1$H NMR (270 MHz): (CDCl3) δ7.68 (m, 3), 7.35 (m, 6), 3.00 (s, 1).

$^{13}$C NMR (67.8 MHz) (CDCl3): δ144.40, 140.22, 133.83, 129.56, 129.20, 128.92, 127.95, 127.49, 126.94, 120.44, 83.08, 80.15.

Mass Spec m/e 179 (M+ +H).

D. (S)-4-[[2-[[1,1'-Biphenyl]-2-yl]ethynyl]methoxyphosphinyl]-3-(t-butyldipehnylsilyloxy)butanoic acid, methyl ester Part C acetylene (0.332 g, 1.86 mmol) was stirred at −78° C. (under argon atmosphere and in 10 ml of THF. Over 5 minutes, n-BuLi (0.75 ml of a 2.5M solution in hexane) was added to the acetylene solution. The reaction was stirred at −78° C. for 1 hour warmed to 0° C. and stirred for 10 minutes and then recooled to −78° C. The acetylenic anion solution was then added dropwise over 8 minutes to a 10 ml THF solution of the Example 1 Part F phosphonochloridate (2.98 mmol) which had been cooled to −78° C. under an argon atmosphere. After the addition was complete, the reaction was stirred at −78° C. for 1 hour and then quenched by the addition of saturated aqueous NH4Cl solution. The quenched reaction was warmed to room temperature, diluted with half-saturated aqueous NaCl solution and extracted 3× with Et2O. The combined Et2O extracts were washed with saturated aqueous NaHCO3 and saturated aqueous NaCl solutions. The Et2O layer was dried over MgSO4 and evaporated to give 1.5 g of a yellow oil. Purification by flash chromatography eluting with 5:1:4 hexane:toluene:EtOAc gave the title acetylenic phosphinate (0.543 g, 48%).

TLC (5:1:4 hexane:toluene:EtOAc, silica gel) Rf=0.20.

IR (CHCl3) 3070, 3053, 3035, 3000, 2952, 2934, 2896, 2859, 2178, 1735, 1474, 1448, 1436, 1429 cm$^{-1}$.

$^1$H NMR (270 MHz) (CDCl3): δ7.65 (m, 3), 7.65–7.28 (m, 16), 4.55 (m, 1), 3.55 (d, 3), 3.40 (dd, 3), 2.80 (m, 1), 2.55 (m, 1), 2.35 (m, 1) 2.08 (m, 1), 1.00 (s, 9).

$^{13}$C (67.8 Mz) (CDCl3): δ170.83, 145.29, 145.19, 139.22, 135.95, 135.59, 133.86, 133.75, 133.16, 132.86, 130.57, 129.56, 129.34, 128.81, 127.92, 127.75, 127.44, 127.39, 126.94, 117.90, 100.91, 100.38, 100.18, 84.51, 81.60, 65.53, 65.42, 60.06, 51.61, 51.50, 51.11, 42.07, 41.90, 38.86, 37.16, 26.56, 20.75, 18.97, 13.97.

Mass Spec m/e 611 (M+ +H).

E. (S)-4-[[2-[[1,1'-Biphenyl]-2-yl-]ethyl]methoxyphosphinyl]-(t-butyldiphenylsilyloxy)butanoic acid, methyl ester Argon was bubbled through a methanol (8 ml) solution of Part D acetylenic phosphinate (0.515 g, 0.85 mmol) for 10 minutes. Addition of 10% Pd/C (0.190 g) to the acetylene solution was followed by Parr hydrogenation at 43 psi. After shaking for 25 hours at 43 psi, the methanol solution was filtered through Celite and the filtrated evaporated to give the title phosphinate (0.510 g, 98%) as a colorless oil.

TLC (4:1 EtOAc:hexane) Rf=0.21.

IR (CHCl3) 3071, 3054, 2998, 2954, 2934, 2902, 2859, 1734, 1477, 1462, 1448, 1438, 1428 cm$^{-1}$.

$^1$H NMR (270 MHz) (CDCl3): δ7.65 (m, 3), 7.55–7.00 (m, 16), 4.45 (m, 1), 3.58 (s, 3), 3.30–3.20 (2 doublets, 3, J=11 Hz), 2.88 (m, 1), 2.60 (m, 3), 2.17–1.80 (m, 1), 1.80–1.30 (m, 1), 1.00 (s, 3).

$^{13}$C NMR (67.8 MH) (Diagnostic peaks) (CDCl3) δ171.33, 65.78, 51.36, 42.24, 26.75.

Mass Spec m/e 615 (M+ +H).

F. (S)-4-[2-[[1,1'-Biphenyl]-2-yl]ethyl]methoxyphosphinyl]-3-hydroxybutanoic acid, methyl ester A THF (10 ml) solution of Part E phosphinate (0.500 g, 0.82 mmol) was stirred under an argon atmosphere with HOAc (0.19 ml, 3.3 mmol). At room temperature, nBu4NF (2.45 ml, 1.0M solution THF) was added dropwise. The reaction was stirred at room temperature for 23 hours and then quenched with 15 ml of ice water. The aqueous layer was extracted 3× with EtOAc. The combined organic solutions were washed 2× with saturated aqueous NaHCO3 solution and 1× with saturated aqueous NaCl solution. The organic layer was dried over Na2SO4 and evaporated to give 0.437 g of a colorless oil. Purification by flash chromatography eluting with 7:3 acetone:hexane gave the title alcohol (0.247 g, 81%) as a colorless oil.

TLC (7:3 acetone:hexane, silica gel) Rf=0.22.

IR (CHCl3) 3600–3171 (br), 3064, 3009, 2954, 1731, 1479, 1439, 1237, 1180, 1042, 999 cm$^{-1}$.

$^1$H NMR (270 MHz) (CDCl3) δ7.50–7.10 (m, 9), 4.50–4.15 (m, 1), 3.70 (s, 3), 3.53 and 3.50 (2 doublets, 3, J=11 Hz), 2.88 (m, 2), 2.50 (m, 2), 2.00–1.60 (m, 4).

$^{13}$C NMR (67.8 MHz) (CDCl3) δ171.55, 171.49, 141.39, 141.00, 138.10, 137.88, 129.95, 128.81, 128.06, 127.53, 26.83, 126.22, 63.08, 63.02, 62.85, 51.39, 50.58, 50.47, 42.35, 42.15, 42.07, 41.87, 34.31, 33.06, 33.00, 30.77, 30.52, 29.49, 29.21, 25.41.

Mass Spec m/e 377 (M+ +H).

EXAMPLE 10

(S)-4-[2-[1,1'-Biphenyl-2-yl]ethyl]hydroxyphosphinyl]-3-hydroxybutanoic acid, dilithium salt Example 9 diester (0.239 g, 0.64 mmol) was stirred in dioxane (6.5 ml) under argon atomsphere. At room temperature, 1.9 ml of 1.0M LiOH solution was added. This mixture was stirred at 55° C. After stirring for 2.5 hours, the reaction was cooled to room temperature, and the dioxane and most of the H2O were removed by rotary evaporation. Purification by HP-20 chromatography (18 cm×2.5 cm) eluting first with 100% H2O and then with 1:1 MeOH:H2O gave the title dilithium salt (0.180 g, 79%) as a white solid.

TLC (8:1:1 CH2Cl2:MeOH:AcOH) Rf=0.16; (7:2:1 nPrOH:NH3:H2O) Rf=0.37.

EXAMPLE 11

(R)-4-[[(E)-2-[4'-Fluoro-3,3',5-trimethyl[1,1'-biphenyl]-2-yl]ethenyl]hydroxyphosphinyl]-3-hydroxybutanoic acid, dilithium salt A. (E)-Tributyl[2-[4'-fluoro-3,3',5-trimethyl[1,1'-biphenyl]-2-yl]ethenyl]tin Ref. Miftakov, M. A. et al. Synthesis (Comm.) pp. 496–499 (1985). A mixture of 2-ethynyl-4'-fluoro-3,3',5-trimethyl[1,1'-biphenyl] (1.7 g, 7.13 mmole) and (n-C4H9)3SnH (2.9 ml, 10.7 mmole, 1.5 eq.) was treated with AIBN (7.0 mg, 0.426 mmole) and the solution heated rapidly to 120° C. (oil bath) under argon. After 15 minutes at 120° C. an additional quantity of (n-

$C_4H_9)_3SnH$ (0.39 ml, 1.43 mmole, 0.2 eq.) was added and heating continued for a total of 3 hours. The yellow mixture was cooled and purified by Kugelrohr distillation at 0.1 mmHg, 240° C. to give 3.073 g (81%) of title vinyl stannane as a colorless liquid.

TLC hexane, $R_f$ product=0.45, UV and PMA. Product is unstable on silica gel (streaks to baseline).

$^{13}$C NMR (67.5 MHz, CDCl$_3$): 9.5, 13.6, 14.5, 20.9, 21.1, 27.2, 27.6, 114.0, 114.3, 123.6, 123.9, 128.8, 130.4, 133.0, 135.6, 136.1, 138.1, 140.0, 144.4, 160.3 ($J_{CF}$=244 Hz) ppm.

$^1$H NMR: δ0.8-1.5 ppm (27H, m, Sn(Bu)$_3$); 2.27, 2.31, 2.36 (9H, 3 singlets, aromatic CH$_3$'s); 6.05 (1H, d, J=20 Hz, PhCH=CHSn); 6.68 (1H, d, J=20 Hz, PhCH=CHSn); 6.90-7.13 (5H, m, aromatic protons).

B. (E)-4'-Fluoro-2-(2-iodoethenyl)-3,3',5-trimethyl[1,1'-biphenyl]

A solution of the Part A vinyl stannane (1.537 g, 2.89 mmole) in dry Et$_2$O (20 ml) was treated with iodine (734 mg, 2.9 mmole, 1 eq.) and the brownish solution stirred at room temperature under argon for 2 hours. The mixture was washed with saturated sodium thiosulfate, 10% NH$_4$OH and brine, dried over anhydrous MgSO$_4$ and evaporated to give 1.639 g of a yellow oil. The crude product was purified by flash chromatography on silica gel (160 gm) eluting with hexane. Combined product fractions gave 832 mg (65%) of desired pure title trans vinyl iodide as a pale yellow oil which slowly crystallized on standing, m.p. 53°-55° C.

TLC (hexane) $R_f$ trans olefin=0.31, ($R_f$ cis olefin=0.26), UV and PMA.

$^1$H NMR (270 MHz): δ2.30 and 2.32 ppm (9H, 2 singlets, aromatic methyls); 6.05 (1H, d, J=15 Hz, —HC=CHI); 6.92-7.10 (5H, m, aromatic H's); 7.24 (1H, d, J=15 Hz, PhCH=CHI).

$^{13}$C NMR (67.5 MHz): 14.6, 21.0, 21.1, 81.0 (=CH—I), 114.4, 114.7, 124.2, 124.5, 128.5, 128.7, 130.5, 132.7, 132.8, 133.2, 135.8, 137.2, 140.1, 143.1 (PhCH=CHI), 161.0 ($J_{CF}$=244 Hz) ppm.

Note: An $^1$H NMR (CDCl$_3$, 270 MHz) on mixed fractions indicated the close running impurity to be the cis vinyl iodide. δ6.54 ppm (1H, d, $J_{HaHb}$=7.9 Hz (PhCH$_b$=CH$_a$—I)).

C. (R)-3-[[(1,1-Dimethylethyl)diphenylsilyl]oxy]-4-[[(E)-2-[4'-fluoro-3,3',5-trimethyl[1,1'-biphenyl]-2-yl]ethenyl]methoxyphosphinyl]butanoic acid, methyl ester A −78° C. (dry ice/acetone) solution of the Part B vinyl iodide (812 mg, 2.22 mmole) in dry THF (6 ml) was treated dropwise via syringe with a 1.6M n-BuLi solution in hexanes (1.4 ml, 2.2 mmole, 1 eq.) and the pale yellow mixture stirred under argon at −78° C. for 45 minutes. The anion was then transferred by cannula dropwise over 10 minutes directly into a −78° C. solution of the Example 1 Part F phosphonochloridate (~3.5 mmole, 1.58 eq) in dry THF (6 ml). The yellow mixture was stirred for 30 minutes at −78° C. then warmed to room temperature. The mixture was quenched at room temperature by the addition of saturated NH$_4$Cl (5 ml). The mixture was diluted with Et$_2$O, the ethereal layer washed with saturated NH$_4$Cl and brine, then dried over anhydrous MgSO$_4$ and evaporated to give 2.083 g of a yellow oil. The crude product was purified by flash chromatography on silica gel eluting with (85:15) Hex-acetone. Product fractions were combined and evaporated to give 249 mg (17%) of the desired trans olefinic phosphinate as a pale yellow oil. NMR indicated approximately at (1:1) mixture of diastereomers at phosphorus. TLC (7:3) Hex-acetone, $R_f$=0.35, UV and PMA.

$^1$H NMR: δ3.27 ppm (3H, d, $J_{H-P}$=11.6 Hz,

);

3.57 and 3.60 (3H, 2 singlets, diastereomers, —CO$_2$CH$_3$); 4.33 and 4.50 (1H, 2 multiplets, diastereomers, —CH$_2$CH(OSiR$_3$)CH$_2$—); 4.84 and 5.25 (1H, 2 dd's, diastereomers, $J_{HaHb}$=17.9 Hz, $J_{Ha-P}$=25.3 Hz,

).

D. (R)-4-[[(E)-2-[4'-Fluoro-3,3',5-trimethyl[1,1'-biphenyl]-2-yl]ethenyl]methoxyphosphinyl]-3-hydroxybutanoic acid, methyl ester A solution of the Part C silyl ether (249 mg, 0.370 mmole) in THF (5.0 ml) was treated successively with glacial HOAc (85 μl, 1.48 mmoles, 4.0 eq.) and a 1.0M (n-C$_4$H$_9$)$_4$NF solution in THF (1.1 ml, 1.1 mmole, 3.0 eq) and the yellow mixture was stirred overnight at room temperature under argon. The mixture was diluted with cold H$_2$O (10 ml) and extracted with EtOAc. The organic phase was washed with saturated NaHCO$_3$ and brine then dried over anhydrous Na$_2$SO$_4$ and evaporated to give 243 mg of a yellow oil. The crude product was purified by flash chromatography on silica gel eluting with (55:45) Hex-acetone. Product fractions were combined and evaporated to give 121 mg (75%) of desired title hydroxy diester as a colorless viscous oil.

TLC (6:4) Acetone-Hex, $R_f$=0.26, UV and PMA.

$^1$H NMR: δ1.8-2.06 ppm (2H, m,

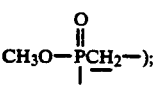

);

2.30, 2.35, 2.40 (9H, 3 singlets, aromatic CH$_3$'s); 2.40-2.60 (2H, m, —CH(OH)CH$_2$CO$_2$CH$_3$); 3.50+3.55 (3H, 2 doublets, diastereomers,

$J_{H-P}$=12 Hz); 3.64 (3H, s, —CO$_2$CH$_3$); 3.77+3.84 (1H, 2 doublets, diastereomers, —CH(OH)—); 4.28+4.38 (1H, 2 broad multiplets, —CH(OH)—); 5.52 (1H, 2 dd's, diastereomers $J_{HH}$ coupling and $J_{HP}$ coupling,

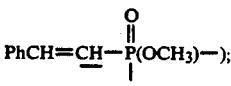

6.90-7.10 (5H, aromatic protons) 7.50 (1H, multiplet, diastereomers and $J_{HH}$ coupling $J_{HP}$ coupling,

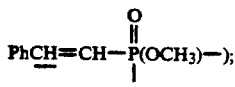

E. (R)-4-[[(E)-2-[4'-Fluoro-3,3',5-trimethyl[1,1'-biphenyl]-2-yl]ethenyl]hydroxyphosphinyl]-3-hydroxybutanoic acid, dilithium salt A solution of Part D hydroxy diester (121 mg, 0.279 mmole) in dioxane (2 ml) was treated with excess 1.0N LiOH (0.98 mg, 0.98 mmole, 3.5 eq) and the clear pale yellow mixture stirred under argon at 50° C. (oil bath) for 1.5 hours. The mixture was cooled, diluted with H$_2$O, filtered and evaporated in vacuo. The residue was taken up in a minimum amount of H$_2$O and chromatographed on HP-20 resin (8 cm bed, 25 mm column diameter) eluting sequentially with H$_2$O (200 ml), (80:20) H$_2$O—CH$_3$OH, and finally (60:40) H$_2$O—CH$_3$OH. Product fractions were evaporated in vacuo, taken up in H$_2$O (50 ml) and lyophilized to give 91 mg of pure title dilithium salt product as a hygroscopic, white lyophilate.

TLC (8:1:1) CH$_2$CH$_2$—CH$_3$OH—HOAc, Rf=0.19, UV and PMA.

EXAMPLES 12 TO 24

Following the procedures as outlined heretofore and as described in the previous working Examples, the following additional compounds may be prepared.

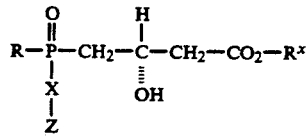

| Ex. No. | R | Z | X | R$^x$ |
|---|---|---|---|---|
| 12. | OH | 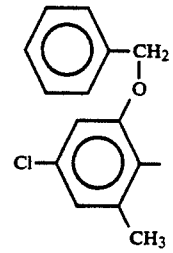 | —CH$_2$CH$_2$— | H |
| 13. | C$_2$H$_5$O | 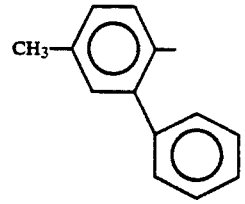 | —CH=CH— | CH$_3$ |
| 14. | OH | 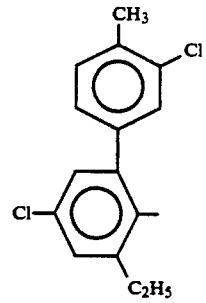 | —C≡C— | H |
| 15. | OLi | 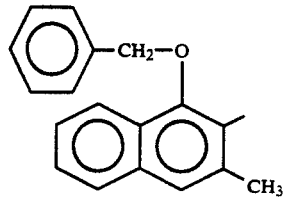 | —CH$_2$CH$_2$— | Li |

-continued

| Ex. No. | R | Z | X | R^x |
|---|---|---|---|---|
| 16. | OH | 2-methyl-1,3-diphenylnaphthalene | —CH=CH— | H |
| 17. | OLi | 1-benzyl-2-methyl-3-phenylindole | —C≡C— | Li |
| 18. | OCH₃ | 3-cyclopentyl-2-methyl-1-phenylindole | —CH₂CH₂— | CH₃ |
| 19. | OK | (2-methylbutanoate ester of a dimethyl-octahydronaphthalenol) with C₂H₅—CH(CH₃)—C(=O)O— group | —CH=CH— | OK |
| 20. | ONa | 1-(benzyloxy)-7-ethyl-8-methyl-octahydronaphthalene | —C≡C— | Na |
| 21. | OH | 1-(benzyloxy)-hydroxy-methyl-octahydronaphthalene | —CH₂CH₂— | H |

| Ex. No. | R | Z | X | R$^x$ |
|---|---|---|---|---|
| 22. | OH | C$_2$H$_5$—C(CH$_3$)—C(CH$_3$)—O—C(=O)—[decalin with OH, CH$_3$, C$_2$H$_5$ substituents] | —CH$_2$CH$_2$— | H |
| 23. | CH$_3$O | phenyl | —CH=CH— | CH$_3$ |
| 24. | OH | 1,2,3-triphenylbenzene group | —C≡C— | H |

EXAMPLE 25

(S)-4-(Hydroxymethoxyphosphinyl)-3-[[(1,1-dimethylethyl)diphenylsilyl]oxy]butanoic acid, methyl ester, dicyclohexylamine (1:1) salt

A. (S)-4-Diisopropyloxyphosphinyl-3-[[(1,1-dimethylethyl)diphenylsilyl]oxy]-butanoic acid, methyl ester The Example 1, Part F(2) iodide (45.1 mmol., 21.70 g) was stirred under high vacuum for 30 minutes. Freshly distilled triisopropyl phosphite (0.451 mol., 93.92 g, 113.37 ml.) was added in one portion and the reaction mixture was stirred under argon and heated in a 155° C. oil bath for 16.5 hours. The mixture was then cooled to room temperature. Excess triisopropyl phosphite and volatile reaction products were removed by short path distillation (10 mm Hg) followed by Kugelrohr distillation (0.50 mm Hg, 100° C., 8 hours). The product was further purified via flash chromatography (95 mm diam. column, 6"/Merck silica gel, 6/3/1 Hexane/acetone/toluene eluent, 2"/min flow rate, 50 ml fractions) to afford 17.68 g (33.96 mmol, 75% yield) of the title isopropylphosphonate as a clear viscous oil.

TLC: Silica gel R$_f$=0.32 (6:3:1 Hexane/acetone toluene).

$^1$H NMR: (270 MHz, CDCl$_3$) δ: 7.70–7.65 (m, 4H); 7.45–7.35 (m, 6H); 4.57–4.44 (m, 3H); 3.59 (s, 3H); 2.94 and 2.88 (2 xd, 1H J=3.7 Hz); 2.65 and 2.60 (2 xd, 1H J=7.4 Hz); 2.24–1.87 (Series of m, 2H); 1.19 and 1.12 (2 xd, 12H J=6.3 Hz); 1.01 (s, 9H).

B. (S)-4-(Hydroxymethoxyphosphinyl)-3-[[(1,1-dimethylethyl)diphenylsilyl]oxy]butanoic acid, methyl ester, dicyclohexylamine (1:1) salt The Part A isopropyl phosphonate (30.5 mmol, 10.66 g) was stirred under argon, at room temperature, in 80 ml of dry CH$_2$Cl$_2$. This solution was treated dropwise (5 min) with bistrimethylsilyltrifluoroacetamide (BSTFA) (32.8 mmol, 8.44 g, 8.71 ml), followed by dropwise addition (10 min) of trimethylsilylbromide (TMSBr) (51.3 mmol, 7.84 g, 6.75 ml). After stirring at room temperature for 20 hours, the reaction mixture was quenched with 200 ml of 5% aqueous KHSO$_4$ and stirred vigorously for 15 minutes. The aqueous layer was extracted 3 times with ethylacetate. The organic extracts were combined, washed once with brine, dried over Na$_2$SO$_4$ and concentrated in vacuo. The residue was azeotroped 2 times with 50 ml of toluene. The precipitate which formed was suspended in toluene and filtered. The filtrate was concentrated and the azeotrope/filter process repeated. The resulting filtrate was evaporated in vacuo and then pumped under high vacuum for 5 hours. The resulting viscous clear oil was stirred under argon, at room temperature, in 50 ml of dry pyridine. This solution was treated in one portion with dicyclohexylcarbodiimide (DCC) (22.6 mmol, 4.65 g), followed by addition of methanol (41.0 mmol, 1.31 g, 1.67 ml). After stirring at room temperature for 20 hours, the reaction mixture was filtered through a celite pad in a sintered glass funnel. The celite was washed with ethyl acetate and the combined filtrates were evaporated in vacuo. The residue was redissolved in ethyl acetate and washed 2 times with 5% aqueous KHSO$_4$ and once with brine. The organic extract was dried over Na$_2$SO$_4$, filtered, the filtrate concentrated and azeotroped 2 times with toluene, suspended in toluene and filtered. The resulting filtrate was again concentrated, azeotroped, filtered and the filtrate evaporated in vacuo and placed under high vacuum for 6 hours to afford the phosphonate monoester as a clear viscous oil (10.2 g, >100% yield). TLC: silica gel R$_f$=0.50 (7:2:1 nPrOH/NH$_4$OH/H$_2$O). The phosphonate monoester [1.21 g was pumped under high vacuum for 4 hours, affording 1.16 g (2.57 mmol)] was dissolved in 10 ml of dry ethyl ether and treated dropwise with dicyclohexylamine (2.65 mmol, 0.481 g, 0.528 ml). The resulting homogeneous solution sat at room temperature for 7 hours resulting in significant crystal formation. The mixture was stored at −20° C. for 16 hours and then warmed to room temperature and filtered. The crystals were washed with cold, dry ethyl ether and then pumped under high vacuum over P$_2$O$_5$ for 18 hours. The crystals were subsequently pumped under high vacuum at 45° C. for 4 hours, affording 1.25 g (1.98 mmol, 77% yield) of the title dicyclohexylamine salt as a white powdery solid, m.p. 155°-156° C.

TLC: Silica gel $R_f=0.57$ (20% MeOH/CH$_2$Cl$_2$) $^1$H NMR: (270 MH$_2$, CDCl$_3$) δ: 7.71-7.65 (m, 4H); 7.40-7.32 (m, 6H); 4.02 (m, 1H); 3.52 (s, 3H); 3.28 and 3.22 (m, 1H); 3.11 (d, 3H J=11 Hz); 2.77-2.64 (m, 2H); 2.62-2.56 (m, 1H); 1.92-1.08 (Series of m, 22H); 1.00 (S, 9H).

Mass Spec: (FAB) 632 (M&H)+.

IR:(KBr) 3466-3457 (broad) 3046, 3016, 2997, 2937, 2858, 2836, 2798, 2721, 2704, 2633, 2533, 2447, 1736, 1449, 1435, 1426, 1379, 1243, 1231, 1191, 1107, 1074, 1061, 1051, 820 CM−1.

Anal Calcd for C$_{22}$H$_{31}$O$_6$PSi·C$_{12}$H$_{23}$N: C, 64.63; H, 8.61; N, 2.22. Found: C, 64.51; H, 8.49; N, 2.18.

EXAMPLE 26

(E)-4-[[2-[4'-Fluoro-3,3',5-trimethyl[1,1'-biphenyl]-2-yl]ethenyl]hydroxyphosphinyl]-3-hydroxybutanoic acid, dilithium salt A. [2-[4'-Fluoro-3,3',5-trimethyl[1,1'-biphenyl]-2-yl]-2-hydroxyethyl]phosphonic acid, dimethyl ester A −78° C. (CO$_2$/acetone) solution of dimethylmethylphosphonate (1.8 ml, 16.5 mmole, 1.6 eq) in dry THF (20 ml) was treated dropwise over 20 minutes with a 1.6M n-butyllithium solution in hexanes (9.7 ml, 15.5 mmole, 1.5 eq) and the resulting white suspension stirred under argon at −78° C. for 60 minutes. Example 1, Part C biphenyl aldehyde (2.5 g, 10.3 mmole, 1 eq) in dry THF (10 ml) was then added dropwise over 15 minutes at −78° C. to give a pale orange suspension. After 30 minutes at −78° C., the mixture was quenched by dropwise addition of sat'd NH$_4$Cl (10 ml) and allowed to warm to room temperature. The mixture was partitioned between ethyl acetate and H$_2$O, the organic phase washed with brine, dried over anydrous Na$_2$SO$_4$ and evaporated in vacuo to give 4.127 g of a yellow oil which slowly crystallized on standing. The crystals were triturated with hexanes to give after filtration and drying in vacuo 3.38 g (89.4%) of pure title hydroxy phosphonate as white needles with mp=98°-100° C. An additional 233 mg (3.613 g total, yield=95.6%) of pure title compound was recovered by a flash chromatography of the mother liquor (603 mg) on LPS-1 silica gel (40:1) eluting with (7:3) hexane-acetone. TLC (1:1) hexane-acetone, $R_f=0.33$, UV+PMA.

Anal Calcd for C$_{19}$H$_{24}$O$_4$PF: C, 62.29; H, 6.60; F, 5.19; P, 8.45. Found: C, 62.66; H, 6.56; F, 5.03; P, 8.68.

B. [2-[4'-Fluoro-3,3',5-trimethyl[1,1'-biphenyl]-2-yl]ethenyl]phosphonic acid, dimethyl ester A solution of the Part A hydroxy phosphonate (3.513 g, 9.6 mmole) in dry (4 Å sieves) toluene (15 ml) was treated with pTsOH.1 H$_2$O (91 mg, 0.48 mmole, 0.05 eq) and refluxed through a Soxhlet apparatus containing 4 Å sieves for 16 hours under argon. Additional pTsOH.H$_2$O was added during the course of the reaction at the following time intervals: 3.5 hours (91 mg), 5.0 hours (91 mg), and 6.5 hours (91 mg). The mixture was cooled, diluted with ethyl acetate and washed with sat'd NaHCO$_3$ to give an aqueous phase, an organic phase and an oily layer between phases. The aqueous phase and oily layer were collected, washed with ethyl acetate, the ethyl acetate layer washed with sat'd NaHCO$_3$ and put aside. The 2 bicarbonate washes were acidified with conc. HCl, extracted with ethyl acetate, the organic phase washed with brine, dried over anhydrous Na$_2$SO$_4$ and evaporated to give 520 mg of recovered phosphonic acid, mono methyl ester. The diester was regenerated by dissolving the oil in trimethyl orthoformate (5 ml) and refluxing the mixture under argon for 4 hours. Excess formate was removed in vacuo to give a yellow oil which was taken up in ethyl acetate and combined with the original neutral organic phase. The ethyl acetate layer was washed with brine, dried over anhydrous Na$_2$SO$_4$ and evaporated to give 3.396 g of a yellow oil. The crude oil was purified by flash chromatography on LPS-1 silica gel (40:1) eluting with (75:25) Hexane-acetone. Product fractions were evaporated to give 2.987 g (89.4%) of the title trans-vinyl dimethyl phosphonate as a golden oil. TLC (1:1) Hex-acetone, $R_f=0.44$, UV and PMA.

$^1$H NMR (CDCl$_3$): δ2.27 (3H, d, $J_{H-F}=1.6$ Hz); 2.33 (3H, s); 2.39 (3H, s); 3.61 (6H, d, $J_{H-P}=11$ Hz); 5.51 (1H, dd, $J_{H-H}=18$ Hz, $J_{H-P}=20.6$ Hz); 6.95-7.09 (5H, m); 7.48 (1H, dd, $J_{H-H}=17.9$ Hz, $J_{H-P}=23.7$ Hz) ppm.

$^{13}$C NMR (CDCl$_3$): δ14.4, 20.9, 52.0 ($J_{C-P}=5.7$ Hz); 114.4, 114.7, 119.2 ($J_{C-P}=185.5$ Hz); 124.3, 124.5, 128.4, 128.5 129.0 130.6; 130.9 132.6, 132.7, 134.6, 137.1, 141.0; 148.2, 148.2 ($J_{C-P}=5.7$ Hz); 160.5 ($J_{C-F}=244.1$ Hz).

C. [2-[4'-Fluoro-3,3',5-trimethyl[1,1'-biphenyl]-2-yl]ethenyl]phosphonic acid, monomethyl ester A solution of Part E vinyl dimethylphosphonate (2.895 g, 8.31 mmole) in dioxane (20 ml) was treated with a 1.0N LiOH solution (12.5 ml, 12.5 mmole, 1.5 eq) and the resulting mixture stirred at 75° C. (oil bath) for 70 minutes under argon. After 15 minutes of heating, the mixture became homogeneous. The mixture was cooled to room temperature, acidified to pH 1 with 1.0N HCl (∼15 ml), extracted (2×) with ethyl acetate, the organic phase washed with brine, dried over anhydrous Na$_2$SO$_4$ and evaporated in vacuo to give 2.663 g (95.8%) of desired title monomethyl ester as a clear, colorless oil. TLC: (8:1:1) CH$_2$Cl$_2$-CH$_3$OH-HOAc, $R_f=0.57$, UV and PMA. Mass Spec (M+H+=335+ observed).

$^1$H NMR (CDCl$_3$): δ2.25 (3H, d, $J_{H-F}=1.6$ Hz); 2.33 (3H, s); 2.39 (3H, s); 3.53 (3H, d, $J_{H-P}=11$ Hz); 5.61 (1H, dd, $J_{H-H}=18$ Hz, $J_{H-P}=20.6$ Hz); 6.90-7.12 (5H, m); 7.38 (1H, dd, $J_{H-H}=18$ Hz, $J_{N-P}=24$ Hz) ppm.

D. 4-[[2-[4'-Fluoro-3,3',5-trimethyl[1,1'-biphenyl]-2-yl]ethenyl]methoxyphosphinyl]-3-oxobutanoic acid, methyl ester Distilled methyl acetoacetate (420 μl, 3.9 mmole, 1.3 eq) was added dropwise over 15 minutes to a stirred suspension of 60% NaH dispersion in mineral oil (168 mg, 4.2 mmole, 1.4 eq) in dry THF (10 ml) at 0° C. (ice bath) under argon. The resulting clear solution was stirred 15 minutes at 0° C., then treated with 1.6M n-butyllithium solution in hexanes (2.25 m, 3.6 mmole, 1.2 eq) over 10 minutes. The yellow dianion solution was stirred for 15 minutes at 0° C., then cooled to −78° C. in preparation for treatment with phosphonochloridate.

Phosphonochloridate was prepared from title Part C mono methyl ester according to the following method. A solution of the Part C phosphonic mono methyl ester (960 mg, 2.87 mmole) in dry CH$_2$Cl$_2$ (8 ml) was treated with distilled trimethylsilyldiethylamine (750 μl, 5.98 mmole, 2 eq) and the clear mixture stirred under argon at room temperature for 1 hour. The mixture was evaporated in vacuo, azeotroped with benzene (2×15 ml) and the viscous oil left on the vacuum pump for 15 minutes. The oil was taken up in dry CH$_2$Cl$_2$ (8 ml) and dry DMF (1 drop), cooled to 0° C. (ice bath) and treated with distilled oxalyl chloride (290 μl, 3.3 mmole, 1.1 eq) dropwise over 5 minutes under argon. After 15 minutes at 0° C., the mixture was stirred at room temperature for 45 minutes then evaporated in vacuo. The crude oil was azeotroped with dry benzene (2×15 ml) to give after evaporation and drying on the vacuum pump for 15 minutes crude phosphonochloridate as a pale yellow oil.

Phosphonochloridate (~2.9 mmole, 1 eq) in dry THF (8 ml) at −78° C. was transferred via cannula dropwise over 30 minutes to a −78° C. solution of methyl acetoacetate dianion. After 30 minutes at −78° C. the orange brown reaction mixture was quenched by dropwise addition of saturated NH₄Cl (8 ml) and allowed to warm to room temperature. The mixture was diluted with ethyl acetate, washed with sat'd NaHCO₃ and brine, then dried over anhydrous Na₂SO₄ and evaporated in vacuo to give 1.481 g of an orange oil. The crude oil was purified by flash chromatography on Merck silica gel eluting with (9:1) Hexane-Acetone, followed by (1:1) Hexane-Acetone. Product fractions were combined and evaporated to give 813 mg (62.9%) of desired title vinyl phosphinic diester as a viscous, pale yellow oil. TLC (1:1) Hex-Acetone, $R_f$=0.42, UV and PMA.

¹H NMR (CDCl₃): δ2.28 (3H, s); 2.34 (3H, s); 2.40 (3H, s); 3.15 (2H, dd, $J_{H-H}$=4.7 Hz, $J_{H-P}$=18.2 Hz); 3.54 (3H, d, $J_{H-P}$=11.6 Hz); 3.63 (2H, s); 3.72 (3H, s); 5.57 (1H, dd, $J_{H-H}$=17.9 Hz, $J_{H-P}$ 25.3 Hz); 6.95–7.09 (5H, m); 7.52 (1H, dd, $J_{H-H}$=17.9 Hz, $J_{H-P}$=22.7 Hz) ppm.

¹³NMR (CDCl₃): δ14.0 ($J_{C-F}$=3.9 Hz), 20.6, 45.3 ($J_{C-P}$=85.9 Hz), 49.6, 50.9 ($J_{C-P}$=5.8 Hz), 5.18, 113.6, 115.0 121.4 ($J_{C-P}$=128.9 Hz), 123.6, 124.7, 128, 187.7, 129.5, 130.3, 130.8, 132.1, 132.4, 136.4, 136.8, 138.2, 140.7, 149.2 ($J_{C-P}$=4.9 Hz), 160.3 ($J_{C-F}$=245.1 Hz), 166.7, 194.4 ($J_{C-P}$=4.9 Hz) ppm.

E. (E)-4-[[2-[4'-Fluoro-3,3',5-trimethyl[1,1'-biphenyl]-2-yl]ethenyl]methoxyphosphinyl]-3-hydroxybutanoic acid, methyl ester A 0° C. (ice bath) solution of the Part D, ketone (585 mg, 1.35 mmole) in dry THF (4 ml) was treated with solid NaBH₄ (51 mg, 1.35 mmole, 1 molar eq.) followed by dropwise addition of dry CH₃OH (1 ml, 3 Å sieves) and the yellow mixture stirred under argon at 0° C. for 30 minutes. The mixture was quenched at 0° C. by addition of reagent acetone (6.5 ml) followed by addition of CC-4 silica gel (500 mg). The suspension was warmed to room temperature, filtered through sintered glass, rinsed with ethyl acetate and evaporated in vacuo to give 607 mg of a yellow oil. The crude oil was purified by flash chromatography on Merck silica gel (30:1) eluting with neat ethyl acetate. Product fractions were evaporated to give 340 mg (57.6%) of desired title alcohol as a pale yellow oil.

TLC (neat EtOAc), $R_f$=0.19, UV+PMA.

Mass Spec (M+H+ =435 observed).

¹H NMR (CDCl₃): δ1.90 (2H, m), 2.27+2.28 (3H, 2 singlets), 2.34 (3H, s), 2.39+2.40 (3H, singlets), 2.56 (2H, d), 3.52 (3H, d, $J_{H-P}$=11.1 Hz), 3.69+3.70 (3H, 2 singlets), 3.79+3.90 (1H, 2 doublets), 5.52+5.54 (1H, 2dd, $J_{H-H}$=18 Hz, $J_{H-P}$=2.48 Hz), 6.95–7.02 (5H, m), 7.52–7.54 (1H, 2dd, $J_{H-H}$=18 Hz, $J_{H-P}$=21.6 Hz) ppm.

¹³C NMR (CDCl₃) (R,S mixture): δ14.3 ($J_{C-F}$=3.9 Hz), 20.8, 35.4+35.8 ($J_{C-P}$=100.6 Hz), 42.0 ($J_{C-P}$=12.7 Hz), 50.7 ($J_{C-P}$=6.8 Hz), 56.5, 63.2 ($J_{C-P}$=3.9 Hz), 113.8, 115.3, 122.9+123.2 ($J_{C-P}$=122.1 Hz) 123.8, 128.2, 128.7, 129.0, 130.4, 131.4, 132.3, 132.7, 136.6, 137.0, 138.2, 140.8, 148.2+148.8 ($J_{C-P}$=4.9 Hz), 160.5 ($J_{C-F}$=245.1 Hz), 171.8 ppm.

F. (E)-4-[[2-[4'-Fluoro-3,3',5-trimethyl[1,1'-biphenyl]-2-yl]ethenyl]hydroxyphosphinyl]-3-hydroxybutanoic acid, dilithium salt A solution of the Part E diester (339 mg, 0.781 mmole) in dioxane (8 ml) was treated with excess 1.0N LiOH (2.3 ml, 2.3 mmole, 3 eq) and the mixture heated at 50° C. (oil bath) for 1.5 hours under argon. A white precipitate was evident after 15 minutes. While still warm, the mixture was diluted with H₂O until all solids dissolved then filtered. The filtrate was evaporated in vacuo, taken up in a minimum amount of H₂O and chromatographed on HP-20 resin eluting with a neat H₂O→neat CH₃OH linear gradient. Product fractions were evaporated, the white residue taken up in H₂O (50 ml), filtered and lyophilized to give 270 mg (82.7%) of desired) title dilithium salt as a hygroscopic, white lyophilate.

TLC (8:1:1) CH₂Cl₂-CH₃OH-HOAc, $R_f$=0.33, UV+PMA.

Anal for C₂₁H₂₂O₅FP.2Li+0.63 moles H₂O (MW 429.57): Calcd: C, 58.71; H, 5.46; F, 4.42; P, 7.21. Found: C, 58.71; H, 5.70; F, 4.18, P, 6.96, ¹H NMR (CDCl₃) δ1.59 (2H, multiplet), 2.24–2.37 (2H, 3 multiplet, $J_{H-H}$=8.5 Hz+4.4 Hz), 2.28 (3H, doublet, $J_{H-F}$=1.8 Hz), 2.30+2.39 (6H, 2 singlets), 4.14 (1H, multiplet), 5.78 (1H, $J_{H-H}$=17.9 Hz, $J_{H-P}$=20.5 Hz), 6.88–7.21 (6H, multiplet),

EXAMPLE 27

4-[[2-[4'-Fluoro-3,3',5-trimethyl[1,1'-biphenyl]-2-yl]ethyl]hydroxyphosphinyl]-3-hydroxybutanoic acid, dilithium salt A. 4-[[2-[4'-Fluoro-3,3'-trimethyl[1,1'-biphenyl]-2-yl]ethyl]methoxyphosphinyl]-3-hydroxybutanoic acid, methyl ester An argon purged solution of the Example 6 Part E trans vinyl phosphinate (297 mg) in CH₃OH (6 ml) was treated with 10% Pd/c (74 mg, 25% by weight) and the black suspension shaken on a Parr apparatus under 40 psi H₂ for 3 hours. Catalyst was removed by filtration through packed Celite and the filtrate evaporated in vacuo to an oil. The oil crystallized from hexanes giving, after filtration and drying in vacuo, 267 mg (89.5%) of title saturated phosphinate as a white crystalline solid. TLC (EtOAc), $R_f$=0.20, UV+PMA.

¹H NMR (CDCl₃, 270 MHz), IR (KBr pellet),

Mass Spec (M+M+ =437+ observed).

¹H NMR (CDCl₃): δ1.55–1.87 (4H, m), 2.29+2.30+2.31 (6H, 3 singlets), 2.35 (3H, d, $J_{H-F}$=2.1 Hz), 2.52 (2H, m), 2.78 (2H, m), 3.50+3.55 (3H, 2 doublets $J_{H-P}$=4.3 Hz), 3.71 (3H,s), 3.86+3.91 (1H, 2 singlets), 4.25+4.39 (1H, 2 broad multiplets) ppm.

B. 4-[[2-[4'-Fluoro-3,3',5-trimethyl[1,1'-biphenyl]-2-yl]ethyl]hydroxyphosphinyl]-3-hydroxybutanoic acid, dilithium salt A solution of the Part A diester (250 mg, 0.573 mmole) in dioxane (6 ml) was treated with excess 1.0N LiOH (1.72 ml, 3 eq) and the mixture heated at 50° C. (oil bath) under argon for 1.5 hours. A white precipitate was evident after 15 minutes. The mixture was diluted with H₂O, while still warm until all solids dissolved and then filtered. The filtrate was evaporated in vacuo, the white residue dissolved in a minimum amount of H₂O and chromatographed on HP-20 resin eluting with neat H₂O (until neutral), followed by neat CH₃OH. Product fractions were evaporated in vacuo to a white solid which was azeotroped (2×) with CH₃CN and dried in vacuo to give 131 mg (55%) of desired title dilithium salt as a white solid. TLC (8:1:1) $CH_2Cl_2$—$CH_3OH$—acetic acid, $R_f$=0.34, Uv+PMA.

Anal Calcd for $C_{21}H_{24}O_5FPLi_2$+0.95 moles $H_2O$ (MW 437.30): C, 57.67; H, 5.97; F, 4.34; P, 7.08. Found: C, 57.67; H, 5.90; F, 3.92; P. 7.39.

$^1$H NMR ($CD_3OD+D_2O$): $\delta$1.39–1.57 (4H, multiplet) ppm, 2.22–2.37 (2H, multiplet), 2.26+2.38 (6H, 2 singlets), 2.31 (3H, doublet, $J_{H-F}$=1.8 Hz), 2.71–2.77 (2H, multiplet), 4.13–4.20 (1H, multiplet), 6.73–7.11 (5H, multiplet, aromatic H's).

EXAMPLE 28

(E)-4-[[2-[3-(4-Fluorophenyl)-1-(1-methylethyl)1H-indol-2-yl]ethenyl]hydroxyphosphinyl]-3-hydroxybutanoic acid, dilithium salt A. [2-[3-(4-Fluorophenyl)-1-(1-methylethyl)-1H-indol-2-yl]-2-hydroxyethyl]phosphonic acid, dimethyl ester A −78° C. (acetone/$CO_2$) solution of methyl dimethylphosphonate (1.35 ml, 12.42 mmole, 1.6 eq.) in dry THF (20 ml) was treated dropwise over 15 minutes with a 1.6M n-BuLi solution in hexanes (7.3 ml, 11.6 mmole, 1.5 eq.) and the resulting white suspension stirred under argon at −78° C. for 1 hour. The Example 7 Part E indole aldehyde (2.183 g, 7.76 mmole) in dry THF (8 ml) was added dropwise over 10 minutes to the anion at −78° C. and the resulting light orange suspension stirred for 30 minutes at −78° C. The mixture was quenched by dropwise addition of saturated $NH_4Cl$ (10 ml), warmed to room temperature, partitioned between $H_2O$ and ethyl acetate, the organic phase washed with brine, dried over anhydrous $Na_2SO_4$ and evaporated to give 3.19 g of a white solid. The crude solid was triturated with warm hexane to give 2.967 g (94.3%) of pure title hydroxy phosphonate as a white solid with m.p.=161°–162° C. TLC (1:1) Hex-Acetone, $R_f$=0.29, UV+PMA.

Anal Calcd for $C_{21}H_{25}O_4NPF$: C, 62.21; H, 6.22; N, 3.46; F, 4.69; P. 7.64. Found: C, 62.34; H, 6.32; N, 3.30; F, 4.61; P. 7.32.

$^1$H NMR ($CDCl_3$): $\delta$1.69+1.74 (6H, 2 doublets), 2.18+2.56 (2H, 2 multiplets), 3.61 (1H), 3.67+3.71 (6H, 2 doublets, $J_{H-P}$=11 Hz), 5.32 (1H, m), 5.50 (1H, m), 7.04–7.25 (4H, m), 7.33–7.39 (2H quartet), 7.52 (2H, AB quartet) ppm.

$^{13}$C NMR ($CDCl_3$): $\delta$21.1, 21.3, 33.1 ($J_{C-P}$=136.3 Hz), 48.3, 52.6+52.7 ($J_{C-P}$=5.7 Hz), 62.1 ($J_{C-P}$=3.8 Hz) 112.5, 114.3, 115.1, 115.4, 119.5, 120, 122, 128.1, 130.6, 131.9, 132.0, 134.8, 134.9, 135.2, 161.8 ($J_{C-F}$=246.1 Hz) ppm.

B. (trans)-[2-[3-(4-Fluorophenyl)-1-(1-methylethyl)-1H-indol-2-yl]ethenyl]phosphonic acid, dimethyl ester The Part A hydroxy phosphonate (2.60 g, 6.43 mmole) dissolved in warm benzene (20 ml) was treated with pTsOH.$H_2O$ (122 mg, 0.1 eq.) and the mixture refluxed through a Soxhlet containing 4 Å sieves for 1 hour under argon. The yellow solution was cooled, diluted with ethyl acetate, the organic phase washed with saturated $NaHCO_3$ (2×) and brine then dried over anhydrous $Na_2SO_4$ and evaporated to give 2.47 g of crude olefin as a yellow solid. One recrystallization from ethyl acetate-hexanes gave 2.238 g (89.9%) of pure title trans vinyl phosphonate as pale yellow plates with m.p.=153°–155° C.

TLC (1:1) Hex-Acetone, $R_f$=0.33, UV+PMA, Mass Spec (M+H+388+ observed).

Anal Calcd for $C_{21}H_{23}O_3PNF$: C, 65.11; H, 5.98; N, 3.62; F, 4.90; P. 7.99. Found: C, 65.27; H, 6.03; N, 3.48; F, 5.11; P. 7.98.

$^1$H NMR($CDCl_3$): $\delta$1.67 (6H, doublet), 3.68 (6H, d, $J_{H-P}$=11.6 Hz), 4.90 (1H, septet), 5.73 (1H, dd, $J_{H-H}$(trans)=18 Hz, $J_{H-P}$=18.2 Hz), 7.05–7.56 (8H, m), 7.64 (1H, dd, $J_{H-H}$=17.9 Hz, $J_{H-P}$=23.7 Hz) ppm.

$^{13}$C NMR ($CDCl_3$): $\delta$21.7, 47.8, 52.2 ($J_{C-P}$=5.7 Hz) 111.8, 115.4, 115.7, 118.5 ($J_{C-P}$=43.5H) 120.1, 120.2, 123.4, 128.2, 130.5, 130.7, 131.1, 131.7, 135.9, 137.9 ($J_{C-P}$=7.6 Hz) 161.9 ($J_{C-F}$=246 Hz) ppm.

C. (trans)-[2-[3-(4-Fluorophenyl)-1-(1-methylethyl)-1H-indol-2-yl]ethenyl]phosphonic acid, monomethyl ester The Part B vinyl dimethylphosphonate (1.787 g, 4.61 mmole) was dissolved in warm dioxane (12 ml), treated with 1.0N LiOH (6.9 ml, 6.9 mmole, 1.5 eq.) and heated at 75° C. (oil bath) under argon for 30 minutes. The mixture was cooled, acidified with 1.0N HCl (8 ml), extracted with ethyl acetate (2×), washed with $H_2O$ (2×) and brine, dried over anhydrous $Na_2SO_4$ and evaporated to give 1.859 g of a yellow oil. The oil was dissolved in warm hexane, cooled, and crystallized to give 1.657 g (96.1%) of mono acid as a pale yellow solid with m.p.=181°–183° C.

Anal Calcd for $C_{20}H_{21}O_3PNF$: C, 64.02; H, 5.70; N, 3.73; F, 5.06; P, 8.25. Found: C, 64.02; H, 5.87, N, 3.64, F, 5.26, P. 7.90.

TLC (20:1:1) $CH_2Cl_2$-$CH_3OH$-acetic acid, $R_f$=0.26, UV+PMA.

$^1$H NMR ($CDCl_3$): $\delta$1.66 (6H, doublet), 3.64 (3H, doublet, $J_{H-P}$=11.6 Hz), 4.89 (1H, septet), 5.81 (1H, dd, $J_{H-H}$=17.9 Hz, $J_{H-P}$=18.5 Hz) 7.06–7.64 (9H, multiplet) ppm.

$^{13}$C NMR ($CDCl_3$): $\delta$21.8, 47.9, 52.1 ($J_{C-P}$=5.7 Hz), 112.0, 115.5, 115.8, 116.1, 119.0 ($J_{C-P}$=9.5 Hz), 120.2, 120.4, 123.5, 128.3, 130.4, 130.8, 131.2, 131.8, 131.9, 136.2, 136.8 ($J_{C-P}$=7.6 Hz), 161.9 ($J_{C-F}$=246 Hz) ppm.

D. 4-[[2-[3-(4-Fluorophenyl)-1-(1-methylethyl)-1H-indol-2-yl]ethenyl]methoxyphosphinyl]-3-oxobutanoic acid, methyl ester Phosphonochloridate was prepared according to the following method. A solution of Part C phosphonic mono methyl ester (1.564 g, 4.19 mmole, 1 eq) in dry $CH_2Cl_2$ (10 ml) was treated with distilled diethylamino trimethylsilane (1.05 ml, 8.38 mmole, 2 eq) and the mixture stirred under argon at room temperature for 1 hour. The mixture was evaporated in vacuo, taken up in benzene (20 ml), evaporated in vacuo and the viscous oil left on the vacuum pump for 15 minutes. A solution of the crude silylated acid in dry $CH_2Cl_2$ (10 ml) and dry DMF (1 drop) was cooled to 0° C., treated dropwise with distilled $(COCl)_2$ (400 ml, 4.61 mmole, 1.1 eq), stirred 15 minutes at 0° C., then at room temperature for 45 minutes under argon. The yellow mixture was evaporated in vacuo, taken up in benzene (20 ml), evaporated in vacuo and left on the vacuum pump for 15 minutes to give crude phosphonochloridate as a viscous yellow oil. A solution of the phosphonochloridate in dry THF (8 ml) at −78° C. was transferred by cannula dropwise over 20 minutes to a −78° C. solution of the methyl acetoacetate dianion prepared as described in Example 26 from methyl acetoacetate (590 μl, 5.45 mmole, 1.3 eq), 60% NaH oil dispersion (235 mg, 5.87 mmole, 1.4 eq), 1.6M n-butyllithium (3.1 ml, 5.03 mmole, 1.2 eq), THF (10 ml). The orange reaction mixture was stirred 30 minutes at −78° C. then quenched by dropwise addition of saturated NH₄Cl and allowed to warm to room temperature. The mixture was partitioned between ethyl acetate and H₂O, the organic phase washed with saturated NaHCO₃ and brine then dried over andhydrous Na₂SO₄ and evaporated to give 2.080 g of a yellow oil. The crude oil was purified by flash chromatography on Merck silica gel eluting with (7:3) CH₂Cl₂-EtOAc. Product fractions were combined and evaporated to give 519 mg (26.3%) of desired title trans phosphinate as a light yellow oil.

TLC (1:1) Hex-Acetone, $R_f$=0.48, UV+PMA.
Mass Spec (M+H⁺=472⁺ observed).

¹H NMR (CDCl₃): δ1.66+1.71 (6H, 2 doublets), 1.68 (2H, m), 3.23 (2H doublet), 3.54 (3H, d), 3.72 (3H, s), 4.90 (1H, septet), 5.76 (1H, dd, $J_{H-H}$=18 Hz), 7.10–7.58 (8H, m), 7.66 (1H, dd, $J_{H-H}$=18 Hz) ppm.

¹³C NMR (CDCl₃): δ21.8, 45.7 ($J_{C-P}$=87.1 Hz), 47.9, 50.0, 51.5 ($J_{C-P}$=5.7 Hz), 52.3, 111.9, 115.5, 118.8 ($J_{C-P}$=104.1 Hz) 119.8, 120.2, 120.3, 123.6, 128.2, 130.4, 130.8, 131.8, 131.9, 136.1, 139.2, ($J_{C-P}$=5.6 Hz), 161.9 ($J_{C-F}$=246 Hz), 167.0, 194.6 ($J_{C-P}$=3.8 Hz) ppm.

E. (E)-4-[[2-[3-(4-Fluorophenyl)-1-(1-methylethyl)-1H-indol-2-yl]ethenyl]methoxyphosphinyl]-3-hydroxybutanoic acid, methyl ester A −15° C. (salt/ice bath) solution of the Part D ketone (519 mg, 1.1 mmole) in dry absolute EtOH (3 Å sieves 8 ml) was treated with solid NaBH₄ (42 mg, 1.1 mmole) and the yellow mixture stirred under argon at −15° C. for 20 minutes. The mixture was quenched by addition of acetone (0.5 ml) followed by CC-4 silica gel (500 mg). The mixture was warmed to room temperature, filtered, rinsed with ethyl acetate and evaporated in vacuo to give 512 mg of a yellow foam. The crude foam was purified by flash chromatography on Merck silica gel eluting with (4:1) ethyl acetate-acetone followed by neat acetone. Product fractions were evaporated to give 317 mg (60.9%) of desired title alcohol as a yellow oil. TLC (4:1) EtOAc-Acetone, $R_f$=0.21, UV+PMA.

Mass Spec (M+H⁺=4.74⁺ observed). ¹H NMR (CDCl₃): δ1.68 (6H, doublet), 1.97 (2H, m), 2.58 (2H, d), 3.61 (3H, d, $J_{H-P}$=11 Hz), 3.68 (3H, s), 3.95+4.04 (1H, 2 doublets), 4.40 (1H, bm), 4.95 (1H, septet), 5.78 (1H, dd, $J_{H-H}$=17.4 Hz, $J_{H-P}$=23.2 Hz), 7.05–7.77 (9H, m) ppm.

¹³C NMR (CDCl₃): δ21.7, 34.9+36.3 ($J_{C-P}$=20.8 Hz), 42.0 ($J_{C-P}$=13.2 Hz), 47.8, 50.8 ($J_{C-P}$=5.6 Hz), 51.6, 63.1 ($J_{C-P}$=15.1 Hz), 111.8, 115.4, 115.7, 118.6, 119.9+121.8 ($J_{C-P}$=18.9 Hz) 120.1, 123.4, 128.2, 130.6, 130.7, 131.1, 131.7, 131.9, 135.8, 138.0+138.5 ($J_{C-P}$=5.7 Hz), 161.8 ($J_{C-F}$=246.1 Hz), 171.7, 171.8 ppm.

F. (E)-4-[[2-[3-(4-Fluorophenyl)-1-(1-methylethyl)-1H-indol-2-yl]ethenyl]hydroxyphosphinyl]-3-hydroxybutanoic acid, dilithium salt A stirred solution of the Part E hydroxy diester (264 mg, 0.558 mmole) in dioxane (6 ml) was treated with 1.0N LiOH (1.95 ml, 3.5 eq) and heated at 70° C. (oil bath) for 20 minutes under argon. The mixture was allowed to cool, diluted with H₂O, filtered, evaporated in vacuo, taken up in a small amount of H₂O (1–2 mls) and chromatographed on HP-20 eluting with H₂O (until neutral, 3–4 column volumes) followed by (75:25) CH₃OH-H₂O. Product fractions were evaporated, taken up in H₂O (50 ml), filtered and lyophilized to give 217 mg (85.1%) of desired title dilithium salt as a white lyophilate. TLC (8:1:1) CH₂Cl₂-CH₃OH-acetic acid, $R_f$0.08, UV+PMA.

Anal Calcd for C₂₃H₂₃O₅NPF.2 Li+1.62 moles H₂O (MW 486.46): C, 56.78; H, 5.44; N, 2.88; F, 3.91; P, 6.37. Found: C, 56.76; H, 5.64; N, 2.58; F, 3.60; P, 6.77.

¹H NMR (400 MHz, CDCl₃): δ1.67 (6H, doublet), 1.73 (2H, multiplet), 2.38 (2H, doublet of AB quartet, $J_{AB}$=15 Hz, $J_{AX}$=8 Hz, $J_{BX}$=4.8 Hz), 4.24 (1H, multiplet), 5.06 (1H, septet), 6.09 (1H, $J_{HH}$=17.6 Hz, $J_{HP}$=19.4 Hz), 7.02–7.61 (9H, multiplet).

EXAMPLE 29

(S)-4-[[2-[1-(4-Fluorophenyl)-3-(1-methylethyl)-1H-indol-2-yl]ethyl]hydroxyphosphinyl]-3-hydroxybutanoic acid, dilithium salt A. 4-Methyl-2-oxopentanoic acid, ethyl ester 4-Methyl-2-oxopentanoic acid, sodium salt (25 g) was dissolved in a minimum amount of H₂O, acidified to pH 1 with concentrated HCl and then extracted several times with CH₂Cl₂. The aqueous phase was saturated with NaCl and back extracted (2×) with CH₂Cl₂. The combined organic phases were washed with brine, dried over anhydrous Na₂SO₄ and evaporated to give 17.7 g of the free acid as a viscous oil.

A mixture of the acid (17.7 g, 136 mmole) in dry benzene (200 ml) was treated with diazabicycloundecane (DBU) (20.4 ml, 136.2 mmole, 1 eq.) giving an exothermic reaction and a gel-like crystalline salt formed. The mixture was treated with ethyl iodide (10.9 ml, 1 eq.) and mechanically stirred under argon for 3 hours. Precipitated salts were removed by filtration, the filtrate washed once with a small amount of H₂O (50 ml) and brine then dried over anhydrous Na₂SO₄. Benzene was removed by distillation at atmospheric pressure and the yellow liquid remaining was vacuum distilled to give 6.46 g (35.1%) of desired title ester as a clear, pale yellow liquid with bp=65°–66° C. (5 mmHg). TLC (9:1) Hexane-acetone, $R_f$=0.55, PMA (pale blue) Mass Spec (M+H⁺=159⁺ observed).

B. 4-Methyl-2-(2-phenylhydrazono)pentanoic acid, ethyl ester

A solution of the Part A ethyl ester (5 g, 31.6 mmole) in dry CH₂Cl₂ (30 ml) was treated with phenylhydrazine (3.3 ml, 33.2 mmole, 1.05 eq) dropwise over 5 minutes and the resulting yellow mixture stirred under argon at room temperature over 4 Å sieves for 3 hours. The mixture was dried over anhydrous Na₂SO₄, filtered and evaporated in vacuo to give 8.105 g of an orange oil. The oil was purified by flash chromatography on LPS-1 silica gel eluting with Hexane-ethyl acetate. Product fractions were evaporated to give 6.8 g (86.7%) of pure title hydrazone and 848 mg (10.8%) of the geometrical isomer of the title hydrazone. Total yield=97.5%, TLC (9:1) Hexane-Acetone, $R_f$ geometrical isomers=0.42+0.64, UV+PMA, Mass Spec (M+H⁺=249⁺ observed).

C. 3-(1-Methylethyl)-1H-indole-2-carboxylic acid, ethyl ester

Gaseous HCl was bubbled (gas dispersion tube) into an absolute ethanolic (50 ml, over 3 Å sieves) solution of the Part B hydrazone (6.8 g, 27.4 mmole) for 30 minutes at room temperature. The exothermic reaction was characterized by color changes from yellow to red to deep green followed by precipitation of NH₄Cl. The suspension was stirred an additional 20 minutes under Drierite, then dumped into ice cold H₂O (50 ml). Ethanol was removed in vacuo and the residue partitioned between ethyl acetate and H₂O. The aqueous layer was extracted with ethyl acetate (2×), the combined organic phases washed with H₂O and brine, then dried over anhydrous MgSO₄ and evaporated to give 4.969 g of a green solid. The crude solid was dissolved in hot hexane, treated with Darco, filtered through packed Celite, concentrated to a 30–50 ml volume and the yellow solution allowed to crystallize. Precipitated crystals were collected by filtration, rinsed with cold hexane and dried to give 4.34 g (68.5%) of pure title indole as white needles with mp80°–81° C. and with consistent $^1$H NMR (CDCl₃, 270 MHz). TLC (9:1) Hexane-Acetone, $R_f$=0.42, UV+PMA. Note: $R_f$ of hydrazone and indole are identical but indole has bright purple fluorescence. (M+H+ =232+ observed).

Anal Calcd for $C_{14}H_{17}NO_2$: C, 72.70; H, 7.41, N, 6.06. Found: C, 72.67; H, 7.57; N, 6.00.

D. 1-(4-Fluorophenyl-3-(1-methylethyl)-1H-indole-2-carboxylic acid, ethyl ester

A solution of the Part C indole (3.937 g, 17 mmole) and 1-bromo-4-fluorobenzene 9.34 ml, 85 mmole, 5 eq) in dry DMF (15 ml) was treated with cuprous oxide (245 mg, 1.7 mmole, 0.1 eq) and refluxed under argon for 17 hours. Additional bromide (9.34 ml, 5 eq) and Cu₂O (245 mg, 0.1 eq) were added, refluxing continued for 6 hours, more Cu₂O added (730 mg, 5.1 mmole) and refluxing continued for 60 more hours. DMF and excess bromide were distilled off in vacuo and the orange residual oil taken up in ethyl acetate, filtered through packed Celite, washed with saturated NaHCO₃ and brine then dried over anhydrous Na₂SO₄ and evaporated to give 5.385 g (97.2%) of desired crude title indole as an orange oil.

TLC (9:1) Hexane-Acetone, $R_f$=0.29, UV+PMA.

E. 1-(4-Fluorophenyl)-3-(1-methylethyl)-1H-indole-2-methanol

To cold (0° C., ice bath) dry ether (24 ml) under argon was added solid LiALH₄ (907 mg, 23.9 mmole, 1.5 molar equivalent) followed by dropwise addition of the Part D indole ester (5.185 g, 15.9 mmole) in dry Et₂O (10 ml) over 10 minutes. The mixture was stirred for 1 hour at 0° C., then quenched at 0° C. by sequential dropwise addition of H₂O (910 μl), 15% NaOH (910 μl) and H₂O (2.73 ml). The suspension was filtered through anhydrous MgSO₄ over packed Celite and the filtrate evaporated to a clear, colorless oil. The oil gradually crystallized from hexane to give in 2 crops (3.771 g + 0.333 g) 4.10 g (90.9%) of pure title indole alcohol as white, granular crystals with mp=81°–82° C.

Mass Spec (M+H+ =284+ observed).

Anal Calcd for $C_{18}H_{18}NOF$: C, 76.30; H, 6.40; N, 4.94; F, 6.71. Found: C, 76.59; H, 6.31; N, 4.93; F, 6.49.

F. 1-(4-Fluorophenyl)-3-(1-methylethyl)-1H-indole-2-carboxaldehyde

A solution of Dess-Martin periodinane (6.46 g, 15.24 mmole) in dry CH₂Cl₂ (30 ml) was treated with dry t-butanol (4 Å sieves, 1.44 ml, 15.24 mmole, 1 eq.) and the mixture stirred under argon for 15 minutes at room temperature. A solution of the Part E indole alcohol (3.599 g, 12.7 mmole) in dry CH₂Cl₂ (13 ml) was added dropwise over 10 minutes and the pale yellow mixture stirred under argon at room temperature for 30 minutes. The reaction mixture was added to a solution of sodium thiosulfate (14.06 g, 89 mmole, 7 eq) in freshly prepared 1N NaHCO₃ (40 ml) and stirred for 10 minutes. The aqueous phase was drawn off, the organic phase washed with 1.0N NaHCO₃ (2X), H₂O and brine, then dried over anhydrous Na₂SO₄ and evaporated to give 3.877 g of a yellow oil. The crude oil was purified by flash chromatography on LPS-1 silica gel eluting with (40:1) Hexane-ether. Product fractions were evaporated to give 3.118 g (87.3%, crude yield) of crude product. One recrystallization from hot hexane gave 2.643 g (74%) of pure title aldehyde as white fluffy needles with mp=114°–116° C.

Mass Spec (M+H+ =282+ observed). TLC (7.3) Hex-Et₂O, $R_f$=0.51, UV+PMA.

Anal Calcd for $C_{18}N_{16}NOF$: C, 76.85; H, 5.73; N, 4.98; F, 6.75. Found: C, 76.87; H, 5.63; N, 4.89; F, 6.88.

G. 2-(2,2-Dibromoethenyl)-1-(4-fluorophenyl)-3-(1-methylethyl)-1H-indole

A −15° C. (salt/ice bath) solution of the Part F aldehyde (1.615 g, 5.74 mmole) and triphenylphosphine (4.52 g, 17.22 mmole, 3 eq) in dry CH₂Cl₂ (25 ml) was treated dropwise over 10 minutes with a CBr₄ (2.86 g, 8.61 mmole, 1.5 eq) solution in dry CH₂Cl₂ (10 ml) and the resulting dark orange red solution stirred under argon at −15° C. for 15 minutes. The mixture was quenched at −15° C. by the addition of saturated NaHCO₃, diluted with CH₂Cl₂, the organic phase washed with saturated NaHCO₃ and brine then dried over anhydrous Na₂SO₄ and evaporated to give 8.9 g of a red solid. The crude solid was purified by flash chromatography on LPS-1 silica gel eluting with (100:1) Hexane-ether. Product fractions were evaporated to give 2.017 g (80.6%) of pure title vinyl dibromide as pale yellow crystals with mp=123°–124° C.

TLC (9:1) Hexane-ether, $R_f$=0.67, UV and PMA.

Mass Spec (M&H+ =438+ observed).

Anal Calcd for $C_{19}H_{16}NFBr_2$: C, 52.20; H, 3.69; N, 3.20; F, 4.35; Br, 36.56. Found: C, 52.25; H, 3.69; N, 3.18; F, 4.24; Br, 36.59.

H. 2-Ethynyl-1-(4-fluorophenyl)-3-(1-methylethyl)-1H-indole

A −78° C. (CO₂/acetone) solution of dry THF (10 ml) was treated with a 1.6M n-butyl lithium solution in hexanes (5.5 ml, 8.8 mmole, 2.2 eq) and a solution of Part G vinyl dibromide (1.749 g, 4 mmole) in dry THF (10 ml) was added dropwise over 15 minutes under argon. The yellow mixture was stirred 20 minutes at −78° C., then quenched by the addition of sat'd. NH₄Cl (10 ml). After warming to room temperature, the mixture was diluted with ethyl acetate, the organic phase washed with sat'd. NH₄Cl and brine, then dried over anhydrous Na₂SO₄ and evaporated to give 1.216 g of a dark green-brown oil. The crude oil was purified by flash chromatography on Merck silica gel eluting with (300:1) Hexane-ether. Product fractions were evaporated to give 1.084 g (97.5) of title indole acetylene as a fluorescent green oil. $^1$H NMR (CDCl₃, 270, MHZ) indicated an (18:1) mixture of desired acetylene to undesired terminal olefin. TLC (50:1) Hex-Et₂O, $R_f$=0.55, UV and PMA.

J. (S)-4-[[2-[1-(4-Fluorophenyl)-1-(1-methylethyl)-1H-indol-2-yl]-ethynyl]methoxyphosphinyl]-3-[[(1,1-dimethylethyl)diphenylsilyl]-oxy]butanoic acid, methyl ester Phosphonochloridate was prepared from the Example 25 phosphonic mono methyl ester, dicylohexylamine salt by the following procedure. The free acid was regenerated from the dicyclohexylamine salt (4.32 g, 6.83 mmole, 1.75 eq) by partitioning between 1.0N HCl and ethyl acetate, washing the organic phase with 1.0 HCl (2X) and brine then drying over anydrous Na₂SO₄ and evaporating in vacuo to give the free acid (6.8 mmole) as a clear, viscous oil. The phosphonic acid, mono methyl ester (6.8 mmole) in dry CH₂Cl₂ (10 ml) was treated with distilled trimethylsilyl diethylamine (1.72 ml, 13.7 mmole, 2 eq) and the clear solution stirred under argon at room temp. for 1 hour. The mixture was evaporated in vacuo, chased with dry benzene (2×20 ml) and left on the vacuum pump for 15 minutes. The crude silylated acid in dry $CH_2Cl_2$ (10 ml) and dry DMF (1 drop) was cooled to 0° C. (ice bath) and treated dropwise over 5 minutes with distilled $(COCl)_2$ (655 μl, 7.5 mmole, 1.1 eq). The yellow mixture was stirred at 0° C. for 15 minutes and 45 minutes at room temp. under argon. The mixture was evaporated in vacuo, chased with benzene (2 x 20 m) and left on the vacuum pump for 15 minutes giving crude phosphonochloridate as a yellow, viscous oil.

A −78° C. solution ($CO_2$/acetone) of the Part H indole acetylene (1.084 g, 3.90 mmole, 1 eq) in dry THF (10 ml) was treated dropwise over 10 minutes with a 1.6M n-butyllithium in hexanes solution (2.44 ml, 3.9 mmole, 1 eq) and the purple suspension stirred under argon at −78° C. for 30 minutes. The anion was added dropwise via cannula over 30 minutes at −78° C. to a −78° C. solution of the phosphonochloridate in dry THF (10 ml). The dark brown mixture was stirred at −78° C. for 30 minutes then quenched by dropwise addition of sat'd $NH_4Cl$ (10 ml). The mixture was warmed to room temperature, partitioned between ethyl acetate, and sat'd $NH_4Cl$, washed with brine, dried over anhydrous $Na_2SO_4$ and evaporated to give 1.968 g (71.1%) of title acetylenic phosphinate as a light yellow oil.

TLC (7:3) Hexane-Acetone, $R_f$=0.25, UV and PMA. Mass Spec. ($M+H^+$ =710+ observed).

K. (S)-3-[[(1,1-Dimethylethyl)diphenylsilyl]oxy]-4-[[2-[1-(4-fluorophenyl)-3-(1-methylethyl)-1H-indol-2-yl]ethyl]methoxyphosphinyl]butanoic acid, methyl ester An argon purged solution of Part J acetylene (950 mg) in $CH_3OH$ (10 ml) was treated with 10% Pt/C (238 mg, 25% by weight) and the black suspension stirred under an $H_2$ atmosphere (1 atm) overnight. Catalyst was removed by filtration through a Millipore polycarbonate filter (0.4 μm) and prefilter and the filtrate evaporated in vacuo to a yellow oil. The crude oil was purified by flash chromatography on Merck silica gel eluting with (8:2) Hexane-ethyl acetate. Product fractions were evaporated to give 915 mg (86.7%) of pure title saturated phosphinate as a white foam.

TLC (4:1) EtOAc-Hexane, $R_f$=0.39, UV+PMA. Mass Spec ($M+H^+$ =714+ observed).

L. (S)-4-[[2-[1-(4-Fluorophenyl)-3-(1-methylethyl)-1H-indol-2-yl]ethyl]methoxyphosphinyl]-3-hydroxybutanoic acid, methyl ester A solution of the Part K silyl ether (915 mg, 1.22 mmole) in THF (10 ml) was treated successively with glacial acetic acid (280 μl, 4.88 mmole, 4 eq) and a 1.1M n-$C_4H_9NF$ solution in the THF (3.3 ml, 3.66 mmole, 3 eq) and the mixture stirred under argon at room temperature overnight. Ice cold $H_2O$ (8 ml) was added, the mixture extracted with ethyl acetate, the organic phase washed with 5% $KHSO_4$ (2×), saturated $NaHCO_3$ and brine then dried over anhydrous $Na_2SO_4$ and evaporated in vacuo to give 955 mg of a yellow oil. The crude oil was purified by flash chromatography on Merck silica gel eluting with (1:1) Hexane-Acetone. Product fractions were evaporated to give 521 mg (85.5%) of desired title alcohol as a pale yellow oil. TLC (3:2) Acetone-Hexane, $R_f$=0.21, UV+PMA. Mass Spec ($M+H^+$ =476+ observed).

M. (S)-4-[[2-[1-(4-Fluorophenyl)-3-(1-methylethyl)-1H-indol-2-yl]ethyl]hydroxyphosphinyl]-3-hydroxybutanoic acid, dilithium salt A solution of Part L diester (505 mg, 1.06 mmole) in dioxane (10 ml) was treated with excess 1.0N LiOH (3.7 ml, 3.7 mmole, 3.5 eq) and the mixture heated at 65° C. (oil bath) under argon for 1.5 hours. The mixture was diluted with $H_2O$, filtered, and evaporated in vacuo to a light yellow solid. The crude solid was suspended in a small amount of $H_2O$ and chromatographed on HP-20 resin (15 cm bed, 25 mm dia. column) eluting with $H_2O$ until neutral followed by $CH_3OH$. Product fractions were combined, evaporated, taken up in $H_2O$ (50 ml) and lyophilized to give 484 mg (95.4%) of desired title dilithium salt as a white lyophilate.

TLC (8:1:1) $CH_2Cl_2$-$CH_3OH$-acetic acid, $R_f$=0.39, UV+PMA.

Anal Calcd for $C_{23}H_{25}NO_5FP.2Li+1.03$ moles $H_2$(MW=477.91): C, 57.80; H, 5.72; N, 2.93; F, 3.97; P, 6.48. Found: C, 57.80; H, 6.01, N. 3.01; F, 3.93, P, 6.41.

EXAMPLE 30

(S)-4-[[2-[1-(4-Fluorophenyl)-3-(1-methylethyl)-1H-indol-2-yl]ethynyl]hydroxyphosphinyl]-3-hydroxybutanoic acid, dilithium salt A. (S)-4-[[2-[1-(4-Fluorophenyl)-3-(1-methylethyl)-1H-indol-2-yl]ethynyl]methoxyphosphinyl]-3-hydroxybutanoic acid, methyl ester A solution of the Example 30 Part J silyl ether (987 mg, 1.39 mmole) in dry THF (12 ml) was treated successively with glacial acetic acid (320 μl, 5.6 mmol, 4 eq) followed by a 1.1M n-$C_4H_9NF$ solution in THF (3.8 ml, 4.17 mmole, 3 eq) and the mixture stirred overnight under argon at room temperature. The mixture was diluted with ice cold $H_2O$ (10 ml) and extracted with ethyl acetate. The organic phase was washed with 5% $KHSO_4$ (3×), saturated $NaHCO_3$ and brine then dried over anhydrous $Na_2SO_4$ and evaporated to give 1.0 g of a yellow oil. TLC indicated formation of some mono acid which was converted back to the methyl ester by treatment with ethereal solution of $CH_2N_2$. Excess $CH_2N_2$ was quenched with glacial acetic acid and the mixture evaporated in vacuo to give 1.012 g of a brown oil. The crude oil was purified by flash chromatography on Merck silica gel eluting with (8:2) Hexane-Acetone (600 ml) followed by (1:1) Hexane-Acetone. Product fractions were evaporated to give 516 mg (78.7%) of free title alcohol as a light brown oil. TLC (9:1) $CH_2Cl_2$-$CH_3OH$, $R_f$=0.41, UV+PMA. Mass Spec ($M+H^+$ =472+ observed).

B. (S)-4-[[2-[1-(4-Fluorophenyl)-3-(1-methylethyl)-1H-indol-2-yl]ethynyl]hydroxyphosphinyl]-3-hydroxybutanoic acid, dilithium salt A solution of the Part A diester (516 mg, 1.09 mmole) in dioxane (10 ml) was treated with a 1.0 N LiOH solution (3.8 ml, 3.8 mmole, 3.5 eq) and the clear mixture heated and stirred at 60° C. (oil bath) for 1.5 hours under argon. The mixture was diluted with $H_2O$, filtered, evaporated in vacuo, the residual oil taken up in a minimum amount of $H_2O$ and chromatographed on HP-20 resin (15 cm bed, 25 mm column diameter) eluting with neat $H_2O$ (until neutral) followed by (1:1) $H_2O$—$CH_3OH$. Product fractions were evaporated in vacuo, taken up in $H_2O$ (50 ml), filtered and lyophilized to give 447 mg (82.3%) of desired title di-lithium salt as a white lyophilate. TLC (8:1:1) $CH_2Cl_2$-$CH_3OH$-acetic acid, $R_f$=0.39, UV+PMA.

Anal Calcd for $C_{23}H_{21}O_5PNF \cdot 2Li + 2.27$ moles $H_2O$ (MW 496.19): C, 55.67; H, 5.19; N, 2.82; F, 3.83; P, 6.24. Found: C, 55.69; H, 5.37; N, 2.82; , F, 3.85; P, 6.19.

EXAMPLE 31

(S)-4-[[[2,4-Dimethyl-6-[(4-fluorophenyl)methoxy]-phenyl]ethynyl]hydroxyphosphinyl]-3-hydroxybutanoic acid, dilithium salt

A. 1-(Methoxymethoxy)-3,5-dimethylbenzene

A THF solution (12 ml) of 3,5-dimethylphenol (10.42 g, 85.3 mmol) was added dropwise over 10 minutes to a suspension of NaH (85.3 mmol) (prewashed with pentane) in THF (150 ml) under an argon atmosphere and cooled to 0° C. After completion of the addition of the phenol, the reaction was stirred at 0° C. for 10 minutes warmed to room temperature and stirred for 20 minutes. To the alkoxide solution was added 42 ml of dry DMF followed by the slow addition of a 10 ml THF solution of bromomethyl methyl ether (11.19 g, 89.6 mmol). A white precipitate formed. After stirring for 2.5 hours at room temperature, the reaction was quenched by the slow addition of 25 ml of 1N NaOH. The THF was removed from the reaction mixture by rotary evaporation and the resulting solution was diluted with saturated NaCl solution and then extracted 3 times with ether. The combined ether extracts were dried over $Na_2SO_4$ and filtered. Solvent removal gave an orange oil. Purification by flash chromatography eluting with 5% ether/hexanes gave the title methoxymethyl (MOM) ether (12.0 g, 85% yield) as a clear oil.

TLC $R_f=0.45$ (15% $Et_2O$/Hexane, silica gel).

Mass Spec m/e 166 $(M^+)$, 165 $(M^+-H)^-$.

B. 2-(Methoxymethoxy)-4,6-dimethylbenzaldehyde

Tetramethylethylenediamine (7.70 g, 79.45 mmol) was added slowly to a solution of n-butyllithium (26.5 ml, of a 2.5M solution of hexane) in cyclohexane (30 ml) under argon atmosphere. The solution was cooled to 0° C. and the Part A MOM-ether (11.00 g, 66.21 mmol) was added dropwise over 20 minutes. After the addition was complete, the reaction was stirred at 0° C. for 30 minutes, warmed to room temperature and stirred for 10 minutes. The anion was then added via addition funnel to a 100 ml dry cyclohexane solution of DMF (5.81 g, 79.45 mmol) under argon atmosphere and at room temperature. The reaction was stirred at room temperature for 2 hours then quenched with methanol. The reaction solvent was removed on the rotavap, and the resulting orange oil was dissolved in a 1:1 ether/water mixture. The water layer was extracted 3 times with ether and the combined ether extracts were dried over $MgSO_4$. Filtration and solvent removal gave an orange oil. Purification of the oil by flash chromatography eluting with 20% ether/Hexane gave the desired title aldehyde (7.7 g, 60%) as a clear oil.

TLC $R_f=0.14$ (15% $Et_2O$/Hexane, silica gel).

Mass Spec. m/e 195 $(M+H)^+$, 179 $(M-CH_3)^+$, 163 $(M-OCH_3)^+$, 149 $(M-O_2CH_5)^+$.

C. 2-Hydroxy-4,6-dimethylbenzaldehyde

A 1M HCl solution (35.5 ml) was added to a dioxane (130 ml) solution of the Part B MOM-ether (6.89 g, 35.5 mmol) at room temperature. The reaction was warmed to a gentle reflux and stirred for 30 minutes. The reaction was cooled to room temperature, and the dioxane was removed via rotary evaporation. The resulting aqueous solution was diluted with $H_2O$ and extracted with ether. The aqueous layer was then saturated with NaCl and reextracted 2 times with ether. The ether extracts were combined and then dried over $MgSO_4$. Filtration and solvent removal gave a greenish solid which was purified by recrystallization from hexane (4.01 g, 75%). TLC $R_f=0.48$ (25% $Et_2O$/Hexane, silica gel) mp 46°-48° C. Mass Spec. m/e 151 $(M+H)^+$, 135 $(M-CH_3)^+$

D. 2-[(4-Fluorophenyl)methoxy]-4,6-dimethylbenzaldehyde

A solution of the Part C phenol (4.0 g, 26.7 mmol) and dry DMF (30 ml) was stirred under argon atmosphere. At room temperature, solid $K_2CO_3$ (4.43 g, 32 mmol) was added to the phenol solution and then warmed to 60° C. for 35 minutes. The resulting orange solution was cooled to room temperature and the p-fluorobenzyl bromide (5.55 g, 29.3 mmol) was added. The reaction was warmed to 60° C. and stirred for 2 hours. The reaction mixture was poured into 50 ml of ice water and this mixture was extracted several times with ether. The combined ether extracts were dried over $MgSO_4$ and filtered to give a yellow solid after solvent removal. Purification by flash chromatography eluting with 15% ether/Hexane gave the title benzyl ether (4.48 g, 60%) as a white solid.

TLC $R_f=0.34$ (25% $Et_2O$/Hexane, silica gel).

Mass Spec. m/e 259 $(M+H)^+$, 231 $(M-CHO)^+$, 109 $(M-C_7H_6F)^+$.

E. 1-(2,2-Dibromoethenyl)-2,4-dimethyl-6-(phenylmethoxy)benzene

A 170 ml dry $CH_2Cl_2$ solution of the Part D aldehyde (4.42 g, 17.13 mmol) under argon atmosphere was cooled in an ice-salt bath. To the cooled solution was added triphenyl phosphine (14.4 g, 55.0 mmol) and the mixture was stirred until all of the solid dissolved. A 50 ml $CH_2Cl_2$ solution of $CBr_4$ (8.52 g, 25.7 mmol) was added via an addition funnel over a 12 minute period. After the addition was complete, the orange reaction solution was stirred at 0° C. for 1 hour 15 minutes. The reaction was quenched with 60 ml of saturated aqueous $NaHCO_3$ solution and stirred vigorously. The aqueous layer was removed and extracted 2 times with $CH_2Cl_2$. The combined $CH_2Cl_2$ solutions were washed once with saturated aqueous $NaHCO_3$ solution, dried over $MgSO_4$ and filtered to give the title dibromide in the form of a tan solid (13 g). The title dibromide was purified by flash chromatography eluting with 2% ether/hexane providing 5.49 g, 77% yield of the title dibromide.

TLC $R_f=0.28$ (2% $Et_2O$/Hexane, silica gel).

Mass Spec. m/e 413 $(M+H)^+$, 333, 335 $(M-Br)^+$, 317 $(M-C_6H_4F)$, 109 $(M-C_{10}H_9OBr_2)^+$.

F. 1-Ethynyl-2-[(4-fluorophenyl)methoxy]-4,6-dimethylbenzene

A 70 ml THF solution of the Part G dibromide (5.48 g, 13.3 mmol) under argon atmosphere was cooled to −78° C. n-Butyllithium (10.6 ml of a 2.5M solution in hexane, 26.5 mmol) was added to the dibromide solution over 10 minutes. The reaction was stirred at −78° C. for 1 hour and then quenched at −78° C. with saturated aqueous $NH_4Cl$ solution. After the reaction was warmed to room temperature, it was diluted with 60 ml of $H_2O$, and the aqueous layer was extracted 2 times with ether. All of the organic layers were combined and dried over $MgSO_4$. Filtration and solvent removal gave 3.8 g of title benzyloxyacetylene in the form of a yellow solid. The title benzyloxyacetylene was purified by flash chromatography eluting with 3% ether/hexane. Title acetylene was obtained in 85% yield (2.76 g) as a white solid.

TLC R$_f$=0.17 (2% Et$_2$O/Hexane, silica gel).

Mass Spec. m/e 255 (M+H)+, 159 (M-C$_6$H$_4$F)+, 109 (M-C$_{10}$H$_9$O)+.

G. (S)-4-[[[2,4-Dimethyl-6-[(4-fluorophenyl)methoxy]phenyl]ethynyl]hydroxyphosphinyl]-3-(t-butyldiphenylsilyloxy)butanoic acid, dilithium salt A 40 ml THF solution of the Part F acetylene (2.76 g, 11 mmol) under argon atmosphere was cooled to −78° C. At −78° C., n-butyllithium (4.4 ml of a 2.5M solution in hexane) was added over 8 minutes. The reaction was stirred at −78° C. for 40 minutes.

The Example 25 phosphonylchloridate (17.4 mmol), in 60 ml of THF and under argon atmosphere was cooled to −78° C. The above generated acetylenic anion was then added over 8 minutes. After stirring for 1 hour at −78° C., the reaction was quenched at −78° C. with saturated aqueous NH$_4$Cl solution and allowed to warm to room temperature. The aqueous layer was diluted with H$_2$O and extracted 2 times with ether. The THF was removed from the THF reaction layer, and the resulting orange oil was taken up in ether. All of the ether solutions were combined and washed once with saturated aqueous NaHCO$_3$ solution and once with saturated NaCl solution. The organic layer was dried over MgSO$_4$ and filtered leaving 9.4 g of title acetylenic phosphinic acid in the form of an orange gum after solvent removal. The title acetylenic phosphinic acid was purified by flash chromatography by eluting with a 5/1/4 hexane/toluene/ethyl acetate mixture. Title acetylenic phosphinic acid (4.23 g) was obtained in 56% yield as a clear gum.

TLC R$_f$=0.28 (5/1/4 Hexane/toluene/ethylacetate silia gel).

Mass Spec. m/e 609 (M+H-C$_6$H$_5$)+, 255 (C$_{14}$H$_{19}$SiO)+.

H. (S)-4-[[[2,4-Dimethyl-6-[(4-fluorophenyl)methoxy]phenyl]ethynyl]methoxyphosphinyl]-3-hydroxybutanoic acid, methyl ester Part G acetylenic phosphinate (0.455 g, 0.66 mmol) was stirred in 10 ml of THF under argon atmosphere. Acetic acid (0.16 g, 2.66 mmol) was added at room temperature followed by the dropwise addition over 5 minutes of n-C$_4$H$_9$NF (1.8 ml of a 1.1M THF solution, 2.0 mmol). After stirring for 24 hours at room temperature, the reaction was quenched by the addition of 30 ml of ice-water. The aqueous layer was removed and extracted 2 times with ethyl acetate. The THF was removed from the reaction organic layer, and the resulting oil was dissolved in ethyl acetate and combined with the extracts of the aqueous layer. This ethyl acetate solution was washed 2 times with saturated aqueous NaHCO$_3$ solution and once with saturated NaCl solution and then dried over Na$_2$SO$_4$. Filtration and solvent removal gave 0.40 g of title hydroxy acetylenic phosphinate in the form of an oil. The title hydroxy acetylenic phosphinate was purified by flash chromatography eluting with 100% ethyl acetate. Title hydroxy acetylenic phosphinate was obtained in 79% yield. TLC R$_f$=0.56 (7:3 acetone/Hexane, silica gel). Mass Spec. m/e 449 (M+H)+, 431 (M-OH)+, 417 (M-OCH$_3$)+

J. (S)-4-[[[2,4-Dimethyl-6-[(4-fluorophenyl)methoxy]phenyl]ethynyl]hydroxyphosphinyl]-3-hydroxybutanoic acid, dilithium salt To a 6.0 ml dioxane solution of Part H acetylenic phoshinate (0.191 g, 0.43 mmol) at room temperature was added 1.4 ml of 1N LiOH solution. The reaction was warmed to 55° C. and stirred for 2 hours. The reaction was cooled to room temperature and evaporated to dryness to obtain the title compound. The title compound was purified on a 130 mm×30 mm diameter column of HP-20 eluting first with 100 ml of H$_2$O then with a 1:1 MeOH/H$_2$O mixture. Title compound was obtained in 91% yield (0.170 g) as a white lyophilate. TLC R$_f$=0.37 (7:2:1 nPrOH/NH$_4$OH/H$_2$O, silica gel).

Mass Spec (FAB) m/e 421 (M+H)+, 427 (M+Li)+, 433 (M+2Li)+

Anal Calcd for C$_{21}$H$_{20}$O$_6$FPLi$_2$.1.4 H$_2$O: C, 55.09; H, 4.98; F, 4.15; P, 6.78. Found: C, 55.13; H, 5.25; F, 4.08; P, 6.91.

EXAMPLE 32

(S)-4-[[[2,4-Dimethyl-6-[(4-fluorophenyl)methoxy]phenyl]ethyl]hydroxyphosphinyl]-3-hydroxy-butanoic acid, dilithium salt A. (S)-3-[[(1,1-Dimethylethyl)diphenylsilyl]oxy]-4-[[2-[2-[(4-fluorophenyl)methoxy]-4,6-dimethylphenyl]ethyl]-methoxyphosphinyl]butanoic acid, methyl ester The Example 31 of Part G acetylenic phosphinate (1.34 g, 1.95 mmole) was stirred in methanol (12 ml) and PtO$_2$ (0.040 g) was added Hydrogen gas was bubbled through the methanol solution for 10 minutes and then a H$_2$(g) atmosphere was maintained with a balloon. After 5 hours, 15 minutes at room temperature, the reaction was complete and argon was bubbled through the reaction solution. The reaction was filtered through a celite pad in a fine sintered glass funnel, and the catalyst was washed with methanol. Solvent was removed from the filtrate to give 1.4 g of a title saturated phosphinate in the form of a clear gum. The title saturated phosphinate was purified by flash chromatography eluting with 60% ethyl acetate/hexane and then rechromatographing material from slightly impure fractions with 6/2.5/1.5 hexane/acetone/toluene. Title saturated phosphinate was obtained in 86% yield (1.17 g).

TLC R$_f$=0.45 (80% ethyl acetate/hexane, silica gel). Mass Spec. m/e 691 (M+H)+, 659 (M-OCH$_3$)+, 635 (M-C$_9$H$_{19}$OSi)+

B. (S)-4-[[[2,4-Dimethyl-6-[(4-fluorophenyl)methoxy]phenyl]ethyl]methoxyphosphinyl]-3-hydroxybutanoic acid, methyl ester The Part A phosphinate (1.16 g, 1.68 mmol) was stirred in THF (25 ml) under argon atmosphere and at room temp. Glacial acetic acid (0.40 ml) was added dropwise to the phosphinate solution, and then n-C$_4$N$_9$NF (4.6 ml of a 1.1M THF solution) was added dropwise over 5 minutes. The reaction was stirred at room temperature overnight (18 hours) and then quenched with 50 ml of ice-water. After stirring for several minutes, sat'd NaCl solution was added, and the layers were separated. The organic layer was rotary evaporated to remove the THF, and the resulting residue was dissolved in ethyl acetate. The aqueous layer was extracted 2 times with ethyl acetate, and all of the ethyl acetate solutions were combined and washed 2 times with sat'd aqueous NaHCO$_3$ solution and once with sat'd NaCl solution, then dried over Na$_2$SO$_4$. Filtration and solvent removal gave 1.13 g of title hydroxy phosphinate in the form of a clear oil. The title hydroxy phosphinate was purified by flash chromatography eluting with 100% ethyl acetate and gave the title hydroxy phosphinate as a clear oil in 83% yield.

TLC R$_f$=0.27 (6:4 Acetone/hexane, silica, gel).

Mass Spec. m/e 453 (M+H)+, 343 (M-C$_7$H$_6$F)+.

C. (S)-4-[[[2,4-Dimethyl-6-[(4-fluorophenyl)methoxy]phenyl]ethyl]-hydroxyphosphinyl]-3-hydroxybutanoic acid, dilithium salt The Part B phosphinate (0.594 g, 1.3 mmole) was stirred in 19 ml of dioxane at room temperature 1N LiOH (4.0 ml) was added with stirring at room temp. and the reaction was warmed to 55° C. After 20 minutes at 55° C., a white thick precipitate formed and 4.0 ml of dioxane was added, and the resulting suspension was stirred at 55° C. After 2.5 at 55° C., 3 ml of $H_2O$ were added and the reaction mixture became clear. After 3 hours at 55° C., the reaction was cooled to room temperature, and the dioxane and water were removed by rotary evaporation leaving title diacid in the form of white solid which was placed under high vacuum for 15 minutes. The title diacid was purified by HP-20 chromatography eluting first with 100 ml of $H_2O$ followed by elution with 1:1 MeOH/$H_2O$ solution. Title diacid was obtained as a white lyophilate in 67% yield. TLC $R_f=0.36$ (7:2:1 n-propanol/$NH_4OH$/$H_2O$, silica gel).

Mass Spec. m/e (FAB), 425 $(M+H)^+$, 437 $(M+H+2 Li)^+$.

Anal Calcd for $C_{21}H_{24}O_6FP$. 1.15 $H_2O$: C, 55.19; H, 5.80; F, 4.16; P, 6.78. Found: C, 55.19; H, 5.80; F, 4.29; P. 6.83.

EXAMPLE 33

(S)-4-[[2-[[1,1'-Biphenyl]-2-yl]ethynyl]hydroxy-phosphinyl]-3-hydroxybutanoic acid, dilithium salt A. (S)-4-[[2-[[1,1'-Biphenyl]-2-yl]ethynyl]hydroxyphosphinyl]-3-hydroxy butanoic acid, methyl ester The Example 9, Part D phosphinate (1.61 mmole, 0.985 g) was stirred under argon, at room temperature in 19.6 ml of dry THF. This solution was treated dropwise with glacial acetic acid (6.44 mmol, 0.386 g, 0.368 ml), followed by dropwise addition (8 min) of n-$C_4H_9NF$ (4.84 mmol, 4.40 ml of a 1.1M solution in THF). After stirring at room temp. for 18 hours, the reaction mixture was quenched with 30 ml of ice water. The aqueous layer was extracted with ethyl acetate. The organic extracts were combined, washed 2 times with saturated aqueous $NaHCO_3$, once with brine, dried over $MgSO_4$, filtered and evaporated. The product was isolated via flash chromatography (50 mm column, 6" Merck silica gel, 40% acetone/hexane eluent, 2"/min flow rate). Product fractions were concentrated, azeotroped with toluene, and evaporated in vacuo to afford (0.369 g, 0.991 mmol, 62% yield) of the title alcohol as a viscous yellow oil. (Also obtained 0.098 g, 0.263 mmol, 16% of slightly impure product) TLC: Silica gel $R_f=0.35$ (50% acetone/hexane).

Mass Spec. CI m/e 373 $(M+H)^+$.

B. (S)-4-[[2-[[1,1'-Biphenyl]-2-yl]ethynyl]hydroxyphosphinyl]-3-hydroxybutanoic acid, dilithium salt The Part A diester (0.739 mmol, 0.275 g) was stirred under argon in 7.57 ml of dioxane and treated with 1M LiOH (2.22 mmol, 2.22 ml). This cloudy reaction mixture was heated in a 55° C. oil bath for 45 minutes. The mixture was cooled to room temp. The solvents were removed via rotary evaporation and high vacuum (90 minutes). The resulting yellow foam was dissolved in 4 ml of distilled $H_2O$ and eluted through an HP-20 chromatography column (2.5 cm × 19 cm), collecting 10 ml fractions every 1.4 minutes. The column was eluted with $H_2O$ until 15 fractions were collected (no longer basic) and then elution with 45/55 methanol/$H_2O$ afforded (after lyophilization (2×) and high vacuum pump over $P_2O_5$ for 16 hours) 0.231 g (0.649 mmol, 88% yield) of the title diacid as a white lyophilate TLC: Silica gel $R_f=0.55$ (7:2:1 n-propanol/$NH_4OH$/$H_2O$)

Mass Spec. (FAB m/e 345 $(M+H)^+$, 351 $(M+Li)^+$, 357 $(M+2 Li)^+$.

Anal Calcd for $C_{18}H_{15}O_5PLi_2+1.42$ moles $H_2O$ MW=381.75: C, 56.63; H, 4.71; P, 8.07. Found: C, 56.62; H, 4.70; P, 8.07.

EXAMPLE 34

(S)-4-[[2-[3,5-Dimethyl[1,1'-biphenyl]-2-yl]ethyl]hydroxyphosphinyl]-3-hydroxybutanoic acid, dilithium salt A. 3,5-Dimethyl[1,1'-biphenyl]-2-carboxaldehyde Phenylmagnesium bromide was obtained from Aldrich (Cat. No. 17, 156-5) as a 3M solution in ethyl ether.

A mixture of Example 1, Part B dipalladium complex (4.48 mmol, 3.35 g) and triphenylphosphine (35.85 mmol, 9.40 g) was stirred at room temperature under argon in 67.2 ml of anhydrous toluene for 30 minutes. This reaction mixture was cooled to 0° C. and phenylmagnesium bromide Grignard reagent (Aldrich) (35.84 mmol, 11.95 ml of a 3M solution in ether was added portionwise (quickly). The resulting mixture was stirred at room temp. for 1.5 hours. The mixture was then cooled at 0° and treated in one portion with 22.4 ml of 6.0N HCl, and stirred at room temp. for 1 hour. The aqueous layer was separated and extracted with ether. The organic extracts were combined, filtered through Celite (washed with ether) and the filtrate washed with brine, azeotroped with toluene, and evaporated in vacuo to afford a yellow solid. Attempted product purification via (2×) flash chromatography (95 mm diameter column, 6" Merck silica gel, 100% Hexane→3% ether/Hexane eluent, 2"/min flow rate afforded 2.95 g of a yellow solid (1.88 g, 8.96 mmol 100% yield of the title aldehyde and 1.06 g of triphenylphosphine). This compound mixture was used directly in the preparation of the Part B compound. TLC: Silica gel, $R_f=0.30$ (5% ether/Hexane) Mass Spec. (CI) m/e 211 $(M+H)^+$, 263 $(M_2+H)^+$, 473 $(M_1+M_2+H)^+ M_1=$Part A aldehyde, $M_2=$triphenylphosphine.

B. 2-(2,2-Dibromoethenyl)-3,5-dimethyl[1,1'-biphenyl]

A mixture of Part A aldehyde (8.96 mmol, "1.88 g") and triphenylphosphine (26.4 mmol, 6.90 g) was stirred in 88 ml of dry $CH_2CH_2$ at −5° C. for 10 minutes. This reaction mixture was maintained at −5° C. as a solution of $CBr_4$ (13.2 mmol, 4.38 g) in 32 ml of dry $CH_2Cl_2$ was added dropwise (20 min). The resulting reaction mixture was stirred at −5° C. for 1 hour and became progressively darker orange with time. The mixture was then quenched with 85 ml of saturated aqueous $NaHCO_3$. The aqueous layer was extracted with $CH_2Cl_2$. The organic extracts were combined, washed once with saturated $NaHCO_3$ (aqueous), and once with brine, dried over $MgSO_4$, filtered and evaporated in vacuo. The product was purified by preabsorbing the crude product in $CH_2Cl_2$ onto 25 g of Merck silica gel and applying this to a flash chromatography column (50 mm diameter, 6" Merck silica gel, 4% $CH_2Cl_2$/Hexane eluent, 2"/min flow rate), affording 2.18 g (5.96 mmol, 68% yield) of the title vinyl dibromide as a viscous colorless oil. TLC: Silica gel $R_f=0.37$ (4% $CH_2Cl_2$, Hexane) Mass Spec. (CI) m/e 365/367/369 $(M+H)^+$.

C. 3,5-Dimethyl-2-(1-propynyl)[1,1'-biphenyl]

A solution of the Part B vinyl dibromide (5.74 mmol, 2.10 g) in 29.11 ml of anhydrous THF was stirred under argon and cooled to −78° C. This solution was treated dropwise (20 minutes) with n-butyllithium (11.47 mmol, 4.59 ml of a 2.5M solution in hexanes) resulting in a deep purple solution. After stirring at −78° C. for an additional hour, the reaction mixture was quenched at −78° C. with 25 ml of saturated $NH_4Cl$ (aqueous), warmed to room temp. diluted with $H_2O$, and the aqueous layer extracted with 1:1 ether/hexane. The organic extracts were combined, dried over $MgSO_4$, filtered, and evaporated in vacuo. The product was isolated via flash chromatography (50 mm column, 6″ Merck silica gel, 1% ether/hexane eluent) to afford 1.08 g (5.23 mmol, 91% yield) of the title acetylene as a colorless oil which became blue when stored 16 hours at −20° C. TLC: Silica gel $R_f$=0.32 (100% hexane).

Mass spec. (CI) m/e 207 (M+H)+.

D. (S)-3-[[(1,1-Dimethylethyl)diphenylsilyl]oxy]-4-[[2-[3,5-dimethyl[1,1'-biphenyl]-2-yl]methoxyphosphinyl]butanoic acid, methyl ester A solution of the Part C acetylene (4.61 mmol, 0.950 g) in 27.3 ml of dry THF was stirred under argon and cooled to −78° C. n-Butyllithium (4.61 mmol, 1.84 ml of a 2.5M solution in hexanes) was added dropwise (20 min) resulting in a dark purple/brown solution. The reaction mixture was stirred at −78° C. for 1 hour (reaction mixture became a slurry) warmed to 0° C. and stirred 15 min. (reaction mixture returned to a dark purple homogeneous solution) and finally recooled to −40° C. (remained homogeneous). This acetylenic anion solution at −40° C. was then added dropwise (25 min) to a solution of the Example 1, Part F phosphinyl chloridate (8.12 mmol) in 27.3 ml of dry THF which had been cooled to −78° C. as it was stirred under argon. After the addition of the acetylenic anion solution to the phosphinyl chloridate solution was complete, the dark orange reaction mixture was stirred at −78° C. for 1 hour and then quenched at −78° C. with 50 ml of saturated $NH_4Cl$, warmed to room temp. and diluted with $H_2O$. The aqueous layer was extracted with ether. The organic extracts were combined, washed once with saturated $NaHCO_3$ (aqueous), once with brine, dried over $MgSO_4$, filtered and evaporated in vacuo. The product was isolated via flash chromatography (50 mm diameter column, 6″ Merck silica gel, 50% ethyl acetate/hexane eluent, 2″/min flow rate) to afford 0.609 g (0.945 mmol, 21%) of the title phosphinate as a golden orange oil.

TLC: Silica gel $R_f$=0.32 (50% ethyl acetate/Hexane).

Mass Spec. (CI) m/e 639 (M+H)+.

E. (S)-4-[[2-[3,5-Dimethyl[1,1'-biphenyl]-2-yl]ethyl]hydroxyphosphinyl]-3-(t-butyldiphenylsilyloxy)-butanoic acid, dilithium salt Argon was bubbled through a methanol (13 ml) solution of the Part D acetylenic phosphinate (1.37 mmol, 0.876 g) for 10 minutes. 10% Pd/C (0.315 g) was added and the reaction mixture was subjected to Parr hydrogenation at 40 psi. After shaking for 24 hours, the reaction mixture was filtered through a Celite pad in a sintered glass funnel. The Celite was washed with methanol and the filtrate was evaporated in vacuo to afford 0.896 g of a yellow oil which was purified via flash chromatography (50 mm diameter column, 6″ Merck silica gel, 40%→50% ethyl acetate/Hexane eluent) to afford 0.680 g (1.06 mmol, 77% yield) of the title saturated phosphinate as a pale yellow foam. Stripping the flash column by eluting with methanol produced an additional 0.087 g of slightly impure product. TLC: $R_f$=0.27, Silica gel (50% acetone/hexane).

Mass Spec. (CI) m/e 643 (M+H)+.

F. (S)-4-[[2-[3,5-Dimethyl[1,1'-biphenyl]-2-yl]ethyl]hydroxyphosphinyl]-3-hydroxybutanoic acid, dilithium salt The Part E phosphinate (1.03 mmol, 0.66 g) was stirred under argon at room temp. in 12.65 ml of dry THF. This solution was treated dropwise with glacial acetic acid (4.12 mmol, 0.247 g, 0.236 ml), followed by dropwise addition of n-$C_4N_9NF$ (3.09 mmol, 2.81 ml of a 1.1M solution of THF). After stirring at room temperature for 16 hours, the reaction mixture was quenched with 25 ml of ice water. The aqueous layer was extracted with ethyl acetate. The organic extracts were combined, washed 2 times with saturated aqueous $NaHCO_3$, once with brine, dried over $MgSO_4$, filtered and evaporated in vacuo. The product was purified via flash chromatography (40 mm column, 6″ Merck silica gel, 50% acetone/Hexane eluent) to afford 0.363 g (0.898 mmole, 87% yield) of the title alcohol as a white solid. TLC: Silica gel, $R_f$=0.30 (50% acetone/Hexane).

Mass Spec (FAB) m/e 405 (M+H)+.

G. (S)-4-[[2-[3,5-Dimethyl[1,1'-biphenyl]-2-yl]ethyl]hydroxyphosphinyl]-3-hydroxybutanoic acid, dilithium salt The Part F diester (0.878 mmol, 0.355 g) was stirred under argon in 9 ml of dioxane and treated with 1M LiOH (2.63 mmol, 2.63 ml). This homogeneous reaction mixture was heated in a 55° C. oil bath. After stirring at 55° C. for 10 minutes, the reaction mixture became a white suspension. An additional 9 ml of dioxane and 2 ml of $H_2O$ were added, and the suspension was heated at 55° C. for 45 minutes, then cooled to room temperature. The solvents were removed by rotary evaporation and high vacuum (1 hour). The resulting white solid was eluted through an HP-20 chromatography column (18 cm×2.5 cm). 10 ml fractions were collected every 1.4 minutes. The column was eluted with $H_2O$ until 15 fractions were collected and then elution with 1:1 methanol/$H_2O$ afforded [after lyophilization (3×) and high vacuum pump over $P_2O_5$ (4×8 hours)] 0.289 g (0.744 mmol, 85% yield) of the title diacid as a white lyophilate.

TLC: silica gel, $R_f$=0.56 (7:2:1, n-propanol/$NH_4OH$/$H_2O$).

Anal Calcd for $C_{20}H_{23}O_5PLi_2$+0.34 moles of $H_2O$ M.W.=394.31: C, 60.92; H, 6.05. Found: C, 60.95; H, 6.18.

Mass Spec. (FAB) m/e 389 (M+H)+.

EXAMPLE 35

(S)-4-[[2-[4'-Fluoro-3,5-dimethyl[1,1'-biphenyl]-2-yl]ethyl]hydroxyphosphinyl]-3-hydroxybutanoic acid, dilithium salt A. Bromo(4-fluorophenyl)magnesium Magnesium metal turnings (44.35 mmol, 1.08 g) were flame dried, then stirred under argon in 40 ml of anhydrous ether. With vigorous stirring, 1-bromo-4-fluorobenzene (40.3 mmol) was added dropwise to the magnesium. The reaction was initiated in an ultrasound device and then the halide was added dropwise at a rate sufficient to maintain reflux. After addition of the bromide was complete, the reaction mixture was stirred at room temperature for 20 minutes, then heated to reflux and finally cooled to room temperature. This procedure yielded a golden orange transparent Grignard solution containing 40.32 mmol of title Grignard as a 0.91M solution in ether.

B. 4'-Fluoro-3,5-dimethyl[1,1'-biphenyl]-2-carboxaldehyde

Reference: Stockker et al, *Journal of Med. Chem.*, 29, 170–181 (1986).

A mixture of the Example 26 Part B palladium complex (4.35 mmol, 3.20 g) and triphenylphosphine (40.32 mmol, 10.58 g) was stirred at room temperature under argon in 67.2 ml of anhydrous toluene for 30 minutes. Then this reaction mixture was cooled to 0° C. and the Part A Grignard reagent (40.32 mmol, 44.43 ml) was added portionwise (quickly). The resulting mixture was stirred at room temperature for 1.5 hours. The mixture was then cooled to 0° C. and treated in one portion with 21.75 ml of 6.0N HCl and stirred at room temperature for 1 hour. The aqueous layer was separated, extracted with ether and the combined organic extracts filtered through Celite. The celite was washed with ether and the combined filtrates were washed with brine, azeotroped 2 times with toluene, and stripped, to afford an orange-yellow solid. Attempts at isolating the title aldehyde by flash chromatography using a 95 mm diameter column, 6" Merck silica gel, hexane eluent followed by 3% Et$_2$O/hexane eluent, 2"/min flow rate, resulted in a final reaction product mixture of the desired title aldehyde and triphenylphosphine as a pale yellow solid (3.70 g-assume this contains 8.7 mmol, 1.99 g, 100% yield of title aldehyde+1.70 g of triphenylphosphine). This compound mixture was used directly in the preparation of Part C compound.

TLC: silica gel R$_f$=0.25 (5% ether/Hexane).
$^1$H NMR: (270 MHz, CDCl$_3$).

C. 2-(2,2-Dibromoethenyl)-4'-fluoro-3,5-dimethyl[1,1'-biphenyl]

A mixture of the Part B aldehyde (8.70 mmol, "1.99 g") and triphenylphosphine (26.1 mmol, 6.85 g) was stirred in 87 ml of dry CH$_2$Cl$_2$ at −5° C. for 10 minutes. This reaction mixture was maintained at −5° C. as a solution of CBr$_4$ (13.05 mmol, 4.33 g) in 43 ml of dry CH$_2$Cl$_2$ was added dropwise over 25 minutes. The resulting reaction mixture was stirred at −5° C. for 1 hour producing a dark orange solution which was then quenched with 80 ml of saturated aqueous NaHCO$_3$. The aqueous layer was extracted 4 times with CH$_2$Cl$_2$. The combined organic extracts were washed once with saturated aqueous NaHCO$_3$ and once with brine. The CH$_2$Cl$_2$ extract was dried over MgSO$_4$, filtered and the filtrate combined with 25 g of Merck silica gel. The solvent was evaporated and the preabsorbed product was purified via flash chromatography (50 mm diameter column, 6" Merck silica gel, 4% CH$_2$Cl$_2$/Hexane eluent, 2"/min flow rate) to afford 2.32 g (6.04 mmol, 69% yield) of the title vinyl dibromide as a colorless oil.

TLC: silica gel, R$_f$=0.43 (5% CH$_2$Cl$_2$/Hexane).
Mass Spec. (CI) m/e 383/385/387 (M+H)$^+$.

D. 4'-Fluoro-3,5-dimethyl-2-(1-propynyl)-[1,1'-biphenyl]

A solution of the Part C vinyl dibromide (5.99 mmol, 2.30 g) in 33 ml of anhydrous THF was stirred under argon and cooled to −78° C. This solution was treated dropwise (25 minutes) with n-butyllithium (11.97 mmol, 4.79 ml of a 2.5M solution in hexanes), resulting in a deep purple solution. After stirring at −78° C. for an additional hour, the reaction mixture was quenched at −78° C. with 25 ml saturated aqueous NH$_4$Cl, warmed to room temperature and diluted with 25 ml of H$_2$O. The aqueous layer was extracted 4 times with 1:1 ether/hexane. The organic extracts were combined, dried over MgSO$_4$, filtered and evaporated. The product was isolated via flash chromatography (50 mm column, 6" Merck silica gel, 0.50% ether/hexane eluent, 2"/mm flow rate) to afford 1.25 g (5.57 mmol, 93% yield) of the title acetylene, as a colorless oil which turns blue when stored at 20° C.

TLC: silica gel, R$_f$=0.25 (100% hexane).
Mass Spec. (CI) m/e 225 (M+H)$^+$.

E. (S)-4-[[2-[4'-Fluoro-3,5-dimethyl[1,1'-biphenyl]-2-yl]ethynyl]hydroxyphosphinyl]-3-(t-butyldiphenylsilyloxy)butanoic acid, methyl ester A solution of the Part D acetylene (5.24 mmol, 1.18 g) in 28 ml of dry THF was stirred under argon and cooled to −78° C. n-Butyllithium (5.24 mmol, 2.10 ml of a 2.5M solution in hexane) was added dropwise (25 min) as the reaction mixture became dark purple/brown. The reaction mixture was then stirred at −78° C. for 1 hour, warmed to 0° C., stirred for 10 minutes, and recooled to −78° C. This acetylenic anion solution at −78° C. was then added dropwise (20 minutes) to a solution of the Example 1 Part F phosphinyl chloridate (8.32 mmol) in 28 ml of anhydrous THF which had been cooled to −78° C. as it was stirred under argon. After the addition was complete, the dark orange reaction mixture was stirred at −78° C. for 1 hour and then quenched at −78° C. with saturated aqueous NH$_4$Cl, warmed to room temperature and diluted with H$_2$O. The aqueous layer was extracted 4 times with ether. The organic extracts were combined and washed once with saturated aqueous NaHCO$_3$, once with brine, dried over MgSO$_4$, filtered, and evaporated. The product was isolated via flash chromatography (50 mm diameter column, 6" Merck silica gel, 40% ethyl acetate/hexane eluent, 2"/min flow rate) to afford 0.730 g (1.11 mmol, 21% yield) of the title acetylenic phosphinate as a green viscous oil.

TLC: silica gel R$_f$=0.36 (50% ethyl acetate/hexane).
Mass Spec (CI) m/e 657 (M+H)$^+$.

F. (S)-4-[[2-[4'-Fluoro-3,5-dimethyl[1,1'-biphenyl]-2-yl]ethyl]hydroxyphosphinyl]-3-(t-butyldiphenylsilyloxy)butanoic acid, methyl ester Argon was bubbled through a methanol 9.9 ml solution of the Part E acetylenic phosphinate (1.04 mmol, 0.685 g) for 10 minutes. 10% Pd/C 0.239 g was added and the reaction mixture was subjected to Parr hydrogenation at 40 psi. After shaking for 24 hours, the reaction mixture was filtered through a Celite pad in a sintered glass funnel, the Celite was washed with methanol, and the filtrate was evaporated to afford 0.638 g of a green oil. The product was purified via flash chromatography (40 mm diameter column, 6" Merck silica gel, 45% ethyl acetate/hexane eluent, 2"/min flow rate) to afford 0.530 g (0.802 mmol 77% yield) of the title saturated phosphinate as a pale yellow foam. Also obtained 0.09 g (0.136 mmol, 13%) of slightly impure product.

TLC: silica gel. R$_f$=0.30 (50% ethyl acetate/hexane).
Mass spec. (CI) m/e 661 (M+H)$^+$.

G. (S)-4-[[2-[4'-Fluoro-3,5-dimethyl[1,1'-biphenyl]-2-yl]ethyl]methoxyphosphinyl]-3-hydroxybutanoic acid, methyl ester The Part F phosphinate (0.794 mmol, 0.525 g) was stirred under argon at room temperature in 9.74 ml of anhydrous THF. This solution was treated dropwise with glacial acetic acid (3.18 mmol, 0.191 g, 0.182 ml), followed by dropwise addition of n-C$_4$H$_9$NF (2.38 mmol, 2.17 ml of a 1.1M solution in THF). After stirring at room temperature for 16 hours, the reaction mixture was quenched with 15 ml of ice water. The aqueous layer was extracted 3 times with ethyl acetate. The organic extracts were combined, washed 2 times with saturated aqueous NaHCO$_3$, 1 time with brine, dried over MgSO$_4$, filtered and evaporated. The product was purified via flash chromatography (40 mm diameter column, 6" Merck silica gel, 50% acetone/hexane eluent, 2"/min flow rate). Product fractions were concentrated and azeotroped to dryness with toluene to afford 0.281 g (0.665 mmol, 84% yield) of the title alcohol as a white solid. An impurity visible by 270 MHz $^1$H NMR was not separable/visible in various TLC systems.

TLC: Silica gel, R$_f$=0.31 (50% acetone/hexane) $^1$H NMR: (270 MHz, CDCl$_3$).

Mass Spec. (CI) m/e 423 (M+H)$^+$.

H. (S)-4-[[2-[4'-Fluoro-3,5-dimethyl[1,1'-biphenyl]-2-yl]ethyl]hydroxyphosphinyl]-3-hydroxybutanoic acid, dilithium salt The Part G diester (0.473 mmol, 0.20 g) was stirred under argon in dioxane (4.84 ml) and treated with 1M LiOH (1.42 mmol, 1.42 ml). This homogeneous reaction mixture was heated in a 55° C. oil bath. After stirring at 55° C. for 10 minutes, the reaction mixture became a white suspension. The mixture was maintained at 55° C. for an additional 45 minutes, then cooled to room temperature. The solvents were removed by rotary evaporation and high vacuum (1 hour). The resulting white foam was dissolved in 4 ml of distilled H$_2$O and eluted through an HP-20 chromatography column (16 cm×2.5 cm). 10 ml fractions were collected every 1.4 minutes. The column was eluted with H$_2$ until 15 fractions were collected and then elution with 1:1 methanol/H$_2$O afforded (after lyophilization (2×) and high vacuum pump over P$_2$O$_5$ for 11 hours) 0.158 g (0.389 mmol, 82% yield) of the title diacid as a white lyophilate.

TLC: silica gel R$_f$=0.59 (7:2:1, n-propanol/N-H$_4$OH/H$_2$O).

Mass Spec (FAB) m/e 395 (M+H)$^+$.

Anal Calcd for C$_{20}$H$_{22}$FO$_5$PLi$_2$+0.39 moles H$_2$O: MW=413.25: C, 58.12; H, 5.56. Found: C, 58.14; H, 6.09.

EXAMPLE 36

(S)-4-[[2-[5-(4-Fluorophenyl)-3-(1-methylethyl)-1-phenyl-1H-pyrazol-4-yl]ethynyl]methoxyphosphinyl]-3-hydroxybutanoic acid, methyl ester A. 4-Fluoro-β-oxobenzenepropanoic acid, ethyl ester 60% Sodium hydride in mineral oil (17.4 g, 0.43 mmole) was washed twice with dry hexane, dried in vacuo then treated with neat diethylcarbonate (44.3 ml, 0.36 mmole) followed by the dropwise addition of p-fluoro-acetophenone (22 ml, 0.18 mole). After about 10% of the ketone had been added, 4 drops of ethanol was added to initiate refluxing and the remainder of the p-fluoro-acetophenone was added over 1.0 hour at a rate that maintained reflux conditions. The yellow solid which formed was slurried in dry ether (250 ml) and refluxed for an additional 3.0 hours under argon.

The reaction mixture was cooled in an ice bath, diluted with ether (200 ml) and treated slowly with water (1.3 liters) until all the solids dissolved. The aqueous phase was separated from the organic phase, acidified with 12N HCl (32 ml) to pH 1.0 and extracted with ether (2×500 ml). The combined organic extracts were washed with brine (200 ml), dried (anhydrous MgSO$_4$), filtered and evaporated to dryness. The crude product (44.0 g) was distilled under reduced pressure (3.5 mm) to give title compound as a homogeneous oil (24.88 g, 65.8%).

TLC: R$_f$0.46 (Silica gel; CH$_2$Cl$_2$:hexane-4:1).

B. 4-Fluoro-α-(2-methyl-1-oxopropyl)-β-oxobenzenepropanoic acid, ethyl ester

60% Sodium hydride in mineral oil (10.3 g, 0.26 mmole) was washed twice with dry hexane, dried in vacuo, suspended in dry tetrahydrofuran (245 ml) and cooled down to 0° (ice water bath) under argon. The suspension was treated dropwise with Part A compound (24.5 g, 0.12 mole) over a 20-minute period, warmed to room temperature and stirred for another 30 minutes. The reaction mixture was cooled down to 0° (ice water bath), treated dropwise with isobutyryl chloride (18.62 g, 0.17 mole), warmed to room temperature and stirred for 3.0 hours. The mixture was cooled down to 0° (ice water bath), quenched with water (200 ml) to produce a homogeneous solution and evaporated on a rotary evaporator to remove most of the tetrahydrofuran. The aqueous phase was acidified with 10% HCl (37 ml) to pH 1.0 and extracted with ether (3×100 ml). The combined organic extracts were washed with brine (50 ml), dried (anhydrous MgSO$_4$), filtered and evaporated to dryness, to give an oil (36.85 g) which was a mixture of starting material and two other products.

TLC: R$_f$ 0.46, 0.33, 0.20 (Silica gel; CH$_2$Cl$_2$:hexane-4:1, UV).

C. 5-(4-Fluorophenyl)-3-(1-methylethyl)-1-phenyl-1H-pyrazole-4-carboxylic acid, ethyl ester Crude Part B compound (36.85 g, ≈0.12 mole) was dissolved in glacial acetic acid (151 ml), treated portionwise with 97% phenylhydrazine (18.1 ml, 0.18 mole) under nitrogen and stirred at room temperature for 19 hours. The reaction mixture was poured into water (350 ml), extracted with ether (3×100 ml) and the combined organic extracts were washed with saturated NaHCO$_3$ until the aqueous layer was basic, brine (500 ml), dried (anhydrous MgSO$_4$), filtered and evaporated to dryness.

The dark orange oil was evaporated once from petroleum ether (300 ml) to obtain a yellow solid. This crude product was triturated with petroleum ether (100 ml) to give a crude product (15.3 g) which in turn was chromatographed on a silica gel column (LPS-1), eluting the column with CH$_2$Cl$_2$:hexane (2:1) to give 11.53 g of pure product. The mother liquor (26.4 g) on chromatography on a silica gel column (LPS-1) and trituration of the compound obtained gave an additional 7.12 g of desired product (total yield: 18.65 g or 44.1%). A small amount of title compound was recrystallized from Et$_2$O:hexane to give homogeneous solid, m.p. 92°-93° C.

TLC: R$_f$0.35 (Silica gel: CH$_2$Cl$_2$:hexane-4:1).

Anal Calcd: C, 71.57; H, 6.01; N, 7.95; F, 5.39. Found: C, 71.62; H, 5.99; N, 7.91; F, 5.54.

D. 5-(4-Fluorophenyl)-3-(1-methylethyl)-1-phenyl-1H-pyrazole-4-methanol

A solution of Part C compound (11.53 g, 32.7 mmole) in anhydrous ether (142 ml) was added dropwise over a period of 1.5 hours to a cooled (0°; ice-salt bath) suspension of lithium aluminum hydride (3.67 g, 96.7 mmoles) in anhydrous ether (70 ml) under argon. The greenish suspension was allowed to warm up to room temperature over a period of 1.5 hours, cooled back down to 0° (ice-salt bath) and quenched by the dropwise addition of water (20 ml) until gas evolution ceased. The thick slurry was diluted with ether (100 ml) and filtered, washing the precipitates well with ethyl acetate (3×150 ml). The combined organic extracts were washed with brine (50 ml), dried (anhydrous MgSO$_4$), filtered and evaporated to dryness to give a cream-colored solid (10.3 g, 100% crude yield). 100 mg of the crude product was recrystallized from Et$_2$O:hexane to give title compound (58 mg) as white crystals, m.p. 138°-140°.

TLC: R$_f$ 0.01 (Silica gel; CH$_2$Cl$_2$).

Anal Calcd: C, 73.52; H, 6.17; F, 6.12; N, 9.03. Found: C, 73.16; H, 6.15; F, 6.12; N, 8.90.

MS (M+H)$^+$ = 311.

E. 5-(4-Fluorophenyl)-3-(1-methylethyl)-1-phenyl-1H-pyrazole-4-carboxaldehyde

A solution of crude Part D compound (10.2 g, ~32.7 mmole) in dry dichloromethane (85 ml) was added rapidly to a solution of pyridinium chlorochromate (21.23 g, 98.4 mmoles) in dry dichloromethane (125 ml) and the resulting dark brown solution was stirred at room temperature under nitrogen for 4.0 hours. The mixture was diluted with ether (750 ml) and stirred for 10 minutes. The supernatant solution was decanted from the tar-like residue and the residue was triturated with dichloromethane (2×100 ml). The dichloromethane extracts were diluted with ether (750 ml) and the combined extracts filtered through a silica gel pad. The clear filtrate was evaporated to dryness to give a crude product (10.0 g).

The crude product was chromatographed on a silica gel column (Baker, 60-200 mesh, 400 ml), eluting the column with CH$_2$Cl$_2$:hexane (4:1) to give title compound as a solid (9.6 g, 95.2%). An analytical sample (72 mg, m.p. 108°-110°) was obtained by recrystallizing 100 mg from hexane.

TLC: R$_f$ 0.58 (silica gel; CH$_2$Cl$_2$; UV).

Anal Calcd: C, 74.01; H, 5.56; N, 9.09; F, 6.16 Found: C, 74.10; H, 5.52; N, 9.12; F, 6.29

MS (M+H)$^+$ = 309.

F. 4-(2,2-Dibromoethenyl)-5-(4-fluorophenyl)-3-(1-methylethyl)-1-phenyl-1H-pyrazole A mixture of Part E compound (2.0 g, 6.48 mmole) and triphenylphosphine (5.10 g, 19.2 mmoles) in dry dichloromethane (30 ml) was cooled down to −5° to −10° (ice-salt bath) under argon and treated dropwise over a period of 5 minutes with a solution of carbon tetrabromide (3.22 g, 9.61 mmoles) in dry dichloromethane (10 ml). The reaction mixture was stirred at 15°-20° for 15 minutes then poured onto saturated NaHCO$_3$ (10 ml) and extracted with dichloromethane (3×50 ml). The combined organic extracts were washed with saturated NaHCO$_3$ (10 ml), brine (25 ml), dried (anhydrous MgSO$_4$), filtered and evaporated to dryness.

The crude product mixture (9.33 g) was chromatographed on a silica gel column (LPS-1) eluting the column with CH$_2$Cl$_2$:hexane mixtures (1:9, 1:1; 4:1) to give title compound as a solid (2.75 g, 91.6%). Recrystallization of a small sample of title compound gave white crystals, m.p. 88°-90°.

TLC: R$_f$ 0.85 (silica gel; CH$_2$Cl$_2$:hexane-4:1).

Anal Calcd: C, 51.75; H, 3.69; N, 6.04; F, 4.09; Br, 34.43. Found: C, 51.96; H, 3.51; N, 5.97; F, 4.22; Br, 34.77.

MS (M+H)$^+$ = 465.

G. 4-Ethynyl-5-(4-fluorophenyl)-3-(1-methylethyl)-1-phenyl-1H-pyrazole

A solution of Part F compound (2.64 g, 5.67 mmole) in dry tetrahydrofuran (10.5 ml) was cooled down to −78° (dry ice-acetone) under argon and treated dropwise with 1.6M n-BuLi/hexane (7.16 ml, 11.37 mmoles). The resulting suspension was stirred at −78° for 1 hour and 20 minutes, quenched by the dropwise addition of 25% NH$_4$Cl (10 ml) and allowed to warm up to room temperature. The reaction mixture was extracted with ether (3×50 ml) and the combined organic extracts were washed with brine (20 ml), dried (anhydrous MgSO$_4$), filtered and evaporated to dryness to give title compound as a light brown solid (1.79 g).

The crude product was chromatographed on a silica gel column, eluting the column with Et$_2$O:hexane (5:95) to give title compound as a light gold-colored solid (1.08 g, 97.4%). Recrystallization of a small sample from hexane gave white, fluffy crystals, m.p. 106°-108°.

TLC: R$_f$ 0.70 (silica gel; Et$_2$O:hexane-1:9; developed 2×).

Anal Calcd: C, 78.92; H, 5.63; N, 9.21; F, 6.24. Found: C, 79.22; H, 5.53; N, 9.28; F, 6.23.

MS (M+H)$^+$ = 305.

H. (S)-3-[[(1,1-Dimethylethyl)diphenylsilyl]oxy]-4-[[[5-(4-fluorophenyl)-3-(1-methylethyl)-1-phenyl-1H-pyrazol-4-yl]ethynyl]methoxyphosphinyl]butanoic acid, methyl ester A mixture of the crude Example 1 Part F phosphonic monomethyl ester (2.77 g, 5.55 mmoles) and trimethylsilyldiethylamine (2.1 ml, 11.05 mmoles) in dry dichloromethane (10 ml) was stirred at room temperature under argon for 1.0 hour. The mixture was evaporated to dryness, azeotroped with dry benzene (20 ml) and dried in vacuo (pump) for 15 minutes. The viscous oil was re-dissolved in dry dichloromethane (10 ml), treated with one drop of DMF, cooled down to −10° (ice-salt bath) and treated dropwise with oxalyl chloride (530 μl, 6.08 mmoles). Vigorous gas evolution was observed and the dark yellow solution was stirred at −10° for 15 minutes, then at room temperature for 1.0 hour. The reaction mixture was evaporated to dryness, azeotroped with benzene (20 ml) and dried in vacuo.

A solution of Part G compound (1.12 g, 3.67 mmoles) in dry tetrahydrofuran (9.0 ml) was cooled down to −78° (dry ice-acetone) under argon and treated with 1.6M n-BuLi/hexane (2.3 ml, 3.67 mmoles) and stirred at −78° for 30 minutes. The above phosphochloridate was dissolved in dry tetrahydrofuran (6.5 ml), cooled down to −78° (dry ice-acetone) under argon and treated dropwise by cannula with the solution of the acetylene anion, both solutions being kept at −78° throughout the addition. The reaction mixture was stirred at −78° for 30 minutes, quenched by the dropwise addition of 25% NH$_4$Cl (6.0 ml) then warmed to room temperature. The mixture was extracted with ether (3×100 ml) and the combined organic extracts were washed with 25% NH$_4$Cl (10 ml), brine (25 ml), dried (anhydrous MgSO$_4$), filtered and evaporated to dryness.

The crude product mixture (~4.2 g) was chromatographed on a silica gel column, eluting the column with hexane:acetone (9:1) to give title compound as a light brown oil (1.54 g, 57.0%).

TLC: R$_f$ 0.33 (silica gel; hexane:acetone-7:3).

I. (S)-4-[[2-[5-(4-Fluorophenyl)-3-(1-methylethyl)-1-phenyl-1H-pyrazol-4-yl]ethynyl]methoxyphosphinyl]-3-hydroxybutanoic acid, methyl ester A solution of Part H compound (593.9 mg; 0.81 mmole) in dry tetrahydrofuran (8.0 ml) was treated successively with glacial acetic acid (190 μl, 3.24 mmoles) and 1M Bu$_4$NF (2.54 ml, 2.54 mmoles) and stirred overnight at room temperature under argon. The reaction mixture was cooled down to 0° C. (ice water bath), treated with 5% KHSO$_4$ (8.5 ml) and extracted with ethyl acetate (3×75 ml). The combined organic extracts were washed with 5% KHSO$_4$ (10 ml), brine (20 ml), dried (anhydrous MgSO$_4$), filtered and evaporated to dryness.

The crude product was dissolved in a mixture of ether (14 ml) and dry tetrahydrofuran (10 ml), cooled down to 0° (ice-salt bath), treated with excess diazomethane in ether and stirred at 0° for 3.0 hours. The reaction mixture was quenched by the dropwise addition of glacial acetic acid, evaporated to dryness and dried in vacuo. The crude product was chromatographed on a silica gel column eluting the column with acetone:hexane (1:2) to give title compound as a semisolid (325.6 mg, 80.6% yield).

EXAMPLE 37

(S)-4-[[2-[5-(4-Fluorophenyl)-3-(1-methylethyl)-1-phenyl-1H-pyrazol-4-yl]ethynyl]hydroxyphosphinyl]-3-hydroxybutanoic acid, dilithium salt A solution of Example 36 compound (325 mg, 0.65 mmole) in dioxane (7.7 ml) was treated with 1N LiOH (2.25 ml, 2.25 mmole) stirred at 55° (oil bath) under nitrogen for 1.5 hours then at room temperature for 16 hours. The reaction mixture was evaporated to dryness and dried in vacuo. The crude product was chromatographed on an HP-20 column (1"×5"), eluting the column with steam-distilled water (400 ml) and 50% aqueous CH$_3$OH (500 ml). The desired fractions were combined, evaporated to dryness and dried in vacuo. The solid product was dissolved in steam-distilled water and lyophilized to give title product as a fluffy solid lyophilate (317.1 mg, 96.4%).

TLC: R$_f$ 0.33 (silica gel; i-PrOH:NH$_4$OH:H$_2$O-8:1:1).

Anal Calcd for C$_{24}$H$_{22}$FN$_2$O$_5$P.2 Li.1.3 H$_2$O (Eff. Mol. Wt.=505.861): C, 56.99, H, 4.90;, N, 5.54; F, 3.75; P, 6.12. Found: C, 56.98; H, 5.17; N, 5.46; F, 3.90; P, 6.26.

H$^1$-NMR Spectrum (400 MHz, CD$_3$OD): δ1.40 (d, 6H, J=7 Hz), 1.81-1.98 (m, 2H), 2.35 (dd, 1H, J=9, 15 Hz), 2.48 (dd, 1H, J=4, 15 Hz), 3.35 (septet, 1H, J=7 Hz), 4.42 (m, 1H), 7.08-7.41 (m, 9H).

IR(KBr): 2173 cm$^{-1}$ (C≡C).

EXAMPLE 38

(E)-4-[[2-[5-(4-Fluorophenyl)-3-(1-methylethyl)-1-phenyl-1H-pyrazol-4-yl]ethenyl]methoxyphosphinyl]-3-hydroxybutanoic acid, methyl ester A. [2-[5-(4-Fluorophenyl)-3-(1-methylethyl)-1-phenyl-1H-pyrazol-4-yl]2-hydroxyethyl]phosphonic acid, dimethyl ester A −78° C. (CO$_2$/acetone) solution of dimethyl methylphosphonate (2.81 ml, 25.9 mmole) in dry THF (50 ml) was treated with a 1.6M n-BuLi solution in hexanes (15.2 ml, 24.3 mmole) dropwise over 15 minutes and the white suspension (after ∼15 minutes) stirred under argon at −78° C. for one hour. Example 36 Part E pyrazole aldehyde (5.0 g, 16.2 mmole) in dry THF (15 ml) was added dropwise over 10 minutes and the yellow mixture stirred at −78° C. for 30 minutes. The mixture was quenched with saturated NH$_4$Cl (20 ml) and allowed to warm to room temperature. The mixture was partitioned between H$_2$O and EtOAc, the organic phase washed with brine, dried over anhydrous Na$_2$SO$_4$ and evaporated to give 7.158 g of crude title β-hydroxyphosphonate as a yellow foam. A small sample was crystallized from hexanes to give pure title compound as white crystals with m.p.=126°-128° C.

TLC (1:1) hexane-acetone, R$_f$=0.27.

Mass Spec. (M+H$^+$=433+ observed).

Anal Calcd for C$_{22}$H$_{26}$O$_4$N$_2$PF: C, 61.10; H, 6.06; N, 6.48; F, 4.39; P, 7.16. Found: C, 60.95; H, 6.06; N, 6.41; F, 4.22; P, 7.27.

$^1$H NMR (CDCl$_3$): δ1.42 (6H, d), 1.94-2.40 (2H, m), 3.29 (1H, septet), 3.62+3.63 (2 doublets, J$_{H-P}$=11.1 Hz), 3.91 (1H, s), 5.11 (1H, bm), 6.90-7.30 (9H, m) ppm.

$^{13}$C NMR (CDCl$_3$): δ22.6, 26.5, 32.8 (J$_{C-P}$=136.3 Hz), 52.1 (J$_{C-P}$=5.7 Hz), 60.8, 115.0, 115.4, 119.3, 119.5, 124.7, 126.3, 126.6, 128.5, 132.2, 132.3, 139.4, 139.5, 156.7, 164.5 (J$_{C-P}$=265 Hz) ppm.

B. (E)-[2-[5-(4-Fluorophenyl)-3-(1-methylethyl)-1-phenyl-1H-pyrazol-4-yl]ethenyl]phosphonic acid, dimethyl ester A solution of the crude Part A hydroxy phosphonate (7.158 g) in dry benzene (40 ml) was treated with pTsOH.H$_2$O (304 mg, 1.6 mmole) and the mixture refluxed through a Dean Stark trap containing 4 Å sieves for 2 hours under argon. The mixture was cooled, diluted with EtOAc, the organic phase washed with saturated NaHCO$_3$ (2×) and brine then dried over anhydrous Na$_2$SO$_4$ and evaporated in vacuo to give 6.893 g of a yellow oil. The crude oil was triturated with hexane to give 5.692 g of nearly pure vinyl phosphonate as off-white crystals. One recrystallization from EtOAc-hexane gave in 2 crops 5.655 g (84.2%, total yield from aldehyde) of pure title trans vinyl phosphonate as white needles with m.p. 143°-144° C.

TLC (1:1) hexane-acetone, R$_f$=0.40.

Mass. Spec. (M+H$^+$=415+ observed).

Anal Calcd for C$_{22}$H$_{24}$O$_3$PN$_2$F: C, 63.76; H, 5.84; N, 6.76; F, 4.58, P, 7.47. Found: C, 63.99; H, 5.95; N, 6.76; F, 4.54; P, 7.31.

$^1$H NMR (CDCl$_3$): δ1.42 (6H, d), 3.27 (1H, septet), 3.70 (6H, d, J$_{H-P}$=11.0 Hz), 5.67 (1H, dd, J$_{HH}$=18.4 Hz, J$_{HP}$=18.5 Hz) 7.02-7.30 (9H, m), 7.34 (1H, dd, J$_{HH}$=18 Hz, J$_{HP}$=24.3 Hz) ppm.

$^{13}$C NMR (CDCl$_3$): δ21.8, 27.1, 52.1 (J$_{C-P}$=5.7 Hz), 110.4 (J$_{C-P}$=193.1 Hz), 114.7 (J$_{C-P}$=24.6 Hz), 115.9, 116.2, 122.2, 124.9, 125.5, 127.3, 128.8, 132.0, 139.2, 140.2 (J$_{C-P}$=7.6 Hz), 142.1, 158.0, 163.4 (J$_{C-F}$=249.8 Hz) ppm.

C. (E)-[2-[5-(4-Fluorophenyl)-3-(1-methylethyl)-1-phenyl-1H-pyrazol-4-yl]ethenyl]phosphonic acid, monomethyl ester A solution of the Part B dimethylphosphonate (2.0 g, 4.83 mmole) in dioxane (15 ml) was treated with 1.0N LiOH (7.3 ml) and the mixture refluxed for one hour under argon. The mixture was cooled to room temperature, acidified to pH 1 with 1.0N HCl, extracted with EtOAc (2×), the organic phase washed with 1.0N HCl and brine then dried over anhydrous Na$_2$SO$_4$ and evaporated in vacuo to give crude mono acid which slowly crystallized on standing from hexane. Crystals were collected by filtration and dried in vacuo to give 1.918 (99%) of title mono acid as a white crystalline solid with m.p. 168°-170° C. An analytical sample was prepared by recrystallization from EtOAc-hexane.

TLC (8:1:1) CH$_2$Cl$_2$-CH$_3$OH-HOAc, R$_f$=0.40.

Mass Spec (M+H$^+$=401+ observed).

Anal Calcd for C$_{21}$H$_{22}$O$_3$N$_2$PF: C, 62.99; H, 5.54; N, 7.00; F, 4.75; P. 7.74. Found: C, 62.95; H, 5.57; N, 6.87; F, 4.58; P, 7.58.

$^1$H NMR (CDCl$_3$): δ1.40 (6H, d), 3.26 (1H, septet), 3.65 (3H, d, J$_{H-P}$=11.6 Hz), 5.74 (1H, dd, J$_{H-H}$=17.9 Hz, J$_{H-P}$=19.5 Hz) 7.00-7.36 (10H, m), 8.65 (1H, bs) ppm.

13C NMR (CDCl3): δ21.8, 27.0, 51.8 ($J_{C-P}$=6.3 Hz), 111.7 ($J_{C-P}$=198.7 Hz), 114.6 ($J_{C-P}$=24.6 Hz), 115.8, 116.2, 124.9, 125.4, 127.3, 128.7, 131.9, 132.1, 138.8 ($J_{C-P}$=7.6 Hz), 139.2, 142.0, 157.9, 162.9 ($J_{C-F}$=249.8 Hz) ppm.

D. (E)-4-[[2-[5-(4-Fluorophenyl)-3-(1-methylethyl)-1-phenyl-1H-pyrazol-4-yl]ethenyl]methoxyphosphinyl]-3-oxobutanoic acid, methyl ester The dianion of methyl acetoacetate was prepared according to the method described in Example 26 using the following quantities: methyl acetoacetate (815 µl, 7.53 mmole) 60% NaH dispersion in oil (324 mg, 8.11 mmole), 1.6M N-BuLi in hexanes (4.3 ml, 6.95 mmole), THF (15 ml).

A solution of phosphonic monomethyl ester (2.317 g, 5.79 mmole) and trimethylsilyldiethylamine (TMSDEA) (1.45 ml, 11.6 mmole) in CH2Cl2 (15 ml) was stirred at room temperature for 1 hour. The mixture was evaporated to dryness, chased with benzene (20 ml) and dried in vacuo. The residue was taken up in dry CH2Cl2 (15 ml) treated with (COCl)2 (555 µl, 6.37 mmole) and DMF (1 drop), and stirred at room temperature for 1 hour. The mixture was evaporated to dryness, chased with benzene (20 ml) and dried in vacuo.

A −78° C. (CO2/acetone) solution of the above phosphonochloridate in dry THF (10 ml) was transferred dropwise via cannula over 20 minutes to a −78° C. solution of the methyl acetoacetate dianion in dry THF (15 ml). The brown mixture was stirred for 30 minutes at −78° C. then quenched by dropwise addition of saturated NH4Cl (10 ml) and allowed to warm to room temperature. The mixture was partitioned between H2O and EtOAc, the aqueous phase back-extracted with EtOAc, the combined organic phases washed with saturated NaHCO3 and brine then dried over anhydrous Na2SO4 and evaporated in vacuo to give 3.080 g of an orange foam. The crude product was purified by flash chromatography on Merck silica gel eluting with (5:3:2) hexane-acetone-toluene.

The product fractions were combined and evaporated to give 1.247 g (43.2%) of the desired title β-ketophosphonate as a pale yellow oil.

TLC (4:4:2) acetone-hexane-toluene, $R_f$=0.29.

Mass Spec (M+H+ =499+ observed).

1H NMR (CDCl3): δ1.42 and 1.43 (6H, 2 doublets), 3.24 (2H, m), 3.27 (1H, septet), 3.63 (2H, m), 3.66 and 3.67 (3H, 2 doublets, $J_{H-P}$=11.6 Hz), 3.72 (3H, s), 5.72 (1H, dd, $J_{HH}$=18.7 Hz, $J_{HP}$=24.3 Hz), 7.08-7.30 (9H, m), 7.37 (1H, dd, $J_{HH}$=18.0 Hz, $J_{HP}$=22.7 Hz) ppm.

13C NMR (CDCl3): δ21.8, 27.1, 46.1 ($J_{CP}$=84.1 Hz), 50.0, 51.2 ($J_{C-P}$=5.9 Hz), 52.3, 112.6 ($J_{CP}$=135.0 Hz), 114.5 ($J_{CP}$=23.5 Hz), 116.0, 116.3, 124.9, 125.4, 127.4, 128.8, 132.0, 132.1, 139.1, 141.4 ($J_{CP}$=5.9 Hz), 142.5, 158.2, 163.1 ($J_{CF}$=250.4 Hz), 167.1, 194.9, 195.0 ppm.

E.(E)-4-[[2-[5-(4-Fluorophenyl)-3-(1-methylethyl)-1-phenyl-1H-pyrazol-4-yl]ethenyl]methoxyphosphinyl]-3-hydroxybutanoic acid, methyl ester A −15° (salt/ice bath) solution of the Part D ketone (1.304 g, 2.62 mmole) in absolute EtOH (15 ml) was treated with NaBH4 (100 mg, 2.62 mmole) and the mixture stirred for 15 minutes under argon at −15° C. The reaction was quenched by addition of reagent acetone (0.3 ml) followed by CC-4 silica gel (600 mg), allowed to warm to room temperature, diluted with EtOAc, filtered and evaporated in vacuo to give 1.46 g of a yellow foam. The crude product was purified by flash chromatography on Merck silica gel eluting with (85:15) EtOAc-acetone. Product fractions were evaporated to give 388 mg of pure title alcohol as a white foam plus 228 mg of slightly impure product. Total yield was 616 mg (47%).

TLC (7:3) EtOAc-acetone, $R_f$=0.31.

Mass Spec. (M+H+ =501+ observed).

1H NMR (CDCl3): δ1.42 (6H, d), 2.00 (2H, m), 2.60 (2H, d), 3.27 (1H, d), 3.64 (3H, d, $J_{HP}$=11.1 Hz), 3.69 (3H, s), 3.93 and 4.02 (1H, 2 doublets), 4.42 (1H, 2 broad singlets), 5.72 (1H, dd, $J_{HH}$=18.0 Hz, $J_{H-P}$23.2 Hz), 7.04-7.47 (10H, m) ppm.

13C NMR (CDCl3): δ21.8, 27.1, 35.7 and 36.5 ($J_{CP}$=100.3 Hz), 42.0, 42.2, 50.8 ($J_{CP}$=5.7 Hz), 51.6, 63.4 ($J_{CP}$=20.8 Hz), 114.2 and 114.4 ($J_{CP}$=128.7 Hz), 114.6 ($J_{CP}$=20.8 Hz), 115.9, 116.3, 124.9, 125.4, 127.3, 128.8, 131.9, 132.1, 139.1, 140.1 and 140.6 ($J_{CP}$=5.7 Hz), 142.1, 158.0, 163.0 ($J_{CF}$=251.6 Hz), 171.2, 171.9 ppm.

EXAMPLE 39

(S)-4-[[2-[5-(4-Fluorophenyl)-3-(1-methylethyl)-1-phenyl-1H-pyrazol-4-yl]ethenyl]hydroxyphosphinyl]-3-hydroxybutanoic acid, dilithium salt A solution of the Example 38 diester (487 mg, 0.973 mmole) in dioxane (10 ml) was treated with 1.0N LiOH (3.4 ml, 3.4 mmole) and the resulting mixture was heated and stirred at 70° C. for 30 minutes. The mixture was cooled, diluted with H2O, filtered and evaporated in vacuo to an off-white solid. The crude product was dissolved in a minimum amount of H2O and chromatographed on HP-20 resin (15 cm bed, 25 mm diameter column) eluting with H2O followed by (1:1) CH3OH-H2O. Product fractions were evaporated in vacuo, dissolved in 75 ml of H2O, filtered and lyophilized to give 429 mg (87.3%) of pure title dilithium salt as a fluffy, white lyophilate.

TLC (8:1:1) CH2Cl2-CH3OH-HOAc, $R_f$=0.14.

Anal Calcd for C24H24O5N2PF Li2+1.16 moles H2O (MW 505.233): C, 57.05; H, 5.25; N, 5.55; F, 3.76; P, 6.13. Found: C, 57.05; N, 5.18; N, 5.75; F, 3.89; P, 6.47.

1H NMR (400 MHz, CD3OD): δ1.39 (6H, doublet), 1.71 (2H, m), 2.35 (2H, m), 3.36 (1H, septet), 4.24 (1H, m), 6.00 (1H, dd, $J_{HH}$=17.6 Hz, $J_{HP}$=19.4 Hz), 7.07-7.35 (10H, m).

EXAMPLE 40

(E)-4-[[2-[5-(4-Fluorophenyl)-3-(1-methylethyl)-1-phenyl-1H-pyrazol-4-yl]ethyl]methoxyphosphinyl]-3-hydroxybutanoic acid, methyl ester A. (S)-3-[[(1,1-Dimethylethyl)diphenylsilyl]oxy]-4-[[2-[5-(4-fluorophenyl)-3-(1-methylethyl)-1-phenyl-1H-pyrazol-4-yl]ethyl]methoxyphosphinyl]butanoic acid, methyl ester A solution of Example 36 Part H compound (912.0 mg, 1.24 mmole) in dry methanol (50 ml) was treated with 10% Pd/C and hydrogenated at 50 psi on a Parr hydrogenator overnight. The suspension was filtered through Celite and the filtrate was evaporated to dryness and dried in vacuo to give title compound as a homogeneous oil (908.3 mg, 99.1%).

TLC: $R_f$0.23 (silica gel; Hexane:Acetone-7:3).

B. (S)-4-[[2-[5-(4-Fluorophenyl)-3-(1-methylethyl)-1-phenyl-1H-pyrazol-4-yl]ethyl]methoxyphosphinyl]-3-hydroxybutanoic acid, methyl ester A solution of Part A compound (908.3 mg, 1.23 mmole) in dry tetrahydrofuran (12 ml) was stirred under argon at room temperature and treated successively with glacial acetic acid (0.29 ml, 4.94 mmoles) and 1.0M Bu4NF/hexane (3.89 ml, 3.89 mmoles). The reaction mixture was stirred at room temperature for 20 hours, diluted with ice water (25 ml) and extracted with ethyl acetate (3×100 ml). The combined organic extracts were washed with saturated NaHCO$_3$ (15 ml), brine (25 ml), dried (anhydrous MgSO$_4$), filtered and evaporated to dryness.

The crude product mixture (1.0 g) was chromatographed on a silica gel column (LPS-1; 1"×9.5"), eluting the column with EtOAc:Hexane mixtures (4:1; 9:1), EtOAc and acetone to give title compound as an oil (529.1 mg, 85.6% yield). TLC: R$_f$ 0.17 (silica gel; EtOAc:hexane-4:1).

EXAMPLE 41

(S)-4-[[2-[5-(4-Fluorophenyl)-3-(1-methylethyl)-1-phenyl-1H-pyrazol-4-yl]ethyl]hydroxyphosphinyl]-3-hydroxybutanoic acid, dilithium salt A solution of Example 40 compound (529.0 mg, 1.05 mmoles) in dioxane (12.5 ml) was treated with 1.0N LiOH (3.7 ml, 3.7 mmoles) and stirred at 55° C. (oil bath) under nitrogen for 3.0 hours then at room temperature for 20 hours. The reaction mixture was evaporated to dryness and dried in vacuo. The crude product was chromatographed on an HP-20 column (1"×6"), eluting the column with steam-distilled water (750 ml), 10% aqueous CH$_3$OH (500 ml), 20% aqueous CH$_3$OH (500 ml) and 50% aqueous CH$_3$OH (500 ml). The desired fractions were combined, evaporated to dryness and dried in vacuo. The solid obtained was dissolved in steam-distilled water (35 ml) and lyophilized to give title compound as a fluffy white solid (510.0 mg, 92.4%).

TLC: R$_f$0.38 (silica gel; i-PrOH:NH$_4$OH: H$_2$O-8:1:1).

Anal Calcd for C$_{24}$H$_{26}$FLi$_2$N$_2$O$_5$P.2.2 H$_2$O (Eff. Mo. Wt.=525.899): C, 54.81; H, 5.83; N, 5.33; F, 3.61; P, 5.88. Found: C, 54.81; H, 5.61; N, 5.53; F, 4.06; P, 5.80.

IR (KBr) (1596 cm$^{-1}$, C=O of COO-).

H$^1$-NMR Spectrum (400 MHz, CD$_3$OD): δ1.36 (d, 6H, J=7), 1.60–1.72 (m, 4H), 2.32 (m, 2H), 2.74 (m, 2H), 3.21 (septet, 1H, J=7), 4.23 (m, 1H), 7.06–7.32 (m, 9H).

EXAMPLE 42

(S)-4-[[2-[3-(4-Fluorophenyl)-5-(1-methylethyl)-1-phenyl-1H-pyrazol-4-yl]ethynyl]methoxyphosphinyl]-3-hydroxybutanoic acid, methyl ester A. 4-Fluorobenzoic acid, 2-phenylhydrazide A mixture of phenylhydrazine (25 ml, 0.25 mmole) and triethylamine (35 ml, 0.25 mmole) in anhydrous ether (500 ml) was cooled down to −5° to −10° C. (ice-salt bath) under nitrogen and treated dropwise, over a 30 minute period, with 4-fluorobenzene carbonyl chloride (30 ml, 0.25 mole). The reaction mixture was warmed to room temperature, stirred for 3.0 hours, then filtered, washing the solids well with ether (200 ml). The solids were dissolved in dichloromethane (600 ml), stripped to near dryness, suspended in hexane (600 ml) and filtered. The clear filtrate was evaporated to dryness, triturated with tetrahydrofuran (700 ml) and filtered, washing the solids well with tetrahydrofuran (100 ml). The filtrate was evaporated to dryness and dried in vacuo to give a crude product (34.6 g) contaminated with two other components.

The crude product was recrystallized from acetone to give title compound as white crystals (22.36 g, 38.8%), m.p. 182°–184° C.

The filtrate and mother liquor were combined, chromatographed on a silica gel column (Baker, 60–200 mesh, 400 ml), eluting the column with EtOAc:CH$_2$Cl$_2$ (1:9) to give an additional 9.78 g of title compound (55.8%).

TLC: R$_f$0.63 (silica gel: EtOAc:CH$_2$Cl$_2$-1:4).

Anal Calcd for C$_{13}$H$_{11}$FN$_2$O: C, 67.81; H, 4.82; N, 12.17, F, 8.25. Found: C, 67.86; H, 4.88; N, 12.14; F, 8.10

MS (M+H)$^+$ =231.

B. 4-Fluoro-N-phenylbenzenecarbohydrazonoyl chloride

A solution of Part A compound (6.16 g, 26.8 mmole) in anhydrous ether (46 ml) was treated with phosphorus pentachloride (6.6 g, 31.7 mmoles) and the reaction mixture was refluxed under nitrogen for 16.0 hours. The reaction mixture was cooled to room temperature, treated with a solution of phenol (11.5 g, 122.2 mmoles) in ether (15 ml), stirred for 5 minutes then treated dropwise with methanol (11.4 ml). The mixture was concentrated at ~75° in a rotary evaporator and the resulting oil cooled at 5°. The solid obtained was triturated with 5% aqueous acetone (20 ml) and filtered, washing the precipitates well with 5% aqueous acetone (30 ml). The precipitates were dried in vacuo to give title compound as a solid (2.2 g), m.p. 118°–120°.

The clear filtrate was evaporated to dryness and the product mixture chromatographed twice on a silica gel column (Baker, 60–200 mesh, 400 ml), eluting the column with CH$_2$Cl$_2$:Hexane mixtures (1:3; 1:1), to give more title compound (total amount=5.66 g of 85%).

TLC: R$_f$0.90 (silica gel; CH$_2$Cl$_2$:Hexane-4:1).

Anal Calcd for C$_{13}$H$_{10}$FN$_2$: C, 62.78; H, 4.05; N, 11.27; F, 7.64; Cl, 14.26 Found: C, 62.87; H, 3.97; N, 11.34; F, 7.51; Cl, 13.95,

MS (M+H)$^+$ =249.

C. 3-(4-Fluorophenyl)-5-(1-methylethyl)-1-phenyl-1H-pyrazole-4-carboxylic acid, ethyl ester A solution of sodium ethoxide (from 0.28 g of 12 mmoles of sodium metal and 40 ml of absolute ethanol) is treated dropwise under nitrogen with ethyl isobutyrylacetate (2.0 ml, 12 mmoles), stirred for 15 minutes at room temperature then treated with Part B compound (3.0 g, 12 mmoles). The mixture was stirred at room temperature for 4.0 hours, quenched with 10% HCl (10 ml), evaporated to dryness and the resulting solid triturated with ether (3×100 ml). The combined organic extracts were washed with brine (25 ml), dried (anhydrous MgSO$_4$), filtered and evaporated to dryness. The crude product (4.3 g) was chromatographed on a silica gel column, eluting the column with CH$_2$Cl$_2$:hexane (1:1) to give title compound as a reddish-brown syrup (3.27 g, 77.3%).

TLC: R$_f$0.42 (silica gel; CH$_2$Cl$_2$:hexane-4:1).

D. 3-(4-Fluorophenyl)-5-(1-methylethyl)-1-phenyl-1H-pyrazole-4-methanol

A solution of Part C compound (3.26 g, 9.25 mmoles) in dry ether (22 ml) was added to a cooled (0°, ice-salt bath) suspension of lithium aluminum hydride (0.71 g, 18.7 mmoles) in dry ether (32 ml) and the reaction mixture was stirred at 0° under nitrogen for 3.0 hours. The mixture was quenched at 0° by the dropwise addition of ethyl acetate (5.0 ml), followed by 10% HCl (11 ml), decanted and the residue triturated with ether (2×100 ml). The combined organic extracts were washed with brine (20 ml), dried (anhydrous MgSO$_4$), filtered and evaporated to dryness to give title compound (2.87 g, 94.4%).

100 mg of title compound was recrystallized from ether to afford an analytical sample (57 mg, m.p. 145°-147°).

TLC: $R_f$ 0.17 (silica gel; $CH_2Cl_2$:hexane-4:1; developed 2×).

Anal Calcd for $C_{19}H_{19}FN_2O$: C, 73.52; H, 6.17; N, 9.03; F, 6.12. Found: C, 73.26; H, 6.11; N, 8.96; F, 6.09.

MS $(M+H)^+ = 311$.

E. 3-(4-Fluorophenyl)-5-(1-methylethyl)-1-phenyl-1H-pyrazole-4-carboxaldehyde

A solution of Part D compound (2.59 g, 8.34 mmoles( in dry dichloromethane (22.0 ml) was added rapidly to a stirred suspension of pyridinium chlorochromate (5.41 g, 25.1 mmoles) in dry dichloromethane (32 ml) and stirred at room temperature under nitrogen for 4.0 hours. The reaction mixture was diluted with ether (190 ml), stirred for 20 minutes then decanted. The tarry residue was triturated with ether (100 ml) and dichloromethane (30 ml) and the combined organic extracts were filtered through a silica gel pad. The clear filtrate was evaporated to dryness and the crude product chromatographed on a silica gel column (Baker, 60-200 mesh, 300 ml) eluting the column with $CH_2Cl_2$:hexane (4:1) to give title compound (2.40 g, 93.4%) as a solid product.

100 mg of title compound was recrystallized from hexane to give an analytical sample (50 mg, m.p. 103°-105°).

TLC: $R_f$ 0.67 (silica gel; $CH_2Cl_2$).

Anal Calcd for $C_{19}H_{17}FN_2O$: C, 74.01; H, 5.56; N, 9.09; F, 6.16. Found: C, 74.18; H, 5.35; N, 9.11; F, 6.12.

MS $(M+H)^+ = 309$.

F. 4-(2,2-Dibromoethenyl)-3-(4-fluorophenyl)-5-(1-methylethyl)-1-phenyl-1H-pyrazole A mixture of Part E compound (2.296 g, 7.45 mmoles) and triphenylphosphine (5.86 g, 22.1 mmoles) in dry dichloromethane (35.0 ml) was cooled down to −5° to −10° C. (ice-salt bath) under argon, treated dropwise, over a 5 minute period, with a solution of carbon tetrabromide (3.70 g, 11.0 mmoles) in dry dichloromethane (12 ml) and stirred at −10° for 20 minutes. The reaction mixture was warmed up to room temperature, poured into saturated $NaHCO_3$ (12 ml) and extracted with dichloromethane (3×60 ml). The combined organic extracts were washed with saturated $NaHCO_3$ (12 ml), brine (10 ml), dried (anhydrous $MgSO_4$), filtered and evaporated to dryness.

The crude product (11.0 g, solid) was chromatographed on a silica gel column, eluting the column with $CH_2Cl_2$:hexane mixtures (1:1, 4:1) to give title compound (2.96 g, 96.0% corrected yield) and unreacted starting material (250.6 mg).

100 mg of title compound was recrystallized from $Et_2O$:hexane to give an analytical sample (36.5 mg, m.p. 93.5°).

TLC: $R_f$ 0.57 (silica gel; $CH_2Cl_2$:hexane-4:1).

Anal Calcd for $C_{20}H_{17}Br_2FN_2$: C, 51.75; H, 3.69; N, 6.04; Br, 34.43; F, 4.09. Found: C, 51.78; H, 3.54; N, 6.07; Br, 34.40; F, 3.92.

MS $(M+H)^+ = 465$.

G. 4-Ethynyl-3-(4-fluorophenyl)-5-(1-methylethyl)-1-phenyl-1H-pyrazole

A solution of Part F compound (2.87 g, 6.18 mmoles) in dry tetrahydrofuran (11.44 ml) was cooled down to −78° (dry ice-acetone), treated dropwise with 1.6M n-BuLi/hexane (11.7 ml, 18.6 mmoles) under argon then stirred at −78° for 2 hours and 20 minutes. The reaction mixture was quenched at −78° with 25% $NH_4Cl$ (16.5 ml), warmed up to room temperature and extracted with ether (3×60 ml). The combined organic extracts were washed with brine (22 ml), dried (anhydrous $MgSO_4$), filtered and evaporated to dryness. The crude product (1.9 g) was chromatographed on a silica gel column, eluting the column with $Et_2O$:hexane (5:95). The desired fractions were combined and evaporated to dryness to give title compound (1.88 g, 100% yield) as a solid product.

100 mg of title compound was recrystallized from hexane to give an analytical sample (63.5 mg, m.p. 117°-118°).

TLC: $R_f$ 0.37 (silica gel; $Et_2O$:hexane-1:9).

Anal Calcd for $C_{20}H_{17}FN_2$: C, 78.92; H, 5.63; F, 6.24; N, 9.21. Found: C, 79.12; H, 5.60; F, 6.02; N, 9.12.

MS $(M+H)^+ = 305$.

H. (S)-3-[[(1,1-Dimethylethyl)diphenylsilyl]oxy]-4-[[[3-(4-fluorophenyl)-5-(1-methylethyl)-1-phenyl-1H-pyrazol-4-yl]ethynyl]methoxyphosphinyl]butanoic acid, methyl ester A solution of (S)-3-[[(1,1-dimethylethyl)diphenylsilyl]oxy]-4-(hydroxymethoxyphosphinyl)butanoic acid, methyl ester (prepared in Example 1 Part F) (2.77 g, 5.55 mmoles) in dry dichloromethane (10 ml) was treated with trimethylsilyldiethylamine (2.1 ml) and stirred at room temperature for 1.0 hour under argon. The reaction mixture was evaporated to dryness, azeotroped with dry benzene (20 ml) and dried in vacuo. The syrup was re-dissolved in dry dichloromethane (10 ml), cooled down to −10° (ice-salt bath), treated with 1 drop of DMF followed by the dropwise addition of oxalyl chloride (530 μl), stirred at −10° for 15 minutes then at room temperature for 1.0 hours. The mixture was evaporated to dryness, azeotroped with benzene (20 ml) and dried in vacuo.

Part G compound (1.12 g, 3.67 mmoles), was dissolved in dry tetrahydrofuran (9.0 ml), cooled down to −78° (dry ice-acetone bath), treated with 1.6M n-BuLi/hexane (2.3 ml, 3.68 mmoles) under argon and stirred at −78° for 45 minutes. The above phosphonochloridate was dissolved in dry tetrahydrofuran (6.5 ml), cooled to −78° and treated dropwise, by cannula, with the solution of the acetylene anion both solutions being kept at −78° throughout the addition. The reaction mixture was stirred at −78° for 30 minutes then quenched by the dropwise addition of 25% $NH_4Cl$ (6.0 ml) and allowed to warm up to room temperature. The mixture was extracted with ether (3×100 ml) and the combined organic extracts were washed with 25% $NH_4Cl$ (10 ml), brine (25 ml), dried (anhydrous $MgSO_4$), filtered and evaporated to dryness.

The crude product mixture (4.0 g) was chromatographed on a silica gel column, eluting the column with acetone:hexane mixtures (1:9; 3:7) to give title compound (1.76 g, 65.2%) as an oil. TLC: $R_f$ 0.40 (silica gel; hexane:acetone-7.3).

I. (S)-4-[[2-[3-(4-Fluorophenyl)-5-(1-methylethyl)-1-phenyl-1H-pyrazol-4-yl]ethynyl]methoxyphosphinyl]-3-hydroxybutanoic acid, methyl ester A solution of Part H compound (700 mg, 0.95 mmoles) in dry tetrahydrofuran (9 ml) was treated successively with glacial HOAc (224 μl, 3.82 mmoles) and 1.0M $(C_4H_9)_4NF$ (3.0 ml, 3.0 mmoles) and stirred overnight at room temperature under argon. The solution was cooled down to 0° (ice-salt bath), treated dropwise with 5% $KHSO_4$ (10 ml) and extracted with ethyl acetate (3×75 ml). The combined organic extracts were washed with 5% $KHSO_4$ (10 ml), brine (25 ml), dried (anhydrous MgSO₄), filtered and evaporated to dryness.

The crude product (890 mg) was dissolved in a mixture of ether (16 ml) and tetrahydrofuran (12 ml), cooled down to 0° (ice-salt bath) and treated with excess diazomethane in ether. The reaction mixture was stirred at 0° for ~3 hours, quenched by the dropwise addition of glacial acetic acid and evaporated to dryness. The crude product mixture (764 mg) was chromatographed on a silica gel column, eluting the column with EtOAc:hexane mixtures (1:1; 4:1; 9:1) to give title compound as a semi-solid (347 mg, 73.2%). TLC: $R_f$ 0.28 (silica gel; EtOAc:hexane-4:1).

EXAMPLE 43

(S)-4-[[2-[3-(4-Fluorophenyl)-5-(1-methylethyl)-1-phenyl-1H-pyrazol-4-yl]ethynyl]hydroxyphosphinyl]-3-hydroxybutanoic acid, dilithium salt A solution of Example 42 compound (347 mg, 0.7 mmoles) in dioxane (8.3 ml) was treated with 1.0N LiOH (2.4 ml, 2.4 mmoles) and stirred at 55° C. (oil bath) under nitrogen for 45 minutes. The reaction mixture was evaporated to dryness and dried in vacuo. The resulting semi-solid was chromatographed on an HP-20 column (1"×3"), eluting the column with steam-distilled water (350 ml), 50% aqueous methanol (250 ml). The desired fractions were combined, evaporated to dryness and dried in vacuo. The product was dissolved in steam-distilled water and lyophilized to give title compound as a white solid lyophilate (338 mg, 97.5%). TLC: $R_f$ 0.50 (silica gel; i-PrOH:NH₄OH:H₂O-7:2:1).

Anal Calcd for C₂₄H₂₂FLi₂N₂O₅P.1.95 H₂O: C, 55.71; H, 5.04; N, 5.42; F, 3.67; P, 5.99. Found: C, 55.90; H, 5.46; N, 5.30; F, 3.95; P, 5.96.

H¹-NMR Spectrum (400 MHz, CD₃OD): δ1.45 (d, 6H, J=7), 1.89-2.05 (m, 2H), 2.38 (dd, 1H, J=9, 15), 2.52 (dd, 1H, J=4, 15), 3.06 (septet, 1H, J=7), 4.48 (m, 1H), 7.16-8.11 (m, 9H).

EXAMPLE 44

(S)-4-[[2-[3-(4-Fluorophenyl)-5-(1-methylethyl)-1-phenyl-1H-pyrazol-4-yl]ethyl]methoxyphosphinyl]-3-hydroxybutanoic acid, methyl ester A. (S)-3-[[(1,1-Dimethylethyl)diphenylsilyl]oxy]-4-[[2-[3-(4-fluorophenyl)-5-(1-methylethyl)-1-phenyl-1H-pyrazole-4-yl]ethyl]methoxyphosphinyl]butanoic acid, methyl ester A solution of Example 42 Part I compound (1.0 gm, 1.36 mmole) in dry methanol (72 ml) was treated with 10% Pd/C (250 mg) and hydrogenated in a Parr hydrogenator overnight at ~40 psi. The reaction mixture was filtered through Celite and the clear filtrate was evaporated to dryness to give title compound as a homogeneous oil (1.0 gm, 100% crude yield).

TLC: $R_f$ 0.27 (silica gel; hexane:acetone-7:3).

B. (S)-4-[[2-[3-(4-Fluorophenyl)-5-(1-methylethyl)-1-phenyl-1H-pyrazol-4-yl]ethyl]methoxyphosphinyl]-3-hydroxybutanoic acid, methyl ester A solution of Part A compound (1.05 g, 1.41 mmoles) in dry tetrahydrofuran (14.0 ml) was treated successively with glacial acetic acid (334 μl, 5.83 mmoles) and 1.0M (C₄H₉)₄NF/THF (4.46 ml, 4.46 mmoles) and stirred at room temperature under argon for ~19 hours. The reaction mixture was diluted with ice-water (28 ml) and extracted with ethyl acetate (3×100 ml). The combined organic extracts were washed with saturated NaHCO₃ (15 ml), brine (25 ml), dried (anhydrous MgSO₄), filtered and evaporated to dryness. The crude product mixture (1.14 g) was chromatographed on a silica gel column (Baker, 60–200 mesh, 150 ml), eluting the column with EtOAc:hexane mixtures (2:1, 4:1, 9:1), ethyl acetate and acetone to give title compound as a semi-solid (623.5 mg, 88.0%). TLC: $R_f$ 0.18 (silica gel; EtOAc:hexane —4:1).

EXAMPLE 45

(S)-4-[[2-[3-(4-Fluorophenyl)-5-(1-methylethyl)-1-phenyl-1H-pyrazol-4-yl]ethyl]hydroxyphosphinyl]-3-hydroxybutanoic acid, dilithium salt A solution of Example 44 compound (623.5 mg, 1.24 mmoles) in dioxane (14.7 ml) was treated with 1.0N LiOH (4.28 ml, 4.27 mmoles) under nitrogen, heated at 55° C. (oil bath) for 2 hours then stirred at room temperature for ~20 hours. The reaction mixture was evaporated to dryness, dried in vacuo and chromatographed on an HP-20 column (1"×6"), eluting the column with steam-distilled water (750 ml), 10% aqueous CH₃OH, 20% aqueous CH₃OH (500 ml) and 50% aqueous CH₃OH (500 ml). The desired fractions were combined and evaporated to dryness to give the desired product (560 mg, 92.8%). TLC: $R_f$ 0.42 (silica gel; i-PrOH:N-H₄OH:H₂O-8:1:1).

Anal Calcd for C₂₄H₂₆FLi₂N₂O₅P.1.16 H₂O: (Eff. M.W.=507.197): C, 56.83; H, 5.62; N, 5.52; F, 3.74; P, 6.11. Found: C, 56.83; H, 5.80; N, 5.76; F, 3.46; P, 6.19.

H¹-NMR Spectrum (400 MHz, CD₃OD): δ1.30 (d, 6H, J=7), 1.60-178 (d, 4H), 2.36 (m, 2H), 2.96-2.99 (m, 2H), 3.14 (m, 1H), 4.26 (m, 1H), 7.14-7.68 (m, 9H).

EXAMPLE 46

(S)-4-[[[4-(4-Fluorophenyl)-1-(1-methylethyl)-3-phenyl-1H-pyrazol-5-yl]ethynyl]methoxyphosphinyl]-3-hydroxybutanoic acid, methyl ester A. 2-(4-Fluorophenyl)-1-phenylethanone A suspension of magnesium turnings (928 mg, 38 mmoles) in dry ether (38 ml) under argon was treated dropwise with 4-fluorobenzylbromide (5.3 ml, 42 mmoles) over a period of 45 minutes at a rate maintaining gentle reflux. When addition was completed, the mixture was refluxed for another 30 minutes, cooled down to room temperature and treated with a solution of benzonitrile (2.96 ml, 29 mmoles) in dry ether (5 ml). The mixture was stirred at room temperature for 4.5 hours, poured slowly into cold 10% HCl (40 ml) and the resulting suspension was extracted with ether (5×50 ml) and ethyl acetate (2×100 ml). The combined organic extracts were washed with saturated NaHCO₃ (50 ml), brine (50 ml), dried (anhydrous MgSO₄), filtered and evaporated to dryness.

The crude product (9.8 g) was chromatographed on a silica gel column (Baker, 60–200 mesh, 400 ml), eluting the column with CH₂Cl₂:hexane mixtures (1:4, 1:2). The desired fractions were combined and evaporated to dryness to give title compound as a white solid (3.29 g, m.p. 106°-8°). (An additional 2.60 g was obtained from other fractions containing a trace of starting material to give a total yield of 94.8%.) TLC: $R_f$ 0.60 (silica gel; CH₂Cl₂:hexane-1:1).

Anal Calcd for C₁₄H₁₁FO: C, 78.49; H, 5.18; F, 8.87. Found: C, 78.22; H, 5.22; F, 9.21.

MS (M+H)⁺=215.

B. 2-(4-Fluorophenyl)-1-phenylethanone, (1-methylethyl)hydrazone

A solution of Part A compound (4.45 g, 21 mmoles) in a mixture of 95% ethanol (34 ml) and glacial acetic acid (0.74 ml) was treated with isopropylhydrazine (3.63 ml, ~42 mmoles) and heated at 80° (oil bath) under $N_2$ for 1.4 hours. Thin layer chromatography indicated that some starting material was still present so the reaction mixture was treated with additional isopropylhydrazine (2.0 ml, ~23 mmoles) and heated at 80° (oil bath) for another hour. The reaction mixture was cooled down to room temperature, evaporated in a rotary evaporator to remove most of the solvent then diluted with dichloromethane (200 ml). The organic solution was washed with brine (25 ml), dried (anhydrous $MgSO_4$), filtered and evaporated to dryness. The yellow oil obtained was evaporated once from toluene (150 ml) to give title compound as a crude product (5.63 g) contaminated with some starting material and traces of two other components. TLC: $R_f$ 0.28 (silica gel; $CH_2Cl_2$:hexane-1:1).

Isopropylhydrazine was prepared as follows: Iodopropane (10.3 ml, 0.10 mole) was added over a period of 2.0 hours to hydrazine hydrate (48.4 ml, 1.0 mole) under $N_2$. The mixture was then stirred at 60° (oil bath) under $N_2$ for 3 hours, cooled and extracted with ether (250 ml) for 20 hours (liquid-liquid extractor). The ethereal extract was evaporated to give isopropylhydrazine (5.63 ml or 5.3 g).

C. Acetic acid, 2-[2-(4-fluorophenyl)-1-phenylethylidene]-1-(1-methylethyl)hydrazide A mixture of crude Part B compound (5.63 g, ≈21 mmoles) and triethylamine (5.85 ml, 42 mmoles) in dry toluene (210 ml) was cooled down to 0° (ice-salt bath) under $N_2$ and treated with acetyl chloride (1.86 ml, 26.3 mmoles). The reaction mixture was stirred with gradual warming to room temperature for 1.5 hours, diluted with ether (700 ml) and filtered. The clear filtrate was dried (anhydrous $Na_2SO_4$), filtered, evaporated to dryness and evaporated once from toluene (300 ml). The semi-solid obtained (7.1 g) was chromatographed on a silica gel column (Baker, 60-200 mesh, 400 ml), eluting the column with $CH_2Cl_2$:hexane mixtures (1:1, 2:1), $CH_2Cl_2$ and $CH_2Cl_2$:$CH_3OH$ (9:1) to give title compound as a crude product (4.11 g). The crude product was rechromatographed on another silica gel column, eluting the column with EtOAc:hexane (4:1). The desired fractions were combined and evaporated to dryness to give title compound as a thick yellow oil (3.89 g). TLC:$R_f$ 0.47 (silica gel:EtOAc:hexane-1:1).

D. 4-(4-Fluorophenyl)-5-methyl-1-(1-methylethyl)-3-phenyl-1H-pyrazole

A solution of Part C compound (1.50 g, 4.80 mmoles) in bis (2-methoxyethyl)ether (48 ml) was treated with solid potassium hydroxide (615 mg, 10.96 mmoles) and heated at 80° (oil bath) under $N_2$ for 2.0 hours. The reaction mixture was treated with a second batch of potassium hydroxide (700 mg, 12.5 mmoles), heated at 80° for 2 hours and then stirred at room temperature for 16 hours. The mixture was poured into water (300 ml) and extracted successively with ether (3×150 ml) and ethyl acetate (200 ml). The organic solutions were combined, washed with cold 3% HCl (500 ml), brine (2×100 ml), dried (anhydrous $MgSO_4$), filtered and evaporated to dryness. The crude product (3.5 g) was chromatographed on a silica gel column (Baker, 60-200 mesh, 500 ml), eluting the column with EtOAc:hexane (1:4) to give title compound as a cream-colored solid (1.33 g, 94.3%), m.p. 135°-7°.

TLC: $R_f$ 0.63 (silica gel; EtOAc:hexane-1:4).

E. 4-(4-Fluorophenyl)-1-(1-methylethyl)-3-phenyl-1H-pyrazole-5-carboxaldehyde

A mixture of $CuSO_4.5H_2O$ (2.21 g, 8.85 mmoles) and potassium persulfate (9.53 g, 35.3 mmoles) in acetonitrile (65 ml) and water (39 ml) was heated to 65° (oil bath) under $N_2$ and treated with Part D compound (2.6 g, 8.83 mmoles). The bath temperature was slowly raised to 75°, kept at 75° for 40 minutes then cooled to room temperature, using a water bath. The reaction mixture was diluted with dichloromethane (45 ml), stirred for 10 minutes and decanted, extracting the aqueous suspension with more dichloromethane (3×45 ml). The combined organic extracts were washed with brine (2×30 ml), dried (anhydrous $MgSO_4$), filtered and evaporated to dryness. The crude product (2.75 g) was chromatographed on a silica gel column (LPS-1), eluting the column with EtOAc:hexane (1:9) to give title compound as a solid (1.57 g, 57.7%). TLC: $R_f$ 0.72 (silica gel; EtOAc:hexane-1:4).

F. 5-(2,2-Dibromoethenyl)-4-(4-fluorophenyl)-1-(1-methylethyl)-3-phenyl-1H-pyrazole A mixture of Part E compound (1.75 g, 5.68 mmoles) and triphenylphosphine (4.6 g, 16.8 mmoles) in dry dichloromethane (27.0 ml) was cooled down to −5° to −10° (ice-salt bath) under argon, treated dropwise, over a 5 minute period with a solution of carbon tetrabromide (2.82 g, 8.42 mmoles) in dry dichloromethane (9 ml) and stirred at −10° for 20 minutes. The reaction mixture was warmed up to room temperature, poured onto saturated $NaHCO_3$ (9.0 ml) and extracted with dichloromethane (3×50 ml). The combined organic extracts were washed with saturated $NaHCO_3$ (10 ml), brine (10 ml), dried (anhydrous $MgSO_4$), filtered and evaporated to dryness.

The crude product was chromatographed on silica gel eluting with $CH_2Cl_2$:hexane mixtures (1:0, 1:4). The desired fractions were combined to give title compound (2.35 g, 91.4%) as an oil. TLC: $R_f$ 0.32 (silica gel: $CH_2Cl_2$:hexane-1:1).

G. 5-Ethynyl-4-(4-fluorophenyl)-1-(1-methylethyl)-3-phenyl-1H-pyrazole

A solution of Part F compound (1.89 g, 4.08 mmoles) in dry tetrahydrofuran (7.6 ml) was cooled down to −78° (dry ice-acetone), treated dropwise with 1.6M BuLi/hexane (5.2 ml, 8.18 mmoles, 2 eq.) under argon and stirred at −78° for 1 hour and 20 minutes. The reaction mixture was quenched at −78° with 25% $NH_4Cl$ (11.0 ml), warmed up to room temperature and extracted with dichloromethane (3×50 ml). The combined organic extracts were washed with brine (15 ml), dried (anhydrous $MgSO_4$), filtered and evaporated to dryness. The crude product (1.77 g) was chromatographed on a silica gel column, eluting the column with $CH_2Cl_2$:hexane mixtures (1:4, 1:1) to give title compound (648 mg) along with mixed fractions containing title compound and Part F compound. The mixed fractions were combined with the product from another run (490 mg from 1.1 mmoles of Part F compound) and chromatographed on a second column, eluting the column with $CH_2Cl_2$:hexane (1:9). The desired fractions were combined and evaporated to dryness to give title compound as an oil (1.02 g, 71.5% corrected for recovered starting material). TLC: $R_f$(silica gel; $CH_2Cl_2$:hexane-1:1).

H. (S)-3-[[(1,1-Dimethylethyl)diphenylsilyl]oxy]-4-[[[4-(4-fluorophenyl)-1-(1-methylethyl)-3-phenyl-1H-pyrazol-5-yl]ethynyl]methoxyphosphinyl]butanoic acid, methyl ester A solution of the Example 1 Part F phosphonic monomethyl ester (2.341 g, 5.01 mmoles) and trimethylsilylethylamine (1.90 ml, 10 mmoles) in dry dichloromethane (9.5 ml) was stirred at room temperature under argon for 1 hour. The mixture was evaporated to dryness, azeotroped with dry benzene (15 ml) and dried in vacuo. The viscous oil was re-dissolved in dry dichloromethane (9.5 ml), treated with one drop of DMF, cooled down to −10° to 0° (ice-salt bath) and treated dropwise with oxalyl chloride (480 μl, 5.47 mmoles). Vigorous gas evolution was observed and the dark yellow solution was stirred at −10° to 0° for 15 minutes then at room temperature for 1.0 hour. The reaction mixture was evaporated to dryness, azeotroped with benzene (18 ml) and dried in vacuo.

A solution of Part G compound (1.016 g, 3.34 mmoles) in dry tetrahydrofuran (8 ml) was cooled down to −78° (dry ice-acetone) under argon and treated with 1.6M n-BuLi/hexane (2.1 ml, 3.36 mmoles) and stirred at −78° for 1.0 hour. The above phosphonochloridate was dissolved in dry tetrahydrofuran (8 ml), cooled down to −78° (dry ice-acetone) under argon and treated dropwise by cannula with the solution of the acetylene anion both solutions being kept at −78° throughout the addition. The reaction mixture was stirred at −78° for 1.0 hour, quenched by the dropwise addition of 25% NH$_4$Cl (9 ml) then warmed up to room temperature. The mixture was extracted with ether (3×100 ml) and the combined organic extracts were washed with 25% NH$_4$Cl (10 ml), brine (25 ml), dried (anhydrous MgSO$_4$), filtered and evaporated to dryness.

The crude product was chromatographed on a silica gel column, eluting the column with acetone:hexane mixtures (1:9, 1:4) to give title compound as an oil (1.595 g, 64.8%). TLC: R$_f$0.43 (silica gel; acetone:hexane-3:7).

I. (S)-4-[[[4-(4-Fluorophenyl)-1-(1-methylethyl)-3-phenyl-1H-pyrazol-5-yl]ethynyl]methoxyphosphinyl]-3-hydroxybutanoic acid, methyl ester A solution of Part H compound (1.0 g, 1.36 mmoles) in dry tetrahydrofuran (13 ml) was treated successively with glacial acetic acid (320 μl, 5.46 mmoles) and 1M (C$_4$H$_9$)$_4$NF (4.26 ml, 4.26 mmoles) and stirred overnight at room temperature under argon. The reaction mixture was cooled down to 0° (ice-salt bath), treated with 5% KHSO$_4$ (15 ml) and extracted with ethyl acetate (3×125 ml). The combined organic extracts were washed with 5% KHSO$_4$ (2×25 ml), brine (25 ml), dried (anhydrous MgSO$_4$), filtered and evaporated to dryness.

The crude product (1.06 g) was dissolved in a mixture of ether (23 ml) and tetrahydrofuran (18 ml), cooled down to 0° (ice-salt bath), treated with excess diazomethane in ether and stirred at 0° for 4 hours. The reaction mixture was quenched by the dropwise addition of glacial acetic acid, evaporated to dryness and dried in vacuo. The crude product was chromatographed on a silica gel column, eluting the column with acetone:hexane (1:2). The desired fractions were combined and evaporated to dryness to give title compound as an oil (330 mg, 48.7%). TLC: R$_f$0.23 (silica gel; EtOAc:hexane-4:1).

EXAMPLE 47

(S)-4-[[[4-(4-Fluorophenyl)-1-(1-methylethyl)-3-phenyl-1H-pyrazol-5-yl]ethynyl]hydroxyphosphinyl]-3-hydroxybutanoic acid, dilithium salt A solution of Example 46 compound (330 mg, 0.66 mmole) in dioxane (7.8 ml) was treated with 1N LiOH (2.29 ml, 2.29 mmole) stirred at 55° (oil bath) under argon for 1.5 hours then at room temperature for 16 hours. The reaction mixture was evaporated to dryness and dried in vacuo. The crude product was chromatographed on an HP-20 column (1"×10"), eluting the column with steam-distilled water (750 ml), 10% aqueous CH$_3$OH (500 ml), 20% aqueous CH$_3$OH (500 ml) and 50% aqueous CH$_3$OH (500 ml). The desired fractions were combined, evaporated to dryness and dried in vacuo. The solid product was dissolved in steam-distilled water and lyophilized to give title compound as a fluffy solid lyophilate (275 mg, 99.5%).

TLC: R$_f$0.57 (silica gel; i-PrOH;NH$_4$OH:H$_2$O-8:1:1).

Anal Calcd for C$_{24}$H$_{22}$FLi$_2$N$_2$O$_5$P.2.28 (Eff. mol. wt=523.310): C, 55.08; H, 5.11; N,5.35; F, 3.63; P, 5.92. Found: C, 55.08; H, 4.98; N, 5.47; F, 3.66; P, 5.99.

IR (KBr): 2172 cm$^{-1}$ (C≡C).

H$^1$-NMR spectrum (400 MHz, CD$_3$OD): δ1.57 (d, 6H, J=7 Hz), 1.86-2.01 (m, 2H), 2.37 (dd, 1H, J=8), 2.50 (dd, 1H, J=4), 4.40 (m, 1H), 5.01 (septet, 1H, J=7), 7.04-7.39 (m, 9H). z

EXAMPLE 48

(S)-4-[[2-[4-(4-Fluorophenyl)-1-(1-methylethyl)-3-phenyl-1H-pyrazol-5-yl]ethyl]methoxyphosphinyl]-3-hydroxybutanoic acid, methyl ester A. (S)-3-[[[(1,1-Dimethylethyl)diphenylsilyl]oxy]-4-(4-fluorophenyl)-1-(1-methylethyl)-3-phenyl-1H-pyrazol-5-yl]ethyl]methoxyphosphinyl]butanoic acid, methyl ester A solution of Example 47, Part H compound (608 mg, 0.85 mmole) in dry methanol (63 ml) was treated with 10% Pd/C (155 mg) and hydrogenated at room temperature on a Parr hydrogenator at ∼40 psi overnight. The suspension was diluted with methanol (50 ml) and filtered through a celite pad in a millipore unit, washing the pad well with methanol. The clear filtrate was evaporated to dryness and dried in vacuo to give title compound as a homogeneous oil (559 mg, 90.9%) with consistent H$^1$-NMR and C$^{13}$-NMR spectral data. RC: R$_f$0.20 (silica gel:acetone:hexane 3:7; UV).

B. (S)-4-[[2-[4-(4-Fluorophenyl)-1-(1-methylethyl)-3-phenyl-1H-pyrazol-5-yl]ethyl]methoxyphosphinyl]-3-hydroxybutanoic acid, methyl ester A solution of Part A compound (559 mg, 0.75 mmole) in dry tetrahydrofuran (7.5 ml) was treated successively with glacial acetic acid (176 μl, 3.0 mmoles, 4 eq) and 1.0M (C$_4$H$_9$)$_4$ NF/hexane (2.34 ml, 2.34 mmoles, 3.1 eq) under nitrogen and stirred at room temperature for ∼20 hours. The reaction mixture was diluted with ice-water (20 ml), extracted with ethyl acetate (3×70 ml), and the combined organic extracts were washed with saturated NaHCO$_3$ (10 ml), brine (20 ml), dried (anhydrous MgSO$_4$), filtered and evaporated to dryness. The crude product (580 mg) was chromatographed on a silica gel column, eluting the column with EtOAc:hexane (1:4), EtOAc and acetone:hexane (4:1). The desired fractions were combined, evaporated to dryness and dried in vacuo to give title compound as a homogeneous oil (337 mg, 89.4%).

TLC: R_f 0.18 (silica gel; acetone:hexane-1:1; UV).

EXAMPLE 49

(S)-4-[[2-[4-(4-Fluorophenyl)-1-(1-methylethyl)-3-phenyl-1H-pyrazol-5-yl]ethyl]hydroxyphosphinyl]-3-hydroxybutanoic acid, dilithium salt A solution of Example 48 compound (337.0 mg, 0.67 mmole) in dioxane (8.0 ml) was treated with 1.0N LiOH (2.32 ml, 3.5 eq) under argon, stirred at 55° (oil bath) for 3.0 hours then at room temperature for 20 hours. The reaction mixture was evaporated to dryness and dried in vacuo (pump) for 1.0 hour. The crude product was chromatographed on an HP-20 column (1"×8"), eluting the column with steam-distilled water (500 ml), 10% aqueous $CH_3OH$ (500 ml), 20% aqueous $CH_3OH$ (500 ml) and 50% aqueous $CH_3OH$. The desired fractions were combined, evaporated to dryness and dried in vacuo. The resulting solid was dissolved in steam-distilled water, frozen and lyophilized overnight to give title compound as a fluffy white lyophilate (280.4 mg, 82.4%) with consistent analytical, mass spectrum, IR and $H^1$-NMR spectral data.

TLC: $R_f$ 0.45 (silica gel; i-PrOH: $NH_4OH$: $H_2O$-8:1:1; UV). An additional 24 mg of slightly impure product was obtained from other fractions.

Anal Calcd for $C_{24}H_{26}FLi_2N_2O_5P \cdot 1.19 H_2O$ (Effective mol weight)=507.733: C, 56.77; H, 5.63; N, 5.51; F, 3.74; P, 6.10. Found: C, 52.77; H, 5.69; N, 5.49; F, 3.91; P, 6.50.

IR (KBr) #69377 (1589 $CM^{-1}$, C=O of COO−).

$H^1$-NMR Spectrum (400 MHz, $CD_3OD$): δ1.55 (d, 6H, J=7, $H_j$), 1.64-1.84 (m, 4H, -, $H_c + H_d$), 2.34 (m, 2H, -, $H_a$), 2.91 (pseudo quartet, 2H, -, $H_e$), 4.25 (m, 1H, -, $H_6$), 4.77 (septet, 1H, partially buried under HOD signal, -, $H_1$), 7.05-7.32 (m, 9H, aromatic protons).

EXAMPLE 50

(S)-4-[[[1-(4-Fluorophenyl)-4-(1-methylethyl)-2-phenyl-1H-imidazol-5-yl]ethynyl]methoxyphosphinyl]-3-hydroxybutanoic acid, methyl ester

A. N-Benzoylvaline

A solution of valine (20 g, 0.17 mole) in tetrahydrofuran (20 ml) and 2N NaOH (111 ml) was cooled down to 10° (ice-water bath) under nitrogen and treated dropwise with benzoyl chloride (23.8 ml, 0.21 mole). The reaction mixture was warmed up to room temperature, stirred for 3.0 hours then cooled back down to 0° (ice-salt bath) and treated with concentrated sulfuric acid (8.0 ml). The mixture was extracted with ethyl acetate (3×200 ml). The combined organic extracts were washed with water (100 ml), brine (50 ml), dried (anhydrous $MgSO_4$), filtered and evaporated to dryness to give title compound as a solid (41.97 g, 100% crude yield).

A small amount (260 mg) of the product was recrystallized from ethyl acetate and petroleum ether to give title compound as an analytical sample (205 mg, m.p. 132°-3°).

TLC: $R_f$ 0.10 (silica gel; acetone:hexane-1:1).

Anal Calcd: C, 65.14; N, 6.83; N, 6.33. Found: C, 64.81; N, 6.79; N, 6.29.

MS $(M+H)^+=222$.

B. N-(1-Acetyl-2-methylpropyl)benzamide

A mixture of Part A compound (41.7 g, ≈0.17 mole) and triethylamine (47.3 ml, 0.34 mole) in acetic anhydride (48 ml) was treated with two portions of 4-dimethylaminopyridine (2.07 g, 0.017 mole) and stirred at room temperature for 16 hours under nitrogen. The reaction mixture was cooled down to 0° (ice-salt bath), quenched with methanol and stirred for 30 minutes. The light brown precipitates that formed were filtered off, washed well with water (1.1 l.) and re-dissolved in dichloromethane (750 ml). The solution obtained was dried (anhydrous $MgSO_4$), filtered and evaporated to dryness to give a crude product (35.9 g).

The crude product was dissolved in ether (1.3 l.), filtered to remove the insoluble solids and the clear filtrate was concentrated down to a volume of ~300 ml and cooled in an ice-bath. Title compound in the form of a cream colored precipitate (21.35 g, m.p. 88°-90°) was filtered off. Purification of the solid obtained by evaporation of the filtrate on a silica gel column (Baker, 600-200 mesh, 600 ml), eluting the column with EtOAc:hexane mixtures (1:7, 1:4) gave an additional 4.77 g of title compound. A small amount of title compound was recrystallized from ether, m.p. 88°-89° C.

TLC: $R_f$ 0.75 (silica gel; acetone:hexane-1:1).

Anal Calcd: C, 70.20; H, 7.81; N, 6.39. Found: C, 70.79; H, 7.68; N, 6.31.

MS $(M+H)^+=220$.

C. N-[1-[1-[(4-Fluorophenyl)imino]ethyl]-2-methylpropyl]benzamide

A solution of Part B compound (25.0 g, 0.114 mole) in dry toluene (250 ml) was treated with 4-fluoroaniline (12 ml, 0.127 mole, 1.11 ca.) and p-toluenesulfonic acid hydrate (125 mg) and the reaction mixture was refluxed under $N_2$ with a Dean-Starke distilling receiver for 20 hours. The reddish-brown solution was cooled down to −10° C. (ice-salt bath) and used as is for the next step in the sequence.

D. 1-(4-Fluorophenyl)-5-methyl-4-(1-methylethyl)-2-phenyl-1H-imidazole

The cooled solution of Part C compound (≈0.114 mole) was diluted at −10° (ice-salt bath) with dry dichloromethane (200 ml) and treated portionwise with phosphorus pentachloride (47.5, 0.228 mole). The cream-colored slurry was warmed up, refluxed for 2.5 hours under $N_2$, cooled down to room temperature and poured slowly into a mixture of ice (400 g) and 50% NaOH (105 ml). The organic phase was separated and the aqueous phase extracted with dichloromethane (2×200 ml). The combined organic extracts were washed with brine (2×100 ml), dried (anhydrous $MgSO_4$), filtered and evaporated to dryness.

The crude product mixture (35.0 g) was chromatographed on a silica gel column (Baker, 60-200 mesh, 600 ml), eluting with EtOAc:hexane mixtures (1:9, 1:4) to give title compound as white needles (29.24 g, m.p. 146°-8°, 87%).

TLC: $R_f$ 0.40 (silica gel; EtOAc:hexane-1:4).

Anal Calcd: C, 77.52; H, 6.51; N, 9.52; F, 6.45. Found: C, 77.48; H, 6.69; N, 9.40, F, 6.45.

MS $(M+H)^+=295$.

E. 1-(4-Fluorophenyl)-4-(1-methylethyl)-2-phenyl-1H-imidazole-5-carboxaldehyde A mixture of cupric sulfate hydrate (8.50 g, 34.0 mmoles) and potassium persulfate (36.8 g, 0.136 mole) in a solvent mixture of acetonitrile (250 ml) and water (150 ml) was heated to 65° (oil bath) under $N_2$ and treated with Part D compound (10 g, 34.0 mmoles). The reaction mixture was slowly heated up to 75°, kept there for 40 minutes then cooled to room temperature. The solution was decanted from the solids, extracting both aqueous phase and solid with dichloromethane (3×200 ml). The combined organic extracts were washed with brine (2×100 ml), dried (anhydrous MgSO₄), filtered and evaporated to dryness. The crude product (17.0 g) was chromatographed on a silica gel column (Baker, 60-200 mesh, 600 ml) eluting the column with EtOAc:hexane mixtures (5:95, 1:7) to give title compound as a solid (6.27 g, 59.8%).

200 mg of title compound was recrystallized from Et₂O:hexane to give an analytical sample (76 mg, m.p. 160°-1°).

TLC: $R_f$ 0.34 (silica gel; EtOAc:hexane-1:4).

Anal Calcd: C, 74.01; H, 5.56; N, 9.09; F, 6.16. Found: C, 73.98; H, 5.68; N, 9.04; F, 6.09.

MS (M+N+)=309.

F. 5-(2,2-Dibromoethenyl)-1-(4-fluorophenyl)-4-(1-methylethyl)-2-phenyl-1H-imidazole A solution of Part E compound (1.75 g, 5.68 mmoles) and triphenylphosphine (4.46 g, 16.8 mmoles) in dry dichloromethane (27.0 ml) was cooled down to −5° to −10° (ice-salt bath) under argon and treated dropwise over a period of 5 minutes with a solution of carbon tetrabromide (2.82 g, 8.42 mmoles) in dry dichloromethane (9 ml). The mixture was stirred at −10° for 20 minutes then poured onto saturated sodium bicarbonate (9.0 ml) and extracted with dichloromethane (3×50 ml). The combined organic extracts were washed with saturated NaHCO₃ (10 ml), brine (10 ml), dried (anhydrous MgSO₄), filtered and evaporated to dryness. The crude product (8.07 g) was chromatographed on a silica gel column, eluting the column with CH₂Cl₂:hexane mixtures (1:7; 1:4) to give title compound as a solid (2.35 g, 91.4%).

100 mg of Part F compound was recrystallized from Et₂O:hexane to give an analytical sample (49 mg, m.p. 164°-5°).

TLC: $R_f$ 0.32 (silica gel; CH₂Cl₂:hexane-1:1).

Anal Calcd: C, 51.75; H, 3.69: N, 6.04; F, 4.09; Br, 34.43. Found: C, 51.80; H, 3.71; N, 6.02; F, 4.08; Br, 34.25.

MS (M+H)+ =465.

G. 5-Ethynyl-1-(4-fluorophenyl)-4-(1-methylethyl)-2-phenyl-1H-imidazole

A solution of Part F compound (3.065 g, 6.60 mmoles) in dry tetrahydrofuran (12.5 ml) was cooled down to −78° (dry ice-acetone) and treated with 1.6M n-BuLi/hexane (8.4 ml, 13.4 mmoles) under argon. The reaction mixture was stirred at −78° for 1 hour and 20 minutes, quenched by the dropwise addition of 25% NH₄Cl (18 ml), warmed up to room temperature and extracted with ether (3×100 ml). The combined organic extracts were washed with brine (25 ml), dried (anhydrous MgSO₄), filtered and evaporated to dryness. The crude product (2.08 g) was chromatographed on a silica gel column (Baker, 60-200 mesh, 400 ml), eluting the column with EtOAc:hexane mixtures (1:9, 1:4). The desired fractions were combined and evaporated to dryness to give title compound as a solid (1.97 g, 97.8%).

92 mg of Part G compound was recrystallized from hexane to give an analytical sample (59 mg, m.p. 148°-150°).

TLC: $R_f$ 0.60 (silica gel; EtOAc:hexane-1:4).

Anal Calcd: C, 78.92; H, 5.63; N, 9.21; F, 6.24. Found: C, 78.95; H, 5.83; N, 9.07; F, 6.63.

MS (M−H)− =303.

H. (S)-3-[[(1,1-Dimethylethyl)diphenylsilyl]oxy]-4-[[[1-(4-fluorophenyl)-4-(1-methylethyl)-2-phenyl-1H-imidazol-5-yl]ethynyl]methoxyphosphinylbutanoic acid, methyl ester A mixture of the Example 1 Part F crude phosphonic monomethyl ester (3.54 g, 7.86 mmoles) and trimethylsilyldiethylamine (2.70 ml, 14.21 mmoles) in dry dichloromethane was stirred at room temperature under argon for 1.0 hour. The mixture was evaporated to dryness, azeotroped with dry benzene (26 ml) and dried in vacuo. The viscous oil was re-dissolved in dry dichloromethane (14 ml), treated with 2 drops of DMF, cooled down to −10° (ice-salt bath) and treated dropwise with oxalyl chloride (0.68 ml, 7.79 mmoles). Vigorous gas evolution was observed and the yellowish brown solution was stirred at −10° for 15 minutes then at room temperature for 1.0 hours. The reaction mixture was evaporated to dryness, azeotroped with dry benzene (26 ml) and dried in vacuo.

A solution of Part G compound (1.43 g, 4.7 mmoles) in dry tetrahydrofuran (11.5 ml) was cooled down to −78° (dry ice-acetone) under argon and treated with 1.6M n-BuLi/hexane (2.94 ml, 4.7 mmoles) and stirred at −78° for 30 minutes. The above phosphonochloridate was dissolved in dry tetrahydrofuran (11.5 ml), cooled down to −78° (dry ice-acetone) under argon and treated dropwise by cannula with a solution of the acetylenic anion, both solutions being kept at −78° throughout the addition. The reaction mixture was stirred at −78° for 30 minutes, quenched by the dropwise addition of 25% NH₄Cl (13 ml), allowed to warm up to room temperature then extracted with ether (3×130 ml). The combined organic extracts were washed with 25% NH₄Cl (15 ml), brine (30 ml), dried (anhydrous MgSO₄), filtered and evaporated to dryness.

The crude product mixture (4.3 g) was chromatographed on a silica gel column, eluting the column with acetone:hexane mixtures (5:95; 1:4). The desired fractions were combined and evaporated to dryness to give title compound as a light brown syrup (2.18 g, 62.9%) TLC: $R_f$ 0.13 (silica gel; hexane:acetone-7:3).

I. (S)-4-[[[1-(4-Fluorophenyl)-4-(1-methylethyl)-2-phenyl-1H-imidazol-5-yl]ethynyl]methoxyphosphinyl]-3-hydroxybutanoic acid, methyl ester A solution of Part H compound (974 mg, 1.32 mmoles) in dry tetrahydrofuran (13.0 ml) was treated successively with glacial acetic acid (310 μl, 5.29 mmoles) and 1M (C₄H₉)₄NF (4.14 ml, 4.14 mmoles) and stirred overnight at room temperature under argon. The reaction mixture was cooled down to 0° (ice-water bath), treated with 5% KHSO₄ (14 ml) and extracted with ethyl acetate (3×125 ml). The combined organic extracts were washed with 5% KHSO₄ (16 ml), brine (35 ml), dried (anhydrous MgSO₄), filtered and evaporated to dryness.

The crude product (1.48 g) was dissolved in a mixture of ether (22 ml) and dry tetrahydrofuran (17 ml), cooled down to 0° (ice-water bath), treated with excess diazomethane in ether and stirred at 0° for 4.0 hours. The reaction mixture was quenched by the dropwise addition of glacial acetic acid, evaporated to dryness and dried In vacuo. The crude product was chromatographed on a silica gel column, eluting the column with EtOAc:hexane mixtures (1:1; 4:1). The desired fractions were combined to give title compound as a solid (304 mg, 46.2%).

TLC: $R_f$ 0.33 (silica gel; EtOAc:hexane-4:1).

EXAMPLE 51

(S)-4-[[[1-(4-Fluorophenyl)-4-(1-methylethyl)-2-phenyl-1H-imidazol-5-yl]ethynyl]hydroxyphosphinyl]-3-hydroxybutanoic acid, dilithium salt A solution of Example 50 compound (304 mg, 0.6 mmole) in dioxane (7.1 ml) was treated with 1N LiOH (2.03 ml, 2.08 mmoles), stirred at 55° (oil bath) under argon for 1.5 hours then at room temperature for 24 hours. The reaction mixture was evaporated to dryness and dried in vacuo. The crude product was chromatographed on an HP-20 column (1"×7"), eluting the column with steam-distilled water (750 ml), 10% aqueous $CH_3OH$ (500 ml), 20% aqueous $CH_3OH$ (500 ml) and 50% aqueous $CH_3OH$ (500 ml). The desired fractions were combined, evaporated to dryness and dried in vacuo. The solid product was dissolved in steam-distilled water and lyophilized to give title compound as a fluffy solid lyophilate (257 mg, 84.1%).

Other fractions: TLC: $R_f$ 0.38 (silica gel; i-PrOH:N-$H_4OH:H_2O$-8:1:1).

Anal Calcd for $C_{24}H_{22}FLi_2N_2O_5P \cdot 1.52\ H_2O$: C, 56.56; H, 4.95; N, 5.49; F, 3.73; P, 6.08 Found: C, 56.56; H, 4.94; N, 5.32; F, 3.89; P, 5.99.

$H^1$-NMR spectrum (400 MHz, $CD_3OD$): δ1.37 (d, 6H, J=7 Hz), 1.79 (m, 2H), 2.31 (dd, 1H, J=9.15 Hz), 2.43 (dd, 1H, J=4.15 Hz), 3.24 (septet, 1H, J=7 Hz), 4.26 (m, 1H), 7.17-7.35 (m, 9H).

IR(KBr) 2163 (C≡C), 1590 (C=O) $cm^{-1}$.

EXAMPLE 52

(S)-4-[[2-[1-(4-Fluorophenyl)-4-(1-methylethyl)-2-phenyl-1H-imidazol-5-yl]ethyl]methoxyphosphinyl]-3-hydroxybutanoic acid, methyl ester A. (S)-3-[[(1,1-Dimethylethyl)diphenylsilyl]oxy]-4-[[2-[1-(4-fluorophenyl)-4-(1-methylethyl)-2-phenyl-1H-imidazol-5-yl]ethyl]methoxyphosphin-ylbutanoic acid, methyl ester A solution of Example 50 Part H compound (839 mg, 1.14 mmoles) in dry methanol (86 ml) was treated with 10% Pd/C (213 mg) and hydrogenated at room temperature on a Parr hydrogenator overnight at ~40 psi. The suspension was filtered through celite, the clear filtrate was evaporated to dryness and dried in vacuo to give title compound as a thick syrup (853 mg, 100% yield).

TLC: $R_f$ 0.17 (silica gel; hexane:acetone-7:3).

B. (S)-4-[[2-[1-(4-Fluorophenyl)-4-(1-methylethyl)-2-phenyl-1H-imidazol-5-yl]ethyl]methoxyphosphinyl]-3-hydroxybutanoic acid, methyl ester A solution of Part A compound (853 mg, ~1.14 mmoles) in dry tetrahydrofuran (11.0 ml) was treated successively with glacial acetic acid (270 μl, 4.60 mmoles) and 1.0M $(C_4H_9)_4NF$/hexane (3.62 ml, 3.62 mmoles) and stirred overnight at room temperature under argon. The reaction mixture was diluted with ice-water (25 ml) and extracted with ethyl acetate (3×100 ml). The combined organic extracts were washed with saturated $NaHCO_3$ (15 ml), brine (25 ml), dried (anhydrous $MgSO_4$), filtered and evaporated to dryness.

The crude product (958 mg) was chromatographed on a silica gel column, eluting the column with acetone:hexane mixtures (1:1, 4:1). The desired fractions were combined, evaporated to dryness and dried in vacuo to give title compound as a solid (443 mg, 77.0%).

TLC: $R_f$ 0.13 (silica gel; acetone:hexane-1:1).

EXAMPLE 53

(S)-4-[[2-[1-(4-Fluorophenyl)-4-(1-methylethyl)-2-phenyl-1H-imidazol-5-yl]ethyl]hydroxyphosphinyl]-3-hydroxybutanoic acid, dilithium salt A solution of Example 52 compound (443 mg, 0.88 mmole) in dioxane (10.5 ml) was treated with 1.0N LiOH (3.05 ml, 3.09 mmoles) and stirred at 55° (oil bath) under argon for 3.0 hours then at room temperature for ~20 hours. The reaction mixture was evaporated to dryness and dried in vacuo. The crude product was chromatographed on an HP-20 column (1"×8"), eluting the column with steam-distilled water (750 ml), 10% aqueous $CH_3OH$ (500 ml), 20% aqueous $CH_3OH$ (500 ml) and 50% aqueous $CH_3OH$. The desired fractions were combined and evaporated to dryness. The resulting solid was dissolved in steam-distilled water (30 ml) and lyophilized to give title compound as a fluffy white solid (376.4 mg, 83.9%).

TLC: $R_f$ 0.40 (silica gel; i-PrOH:$NH_4OH:H_2O$-8:1:1)

Anal Calcd for $C_{24}H_{26}FLiH_2N_2O_5P \cdot 0.84\ H_2O$ (Eff. mol. wt.=501.46): C, 57.43; H, 5.76; N, 5.69; F, 3.99; P, 6.08. Found: C, 57.48; N, 5.56; N, 5.59; F, 3.79; P, 6.18.

IR(KBr) (1587 $cm^{-1}$, C=O COO-). $H^{-1}$-NMR spectrum (400 MHz, $CD_3OD$): δ1.33 (d, 6H, J=7 Hz), 1.46-1.61 (m, 4H), 2.30 (m, 2H), 2.76 (m, 2H), 3.13 (septet, 1H, J7 Hz), 4.14 (m, 1H), 7.17-7.30 (m, 9H).

EXAMPLE 54

(S)-4-[[[2-(Cyclohexylmethyl)-4,6-dimethylphenyl]ethynyl]hydroxyphosphinyl]-3-hydroxybutanoic acid, dilithium salt A. N-(2,4-Dimethylbenzylidene)benzeneamine Ref. Merck U.S. Pat. No. 4,375,475, pg. 39.

The title compound was prepared as described in Example 1 Part A.

B.

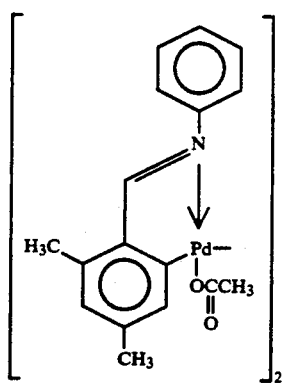

Ref. Merck U.S. Pat. No. 4,375,475, pg. 39.

The title Pd-complex was prepared as described in Example 1 Part B.

C. 2-[(Cyclohexylmethyl)-4,6-dimethylbenzaldehyde

Magnesium turnings (1.44 g, 59.45 mmol) under argon atmosphere were covered with 15 ml of dry $Et_2O$ and sonicated for 5 minutes. Cyclohexylmethylbromide (1.5 ml) was added to the Mg°-turnings and sonication was continued (refluxing began within minutes). Simultaneously via addition funnel 60 ml of dry $Et_2O$ and a 5 ml $Et_2O$ solution of the remainder of the cyclohexylmethylbromide was added with continued sonication (a total of 9.12 ml, 65.3 mmole of cyclohexylmethylbromide was added). After addition was complete, sonication was continued for 15 minutes and then the reaction was refluxed for 40 minutes. This Grignard reagent was cooled to room temperature and then added via cannula to a solution of the Part B Pd-complex (5.55 g, 7.43 mmol) and triphenylphosphine (15.59 g, 59.45 mmol) which had been stirring for 30 minutes under argon atmosphere and at room temperature. Upon the addition of the Grignard reagent the reaction became green and a precipitate formed. This reaction solution was stirred at room temperature for 2 hours followed by the addition of 37 ml of 6N HCl. This mixture was stirred for 1 hour and then filtered through a celite pad in a sintered glass funnel in order to remove solids. The solid was washed with Et$_2$O and the filtrate was rotavapped to remove volatiles. The resulting residue was stirred in Et$_2$O and filtered as above. The filtrate was washed once with saturated NaCl solution, and the organic layer was dried over MgSO$_4$; 14.5 g of a brown oil was obtained. Purification by flash chromatography, eluting with 4% Et$_2$O/hexane gave 1.70 g of a clear oil, 99% yield.

TLC: R$_f$=0.30 (5% Et$_2$O/hexane, silica gel).

IR (CHCl$_3$) 3030, 3008, 2926, 2853, 1679, 1606, 1448, 1147 cm$^{-1}$.

$^1$H NMR (270 MHz-CDCl$_3$): $\delta$10.51 (s, 1), 6.90 (s, 1), 6.85 (s, 1), 2.80 (d, 2, J=6.0 Hz), 2.55 (s, 3), 2.30 (s, 3), 1.80–1.55 (m, 5), 1.55–1.30 (m, 1), 1.30–0.80 (m, 5).

Mass Spec (CI) m/e 231 (M+H)$^+$.

D. 1-(Cyclohexylmethyl)-2-(2,2-dibromoethenyl)-3,5-dimethylbenzene

Part C aldehyde (1.68 g, 7.30 mmol) in 65 ml of dry CH$_2$Cl$_2$ under argon atmosphere was cooled to 0° C. To this solution was added triphenylphosphine (6.13 g, 23.4 mmol) and the solution was stirred until all of the solid was dissolved. At 0° C., CBr$_4$ (3.63 g, 11.0 mmol) was added as a 20 ml CH$_2$Cl$_2$ solution. The reaction solution became orange. The reaction was stirred at 0° C. for 1.5 hours, then quenched with saturated NaHCO$_3$ solution and stirred vigorously. The aqueous layer was removed and extracted 2 times with CH$_2$Cl$_2$. The organic solutions were combined, washed once with saturated NaHCO$_3$ solution, and dried over MgSO$_4$. Filtration and solvent removal gave 9.6 g of a brown solid. Purification by flash chromatography eluting with 100% hexane gave 2.52 g, 90% yield, of a clear oil.

TLC 0.62 (5% Et$_2$O/hexane, silica gel) PMA.

IR (CHCl$_3$) 2925, 2852, 1608, 1472, 869 cm$^{-1}$.

$^1$H NMR (270 MHz, CDCl$_3$); $\delta$7.39 (s, 1), 6.87 (s, 1), 6.80 (s, 1), 2.37 (d, 2, J=6.3 Hz), 2.27 (s, 3), 2.24 (s, 3), 1.70 (m, 5), 1.45 (m, 1), 1.38–1.10 (m, 3), 0.90 (m, 2).

Mass. Spec. (CI) m/e 387 (M+H)$^+$.

E. 1-(Cyclohexylmethyl)-2-ethynyl-3,5-dimethylbenzene

The Part D vinyl dibromide (2.51 g, 6.5 mmol) under argon atmosphere was stirred with THF (30 ml) and cooled to $-78$° C. To the dibromide solution at $-78$° C. was added n-butyllithium (5.20 ml of 2.5M solution in Hexane) over 3 minutes. The resulting pink reaction mixture was stirred at $-78$° C. After 1.5 hours at $-78$° C., the reaction was quenched with saturated aqueous NH$_4$Cl solution and then warmed to room temperature. The aqueous layer was removed and extracted twice with Et$_2$O and once with hexane. All of the organic layers were combined and dried over MgSO$_4$ to give 1.65 g of a brown oil after filtration and solvent removal. Purification by flash chromatography eluting with hexane gave 1.39 g, 95% yield, of title acetylene.

TLC 0.50 (5% toluene/hexane, silica gel), PMA.

IR (CHCl$_3$) 3305, 3007, 2924, 2852, 2096, 1607, 1470, 1448 cm$^{-1}$.

$^1$H NMR (270 MHz, CDCl$_3$); $\delta$6.86 (s, 1), 6.79 (s, 1), 3.39 (s, 1), 2.63 (d, 2, J=6.9 Hz), 2.63 (m, 6), 1.20 (m, 3), 1.00 (m, 2).

Mass Spec (CI) m/e 227 (M+H)$^+$.

F. (S)-4-[[[2-(Cyclohexylmethyl)-4,6-dimethylphenyl]ethynyl]methoxyphosphinyl]-3-[[(1,1-dimethylethyl)diphenylsilyl]oxy]butanoic acid, methyl ester Part E acetylene (1.36 g, 6.0 mmol) in 30 ml of dry THF under argon atmosphere was cooled to $-78$° C. To this solution was added n-BuLi (2.4 ml, of 2.5M solution in hexane); the reaction solution became a burgundy color, stirred for 1 hour at $-78$° C. Example 1 Part F phosphonochloridate (4.68 g, 9.6 mmol) was stirred with 30 ml of dry THF and cooled to $-78$° C. The acetylenic anion was then cannulated into the phosphonochloridate solution over 15 minutes. After the transfer was complete, the reaction was stirred at $-78$° C. for 1 hour, then quenched with saturated aqueous NH$_4$Cl and warmed to room temperature. The THF was removed from the reaction mixture, and the resulting material was dissolved with Et$_2$O and H$_2$O. The aqueous layer was extracted 3 times with Et$_2$O. All the Et$_2$O extracts were combined and washed once with saturated NaHCO$_3$ solution and once with brine, then dried over MgSO$_4$. Filtration and solvent removal gave an orange oil which was purified by flash chromatography eluting with 3.5:5.5:1/EtOAc:Hexane:toluene. The title acetylenic phosphinate (2.80 g, 70% yield) was obtained as a clear oil.

TLC R$_f$=0.37 (5:1:4/Hexane:toluene:EtOAc, silica gel) PMA.

IR (CHCl$_3$) 3025, 3001, 2929, 2856, 2164, 1736, 1607, 1240, 1112, 1039, 823 cm$^{-1}$.

$^1$H NMR (270 MHz, CDCl$_3$): $\delta$7.66 (m, 4), 7.30 (m, 6), 6.87 (s, 1), 6.81 (s, 1), 4.66 (m, 1), 3.70 and 3.66 (d's, 3, J=14.3 Hz), 3.56 (s, 3), 2.95 (m, 1), 2.69 (m, 1), 2.50 (m, 3), 2.32 (m, 2), 2.30 (s, 3), 2.27 (s, 3), 1.60 (m, 6), 1.03 (m, 3), 1.02 (s, 9), 0.95 (m, 2).

Mass Spec (CI) m/e 659 (M+H)$^+$.

G. (S)-4-[[[2-(Cyclohexylmethyl)-4,6-dimethylphenyl]ethynyl]methoxyphosphinyl]-3-hydroxybutanoic acid, methyl ester The Part F acetyleneic phosphinate (0.633 g, 0.96 mmol) was stirred under argon atmosphere at room temperature with 14.0 ml of dry THF. Glacial acetic acid (0.22 ml, 3.84 mmol) was added to the phosphinate solution followed by the dropwise addition over 5 minutes of n-Bu$_4$NF (2.62 ml of 1.1M THF solution). After stirring for 19 hours at room temperature, the reaction was quenched with ice water, and the aqueous layer was extracted 3 times with EtOAc. The combined organic solutions were washed 2 times with saturated aqueous NaHCO$_3$ solution and once with saturated NaCl solution. The organic layer was dried over Na$_2$SO$_4$ and filtered to give a yellow gum (0.658 g) after solvent removal. Purification by flash chromatography eluting with EtOAc provided the title alcohol (0.23 g, 65%) as a clear oil.

TLC R$_f$=0.51 (6:4 Acetone/hexane, silica gel) PMA.

IR (CHCl$_3$) 3450 (br), 3005, 2926, 2852, 2164, 1733, 1607, 1448, 1439, 1039 cm$^{-1}$.

$^1$H NMR (270 MHz, CDCl$_3$): $\delta$6.89 (s, 1), 6.82 (s, 1), 4.63 (m, 1), 3.88 and 3.87 (2 d's, 3, J=12 Hz), 3.69 (s, 3), 2.70 (s, 2), 2.62 (d, 2, J=6.3 Hz), 2.43 (s, 3), 2.32 (s, 3), 2.27 (m, 2), 1.65 (m, 6), 1.19 (m, 3), 1.00 (m, 2).

Mass Spec (CI) m/e 421 (M+H)+.

H. (S)-4-[[[2-(Cyclohexylmethyl)-4,6-dimethylphenyl]ethynyl]hydroxyphosphinyl]-3-hydroxybutanoic acid, dilithium salt The Part G diester (0.212 g, 0.51 mmol) was stirred in dioxane (7 ml) and 1.5 ml of 1N LiOH (1.5 mmol) was added at room temperature. The reaction was warmed to 55° C. and after 20 minutes the resulting precipitate was solubilized by adding 5 ml of dioxane and 4 ml of H$_2$O. After 2 hours 30 minutes at 55° C., the reaction was cooled to room temperature, the solvent was removed under reduced pressure, and the resulting white solid was placed under vacuum for 15 minutes. The product was purified on a 3.0×19 cm column of HP-20 resin eluting first with 100 ml of H$_2$O followed by 1:1 MeOH/H$_2$O. Lyophilization of product Fr's gave 0.145 g (71%) of a white lyophilate.

R$_f$=0.39 (7:2:1 nPrOH/NH$_4$OH/H$_2$O, silica gel) PMA.

IR (KBr) 3700–3100 (br), 2922, 2850, 2167, 1590, 1447, 1179, 1076 cm$^{-1}$.

$^1$H NMR (400 MHz, D$_2$O): δ6.99 (s, 1), 6.94 (s, 1), 4.53 (m, 1), 2.64 (m, 1), 6.22 (d, 2, J=6.2 Hz), 2.39 (s, 3), 2.37 (m, 1), 2.26 (s, 3), 2.02 (m, 2), 1.60 (m, 6), 1.14 (m, 3), 1.00 (m, 2).

Mass Spec (FAB) m/e 409 (M+H)+, 397 (M-2Li+H)+.

Anal Calcd for C$_{21}$H$_{27}$O$_5$P Li$_2$.1.72 H$_2$O: C, 57.96; H, 7.05; P, 7.12. Found: C, 57.96; H, 7.18; P, 6.96.

EXAMPLE 55

4-[[2-[2-(Cyclohexylmethyl)-4,6-dimethylphenyl]ethenyl]hydroxyphosphinyl]-3-hydroxybutanoic acid, dilithium salt A. (E)-[2-[2-(Cyclohexylmethyl)-4,6-dimethylphenyl]ethenyl]phosphonic acid, dimethyl ester Dimethylmethylphosphonate (1.64 g, 13.2 mmol) in dry THF (20 ml) under argon atmosphere was cooled to −78° C. To this solution at −78° C. was added n-butyl lithium (5.0 ml, 2.5M solution in hexane, 12.4 mmol) over 5 minutes. After the addition was complete, the milky white reaction mixture was stirred for 1 hour. To the anion solution at −78° C., a 10 ml THF solution of the Example 54 Part A aldehyde (1.9 g, 8.26 mmol) was added via addition funnel over 10 minutes. After stirring for 35 minutes at −78° C., the reaction was quenched with saturated aqueous NH$_4$Cl (8 ml) and then allowed to warm to room temperature. The organic layer was removed and the aqueous layer was extracted 3 times with EtOAc. The organics were combined and washed once with brine and dried over Na$_2$SO$_4$. Filtration and solvent removal gave 3.25 g of a yellow oil.

The above yellow oil (3.25 g) was dissolved in dry toluene and refluxed through a soxhlet extractor containing 4 Å molecular sieves. p-Toluenesulfonic acid.-H$_2$O (0.080 g, 0.42 mmol) was added at time 0, 3.5 and 18 hours. After 22 hours at reflux, the reaction was cooled to room temperature, and the toluene was removed in vacuo. The resulting yellow residue in EtOAc was washed twice with saturated NaHCO$_3$ solution, dried over Na$_2$SO$_4$ and filtered to give a yellow oil (A) after solvent removal.

The aqueous solution was acidified with concentrated HCl, extracted 3 times with EtOAc, dried over MgSO$_4$, filtered and solvent removed to give 0.535 g of a yellow oil. This yellow oil was then refluxed in 6.0 ml of HC(OCH$_3$)$_3$ for 24 hours followed by removal of excess HC(OCH$_3$)$_3$ under vacuum. This material was combined with yellow oil (A) and purified by flash chromatography eluting with 80% EtOAc/hexane. The title vinyl phosphonate (2.07 g, 73%) was obtained as a white solid.

TLC R$_f$=0.45 (1:1 Acetone/hexane, silica gel) PMA.

IR(KBr) 2921, 2851, 1623, 1447, 1243, 1186, 1060, 1027 cm$^{-1}$.

$^1$H NMR (270 MHz, CDCl$_3$); δ7.65 (dd, 1, J=23.6 Hz, 18.1 Hz), 6.88 (s, 1), 6.82 (s, 1), 5.80 (dd, 1, J=21.0 Hz, 18.1 Hz), 3.79 (d, 6, J=11.5 Hz), 2.49 (d, 2, J=7.2 Hz), 2.29 (s, 3), 2.28 (s, 3) 1.65 (m, 5), 1.45 (m, 1), 1.25–0.80 (m, 5).

Mass Spec (CI) m/e 337 (M+H)+.

B. (E)-[2-[2-(Cyclohexylmethyl)-4,6-dimethylphenyl]ethenyl]phosphonic acid, methyl ester Part A vinyl phosphonate (2.07 g, 6.16 mmol) was stirred with 14 ml of dioxane at room temperature. To this solution was added 1.0N LiOH (9.24 ml, 9.24 mmol), and this mixture was warmed to 75° C. After 3.5 hours at 75° C., the reaction was cooled to room temperature, and the dioxane was removed in vacuo. The resulting residue was stirred with H$_2$O and acidified to pH∼2 with 1N HCl. The aqueous solution was extracted 3 times with EtOAc, dried over Na$_2$SO$_4$, filtered and solvent removed to give 1.95 g of off-white solid. TLC R$_f$=0.58 (8:1:1/CH$_2$Cl$_2$:CH$_3$OH:AcOH, silica gel), PMA.

$^1$H NMR (270 MHz, CDCl$_3$): δ12.11 (s, 1), 7.61 (dd, 1, J=24.17 Hz, 17.58 Hz), 6.87 (s, 1), 6.81 (s, 1), 5.88 (dd, 1, J=21.43 Hz, 17.58 Hz), 3.78 (d, 3, J=11.54 Hz), 2.47 (d, 2, J=6.6 Hz), 2.29 (s, 3), 2.28 (s, 3), 1.65 (m, 5), 1.45 (m, 1), 1.15 (m, 3), 0.95 (m, 2).

C. (E)-4-[[2-[2-(Cyclohexylmethyl)-4,6-dimethylphenyl]ethenyl]methoxyphosphinyl]-3-oxobutanoic acid, methyl ester The Part B monomethyl phosphonate (1.95 g, 6.06 mmol) in 50 ml of dry CH$_2$Cl$_2$ was stirred at room temperature under argon atmosphere with (C$_2$H$_5$)$_2$NSi(CH$_3$)$_3$ (1.76 g, 12.1 mmol) for 1 hour 25 minutes. The CH$_2$Cl$_2$ was removed in vacuo, and the resulting yellow oil was azeotroped once with benzene and placed under high vacuum for 20 minutes. This oil was then dissolved in dry CH$_2$Cl$_2$ (50 ml) under argon atmosphere and cooled to 0° C. Two drops of dry DMF were added followed by slow dropwise addition of oxalylchloride (0.92 g, 7.27 mmol):gas evolution was observed. The reaction was stirred for 15 minutes at 0° C. then warmed to room temperature and stirred for 1 hour. The CH$_2$Cl$_2$ was removed in vacuo from the reaction mixture, and the resulting orange oil was azeotroped twice with dry benzene and pumped under high vacuum for 1 hour thus giving the phosphonochloridate.

The dianion of methylacetoacetate was prepared as follows. Pentane washed NaH (0.25 g oil dispersion, 8.7 mmol) in dry THF (10 ml) under argon atmosphere was cooled to 0° C. Methyl acetoacetate (0.92 g, 7.9 mmol) was added to the NaH suspension as a 10 ml THF solution and stirred for 20 minutes, and then n-butyllithium (2.90 ml, 2.5M in hexane, 7.3 mmol) was added followed by stirring for 45 minutes. The dianion solution was cooled to −78° C. and a 10 ml THF solution of the above prepared phosphonochloridate was cooled to −78° C. and added to the dianion solution over 15 minutes. After stirring at −78° C. for 30 minutes, the reaction was quenched with saturated aqueous NH$_4$Cl solution and warmed to room temperature. The THF was removed from the reaction mixture, and the resulting orange oil was taken up in 1:1 EtOAc/H$_2$O. The aqueous layer was extracted 3 times with EtOAc. The combined EtOAc extracts were combined and washed 2 times with saturated NaHCO$_3$ solution and once with saturated NaCl solution, then dried over Na$_2$SO$_4$. Purification of the crude product (2.75 g) by flash chromatography eluting with EtOAc gave the title keto ester (0.97 g, 42%) as a yellow oil. TLC R$_f$=0.24 (EtOAC, silica gel) PMA.

$^1$H NMR (270 MHz, CDCl$_3$): δ7.71 (dd, 1, J=22.52 Hz, 18.13 Hz), 6.89 (s, 1), 6.83 (s, 1) 5.89 (dd, 1, J=26.37 Hz, 17.58 Hz), 3.79 (s, 2), 3.73 (s(br), 6), 3.36 (dd, 2, J=18.68 Hz, 5.5 Hz), 2.50 (m, 2), 2.30 (s, 3), 2.29 (s, 3), 1.70 (m, 5), 1.45 (m, 1), 1.10–0.80 (m, 5).

D. 4-[[2-[2-(Cyclohexylmethyl)-4,6-dimethylphenyl]ethenyl]methoxyphosphinyl]-3-hydroxybutanoic acid, methyl ester The Part C β-keto phosphonate (0.97 g, 2.31 mmol) was stirred in THF (10 ml) under argon atmosphere and cooled to 0° C. Solid NaBH$_4$ (0.087 g, 2.31 mmol) was added to the THF solution followed by the dropwise addition of 2 ml of CH$_3$OH; gas evolution resulted. After stirring for 50 minutes at 0° C., the reaction was quenched with 2 ml of acetone followed by the addition of CC-4 silica gel. The reaction was warmed to room temperature and filtered through sintered glass. The solvent was removed from the filtrate to give a yellow oil which was purified by flash chromatography eluting with EtOAc. The title alcohol was obtained as a clear oil (0.65 g, 66%).

TLC R$_f$=0.29 (50% Acetone/hexane, silica gel), PMA.

M.P. 80°–83° C.

IR (KBr) 3282 (br), 2923, 2918, 2848, 1743, 1614, 1450, 1442, 1080, 1045 cm$^{-1}$.

$^1$H NMR (270 MHz, CDCl$_3$): δ7.68 (m, 1), 6.88 (s, 1), 6.82 (s, 1), 5.89 (m, 1), 4.50 (m, 1), 4.00 (m, 1), 3.77 and 3.74 (2 d's, 3, J=11.0 Hz), 3.69 and 3.68 (2 s's, 3), 2.65 (d, 2, J=6.0 Hz), 2.50 (m, 2), 2.30 (S(br),3), 2.28 (s, 3), 2.15 (m, 2), 1.68 (m, 5), 1.45 (m, 1), 1.30 to 0.80 (m, 5).

Mass Spec (CI) m/e 423 (M+H)$^+$.

E. 4-[[2-[2-(Cyclohexylmethyl)-4,6-dimethylphenyl]ethenyl]hydroxyphosphinyl]-3-hydroxybutanoic acid, dilithium salt Part D diester (0.565 g, 1.33 mmol) was stirred with 14 ml of dioxane until all of the solid went into solution. 1.0N LiOH (4.0 ml) was added and the solution warmed to 55° C. After 30 minutes, the reaction became turbid. After 2 hours at 55° C., the reaction was cooled to room temperature, and the solvent was removed on the rotavap to give a white solid. The crude product was purified on a 3.0×15 cm column of HP-20 resin eluting first with 100 ml of H$_2$O followed by 75% MeOH/H$_2$O. Lyophilization of product fractions gave title compound in the form of a white lyophilate (0.524 g, 98%).

TLC R$_f$=0.41 (7:2:1 nPrOH/NH$_4$OH/H$_2$O, silica gel) PMA.

IR (KBr) 3700–3100 (br), 2921, 2851, 1591, 1446, 1222, 1195, 1161, 1051 cm$^{-1}$.

$^1$H NMR (400 MHz, D$_2$O) δ7.25 (dd, 1, J=18.68 Hz), 6.98 (s, 1), 6.94 (s, 1), 6.00 (dd, 1, J=17.95 Hz), 4.33 (m, 1), 2.53 (dd, 1, J=15.0 Hz, 4.4 Hz), 2.49 (d, 2, J=7.0 Hz), 2.36 (dd, 1, J=15.0 Hz, 8.43 Hz), 2.27 (s, 3), 2.25 (s, 3), 1.89 (dd, 2, J=14.3 Hz, 6.6 Hz), 1.60 (m, 5), 1.45 (m, 1), 1.13 (m, 3), 0.95 (m, 2).

Mass Spec. (FAB) m/e 407 (M+H)$^+$, 347 (M+-2 Li$^+$+2H).

Anal Calcd for C$_{21}$H$_{29}$O$_5$PLi$_2$.0.38 H$_2$O: C, 61.03; H, 7.45; P, 7.49. Found: C, 61.03; H, 7.63; P, 7.66.

EXAMPLE 56

(S)-4-[[2-[2-(Cyclohexylmethyl)-4,6-dimethylphenyl]ethyl]hydroxyphosphinyl]-3-hydroxybutanoic acid, dilithium salt A. 4-[[[2-(Cyclohexylmethyl)-4,6-dimethylphenyl]ethyl]methoxyphosphinyl]-3-[[(1,1-dimethylethyl)diphenylsilyl]oxy]butanoic acid, methyl ester Argon was bubbled through a 45 ml methanol solution of Example 54 Part F acetylenic phosphinate (1.33 g, 2.02 mmol) for 10 minutes. To this methanol solution in a Parr bottle was added 10% Pd/C (0.34 g). Hydrogenation on a Parr apparatus at 40 psi for 20 hours gave 1.39 g of an oil after filtration through a celite pad in a sintered glass funnel. Purification by flash chromatography eluting with 1:1 EtOAc/hexane gave the title phosphinate (1.25 g, 94%) as a clear oil.

TLC R$_f$=0.21 (5/4/1 Hexane/EtOAc/toluene, silica gel) PMA.

IR (CHCl$_3$) 3600–3200 (br), 3003, 2925, 2853, 1731, 1448, 1440, 1247, 1233, 1179, 1044 cm$^{-1}$.

$^1$H NMR (270 MHz, CDCl$_3$): δ6.83 (s, 1), 6.78 (s, 1), 4.50 (m, 1), 3.80 and 3.77 (2 d's, 3, J=6.3 Hz), 3.72 and 3.71 (2 s's, 3), 3.38 (m, 1), 2.87 (m, 1), 2.60 (m, 2), 2.45 (d, 2, J=6.9 Hz), 2.29 and 2.28 (2 s's, 3), 2.25 (s, 3), 2.00 (m, 4), 1.70 (m, 6), 1.45 (m, 1), 1.30–0.90 (m, 6).

Mass Spec (EI) m/e 424 (M)$^+$.

B. (S)-4-[[2-[2-(Cyclohexylmethyl)-4,6-dimethylphenyl]ethyl]methoxyphosphinyl]-3-hydroxybutanoic acid, methyl ester A solution of the Part A silyl ether (1.2 g, 1.8 mmol) in THF (20 ml) was stirred under argon atmosphere at room temperature. To this solution was added sequentially 0.41 ml of glacial acetic acid and n-Bu$_4$NF (5.0 ml of a 1.1M THF solution, 5.44 mmol) which was added dropwise over 5 minutes. After stirring for 23 hours at room temperature, the reaction was quenched with 50 ml of ice water and stirred vigorously. The THF was removed in vacuo, and the resulting material was diluted with water and extracted 3 times with EtOAc. The EtOAc extract was washed 2 times with saturated NaHCO$_3$ solution and once with brine then dried over Na$_2$SO$_4$. Filtration and solvent removal gave a clear oil (1.3 g). The product was purified by flash chromatography with 100% EtOAc to give the title alcohol (0.55 g, 72%) as a clear oil.

R$_f$=0.22 (EtOAc, silica gel) PMA.

IR (CHCl$_3$) 2999, 2950, 2929, 2856, 1734, 1244, 1195, 1183, 1112, 1105, 1065, 1043 cm$^{-1}$.

$^1$H NMR (270 MHz, CDCl$_3$): δ7.65 (m, 4), 7.28 (m, 6), 6.81 (s, 1), 6.76 (s, 1), 4.51 (m, 1), 3.62 and 3.60 (2 d's, 3, J=5.3 Hz), 3.49 and 3.46 (2 s's, 3), 2.97 (m, 1), 2.65 (m, 2), 2.35 and 2.33 (2 d's, 2, J=6.9 Hz), 2.25 (2 s's, 3), 2.16 (2 s's, 3), 1.84 (m, 1), 1.68 (m, 6), 1.55 (m, 1), 1.18 (m, 2), 1.15 (m, 3), 1.00 and 0.99 (2 s's, 9), 0.91 (m, 2).

Mass Spec (CI) m/e 663 (M+H)$^+$.

C. (S)-4-[[2-[2-(Cyclohexylmethyl)-4,6-dimethylphenyl]ethyl]hydroxyphosphinyl]-3-hydroxybutanoic acid, dilithium salt Part B diester (0.552 g, 1.3 mmol) was stirred in 14 ml of dioxane at room temperature. To this solution was added 1.0N LiOH (3.9 ml, 3.9 mmol) and then the reaction was warmed to 55° C. After stirring for 30 minutes a cake-like precipitate formed which was solubilized by adding 5 ml of H$_2$O. After 2 hours 15 minutes at 55° C., the reaction was cooled to room temperature, and the volatiles were removed in vacuo leaving a white solid. The product was purified on a 3.0×30 cm HP-20 column eluting first with 100 ml of H$_2$O followed by 1:1 CH$_3$OH/H$_2$O. Product fractions were lyophilized to give 0.482 g, 92% yield of white lyophilate.

TLC R$_f$=0.36 (7:2:1 n-PrOH/NH$_4$OH/H$_2$O, silica gel) PMA.

IR (KBr) 3700-3100 (br), 2923, 2852, 1588, 1446, 1410, 1159, 1132, 1048 cm$^{-1}$.

$^1$H NMR (400 MHz, D$_2$O): δ6.93 (s, 1), 6.91 (s, 1), 4.34 (m, 1), 2.80 (m, 2), 2.50 (dd, 1, J=14.7 Hz, 4.4 Hz), 2.48 (d, 2, J=5.12 Hz), 2.38 (dd, 1, J=15.0 Hz, 6.6 Hz), 2.29 (s, 3), 2.26 (s, 3), 1.84 (m, 2), 1.65 (m, 7), 1.48 (m, 1), 1.15 (m, 3), 1.00 (m, 2).

Mass Spec (FAB) m/e 397 (M+H-2L+)+, 409 (M+H)+.

Anal Calcd for C$_{21}$H$_{31}$O$_5$PLi$_2$.0.76 H$_2$O: C, 59.76; H, 7.77; P, 7.34. Found: C, 59.76; H, 7.91; P, 7.53.

EXAMPLE 57

4-[[[[4'-Fluoro-3,3',5-trimethyl[1,1'-biphenyl]-2-yl]oxy]methyl]hydroxyphosphinyl]-3-hydroxybutanoic acid, dilithium salt A. 4'-Fluoro-3,3',5-trimethyl[1,1'-biphenyl]-2-carboxaldehyde Ref. Merck U.S. Pat. No. 4,375,475, pp. 37 and 38.

The title compound was prepared as described in Example 1 Parts A to C.

B. 4'-Fluoro-3,3',5-trimethyl[1,1'-biphenyl]-2-methanol

Part A aldehyde (1.03 g, 4.26 mmol) was stirred in 30 ml of dry CH$_2$Cl$_2$ under argon atmosphere. A 20 ml CH$_2$Cl$_2$ solution of m-Cl-perbenzoic acid (1.06 g, 5.11 mmol) was added dropwise over 15 minutes to the aldehyde solution at room temperature. After stirring for 58 hours at room temperature, the reaction mixture was rotavapped to dryness, and the resulting yellow solid was dissolved in THF and treated with 6.4 ml of 2N KOH. This mixture was stirred at room temperature for 5.5 hours, then the THF was removed from the reaction. The resulting residue was diluted with H$_2$O and the aqueous solution was extracted 3 times with Et$_2$O which was then dried over MgSO$_4$. The crude yellow oil obtained after filtration and solvent removal was purified by flash chromatography eluting with 5% Et$_2$O/hexane. The title phenol was obtained as white solid (0.843 g, 100%).

TLC R$_f$=0.37 (10% Et$_2$O/hexane, silica gel) PMA M.P. 83°-86° C.

IR (KBr) 3512, 3500 (br), 2950, 1504, 1482, 1238, 1231, 1215 cm$^{-1}$.

$^1$H NMR (270 MHz, CDCl$_3$): δ7.20 (m, 2), 7.07 (t, 1, J=9.0 Hz), 6.92 (s, 1), 6.82 (s, 1), 4.95 (s, 1), 2.31 (s, 3), 2.25 (s, 6).

Mass Spec (CI) m/e 231 (M+H)+.

C. [[[4'-Fluoro-3,3',5-trimethyl[1,1'-biphenyl]-2-yl]oxy]methyl]phosphonic acid, diethyl ester A suspension of pentane washed NaH (0.30 g 80% oil disp, 10.3 mmol) in 15 ml of dry DMF under argon atmosphere was cooled in an ice bath. A 10 ml DMF solution of the Part B phenol (2.36 g, 10.3 mmol) was added to the NaH suspension over 15 min:gas evolution was observed. After the addition was complete, the reaction was warmed to room temperature and stirred for 35 minutes. At room temperature, an 11 ml DMF solution of the diethyl tosyloxy methylphosphonate (3.31 g, 10.26 mmol, for prep. see Holy, A., Rosenberg, I., Collection Czechoslovak Chem. Commun., Vol. 47, 1982) was added dropwise over 10 minutes. After 22 hours at room temperature, the reaction was quenched with saturated aqueous NH$_4$Cl solution and the DMF was removed in vacuo. The resulting solid was dissolved in EtOAc and H$_2$O, and the aqueous layer was washed 2 times with EtOAc. The combined EtOAc extracts were washed with saturated aqueous NaHCO$_3$ solution and brine then dried over MgSO$_4$. Filtration and solvent removal gave 4.3 g of crude title ether compound which was purified by flash chromatography eluting with 70% EtOAc/hexane. The title ether (3.2 g, 82%) was obtained as a clear oil.

TLC 0.52 (50% Acetone/hexane, silica gel) PMA.

IR (Film) 2983, 2925, 2910, 1504, 1474, 1213, 1032, 971 cm$^{-1}$.

$^1$H NMR (270 MHz, CDCl$_3$): δ7.33 (m, 2), 7.01 (t, 1, J=10.0 Hz), 6.96 (s, 1), 6.91 (s, 1), 4.07 (m, 4), 3.69 (d, 2, J=9.3 Hz), 2.34 (s, 3), 2.31 (d, 3, J=1.7 Hz), 2.29 (s, 3), 1.31 (t, 6, J=7.0 Hz).

Mass Spec (CI) m/e 381 (M+H)+, 242 (M+-C$_4$H$_{10}$PO$_3$)+.

D. [[[4'-Fluoro-3,3,5'-trimethyl[1,1'-biphenyl]-2-yl]oxy]methyl]phosphonic acid, monoethyl ester Part C diester (3.21 g, 8.45 mmol) in 40 ml of dioxane was stirred with 12.7 ml of 1N LiOH (12.67 mmol) at 70° C. After 3 hours at 70° C., the reaction was cooled to room temperature and the dioxane was removed in vacuo. The aqueous solution was diluted with H$_2$O and cooled in an ice bath, then acidified to pH~1 with 6N HCl leaving a milky white solution. This solution was then extracted 3 times with EtOAc; the EtOAc extract was dried over MgSO$_4$ and filtered to give 3.12 g of a clear gum.

TLC R$_f$=0.20 (9/0.5/0.5 CH$_2$Cl$_2$/AcOH/MeOH, silica gel) PMA.

$^1$H NMR (270 MHz, CDCl$_3$): δ10.26 (s, 1), 7.35 (2), 6.96 (m, 3), 4.05 (dq, 2, J=7.14 Hz, 14.8 Hz), 3.63 (d, 2, J=9.34 Hz), 2.31 (s, 3), 2.29 (s, 3), 2.28 (d, 3, J=2.2 Hz), 1.28 (t, 3, J=7.14 Hz).

E. 4-[Ethoxy[[[4'-fluoro-3,3',5-trimethyl[1,1'-biphenyl]-2-yl]oxy]methyl]phosphinyl]-3-oxobutanoic acid, methyl ester The Part D phosphonic acid (2.96 g, 8.42 mmol) in 75 ml of dry CH$_2$Cl$_2$ under argon atmosphere was stirred at room temperature with (C$_2$H$_5$)$_2$Si(CH$_3$)$_3$ (2.44 g, 16.84 mmol). After stirring for 1 hour 10 min, the CH$_2$Cl$_2$ was removed in vacuo and the resulting oil was azeotroped once with benzene, then placed under high vacuum for 15 minutes. This oil was dissolved in 75 ml of dry CH$_2$Cl$_2$ and cooled to 0° C. under argon atmosphere. Three drops of dry DMF were added to the cooled solution followed by dropwise addition of oxalyl chloride (1.18 g, 9.26 mmol). The reaction was stirred at 0° C. for 20 minutes, warmed to room temperature and stirred for an additional hour. The reaction solvent was removed in vacuo and the maroon oil phosphonochloridate was azeotroped 2 times with benzene then placed under high vacuum for 1 hour.

The dianion of methylacetoacetate was prepared as described in Example 55 Part C [methylacetoacetate (1.27 g, 10.95 mmol), NaH (0.350 g oil disp., 12.05 mmol), n-butyllithium (4.0 ml of 2.5M solution in hexane, 10.07 mmol), THF (35 ml)].

The above prepared phosphonochloridate in 10 ml of THF, cooled to −78° C., was added dropwise over 20 minutes to the dianion solution also at −78° C. After stirring at −78° C. for 40 minutes, the reaction was quenched at −78° C. with saturated aqueous NH₄Cl and allowed to warm to room temperature. The THF was removed in vacuo, and the resulting residue was dissolved in EtOAc and H₂O. The aqueous layer was extracted 2 times with EtOAc, and all of the EtOAc solutions were combined and washed once with saturated NaHCO₃ solution and once with brine then dried over Na₂SO₄. Crude title phosphinate was obtained as an orange oil (4.0 g) which was purified by flash chromatography eluting with 75% EtOAc/hexane. Title phosphinate (1.4 g, 42%) was obtained as a yellow oil.

TLC $R_f$=0.25 (75% EtOAc/hexane, silica gel), PMA.

IR(CHCl₃) 3004, 2954, 2925, 1744, 1718, 1643, 1541, 1503, 1472, 1449, 1438, 1425, 1236, 1037 cm⁻¹.

¹H NMR (270 MHz, CDCl₃): δ7.30 (m, 2), 6.95 (m, 3), 4.05 and 3.90 (2 m's, 2), 3.75 (m, 2), 3.73 and 3.66 (2 s's, 3), 3.55 (m, 1), 3.25 (m, 1), 2.33 and 2.29 (2 s's (br), 9), 1.28 and 1.12 (2 t's, 3, J=7.1 Hz).

Mass Spec (CI) m/e 451 (M+H)⁺.

F.  4-[[[[4'-Fluoro-3,3',5-trimethyl[1,1'-biphenyl]-2-yl]oxy]methyl]ethoxyphosphinyl]-3-hydroxybutanoic acid, methyl ester A solution of Part E ketone (1.39 g, 3.09 mmol) in THF (15 ml) under argon atmosphere was cooled to 0° C. To the cooled solution was added NaBH₄ (0.12 g, 3.09 mmol) followed by slow dropwise addition of CH₃OH (2.8 ml). After 1 hour at 0° C., the reaction was quenched with acetone followed by 1.4 g of CC-4 silica gel and then warmed to room temperature. The reaction was filtered, and the filtrate was rotavapped to give a yellow oil. The oil was flash chromatographed eluting with 90% EtOAc/hexane and product containing fractions were combined and solvent was removed in vacuo. The resulting yellow oil was crystallized from Et₂O/hexane and the resulting crystals were triturated with Et₂O/hexane to give white crystals (0.320 g) of title alcohol.

TLC $R_f$=0.38 (90% EtOAc/hexane, silica gel) PMA.

M.P. 116°-119° C.

IR (KBr) 3288 (br), 3000, 2950, 2920, 1735, 1503, 1473, 1440, 1311, 1232, 1195 cm⁻¹.

¹H NMR (270 MHz, CDCl₃): δ7.28 (m, 2), 7.05 (t, 1, J=6.0 Hz), 6.98 (s, 1), 6.90 (s, 1), 4.42 (m, 1), 4.05 and 3.85 (m, 2), 3.75 (d, 2, J=6.0 Hz), 3.70 (s, 3), 2.55 (m, 2), 2.32 (s, 6), 2.30 (s, 3), 2.00 (m, 2), 1.30 (t, 3, J=7.0 Hz).

Mass Spec (CI) m/e 453 (M+H)⁺, 435 (M-H₂O)⁺

G.  4-[[[[4'-Fluoro-3,3',5-trimethyl[1,1'-diphenyl]-2-yl]oxy]methyl]hydroxyphosphinyl]-3-hydroxybutanoic acid, dilithium salt At room temperature 1N LiOH (2.0 ml) was added to a 13 ml dioxane solution of Part F diester (0.293 g, 0.65 mmol). The reaction mixture was warmed to 55° C. and stirred for 1 hour 45 minutes, then cooled to room temperature. The reaction mixture was rotavapped to dryness and gave a white solid which was then placed under high vacuum for 10 minutes. The crude product was purified by chromatography on a 15 cm×3.0 cm column of HP-20 eluting first with 100 ml of H₂O followed by elution with 50% CH₃OH/H₂O. Pure title dilithium salt was obtained as a white lyophilate (0.295 g, 88%).

TLC $R_f$=0.38 (7:2:1 n-PrOH/NH₄OH/H₂O, silica gel) PMA.

IR (KBr) 3400 (br), 3021, 3011, 2981, 2958, 2924, 1575, 1503, 1475, 1446, 1430, 1401, 1231, 1175, 1087 cm⁻¹.

¹H NMR (270 MHz, D₂O): δ7.20 (m, 2), 7.07 (d, 1, J=9.9 Hz), 7.03 (s, 1), 6.86 (s, 1), 4.03 (m, 1), 3.40 (d, 2, J=8.3 Hz), 2.24 (s, 3), 2.21 (s, 3), 2.20 (m, 2), 2.17 (s, 3), 1.45 (m, 2).

Mass Spec (FAB) m/e 423 (M+H)⁺

Anal Calcd for C₂₀H₂₂O₆FPLi₂.0.95H₂O: C, 54.67; H, 5.48; F, 4.32; P, 7.05. Found: C, 54.37; H, 5.03; F, 4.31; P, 7.55.

EXAMPLE 58

4-[[[4'-Fluoro-3,3',5-trimethyl[1,1'-biphenyl]-2-yl]methyl]hydroxyphosphinyl]-3-hydroxybutanoic acid, dilithium salt A.  4'-Fluoro-3,3',5-trimethyl[1,1'-biphenyl]-2-methanol To a 9 ml EtOH (Abs) solution of NaBH₄ (0.12 g, 3.18 mmol) was added the Example 57 Part A aldehyde (0.70 g, 2.89 mmol) as an Et₂O-EtOH (4.5 ml/3.0 ml) solution. This reaction mixture was stirred at room temperature for 2 hours and then quenched with saturated NH₄Cl solution. The resulting solid precipitate was removed by filtration. The filtrate was rotavapped to dryness and the resulting solid was dissolved in Et₂O and H₂O. The aqueous layer was washed 2 times with Et₂O, and the combined Et₂O solutions were dried over MgSO₄.

After filtration and solvent removal 0.70 g of a white solid was obtained. The solid was purified by flash chromatography eluting with 33% Et₂O/hexane giving 0.675 g (100% yield) of title alcohol.

TLC 0.11 (15% Et₂O/hexane, silica gel) PMA.

M.P. 101°-102° C.

IR (KBr) 3351, 3293, 3267, 3260, 3024, 3016, 2980, 2939, 2921, 1605, 1601, 1502, 1451, 1355, 1243, 1236, 1228, 1189, 1118, 999 cm⁻¹.

¹H NMR (270 MHz, CDCl₃): δ7.15 (m, 2), 7.03 (m, 2), 6.90 (s, 1), 4.55 (d, 2, J=6.0 Hz), 2.48 (s, 3), 2.33 (s, 6).

Mass Spec (CI) m/e 244 (M+), 227 (M+-OH).

B. [[4'-Fluoro-3,3',5-trimethyl[1,1'-biphenyl]-2-yl]methyl]phosphonic acid, diethyl ester A 50 ml CH₂Cl₂ solution of Part A alcohol (1.94 g, 7.95 mmol) under argon atm. was cooled to 0° C. To this cooled solution was added Et₃N (0.965 g, 9.54 mmol) followed by dropwise addition of MsCl (1.00 g, 8.75 mmol). The reaction was stirred at 0° C. for 30 minutes and then warmed to room temperature and stirred overnight. The reaction was quenched with saturated NaHCO₃ solution and stirred vigorously. The organic layer was washed with saturated NaHCO₃ solution and then dried over MgSO₄. Filtration and solvent removal gave 2.1 g of 2-(chloromethyl)-4'-fluoro-3,3',5-trimethyl[1,1'-biphenyl] as a clear oil. TLC $R_f$=0.68 (50% Et₂O/hexane, silica gel) PMA.

¹H NMR (270 MHz, CDCl₃): δ7.22 (m, 2), 7.03 (m, 2), 6.90 (s, 1), 4.50 (s, 2), 2.48 (s, 3), 2.33 (s, 6).

Without further purification the above chloride (2.1 g) was stirred with P(OC₂H₅)₃ (30 ml) at 150° C. under argon atmosphere for 3 hours. The reaction was cooled to room temperature and the excess P(OC₂H₅)₃ was removed by distillation. The crude product was purified by flash chromatography eluting with 70% EtOAc/hexane. Title phosphonate (2.40 g, 83%) was obtained as a clear oil.

TLC $R_f=0.37$ (70% EtOAc/hexane, silica gel) PMA.

IR(CHCl$_3$) 2992, 2928, 2909, 1501, 1474, 1455, 1443, 1392, 1245, 1239, 1119, 1053, 1029, 970, 963 cm$^{-1}$.

$^1$H NMR (270 MHz, CDCl$_3$): δ7.15 (m, 2), 7.00 (m, 2), 6.83 (s, 1), 3.83 (m, 4), 3.22 (d, 2, J=22.52 Hz), 2.47 (s, 3), 2.29 (s, 6), 1.16 (t, 6, J=7.14 Hz). Mass spec (CI) m/e 365 (M+H)+

C. [[4'-Fluoro-3,3',5-trimethyl[1,1'-biphenyl]-2-yl]methyl]phosphonic acid, monoethyl ester Part B phosphonate diester (2.40 g, 6.59 mmol) was stirred in 30 ml of dioxane at room temperature. To this dioxane solution was added 1N LiOH (9.9 ml) and the reaction was warmed to a reflux. Additional 1N LiOH (9.9 ml) was added at each of the 18 hour and 44 hour time points. After 55 hours at reflux the reaction was cooled to room temperature and the dioxane was removed on the rotavap. The resulting aqueous solution was diluted with H$_2$O and extracted 2 times with Et$_2$O to remove any remaining diester. The aqueous layer was then cooled in an ice bath and acidified to pH~1 with 6N HCl. The milky white solution was extracted 3 times with EtOAc, the EtOAc extract was dried over MgSO$_4$, filtered, and the solvent was removed to give 1.89 g, 85% yield of a clear oil.

TLC $R_f=0.26$ (9/0.5/0.5, CH$_2$Cl$_2$/MeOH/AcOH, silica gel) PMA.

IR (CHCl$_3$) 3029, 3023, 3005, 2983, 2925, 1710, 1605, 1500, 1234, 1042, 988 cm$^{-1}$.

$^1$H NMR (270 MHz, CDCl$_3$): δ11.07 (s, 1), 7.05 (m, 2), 6.95 (m, 2), 6.80 (s, 1), 3.71 (dq, 2, J=7.15 Hz, 14.83 Hz), 3.13 (d, 2, J=23.0), 2.38 (s, 3), 2.27 (s, 6), 1.13 (t, 3, J=7.2 Hz).

Mass Spec (CI) m/e 337 (M+H)+

D. 4-[Ethoxy[[4'-fluoro-3,3',5-trimethyl[1,1'-biphenyl]-2-yl]methyl]phosphinyl]-3-oxobutanoic acid, methyl ester A 50 ml CH$_2$Cl$_2$ solution of Part C half acid (1.85 g, 5.50 mmol) under argon atmosphere was stirred with (C$_2$H$_5$)$_2$NSi(CH$_3$)$_3$ (1.60 g, 11.0 mmol) at room temperature for 1 hour 15 minutes. The CH$_2$Cl$_2$ was removed from the reaction mixture and the resulting yellow oil was azeotroped once with benzene and placed under high vacuum for 20 minutes. This oil under argon atmosphere was dissolved in 50 ml of dry CH$_2$Cl$_2$ and cooled to 0° C. Two drops of dry DMF were added to the cooled solution followed by the dropwise addition of oxalyl chloride (0.768 g, 6.06 mmol): gas evolution was observed. The reaction was stirred at 0° C. for 20 minutes, warmed to room temperature and stirred for an additional 1 hour 40 minutes; the reaction turned deep burgundy. The CH$_2$Cl$_2$ was removed from the reaction and the resulting oil was azeotroped 2 times with dry benzene then placed under high vacuum for 1 hour.

The dianion of methylacetoacetate was prepared as described in Example 57 Part E [methylacetoacetate (0.830 g, 7.16 mmol); NaH (0.230 g oil disp., 7.88 mmol); n-BuLi (2.64 ml of 2.5M solution in hexane, 6.59 mmol); 20 ml of THF].

The above prepared phosphonochloridate in 10 ml of dry THF cooled to −78° C. was added via cannula over 20 minutes to the dianion solution cooled to −78° C. After stirring for 40 minutes at −78° C., the reaction was quenched at −78° C. with saturated NH$_4$Cl solution, and warmed to room temperature; the reaction mixture was diluted with H$_2$O in order to dissolve solids and the THF was removed on the rotavap. The resulting mixture was extracted 3 times with EtOAc. The EtOAc extract was washed once with saturated NaHCO$_3$, once with brine, dried over MgSO$_4$ and filtered to give 2.6 g of crude orange oil after solvent removal. The crude product was purified by flash chromatography eluting with 75% EtOAc/hexane. The Part D ketone (0.43 g, 23%) was obtained as an orange foam.

TLC $R_f=0.32$ (50% acetone/hexane, silica gel), PMA.

IR (KBr) 2952, 2925, 1739, 1718, 1654, 1529, 1503, 1472, 1234, 1206, 1166, 1119, 1035 cm$^{-1}$.

$^1$H NMR (270 MHz, CDCl$_3$): δ7.20–6.70 (aromatic H's, 5), 4.00–3.70 (m, 2), 3.70 and 3.55 (2 s's, 3), 3.35 (m, 2), 3.35 (d, 2, J=15 Hz), 2.92 (m, 1), 2.45 and 2.35 (2 s's, 3), 2.25 (s, 6), 1.15 and 0.95 (2 t's, 3, J=7.0 Hz).

Mass Spec (CI) m/e 435 (M+H)+.

E. 4-[Ethoxy[[4'-fluoro-3,3',5-trimethyl[1,1'-biphenyl]-2-yl]methyl]phosphinyl]-3-hydroxybutanoic acid, methyl ester Solid NaBH$_4$ (0.035 g, 0.92 mmol) was added to a 5 ml THF solution of the Part D ketone (0.40 g, 0.92 mmol) under argon atmosphere. Methanol (0.80 ml) was added to the THF solution at room temperature. After 1 hour at room temperature, the reaction was quenched with acetone followed by the addition of 0.4 g of CC-4 silica gel. The reaction mixture was filtered and the solvent was removed. The reaction product still retained some ketone starting material; therefore, the above reaction product was resubjected to the identical reduction conditions described above; however, CO$_2$ (g) was bubbled through the solution prior to the addition of the NaBH$_4$. Workup as before gave 0.250 g of a yellow oil which was purified by flash chromatography eluting with EtOAc. Pure title alcohol was obtained as a clear oil. TLC $R_f=0.26$ (50% acetone/hexane, silica gel) PMA.

$^1$H NMR (270 MHz, CDCl$_3$): δ7.10 (m, 2), 7.00 (m, 2), 6.85 (s, 1), 4.28 and 4.03 (2 m's, 1), 4.10–3.70 (m, 2), 3.67 (s, 3), 3.33 (m, 2), 2.47 (s, 3), 2.40 (m, 2), 2.30 (s, 6), 1.63 (m, 2), 1.17 (t, 3, J=6.6 Hz).

F. 4-[[[4'-Fluoro-3,3',5-trimethyl[1,1'-biphenyl]-2-yl]methyl]hydroxyphosphinyl]-3-hydroxybutanoic acid, dilithium salt Part E diester (0.110 g, 0.252 mmol) in dry CH$_2$Cl$_2$ (5.5 ml) under argon atmosphere was cooled to 0° C. and treated with collidine (0.046 g, 0.38 mmol) followed by dropwise addition of trimethylsilyl iodide (TMSI) (0.182 g, 0.88 mmol). The reaction was stirred at 0° C. for 2 hours then warmed to room temperature. After 24 hours an additional aliquot of both collidine (0.023 g) and TMSI (0.091 g) was added. After stirring for 48 hours at room temperature, the CH$_2$Cl$_2$ was removed, and 6 ml of dioxane was added to the oil followed by 1.7 ml of 1N LiOH. This mixture was refluxed for 16 hours, cooled to room temperature and the dioxane was removed to leave an orange gum. The gum was dissolved in H$_2$O and filtered through sintered glass to remove a solid. The filtrate was lyophilized to give an off-white lyophilate which was purified on a 1.5 cm×15 cm column of HP-20. The column was eluted first with 150 ml of H$_2$O then with 50% MeOH/H$_2$O. Product fractions were lyophilized to give title compound in the form of a white lyophilate (88 mg, 80%)

TLC $R_f=0.38$ (7:2:1 n-PrOH/NH$_4$OH/H$_2$O, silica gel), PMA.

IR (KBr) 3700–3100 (br), 2923, 1591, 1501, 1234, 1147 cm$^{-1}$.

$^1$H NMR (270 MHz, D$_2$O): δ7.20–7.00 (m, 4), 6.82 (s, 1), 3.76 (m, 1), 3.11 (m, 2), 2.35 (s, 3), 2.22 (s, 3), 2.21 (s, 3), 2.05 (m, 2), 1.16 (dd, 2, J=12.32 Hz, 6.45 Hz).

Mass Spec (FAB) m/e 407 (M+H)$^+$.

Anal Calcd for C$_{20}$H$_{22}$FO$_5$PLi$_2$.0.80 H$_2$O: C, 57.11; H, 5.65; F, 4.52; P, 7.36. Found: C, 57.11; H, 6.63; F, 4.44; P, 7.70.

EXAMPLE 59

(S)-4-[[[1-(4-Fluorophenyl)-3-methyl-2-naphthalenyl]ethynyl]hydroxyphosphinyl]-3-hydroxybutanoic acid, dilithium salt A. 1-Methoxy-2-naphthalene carboxylic acid Reference: J. Organomet. Chem., 20 (1969) p. 251–252. n-BuLi (208.60 mmol, 83.44 ml of a 2.5 M solution in hexane, Aldrich) was stirred under argon in 42 ml of dry cyclohexane. This solution was cooled to 0° C. and treated dropwise (10 min.) with distilled tetramethylethylenediamine (TMEDA) (208.6 mmol, 24.24 g, 31.48 ml). The resulting slurry was stirred at 0° C. for 30 minutes, then treated dropwise (20 minutes) with a solution of 1-methoxynaphthalene (208.60 mmol, 33 g, 30.28 ml) (Aldrich Chem. Co., used without further purification) in 84 ml of dry cyclohexane. The resulting bright red homogeneous reaction mixture was warmed to room temperature and stirred for 2 hours. The reaction mixture was cooled to 0° C. and added portionwise over 30 minutes via cannula to a −78° C. solution of dry Et$_2$O (250 ml) saturated with CO$_2$ (g) (CO$_2$ pellets sublimed through drying tube containing SiO$_2$, bubbled into dry Et$_2$O at −78° C.). The resulting white slurry was warmed to ~0° over 45 minutes and then treated with 450 ml of 5% HCl (aqueous). The Et$_2$O layer was separated and the aqueous layer extracted three times with Et$_2$O. The organic extracts were combined and extracted with 3×150 ml saturated NaHCO$_3$ (aqueous). The aqueous layer was filtered through a sintered glass funnel to remove insolubles and the filtrate was cooled to 0° C. and acidified slowly with concentrated HCl until pH=1. The resulting precipitate was filtered, azeotroped with 2×150 ml of toluene, dried under high vacuum at 50° C. for 5 hours to afford 32.52 g (0.161 mol, 77% yield) of the 1-methoxy-2-naphthalene carboxylic acid as an off-white powder, m.p. 118–121.5° C.

TLC: Silica gel, R$_f$=0.35 94:5:1/CH$_2$Cl$_2$:MeOH:CH$_3$CO$_2$H.

$^1$H NMR: (270 MHz, CDCl$_3$) consistent.

$^{13}$C NMR: (67.8 MHz, CDCl$_3$) consistent.

Mass Spec: CI m/e 203+(M+H)$^+$.

IR: KBr consistent.

B. N-(2-Hydroxy-1,1-dimethylethyl)-1-methoxy-2-naphthalenecarboxamide

The 1-methoxy-2-naphthalene carboxylic acid (155.22 mmol, 31.4 g) was stirred under argon in 155 ml of dry CH$_2$Cl$_2$. The solution was then treated with SOCl$_2$ (310.44 mmol, 36.94 g, 22.65 ml). The reaction mixture was stirred at room temperature for 45 minutes then heated to reflux in a 55° C. oil bath for 45 minutes. The reaction mixture was cooled to room temperature and treated with an additional 15 g, 22 mmol (18.47 g, 11.32 ml) of thionyl chloride and again heated to reflux for 45 minutes. The reaction mixture was cooled to 65 room temperature, the excess SOCl$_2$ and CH$_2$Cl$_2$ removed via rotary evaporation at 35° C. (venting to argon atmosphere) and the resulting mustard yellow solid dissolved under argon in 155 ml dry CH$_2$Cl$_2$. This solution was transferred via cannula to an addition funnel and added dropwise (40 minutes) to a solution of 2-amino-2-methyl propanol (310.44 mmol, 27.67 g) in 155 ml dry CH$_2$Cl$_2$ which had been stirring under argon at 0° C. The resulting reaction mixture was warmed to room temperature and stirred for 18 hours. The reaction mixture was then filtered, the precipitate washed with CH$_2$Cl$_2$, the filtrate evaporated in vacuo. The residue was redissolved in 350 ml EtOAc and washed with 1×250 ml H$_2$O, 1×250 ml 5% HCl, 1×250 ml 5% NaOH and 1×250 ml brine. The aqueous extracts were each back-extracted once with EtOAc. The organic extracts were combined, dried over MgSO$_4$, filtered, and evaporated in vacuo to afford an orange oil which was azeotroped with 250 ml toluene and pumped under high vacuum at 55° C. for 8 hours to afford 38.2 g (139.76 mmol, 90% yield) of the title naphthalamide as a light yellow solid.

TLC: Silica gel, R$_f$=0.65 100% EtOAc.

$^1$H NMR (270 MHz, CDCl$_3$): δ8.19 (s, br, 1H), 8.14 (m, 1H), 8.03 (d, 1H, J=8.7 Hz), 7.83 (m, 1H), 7.66 (d, 1H, J=8.7 Hz), 7.55 (m, 2H), 4.00 (s, 3H), 3.74 (s, 2H), 1.47 (s, 6H).

Mass Spec: CI m/e 274 (M+H)$^+$.

IR: (CHCl$_3$ solution): 3365, 3063, 3024, 3005, 2971, 2938, 2873, 1641, 1597, 1540, 1456, 1446, 1387, 1371, 1344, 1291, 1256, 1238, 1223, 1210, 1199, 1183, 1168, 1145, 1079, 981, 833 cm$^{-1}$.

C. 4,5-Dihydro-2-(1-methoxy-2-naphthalenyl)-4,4-dimethyloxazole

The Part B naphthalamide (139 mmol, 38.2 g) was stirred under argon and cooled to 0° C. as thionyl chloride (0.556 mol, 66.15 g, 40.56 ml) was added dropwise (15 minutes). The resulting dark brown oil was stirred at room temperature for 45 minutes. Dry Et$_2$O (500 ml) was added, and the reaction mixture was stirred mechanically for 2.5 hours. The resulting yellow crystalline precipitate was filtered, washed with Et$_2$O and then suspended in 250 ml Et$_2$O. The suspension was cooled to 0° C. and basified with ~200 ml 10% NaOH. The aqueoys layer was extracted 3 times with Et$_2$O and once with EtOAc. The organic extracts were combined, washed once with brine, concentrated, dried over MgSO$_4$ and filtered. The filtrate was azeotroped with toluene in vacuo and the residue pumped under high vacuum at 55° C. for 8 hours to afford 32.10 g (0.126 mol, 90% yield) of the title oxazoline as a golden powder.

TLC: Silica gel R$_f$=0.37 50% EtOAC.

$^1$H NMR: (270 MHz, CDCl$_3$): δ8.25 (m, 1H), 7.84 (d, 1H, J=8.7 Hz), 7.84 (m, 1H), 7.60 (d, 1H, J=8.7 Hz), 7.54 (m, 2H), 4.19 (s, 2H), 4.04 (s, 3H), 1.46 (s, 6H).

Mass Spec: CI m/e 256 (M+H)$^+$.

IR: 2969, 2935, 2896, 1642, 1465, 1447, 1386, 1372, 1349, 1255, 1109, 1074, 991 cm$^{-1}$.

D. 2-[1-(4-Fluorophenyl)-2-naphthalenyl)]-4,5-dihydro-4,4-dimethyloxazole

The Part C oxazoline (117.52 mmol, 30.0 g) was stirred under argon in 352.5 ml of dry THF. This solution was warmed to 45° C. in an oil bath. The heat source was removed and a 2M solution of 4-fluorophenyl magnesium bromide in Et$_2$O (Aldrich) (158.65 mmol, 79.33 ml) was added dropwise (30 minutes) at a rate sufficient to maintain the reaction temperature at ~45° C. After addition was complete, the reaction temperature was maintained at 45° C. as the reaction mixture was stirred for 18 hours. The reaction mixture was cooled to 0° C. and quenched with 200 ml saturated NH₄Cl (aqueous), diluted with 200 ml H₂O and 200 ml EtOAc. The aqueous layer was extracted 4 times with EtOAc. The organic extracts were combined, concentrated, dried over MgSO₄ and filtered. The filtrate was evaporated in vacuo to afford 39 g of a dark golden solid. The product was purified via flash chromatography (95 mm diameter column, 7" Merck silica gel, 25% EtOAc/hexane eluent, 2"/min flow rate) to afford 30.42 g (95.25 mmol, 81% yield) of the title 4-fluorophenyl substituted naphthalene as a pale yellow solid, m.p. 94°-96° C. Also obtained was 3.38 g (10.58 mmol, 9%) of slightly impure product.

TLC: silica gel R$_f$=0.45 50% EtOAc/hexane

¹H NMR: (270 MHz, CDCl₃) δ7.93-7.13 (aromatic, 10H), 3.77 (s, 2H), 1.27 (s, 6H).

Mass Spec: CI m/e 320 (M+H)⁺.

IR:(KBr) 3060, 2966, 2927, 2884, 1667, 1603, 1508, 1462, 1383, 1354, 1335, 1293, 1219, 1185, 1160, 1119, 1083, 978, 842, 830 cm⁻¹.

E. 2-[1-(4-Fluorophenyl)-3-methyl-2-naphthalenyl)]-4,5-dihydro-4,4-dimethyloxazole The Part D 1-4-fluorophenyl-2-oxazolinenaphthyl compound (87.67 mmol, 28 g) was stirred under argon in 585 ml dry Et₂O. This solution was cooled to −25° C. and treated dropwise (1 hour) with n-BuLi (140.27 mmol, 56.1 ml of a 2.5M solution in hexane). The reaction mixture transformed during this hour long addition from a yellow homogeneous solution to a dark red/orange solution to an orange/green solution with a precipitate. The reaction mixture was stirred at −25° C. for an additional 2.5 hours and was then treated with iodomethane (263.01 mmol, 37.33 g, 16.4 ml) added dropwise over 15 minutes. The resulting dark burgundy solution was stirred at −25° C. for 4.5 hours, warmed to 0° C. and stirred for 16 hours and finally warmed to room temperature and stirred for 7 hours. The resulting yellow transparent solution was quenched with 500 ml of ice cold brine. The aqueous layer was extracted 4 times with EtOAc. The organic extracts were combined, concentrated, dried over MgSO₄ and filtered through Florisil (300 ml glass sintered funnel ⅔ full). The Florisil was washed with CH₂Cl₂. The filtrate was concentrated, azeotroped with toluene and evaporated in vacuo and pumped under high vacuum at 55° C. for 3 hours to afford 30.32 g ("90.94 mmol", 100% yield) of the title methylated naphthalene as a yellow solid.

TLC: Silica gel R$_f$=0.50 50% EtOAc/hexane.

¹H NMR: (270 MHz, CDCl₃): δ7.79-7.07 (aromatic, 9H), 3.80 (s, 2H), 2.54 (s, 3H), 1.13 (s, 6H).

Mass Spec: CI m/e 334 (M+H)⁺

IR: (CHCl₃ solution): 3013, 2967, 2931, 2895, 2870, 1667, 1605, 1513, 1497, 1461, 1299, 1280, 1235, 1190, 1158, 1041, 965, 841 cm⁻¹.

F. 2-[1-(4-Fluorophenyl)-3-methyl-2-naphthalenyl)]-4,5-dihydro-3,4,4-trimethyloxazolium iodide The Part E oxazoline (87.67 mmol, 29.23 g) was stirred under argon in 140.28 ml nitromethane. This solution was treated in one portion with iodomethane (0.789 mol, 112 g, 49.2 ml). The resulting brown reaction mixture was heated in a 60° C. oil bath for 1 hour 20 minutes in the absence of light. The iodomethane was removed via simple distillation. The nitromethane was removed via rotary evaporation followed by pumping under high vacuum for 45 minutes. The resulting burgundy solid was stirred mechanically in 250 ml dry Et₂O for 1 hour. The red filtrate was decanted and the solid was again triturated from Et₂O as above. The resulting yellow solid was filtered and pumped under high vacuum for 4 hours (in the absence of light) to afford the title oxazolinium iodide 44 g ("92.63" mmol, 100% yield) as a mustard yellow solid. The title compound was stored in the absence of light at −30° C. for 18 hours and was then used directly in the preparation of the Part G compound.

TLC: Silica gel R$_f$=0.30 10% MeOH/CH₂Cl₂.

G. 1-(4-Fluorophenyl)-3-methyl-2-naphthalenecarboxaldehyde

The Part F oxazolinium iodide (87.67 mmol, 41.67 g) was stirred under argon in 526 ml of dry THF and 210 ml absolute EtOH (dried over 4Å molecular sieves). This solution/suspension was cooled to −15° C. and treated protionwise with NaBH₄ over a one hour period. After addition was complete, the reaction solution was stirred at −10° C. to −15° C. for 2.5 hours. Then, the solution was diluted with 210 ml absolute EtOH and the reaction mixture stirred at −15° C. as 2N HCl (438 ml, 876 mmol) was added dropwise over 45 minutes (add very slowly initially). After addition was complete, the reaction mixture was warmed to room temperature and stirred for 4 hours. Then, dilution with 500 ml H₂O was followed by aqueous extraction with Et₂O. The organic extracts were combined, concentrated, dried over MgSO₄, filtered, concentrated, azeotroped with toluene (2 ×120 ml) and stripped in vacuo to afford 12.9 g, (48.81 mmol, 56% yield) of the title aldehyde as a pale yellow solid.

TLC: Silica gel R$_f$=0.66 50% EtOAc/hexane.

¹H NMR: (270 MHz, CDCl₃): δ10.0 (s, 1H), 7.83–7.18 (aromatic, 9H), 2.81 (s, 3H).

Mass Spec: CI m/e 265 (M+H)⁺.

IR: (CHCl₃ solution) 1685, 1512, 1422, 1237, 862 cm⁻¹.

H. 2-(2,2-Dibromoethenyl)-1-(4-fluorophenyl)-3-methylnaphthalene

The Part G aldehyde (11.35 mmol, 3.0 g) was stirred under argon in 113.5 ml dry CH₂Cl₂. This solution was cooled to 0° C. and then treated in one portion with triphenylphosphine (36.32 mmol, 9.53 g). The reaction mixture was stirred at 0° C. for 20 minutes and then treated dropwise (20 min) with a solution of carbon tetrabromide (18.16 mmol, 6.02 g) in 41 ml dry CH₂Cl₂. The resulting dark orange solution became dark burgundy as it was stirred at 0° C. for 1¼ hours. Then the reaction mixture was quenched with 150 ml saturated NaHCO₃ (aqueous). The aqueous layer was extracted 4 times with CH₂Cl₂. The organic extracts were combined, concentrated in vacuo, washed once with brine, dried over MgSO₄ and filtered. The filtrate was preabsorbed onto Merck silica gel (~28 g) and then applied to a 50 mm diameter flash chromatography column containing 6" Merck silica gel and eluted with 7% EtOAc/hexane eluent, 2"/min flow rate to afford 4.23 g of the title dibromo-olefin as a slightly impure pale yellow solid. Subsequent recrystallization from hexane afforded 3.68 g (8.77 mmol, 77% yield) of the title dibromo-olefin as a white powdery solid. m.p.=134.5–135.5.

TLC: silica gel R$_f$=0.60 20% EtOAc/hexane.

¹H NMR: (270 MHz, CDCl₃): δ7.79–7.11 (aromatic olefinic, 10H) 2.48 (s, 3H).

Mass Spec: CI m/e 419/421/423 (M+H)⁺.

IR: (CHCl₃ solution): 3016, 1604, 1512, 1496, 1234, 1220, 1208, 1158, 886, 858 cm⁻¹.

I. 2-Ethynyl-1-(4-fluorophenyl)-3-methylnaphthalene

The Part H dibromo olefin (8.7 mmol, 3.69 g) was stirred under argon in 47.9 ml dry THF. This solution was cooled to −78° C. and then treated dropwise (15 min) with n-BuLi (17.4 mmol, 6.96 ml of a 2.5M solution in hexane-Aldrich). The reaction mixture was stirred at −78° C. for 1 hour and then was quenched with 40 ml saturated NH$_4$Cl (aqueous). After warming to 0° C., the reaction mixture was diluted with 40 ml of H$_2$O and 40 ml of Et$_2$O. The aqueous phase was extracted 2 times with Et$_2$O and once with EtOAc. The organic extracts were combined, dried over MgSO$_4$, filtered and the solvent evaporated in vacuo. Initial purification via flash chromatography (50 mm diameter column, 6" Merck silica gel, 7% EtOAc/hexane eluent, 2"/min flow rate) afforded 2.32 g of a green oil/solid. 270 MHz $^1$H NMR evidenced impure product. Repurification via flash chromatography (75 mm diameter column, 6" Merck silica gel, 1% EtOAc/hexane eluent, 2"/min flow rate) afforded 2.11 g (8.11 mmol, 93% yield) of the title acetylene as a pale blue solid (pumped under high vacuum 8 hours) m.p.=91.5–94.5.

TLC: Silica gel, PMA R$_f$=0.56 20% EtOAc/hexane $^1$H NMR: (270 MHz, CDCl$_3$): δ7.77–7.13 (aromatic, 9H), 3.18 (s, 1H), 2.62 (s, 3H).

Mass Spec: CI m/e 260M+.

IR: (CH$_2$Cl$_2$ film): 3291, 1604, 1512, 1494, 1383, 1222, 1158, 1150, 1092, 884, 871, 853, 825 cm$^{-1}$.

J. (S)-3-[[(1,1-Dimethylethyl)diphenylsilyl]oxy]-4-[[[1-(4-fluorophenyl)-3-methyl-2-naphthalenyl]ethynyl]methoxyphosphinyl]butanoic acid, methyl ester The Example 25 dicyclohexylamine salt (8.82 mmol, 5.57 g) was partitioned between a 1:1 mixture of EtOAc/5% KHSO$_4$ (150 ml ea.) and shaken vigorously. The layers were separated and the EtOAc layer was washed with 2×100 ml fresh 5% KHSO$_4$. Finally, the organic phase was dried over MgSO$_4$, filtered and the solvent removed in vacuo. The resulting residue was azeotroped with 2×120 ml benzene, evaporated and pumped under high vacuum for 2 hours to afford "4.33 g", "109%" yield, of the phosphonate monoester as a viscous pale yellow oil. This oil was stirred under argon in 24.8 ml dry CH$_2$Cl$_2$ and treated dropwise (8 minutes) with distilled diethyltrimethylsilylamine (17.64 mmol, 2.56 g, 3.34 ml). This solution was stirred at room temperature for 2 hours. Then, the volatiles were removed on the rotavap (vent to argon) and the resulting residue azeotroped with 1×60 ml dry benzene, evaporated in vacuo and pumped under high vacuum for 45 minutes. The residue was then stirred under argon in 24.8 ml of dry CH$_2$Cl$_2$. Two drops of DMF were added and the solution cooled to 0° C. Oxalyl chloride (10.58 mmol, 1.34 g, 0.923 ml) was added dropwise (10 min). The resulting amber solution was stirred at 0° C. for 30 minutes, warmed to room temperature and stirred for 2 hours. The volatiles were removed, the residue azeotroped and pumped under high vacuum as above. Finally, the residue was stirred under argon in 27.7 ml dry THF. This solution was cooled to −78° C. and treated dropwise (15 minutes) with a −78° C. THF solution of the acetylenide anion formed and added to the phosphonochloridate as follows.

The Part I acetylene (5.19 mmol, 1.35 g) was stirred under argon in 27.7 ml of dry THF and cooled to −78° C. This solution was treated dropwise (10 minutes) with n-BuLi (5.19 mmol, 2.08 ml of a 2.5M solution in hexane). The resulting green solution was stirred at −78° C. for 1.5 hours, warmed to 0° C. for 15 minutes and recooled to −78° C. This solution was maintained at −78° C. as it was transferred portionwise to an addition funnel and added dropwise to the −78° C. THF solution of the phosphonochloridate formed above. After completion of addition, the reaction mixture was stirred at −78° C. for 1 hour, then quenched with 50 ml saturated NH$_4$Cl (aqueous) and warmed to 0° C. The reaction mixture was then diluted with 40 ml H$_2$O and 40 ml Et$_2$O. The aqueous layer was extracted with 4×50 ml Et$_2$O. The organic extracts were combined, concentrated, dried over MgSO$_4$, filtered, and the solvent removed in vacuo. The product was isolated via flash chromatography (75 mm diameter column, 6" Merck silica gel, 5:4:1 hexane:EtOAc:toluene eluent, 2"/min flow rate) to afford 1.53 g (2.21 mmol 43% yield) of the title acetylenic phosphinate as a yellow foam. Also recovered 0.589 g of impure starting material.

TLC:Silica gel, PMA R$_f$=0.26 5:4:1. Hexane:EtOAc:toluene.

$^1$H NMR: (270 MHz, CDCl$_3$): δ7.82–7.09 (aromatic, 19H), 4.52 (m, 1H), 3.60 and 3.59 (2×s, 3H), 3.36 and 3.31 (2×d, 3H, J=11.5 Hz), 2.54 and 2.49 (2×s, 3H), 2.87–2.73 (m, 1H), 2.61–2.56 (m, 1H), 2.39–2.22 (m, 1H), 2.12–2.00 (m, 1H), 1.02 (s, 9H).

Mass Spec: CI m/e 693 (M+H)+

IR: (CHCl$_3$ solution): 3004, 2951, 2932, 2858, 2164, 1735, 1605, 1512, 1494, 1472, 1437, 1427, 1237, 1197, 1182, 1158, 1151, 1138, 1110, 1105, 1093, 1038, 1017, 951, 885, 834 cm$^{-1}$.

K. (S)-4-[[[1-(4-Fluorophenyl)-3-methyl-2-naphthalenyl]ethynyl]methoxyphosphinyl]-3-hydroxybutanoic acid, methyl ester The Part J acetylenic phosphinate (0.866 mmol, 0.60 g) was stirred under argon in 10.5 ml dry THF and treated with glacial acetic acid (3.46 mmol, 0.208 g, 0.198 ml) followed by dropwise addition of tetrabutylammonium fluoride (2.60 mmol, 2.36 ml of a 1.1M solution in THF). The reaction mixture was stirred at room temperature for 24 hours, then quenched with 25 ml ice water and diluted with EtOAc. The aqueous layer was extracted 3 times with EtOAc. The organic extracts were combined, washed once with saturated NaHCO$_3$ (aqueous) and once with brine, dried over MgSO$_4$, filtered and evaporated in vacuo. The product was purified via flash chromatography using a 30 mm diameter column; 35:1 Merck silica gel, 100% EtOAc eluent, 2"/min flow rate to afford 0.267 g (0.588 mmol, 68% yield) of the title β-hydroxyphosphinate as a pale yellow foam.

TLC:Silica gel, PMA R$_f$=0.28 100% EtOAc.

$^1$H NMR: (270 MHz, CDCl$_3$): δ7.81–7.18 (aromatic, 9H), 4.38 (m, 1H), 3.71 (s, 3H), 3.59 and 3.58 (2×d, 3H, J=12 Hz), 2.66 and 2.65 (2×s, 3H), 2.62–2.52 (m, 2H), 2.19–1.92 (m, 2H).

Mass Spec: CI m/e 455 (M+H)+.

IR: (film): 3380 (broad), 3065, 3048, 2993, 2951, 2166, 1738, 1604, 1513, 1495, 1457, 1438, 1423, 1401, 1385, 1378, 1334, 1299, 1222, 1179, 1160, 1138, 1095, 1035, 951, 887, 836 cm$^{-1}$ L. (S)-4-[[[1-(4-Fluorophenyl)-3-methyl-2-naphthalenyl]ethynyl]hydroxyphosphinyl]-3-hydroxybutanoic acid, dilithium salt The Part K diester (0.583 mmol, 0.265 g) was stirred under argon in 6 ml dioxane and treated with 1N LiOH (1.75 mmol, 1.75 ml). The reaction mixture was heated in a 70° C. oil bath for 45 minutes. The reaction mixture was cooled to room temperature. The solvents were removed via rotary evaporation followed by pumping under high vacuum for 1 hour. The resulting white solid was dissolved in 4 ml of distilled H₂O and applied to an HP-20 chromatography column (2.5 cm×17.0 cm, equilibrated with H₂O). The column was eluted with 250 ml H₂O followed by eluting with 45:55 MeOH:H₂O. Fractions were collected every 1.3 m (~10 ml). Product fractions were evaporated in vacuo at 35° C., lyophilized, and pumped under high vacuum over P₂O₅ for 8 hours to afford 0.237 g (0.541 mmol, 93% yield) of the title phosphinic acid dilithium salt as a white lyophilate.

TLC:Silica gel, PMA $R_f$=0.40 7:2:1 n-C₃H₇OH/NH₄OH/H₂O.

¹H NMR: (400 MHz, D₂O): δ7.88 (d, 1H, J=8.43 Hz), 7.80 (s, 1H), 7.58–7.29 (aromatic, 7H), 4.14–4.05 (m, 1H), 2.61 (s, 3H), 2.43 (dd, 1H, J=3.67, J=15.39), 2.21 (dd, 1H, J=9.16, J=15.39), 1.84–1.67 (m, 2H).

Mass Spec: FAB m/e 439 (M+2 Li)⁺

IR:(KBr) 3443–3260 (broad), 3066, 2164, 1594, 1512, 1495, 1434, 1222, 1183, 1160, 1071, 834 cm⁻¹.

Anal Calcd for C₂₃H₁₈FO₅PLi₂+0.66 moles H₂O M.W.=450.14: C, 61.38; H, 4.33; F, 4.22; P, 6.88. Found: C, 61.38; H, 4.07; F. 4.42; P, 6.80.

EXAMPLE 60

(E)-4-[[2-[1-(4-Fluorophenyl)-3-methyl-2-naphthalenyl]ethenyl]hydroxyphosphinyl]-3-hydroxybutanoic acid, dilithium salt A. [2-[1-(4-Fluorophenyl)-3-methyl-2-naphthalenyl]-2-hydroxyethyl]phosphonic acid, dimethyl ester Dimethyl methyl phosphonate (24.21 mmol, 3.0 g, 2.62 ml) was stirred under argon in dry THF (47 ml). This solution was cooled to −78° C. and then treated dropwise (15 min) with n-BuLi (22.70 mmol, 9.08 ml of a 2.5M solution in hexane). This reaction mixture was stirred at −78° C. for 1.5 hours and then the resulting milky solution was treated dropwise (15 minutes) with a solution of the Example 59 Part G aldehyde (15.13 mmol, 4.0 g) in dry THF (14 ml). This reaction mixture was stirred at −78° C. for 45 minutes. Finally, the reaction mixture was quenched with saturated NH₄Cl (aqueous) (50 ml), warmed to room temperature, diluted with H₂O (50 ml) and EtOAc (50 ml). The aqueous layer was extracted 4 times with EtOAc. The organic extracts were combined, dried over MgSO₄, filtered, concentrated, azeotroped 2 times with toluene, evaporated in vacuo, and pumped under high vacuum to afford 5.90 g (15.13 mmol, 100% yield) of the title phosphonate as a yellow solid which was used directly in the preparation of Part B compound.

TLC:Silica gel, PMA $R_f$=0.37 50% acetone/hexane

B. (E)-[2-[1-(4-Fluorophenyl)-3-methyl-2-naphthalenyl]ethenyl]phosphonic acid, dimethyl ester The Part A β-hydroxyphosphonate (14.16 mmol, 5.5 g) was stirred under argon in 66.5 ml of dry toluene. This solution was treated with paratoluene sulfonic acid monohydrate (TsOH.H₂O) (3.54 mmol, 0.673 g). The reaction mixture was heated to reflux in a 135° C. oil bath. The condensate was passed through a soxhlet containing dry 4 Å molecular sieves. After 16 hours at reflux additional TsOH.H₂O (2.12 mmol, 0.404 g) was added and the reaction mixture heated as above for an additional 8.5 hours. The reaction mixture was cooled to room temperature and diluted with 100 ml of EtOAC. The mixture was then washed with 100 ml of saturated NaHCO₃ (aqueous). The aqueous layer was extracted 4 times with EtOAc. The organic extracts were combined, dried over MgSO₄, filtered and evaporated in vacuo to afford 4.22 g of crude vinyl phosphonate as a brown solid. The aqueous layer was acidified with 5% HCl and then extracted 3 times with EtOAc. The organic extracts were combined, dried over MgSO₄, filtered and evaporated to afford 1.4 g ("3.92 mmol") of the vinyl phosphonate monoester as a light brown solid. This solid was stirred under argon in trimethyl orthoformate (15 ml) and heated to reflux in a 120° C. oil bath for 16 hours. The reaction mixture was cooled to room temperature. The excess trimethyl orthoformate was removed in vacuo and the residue combined with the 4.22 g of crude vinyl phosphonate (above). The product was purified via flash chromatography (75 mm diameter column, 6" Merck silica gel, 100% EtOAc eluent, 2"/min flow rate) to afford 3.70 g (9.99 mmol, 71% yield) of the title vinyl phosphonate as a peach solid.

TLC:Silica gel, PMA $R_f$=0.48 100% EtOAc.

¹H NMR:(270 MHz, CDCl₃): δ7.79 (d, 1H, J=8.4 Hz), 7.72 (s, 1H), 7.56–7.13 (m, 8H), 5.54 (dd, 1H, J=17.93 Hz, J=20.6 Hz), 3.57 (d, 6H, J=11 Hz), 2.54 (s, 3H).

Mass Spec: CI m/e 371 (M+H)⁺.

IR: (CHCl₃ solution): 3016, 2956, 2857, 1617, 1521, 1500, 1245, 1188, 1162, 1071, 1047, 834 cm⁻¹.

C. (E)-[2-[1-(4-Fluorophenyl)-3-methyl-2-naphthalenyl]ethenyl]phosphonic acid, monomethyl ester The Part B vinyl phosphonate (9.72 mmol, 3.60 g) was stirred under argon in dioxane (23.5 ml) and treated with 1N LiOH (23.32 mmol, 23.32 ml). The reaction mixture was heated in a 75° C. oil bath for 1 hour. Then, the reaction mixture was cooled to room temperature and the solvents removed in vacuo. The resulting residue was diluted with 15 ml of H₂O, cooled to 0° C. and acidified to pH=1 with 5% HCl (aqueous). The aqueous layer was extracted 4 times with EtOAc. The organic extracts were combined, dried over MgSO₄, filtered, concentrated, azeotroped 2 times with benzene and evaporated in vacuo to afford 3.38 g (9.48 mmol, 98% yield) of the title phosphonate monoester as a peach solid.

TLC:Silica gel, PMA $R_f$=0.41 10:1:1 CH₂Cl₂/MeOH/CH₃CO₂H.

¹H NMR: (270 MHz, CDCl₃): δ7.76 (d, 1H, J=8.4 Hz), 7.68 (s, 1H), 7.47–7.09 (m, 8H), 5.61 (dd, 1H, J=18.47 Hz, J=20.58 Hz), 3.48 (d, 3H, J=10.96 Hz), 2.52 (s, 3H).

Mass Spec: FAB m/e 357 (M+H)⁺

IR: (CHCl₃ solution): 3025, 3008, 2951, 1614, 1605, 1511, 1494, 1235, 1210, 1188, 1158, 1050, 987, 833 cm⁻¹.

D. (E)-4-[[2-[1-(4-Fluorophenyl-3-methyl-2-naphthalenyl]ethenyl]methoxyphosphinyl]3-oxobutanoic acid, methyl ester The Part C phosphonate monoester (9.12 mmol, 3.29 g) was stirred under argon in dry CH₂Cl₂ (60 ml) and treated dropwise (10 minutes) with trimethylsilyldiethyl amine (TMSDEA) (18.24 mmol, 2.65 g, 3.45 ml, distilled). The reaction mixture was stirred at room temperature for 1.5 hours. The volatiles were removed on the rotavap (vent to argon) and the residue pumped under high vacuum 40 minutes. Then, the residue was stirred under argon in dry CH₂Cl₂ (25 ml). This solution was cooled to 0° C., treated with 2 drops of dry DMF, followed by dropwise addition (15 minutes) of oxalyl chloride (10.94 mmol, 1.39 g, 0.955 mol). The reaction mixture was stirred at 0° C. for 20 minutes then warmed to room temperature and stirred for 1 hour. The volatiles were removed and the residue pumped as above. Finally, the residue was stirred under argon in dry THF (25 ml), cooled to −78° C. and maintained at −78° C. as this solution was transferred via cannula to an addition funnel and added dropwise (20 minutes) to a −78° C. THF solution of the dianion of methyl acetoacetate. This dianion was generated in the following manner: NaH (13.22 mmol, 0.317 g, 0.397 g of 80% mineral oil dispersion) was washed once with pentane, dried under an argon stream, and then stirred under argon in dry THF (20 ml). This suspension was cooled to 0° C. and treated dropwise (10 minutes) with a solution of methylacetoacetate (12.31 mmol, 1.43 g, 1.33 ml) in dry THF (10 ml). The resulting clear solution was stirred at 0° C. for 20 minutes and was then treated dropwise (10 minutes) with n-BuLi (11.40 mmol, 4.56 ml of a 2.5M solution in hexane). The resulting yellow solution was stirred at 0° C. for 45 minutes then cooled to −78° C. and treated dropwise with the −78° C. THF solution of the phosphonochloridate formed above. After the addition was complete, the reaction mixture was stirred at −78° C. for 45 minutes. Then, the reaction was quenched with saturated NH$_4$Cl (aqueous) (50 ml), warmed to room temperature, diluted with H$_2$O (50 ml) and EtOAc (50 ml). The aqueous layer was extracted 3 times with NaHCO$_3$ (aqueous) and once with CH$_2$Cl$_2$. The organic extracts were combined, washed 3 times with saturated NaHCO$_3$ (aqueous) and once with brine, dried over MgSO$_4$, filtered and evaporated in vacuo to afford 4.0 g of a rust colored foam. Initial purification via flash chromatography (40 mm diameter column, 20:1 Merck silica gel, 100% EtOAc eluent, 2"/min flow rate) afforded 2.0 g of slightly impure title keto-phosphinate as an orange oil. Subsequent chromatography (30 mm diameter column, 25:1 Merck silica gel, 95% EtOAc/hexane eluent, 2"/min flow rate) afforded 1.95 g (4.29 mmol 47% yield) of the title ketophosphinate as an orange foam.

TLC:Silica gel, PMA R$_f$=0.29 100% EtOAc $^1$H NMR:(270 MHz, CDCl$_3$): δ7.78–7.13 (aromatic, olefinic, 10H), 5.62 (dd, 1H, J=17.93 Hz, J=25.84 Hz), 3.71 (s, 3H), 3.63 (s, 3H), 3.48 (d, 3H, J=11.6 Hz), 3.14 and 3.13 (2 x d, 2H, J=18.46 Hz), 2.44 (s, 3H).

Mass Spec: CI m/e 455 (M+H)$^+$.

IR:(film): 1749, 1717, 1623, 1614, 1604, 1511, 1328, 1223, 1159, 1031, 834 cm$^-$.

E. (E)-4-[[2-[1-(4-Fluorophenyl)-3-methyl-2-naphthalenyl]ethenyl]methoxyphosphinyl]-3-hydroxybutanoic acid, methyl ester The Part D ketophosphonate (2.82 mmol, 1.28 g) was stirred under argon in dry THF (12 ml). This solution was cooled to 0° C. and treated with NaBH$_4$ (2.82 mmol, 0.107 g), followed by dropwise addition of methanol (2.45 ml, dried over 4 Å molecular sieves). The reaction mixture was stirred at 0° C. for 1 hour, then quenched with 2.5 ml of acetone. 1.3 g of CC-4 silica gel (Mallinckrodt) were added and the reaction mixture was stirred as it was warmed to room temperature. Finally, the suspension was filtered through a fritted funnel, washed 2 times with EtOAc and 2 times with CH$_2$Cl$_2$. The filtrate was evaporated in vacuo to afford 1.3 g of an orange foam which crystallized upon addition of EtOAc. The product was purified via flash chromatography (30 mm diameter column 30:1 Merck silica gel, 3% MeOH/CH$_2$Cl$_2$ eluent, 2"/min flow rate). Product fractions were combined, evaporated, and azeotroped one time with benzene to afford 0.653 g (1.43 mmol, 51% yield) of the title hydroxyphosphinate as a pale yellow solid. This pure product was triturated from 7:3 EtOAc/hexane to afford 0.516 g of the hydroxyphosphinate as a white solid. m.p.=132°–134.5° C.

TLC:Silica gel, PMA R$_f$=0.38 4% MeOH/CH$_2$Cl$_2$.

$^1$H NMR:(270 MHz, CDCl$_3$): δ7.79–7.16 (aromatic, olefinic, 10H); 5.59 (2 x dd, 1H, J=17.94 Hz, J=24.27 Hz), 4.35 and 4.24 (2 x m, 1H), 3.70 (s, 3H), 3.49 and 3.47 (2 x d, 3H, J=11 Hz), 2.58–2.53 (m, 2H), 2.54 and 2.53 (2 x s, 3H), 2.01–1.74 (m, 2H).

Mass Spec:CI m/e 457 (M+H)$^+$.

IR:(KBr): 3422–3382, 3062, 3051, 2951, 2926, 2913, 1738, 1613, 1604, 1511, 1494, 1457, 1438, 1399, 1373, 1330, 1311, 1307, 1286, 1220, 1194, 1177, 1160, 1092, 1077, 1035, 883, 833 cm$^{-1}$.

F. (E)-4-[[2-[1-(4-Fluorophenyl)-3-methyl-2-naphthalenyl]ethenyl]hydroxyphosphinyl]-3-hydroxybutanoic acid, dilithium salt The Part E diester (1.1 mmol, 0.50 g) was stirred under argon in dioxane (10.45 ml) and treated with 1N LiOH (3.3 mmol, 3.3 ml). The reaction mixture was heated in a 70° C. oil bath for 45 minutes. The resulting white slurry was dissolved in ~100 ml 9:1 H$_2$O/MeOH and rotavapped to dryness at 35° C. The white solid was pumped under high vacuum for 1 hour, then redissolved in 100 ml 9:1 H$_2$O/MeOH and rotavapped to a volume of ~8 ml. This turbid solution was applied directly to an HP-20 chromatography column (17.5 cm×2.5 cm, equilibrated with H$_2$O) and eluted with 250 ml of H$_2$O, followed by 45:55 MeOH/H$_2$O. Fractions were collected every 1.3 minutes (~10 ml). Product fractions were combined, rotavapped at 35° C., redissolved in H$_2$O, lyophilized 16 hours and pumped under high vacuum over P$_2$O$_5$ for 16 hours to afford 0.449 g, 1.02 mmol, 93% yield of the title dilithium salt as a white lyophilate.

TLC:Silica gel, PMA R$_f$=0.49 7:2:1 (n-C$_3$H$_7$OH/NH$_4$OH/H$_2$O).

$^1$H NMR:(400 MHz, D$_2$O): δ7.73 (d, 1H, J=8.06 Hz), 7.64 (s, 1H), 7.43–7.39 (m, 1H), 7.25–7.13 (m, 4H), 7.05–6.95 (m, 3H), 5.62 (dd, 1H, J=17.96 Hz, J=21.2 Hz), 2.43 (s, 3H), 2.38 (dd, 1H, J=4.03 Hz, J=15.39 Hz), 2.22 (dd, 1H, J=9.16 Hz, J=15.39 Hz), 1.59–1.51 (m, 2H).

Mass Spec:FAB m/e 429 (M+H)$^+$, 435 (M+Li)$^+$, 441 (M+2Li)$^+$.

IR:(KBr); 3431 (br), 1603, 1593, 1511, 1494, 1423, 1221, 1158, 1050 cm$^{+1}$.

Anal calcd for C$_{23}$H$_{20}$FO$_5$PLi$_2$.0.87 moles H$_2$O M.W.=455.94: C, 60.60; H, 4.80; F, 4.17; P, 6.79. Found: C, 60.60; H, 4.73; F, 4.24; P, 6.82.

EXAMPLE 61

(S)-4-[[2-[1-(4-Fluorophenyl)-3-methyl-2-naphthalenyl]ethyl]hydroxyphosphinyl]-3-hydroxybutanoic acid, dilithium salt A. (S)-3-[[(1,1-Dimethylethyl)diphenylsilyl]oxy]-4-[[2-[1-(4-fluorophenyl)-3-methyl-2-naphthalenyl]ethynyl]methoxyphosphinyl]butanoic acid, methyl ester The Example 59 Part J acetylenic phosphinate (0.974 mmol, 0.675 g) was dissolved in methanol (14.3 ml). Argon was bubbled through this solution for 10 minutes, then 10% Pd/C (0.270 g) was added and the reaction mixture was shaken on a Parr hydrogenator at 40 psi H$_2$ for 24 hours. The reaction mixture was filtered through a celite pad, washed through with methanol, and the filtrate evaporated in vacuo to afford a white foam. The product was purified via flash chromatography (50 mm diameter column, 4.5" Merck silica gel, 70% EtOAc/hexane eluent, 2"/min flow rate) to afford 0.556 g (0.798 mmol, 82% yield) of the title saturated phosphinate as a white foam. Elution of the column with methanol afforded an additional 0.101 g, (0.145 mmol, 15%) of product.

TLC:Silica gel, PMA $R_f=0.24$ 60% EtOAc/hexane.

$^1$H NMR:(270 MHz, CDCl$_3$): δ7.78–7.14 (aromatic, 19H), 4.44 (m, 1H), 3.61 (s, 3H), 3.35 and 3.23 (2 x d, 3H, J=10.6 Hz), 2.92–2.83 (m, 1H), 2.63–2.54 (m, 3H), 2.21–1.27 (m, 4H), 2.45 and 2.42 (2 x s, 3H), 1.00 (s, 9H).

Mass Spec: CI m/e 697 (M+H)$^+$.

IR:(CHCl$_3$ solution): 3028, 3019, 3007, 2997, 2953, 2933, 2859, 1735, 1510, 1497, 1472, 1463, 1439, 1428, 1378, 1364, 1314, 1236, 1197, 1157, 1142, 1112, 1091, 1073, 1065, 1043, 823 cm$^{-1}$.

B. (S)-4-[[2-[1-(4-Fluorophenyl)-3-methyl-2-naphthalenyl]ethyl]methoxyphosphinyl]-3-hydroxybutanoic acid, methyl ester The Part A silyl ether (0.775 mmol, 0.540 g) was stirred under argon in 9.45 ml of dry THF and treated with glacial acetic acid (3.10 mmol, 0.186 g, 0.177 ml), followed by dropwise addition of tetrabutylammonium fluoride (2.33 mmol, 2.1 ml of a 1.1M solution in THF). The reaction mixture was stirred at room temperature for 16 hours. The reaction mixture was quenched with 30 ml of ice water and diluted with EtOAc. The aqueous layer was extracted 3 times with EtOAc. The organic extracts were combined, washed once with saturated NaHCO$_3$ (aqueous), one time with brine, dried over MgSO$_4$, filtered and evaporated in vacuo. Initial purification via flash chromatography (40 mm diameter column, 6" Merck silica gel, 4% MeOH/CH$_2$Cl$_2$ eluent, 2"/min flow rate afforded 0.40 g of a white solid. This solid was triturated from 100% hexane, filtered and pumped under high vacuum (8 hours) to afford 0.317 g (0.691 mmol, 89% yield) of the title hydroxyphosphinate as a white solid, m.p.=120°-122° C.

TLC:Silica gel R$_f$=0.12 2% MeOH/CH$_2$Cl$_2$ $^1$H NMR: (270 MHz, CDCl$_3$): δ7.76 (d, 1H, J=7.9 Hz), 7.69 (s, 1H), 7.69 (s, 1H), 7.42–7.16 (m, 7H), 4.42 and 4.26 (2x m, 1H), 3.92 and 3.84 (2x d, 1H, J=3.16 Hz), 3.72 (s, 3H), 3.58 and 3.54 (2x d, 3H, J=3.69 Hz), 2.89–2.76 (m, 2H), 2.56 (s, 3H), 2.63–2.41 (m, 2H), 1.92–1.61 (m, 4H).

Mass Spec:CI m/e 459 (M+H)$^+$.

IR: (KBr): 3428 (br), 3287 (br), 3064, 3050, 3017, 2989, 2952, 2921, 1737, 1603, 1510, 1497, 1458, 1438, 1234, 1221, 1191, 1175, 1159, 1042, 826 cm$^{-1}$.

C. (S)-4-[[2-[1-(4-Fluorophenyl)-3-methyl-2-naphthalenyl]ethyl]hydroxyphosphinyl]-3-hydroxybutanoic acid, dilithium salt The Part B diester (0.687 mmol, 0.315 g) was stirred under argon in dioxane (6.9 ml). The solution was treated with 1N LiOH (2.06 mmol, 2.06 ml). The reaction mixture was heated in a 70° C. oil bath for 45 minutes. The reaction mixture was cooled to room temperature. The solvents were removed on the rotavap at 35° C. and the resulting white solid pumped under high vacuum for 1 hour. Then, the solid was dissolved in ~8 ml of distilled H$_2$O and applied to an HP-20 chromatography column (16 cm×2.5 cm equilibrated with H$_2$O. The column was eluted with 250 ml of H$_2$O followed by 45:55 MeOH/H$_2$O. Fractions were collected every 1.4 minutes (~10 ml). Product fractions (37–47) were combined, evaporated on the rotavap at 35° C., lyophilized 16 hours, and pumped under high vacuum over P$_2$O$_5$ for 8 hours to afford 0.286 g (0.647 mmol, 94% yield) of the title dilithium salt as a white lyophilate.

TLC: silica gel, PMA $R_f=0.42$ 7:2:1 (n-C$_3$H$_7$OH/N-H$_4$OH/H$_2$O)

$^1$H NMR: (400 MHz, D$_2$O): δ7.82 (d, 1H, J=8.06 Hz), 7.76 (s, 1H), 7.46–7.42 (m, 1H), 7.30–7.25 (m, 3H), 7.18–7.13 (m, 3H), 4.06 (m, 1H), 2.72–2.66 (m, 2H), 2.54 (s, 3H), 2.34 (dd, 1H, J=4.4 Hz, J=15.22 Hz), 2.22 (dd, 1H, J=8.43 Hz, J=15.02 Hz), 1.59–1.51 (m, 2H), 1.44–1.39 (m, 2H).

Mass Spec: FAB m/e 443 (M+H)$^+$.

IR: (KBr): 3451–3426 (br), 3151, 3124, 1620, 1593, 1509, 1439, 1422, 1403, 1218, 1159, 1050 cm$^{-1}$.

Anal Calcd for C$_{25}$H$_{22}$FO$_5$PLi$_2$.0.60 moles H$_2$O M.W.=453.09: C, 60.96; H, 5.16; F, 4.19; P, 6.83. Found: C, 60.96; H, 5.29; F, 4.12; P, 6.82.

EXAMPLE 62

4-[[3-[4'-Fluoro-3,3',5-trimethyl[1,1'-biphenyl]-2-yl]propyl]hydroxyphosphinyl]-3-hydroxybutanoic acid, dilithium salt A. 3-[4'-Fluoro-3,3'5-trimethyl[1,1'-biphenyl]-2-yl]-2-propenoic acid, ethyl ester Sodium hydride (4.96 mmol, 0.119 g, 0.149 g of an 80% mineral oil dispersion) was washed under argon once with hexane and dried under an argon stream. Then, the NaH was stirred under argon in dry THF (9.1 ml). This suspension was cooled to 0° C. and treated dropwise (5 minutes) with a solution of triethylphosphonacetate (4.96 mmol, 1.11 g, 0.983 ml) in dry THF (2.2 ml). The resulting clear solution was stirred at 0° C. for 15 minutes, then warmed to room temperature and stirred for 30 minutes. Finally, a solution of Example 1 Part C aldehyde (4.13 mmol, 1.0 g) in dry THF (2.5 ml) was added dropwise (8 minutes). The reaction mixture was stirred at room temperature for 1 hour. The mixture was quenched with H$_2$O and the aqueous layer extracted 2 times with EtOAc and 2 times with Et$_2$O. The organic extracts were combined, washed once with brine, dried over MgSO$_4$, filtered and evaporated in vacuo. The product was purified via flash chromatography (50 mm diameter column, 6"Merck silica gel, 6% EtOAc/hexane eluent, 2"/min flow rate) to afford 1.19 g (3.79 mmol, 92% yield) of the title vinylic ester as a pale yellow foam.

TLC:Silica gel, PMA $R_f=0.22$ 4% EtOAc/hexane.

$^1$H NMR (270 MHz, CDCl$_3$): δ7.64 (d, 1H, J=16.35 Hz), 7.09–6.93 (m, 5H), 5.81 (d, 1H, J=16.35 Hz), 4.17 (q, 2H, J=7.12 Hz), 2.42 (s, 3H), 2.33 (s, 3H), 2.28 (s, 3H), 1.25 (t, 3H, J=7.12 Hz).

Mass Spec: CI m/e 313 (M+H)$^+$.

B. 4'-Fluoro-3,3',5-trimethyl[1,1'-biphenyl]-2-butanoic acid, ethyl ester

The Part A vinylic ester (3.68 mmol, 1.15 g) was dissolved in absolute EtOH (36 ml). Argon was bubbled through the solution for 10 minutes. 10% Pd/C (230 mg) was added and H$_2$(g) was bubbled through the solution for 10 minutes. The reaction mixture was stirred under an atmosphere of H$_2$ for 2 hours. The reaction mixture was diluted with EtOH and filtered through a ¼" Celite pad in a 60 ml fritted funnel. The Celite was washed with EtOH. The filtrate was evaporated in vacuo to afford 1.12 g (3.56 mmol, 97% yield) of the title saturated ester as a white solid.

TLC:Silica gel, PMA $R_f=0.29$ 5% EtOAc/hexane.

$^1$H NMR (270 MHz, CDCl$_3$): δ7.09–6.97 (m, 4H), 6.84 (s, 1H), 4.06 (q, 2H, J=7.12 Hz), 2.90–2.84 (m, 2H), 2.37 (s, 3H), 2.30 (2 x s, 6H), 2.32-2.27 (m, 2H), 1.20 (t, 3H, J=7.12 Hz).

Mass Spec: CI m/e 315 (M+H)+.

C. 4'-Fluoro-3,3',5-trimethyl[1,1'-2-propanol

Lithium aluminum hydride (3.5 mmol, 0.133 g) was stirred under argon in dry $Et_2O$ (3.5 ml). This suspension was cooled to 0° C. and treated dropwise (8 minutes) with a solution of the Part B ester (3.5 mmol, 1.1 g) in dry $Et_2O$ (3.5 ml). The reaction mixture was stirred at 0° C. for 15 minutes, then warmed to room temperature and stirred for 45 minutes. The mixture was again cooled to 0° C. and treated dropwise with 0.133 ml of $H_2O$, followed by 0.133 ml of 15% NaOH and finally 0.399 ml of $H_2O$. The suspension was warmed to room temperature over 30 minutes. The resulting white powdery solid was filtered and washed with dry $Et_2O$. The filtrate was concentrated, azeotroped once with benzene and stripped in vacuo to afford 0.950 g of alcohol which was purified via flash chromatography (50 mm diameter column, 6" Merck silica gel, 35% EtOAc/hexane eluent, 2"/min flow rate) to afford 0.906 g (3.33 mmol, 95% yield) of the title alcohol as a colorless oil.

TLC:Silica gel, PMA $R_f$=0.18 20% EtOAc/Hexane.

$^1H$ NMR (270 MHz, $CDCl_3$): δ7.08-6.93 (m, 4H), 6.82 (s, 1H), 3.45-3.40 (m, 2H), 2.60-2.54 (m, 2H), 2.34 (s, 3H), 2.28 (2 x s, 6H), 1.63-1.52 (m, 2H).

Mass Spec: CI m/e 273 (M+H)+.

D. 2-(3-Bromopropyl)-4'-fluoro-3,3',5-trimethyl[1,1'-biphenyl]

A solution of triphenylphosphine (10.1 mmol, 2.65 g) in dry THF (27.5 ml) was cooled to 0° C. and treated dropwise with a solution of carbon tetrabromide (10.71 mmol, 3.55 g) in dry THF (5.5 ml). The resulting yellow/white slurry was stirred at 0° C. for 2 hours. The complex was treated dropwise with a solution of the Part C alcohol (4.04 mmol, 1.1 g) in dry THF (8.2 ml). The reaction mixture was stirred at 0° C. for 1 hour, then warmed to room temperature and stirred 16 hours. The reaction mixture was diluted with $Et_2O$, filtered through a fritted funnel and the precipitate washed with $Et_2O$. The filtrate was washed once with brine, dried over $MgSO_4$, filtered, and evaporated in vacuo. The product was purified via flash chromatography (50 mm diameter, 6" Merck silica gel, 2% EtOAc/hexane eluent, 2"/min flow rate) to afford 1.35 g (4.05 mmol, 100% yield) of the title bromide as a pale yellow oil.

TLC:Silica gel, PMA $R_f$=0.22 100% hexane $^1H$ NMR (270 MHz, $CDCl_3$): δ7.07-6.99 (m, 4H), 6.82 (s, 1H), 3.22 (m, 2H), 2.69-2.63 (m, 2H), 2.36 (s, 3H), 2.30 (s, 3H), 2.28 (s, 3H), 1.90-1.80 (m, 2H).

Mass Spec: CI m/e 235 (M+H)+.

E. [3-[4'-Fluoro-3,3',5-trimethyl[1,1'-biphenyl]-2-yl]propyl]phosphonic acid, dimethyl ester The Part D bromide (3.88 mmol, 1.3 g) was stirred under argon in trimethylphosphite (38.8 ml). The reaction mixture was heated to reflux in a 135° C. oil bath for 36 hours. The excess $(CH_3O)_3P$ was removed via short path distillation and the residue pumped under high vacuum at 100° C. for 1 hour. The resulting yellow oil was subjected to flash chromatography purification (50 mm diameter column, 6" Merck silica gel, 85% EtOAc/hexane eluent, 2"/min flow rate) to afford 1.13 g (3.10 mmol, 80% yield) of the title dimethylphosphonate as a colorless oil.

TLC:Silica gel, PMA, $R_f$=0.28 100% EtOAc.

$^1H$ NMR (270 MHz, $CDCl_3$): δ7.08-6.97 (m, 4H), 6.81 (m, 4H), 3.65 (d, 6H, J=11 Hz), 2.63-2.56 (m, 2H), 2.34 (s, 3H), 2.30 (2 x s, 3H), 2.28 (s, 3H), 1.68-1.50 (m, 4H).

Mass Spec: CI m/e 365 (M+H)+

F. [3-[4'-Fluoro-3,3',5-trimethyl[1,1'-biphenyl]-2-yl]propyl]phosphonic acid, monomethyl ester The Part E phosphonate (3.43 mmol, 1.25 g) was stirred under argon in dioxane (8.23 ml). This solution was treated with 1N LiOH (5.15 mmol, 5.15 ml) and heated in a 95° C. oil bath. After 1 hour, an additional 3.43 mmol of LiOH were added and the reaction mixture again heated to 95° C. for 3.5 hours. The reaction mixture was cooled to room temperature. The solvents were removed in vacuo. The white solid residue was diluted with 25 ml of $H_2O$, the slurry cooled to 0° C. and acidified to pH=1 with 5% HCl (aqueous). The aqueous layer was extracted 4 times with EtOAc. The organic extracts were combined, dried over $MgSO_4$, filtered, and the filtrate concentrated. The residue was azeotroped 2 times with benzene and the resulting viscous oil pumped under high vacuum for 4 hours to afford 1.18 g (3.37 mmol, 98% yield) of the phosphonate mono-methyl ester as a yellow oil.

TLC:Silica gel, PMA, $R_f$=0.46 10:1:1 $CH_2Cl_2$/MeOH/$CH_3CO_2H$.

$^1H$ NMR (270 MHz, $CDCl_3$): δ7.06-6.95 (m, 4H), 6.81 (s, 1H), 3.56 (d, 3H, J=11 Hz), 2.62-2.53 (m, 2H), 2.32 (s, 3H), 2.27 (2 x s, 6H), 1.69-1.48 (m, 4H).

Mass Spec: FAB m/e 351 (M+H)+

G. 4-[[3-[4'-Fluoro-3,3',5-trimethyl[1,1'-biphenyl]-2-yl]propyl]methoxyphosphinyl]-3-oxobutanoic acid, methyl ester The Part F phosphonate monoester (3.22 mmol, 1.13 g) was stirred under argon in dry $CH_2Cl_2$ (12.9 ml). This solution was treated dropwise (8 minutes) with TMSDEA (6.44 mmol, 0.918 g, 1.20 ml freshly distilled). This solution was stirred at room temperature for 1.5 hours. The volaties were removed in vacuo (venting to argon). The residue was azeotroped once with 70 ml of dry benzene and evaporated in vacuo (venting to argon). Finally, the residue was pumped under high vacuum for 50 minutes. Then, the residue was stirred under argon in dry $CH_2Cl_2$ (12.9 ml). Two drops of dry DMF were added and the solution cooled to 0° C. and treated dropwise (8 minutes) with oxalyl chloride (3.70 mmol, 0.470 g, 0.323 ml). This reaction mixture was stirred at 0° C. for 20 minutes, then warmed to room temperature and stirred for 1¼ hours. The volatiles were removed, the residue azeotroped and pumped under high vacuum as above. The rust colored oil was then stirred under argon in dry THF (9.0 ml). This solution was cooled to −78° C. and maintained at −78° C. as it was added dropwise (20 minutes) to a −78° C. THF solution of the dianion of methylacetoacetate generated in the following manner: Sodium hydride (4.85 mmol, 0.116 g, 0.145 g of an 80% mineral oil dispersion) was washed once with hexane and dried under a stream of argon. The solid was then stirred under argon in dry THF (7.1 ml) and this suspension was cooled to 0° C. A solution of methyl acetoacetate (4.36 mmol, 0.506 g, 0.471 ml) in dry THF (3.6 ml) was added dropwise (8 minutes) and the resulting clear solution stirred at 0° C. for 25 minutes. Then, the reaction mixture was treated dropwise (10 minutes) with n-BuLi (4.04 mmol, 1.62 ml of a 2.5M solution in hexane, Aldrich). The resulting yellow solution was stirred at 0° C. for 35 minutes, then cooled to −78° C. and treated dropwise (20 min) with the −78° C. THF solution of the phosphonochloridate formed above. The reaction mixture was stirred at −78° C. for 1 hour, then quenched with saturated NH₄Cl (aqueous) (45 ml) and warmed to room temperature. The mixture was diluted with H₂O (45 ml) and EtOAc. The aqueous layer was extracted 4 times with EtOAc. The organic extracts were combined, washed once with saturated NaHCO₃ (aqueous) and once with brine, dried over MgSO₄, filtered and evaporated in vacuo to afford 2.0 g of a rust oil. The product was isolated via flash chromatography (40 mm diameter column, 35:1) Merck silica gel, 100% EtOAc to 5% MeOH/CH₂Cl₂ eluent, 2"/min flow rate to afford 0.220 g (0.491 mmol, 15% yield) of the title β-ketophosphinate as a rust oil.

TLC: Silica gel, PMA $R_f=0.19$ 100% EtOAc.

¹H NMR (270 MHz, CDCl₃): δ7.08–6.98 (m, 4H), 6.81 (s, 1H), 3.73 (s, 3H), 3.65 (d, 3H, J=11 Hz), 3.64 (s, 2H), 3.10 (dd, 2H, J=5.27 Hz, J=17.41 Hz), 2.67–2.57 (m, 2H), 2.35 (s, 3H), 2.30 and 2.28 (2 x s, 3H), 2.29 (s, 3H), 1.72–1.56 (m, 4H).

Mass Spec: CI m/e 449 (M+H)⁺.

H. 4-[[3-[4'-Fluoro-3,3',5-trimethyl[1,1'-biphenyl]-2-yl]propyl]methoxyphosphinyl]-3-hydroxybutanoic acid, methyl ester The Part G β-ketophosphinate (0.223 mmol, 0.10 g) was stirred under argon in dry THF (1.9 ml). This solution was cooled to 0° C. and then treated with NaBH₄ (0.223 mmol, 0.008 g), followed by dropwise addition of MeOH (0.194 ml, dried over 4 Å mol sieves). The reaction mixture was stirred at 0° C. for 1 hour, then quenched with acetone (0.194 ml) followed by 0.10 g of CC-4 silica gel (Mallinckrodt). The suspension was stirred as it was warmed to room temperature, then filtered through a fritted funnel. The silica was washed with EtOAc. The filtrate was evaporated in vacuo to afford 0.108 g of a golden oil. Two reaction products were isolated via flash chromatography (10 mm diameter column, 35:1 Merck silica gel, 4% MeOH/CH₂Cl₂ eluent, 2"/min flow rate). The desired title β-hydroxyphosphinate was obtained in 58% yield (0.058 g, 0.129 mmol) as a pale yellow oil. Also obtained were 0.019 g (0.043 mmol 20% yield) of the 1,3-butandiol phosphinate.

TLC:Silica gel PMA $R_f=0.19$ 3.5% MeOH/CH₂Cl₂.

¹H NMR (270 MHz, CDCl₃): δ7.08–6.98 (m, 4H), 6.82 (s, 1H), 4.44 and 4.32 (2 x m, 1H), 3.63 and 3.62 (2 x d, 3H, J=10.55 Hz), 3.70 (s, 3H), 2.65–2.50 (m, 4H), 2.35 (s, 3H), 2.30 (2 x s, 3H), 2.29 (s, 3H), 1.89–1.76 (m, 2H), 1.71–1.59 (m, 4H).

Mass Spec: CI m/e 451, (M+H)⁺.

I. 4-[[3-[4'-Fluoro-3,3',5-trimethyl[1,1'-biphenyl]-2-yl]propyl]hydroxyphosphinyl]-3-hydroxybutanoic acid, dilithium salt The Part H diester (0.122 mmol, 0.055 g) was stirred under argon in dioxane (2 ml) and treated with 1N LiOH (0.366 mmol, 0.366 ml). The reaction mixture was heated in a 80° C. oil bath for 45 minutes. The reaction mixture was cooled to room temperature and the solvents were removed on the rotavap. The resulting yellow solid was pumped under high vacuum for 2 hours to afford the title dilithium salt as a yellow solid.

TLC:Silica gel, PMA $R_f=0.29$ 8:1:1 CH₂Cl₂/MeOH/CH₃CO₂H.

¹H NMR (270 MHz, D₂O); δ7.08–7.05 (m, 4H), 6.80 (s, 1H), 4.13 (m, 1H), 2.54–2.47 (m, 2H), 2.38–2.28 (m, 2H), 2.30 (s, 3H), 2.22 (s, 3H), 2.20 (s, 3H), 1.59–1.50 (m, 2H), 1.42–1.29 (m, 4H).

EXAMPLE 63

[1S-[1<a(R*),2<a,4a<b,8<b,8a<a]]-4-[[2-[8-(2,2-Dimethyl-1-oxobutoxy)decahydro-2-methyl-1-naphthalenyl]ethyl]hydroxyphosphinyl]-3-hydroxy butanoic acid, dilithium salt A. [1S-(1<a,2<a,4a<b,8<b,8a<a)]-8-[[(1,1-Dimethylethyl)dimethylsilyl]oxy]-1,2,4a,5,6,7,8,8a-octahydro-2-methyl-1-naphthalenemethanol To dry Et₂O (5 ml) at 0° C. (ice bath) was added lithium aluminum hydride (132 mg, 1 molar eq) followed by the dropwise addition of [1S-(1<a,2<a,-4a<b,8<b,8a<a)]-8-[[(1,1-dimethylethyl)dimethylsilyl]oxy]-1,2,4a,5,6,7,8,8a-octahydro-2-methyl-1-naphthalenecarboxylic, acid, methyl ester, R. L. Funk et al., Tetrahedron Lett. 25, 1655 (1984) (1.175 g, 3.47 mmole) in dry Et₂O (5 ml) and the resulting grey suspension stirred overnight under argon at room temperature. The mixture was quenched by the sequential dropwise addition of H₂O (130 μl), 15% NaOH (130 μl) and H₂O (390 μl). Precipitated salts were removed by filtration through anhydrous MgSO₄ over packed Celite. Evaporation in vacuo gave 1.112 g of a clear oil which was purified by flash chromatography on silica gel eluting with (95:5) Hexane-EtOAc to give 902 mg (85.7%) of desired title alcohol as a clear oil which crystallized on standing, m.p.=79°–81° C.

TLC (9:1) Hexane-EtOAc, $R_f=0.21$.

Anal Calcd for C₁₈H₃₄O₂Si: C, 69.61; H, 11.04. Found: C, 69.64; H, 11.04.

¹H NMR (CDCl₃): δ0.00 (s, 6H), 0.82 (s, 9H), 0.83 (d, 3H), 0.94–1.05 (m, 2H), 1.18 (s, 1H), 1.2–1.42 (m, 2H), 1.67 (m, 3H), 1.89 (m, 1H), 2.25 and 2.37 (2H, 2 multiplets), 3.42 (bt, 1H), 3.80 (dd, 1H), 3.93 (bs, 1H), 5.29 (d, 1H), 5.48 (dq, 1H) ppm.

B. [1S-(1<a,2<a,4a<b,8<b,8a<a)]-8-[[(1,1-Dimethylethyl)dimethylsilyl]oxy]-1,2,4a,5,6,7,8,8a-octahydro-2-methyl-1-naphthalenecarboxaldehyde A solution of Dess-Martin periodinane (895 mg, 2.11 mmole) in dry CH₂Cl₂ (6 ml) was treated with dry t-C₄H₉OH (200 μl) and the white suspension stirred under argon at room temperature for 15 minutes. A solution of the alcohol (596 mg, 1.92 mmole) in dry CH₂Cl₂ (6 ml) was added dropwise over 5 minutes and the mixture stirred under argon at room temperature for 20 minutes. The mixture was added to a solution of sodium thiosulfate (2.12 g) in 1.0N NaHCO₃ (12 ml) and the resulting mixture stirred until all solids dissolved. The organic phase was washed with saturated NaHCO₃, H₂O and brine then dried over anhydrous Na₂SO₄ and evaporated in vacuo to give 1.005 g of a colorless oil. The crude product was combined with a smaller run (1.306 g total) and then purified by flash chromatography on silica gel eluting with (98:2) hexane-EtOAc. Product fractions were evaporated in vacuo to give 667 mg (75.7%) of desired title aldehyde as a colorless oil.

TLC (7:3) Hexane-Et₂O, $R_f=0.70$ PMA.

¹H NMR (CDCl₃): δ0.07 (s, 3H), 0.00 (s, 3H), 0.85 (s, 9H), 0.89 (d, 3H), 0.93–1.10 (m, 2H), 1.38–1.52 (m, 2H), 1.58–1.78 (m, 4H), 2.31 (m, 1H), 2.66 (m, 1H), 2.78 (m, 1H), 4.30 (s, 1H), 5.40 (d, 1H), 5.50 (m, 1H), 9.74 (d, 1H).

C. [1S-(1<a,2<a,4a<b,8<b,8a<a)]-1-(2,2-Dibromoethenyl)-8-[[(1,1-dimethylethyl)dimethylsilyl]oxy]-1,2,4a,5,6,7,8,8a-octahydro-2-methylnaphthalene A −15° C. (salt/ice bath) solution of the Part B aldehyde (667 mg, 2.16 mmole) and triphenylphosphine (1.7 g, 6.48 mmole) in dry CH₂Cl₂ (10 ml) was treated dropwise over 5 minutes with a CH₂Cl₂ (5 ml) solution of carbon tetrabromide (1.7 g, 6.48 mmole) and the deep reddish brown mixture stirred under argon at −15° C. for 30 minutes, at 0° C. for 2 hours and finally overnight at room temperature. The mixture was recooled to 0° C., treated with additional triphenylphosphine (567 mg, 216 mmol) followed by CBr₄ (358 mg, 1.08 mmole) and stirred for 4 hours at room temperature. The mixture was quenched with saturated NaHCO₃ (10 ml), diluted with CH₂Cl₂, the organic phase filtered through sintered glass, washed with saturated NaHCO₃ and brine, dried over anhydrous Na₂SO₄ and evaporated in vacuo to give 3.578 g of a brown solid. The crude product was purified by flash chromatography on silica gel eluting with neat hexanes. Product fractions were evaporated to give 677 mg (67.3%) of pure title vinyl dibromide as a colorless oil.

TLC (9:11 Hexane-acetone, $R_f$=0.73 UV+PMA).

¹H NMR (CDCl₃): δ0.08 and 0.10 (2 singlets, 6H), 0.85 (d, 3H), 0.90 (s, 9H), 0.98 (m, 2H), 1.25-2.52 (m, 5H), 1.74 (m, 1H), 1.82 (m, 1H), 2.39 (m, 1H), 2.56 (m, 1H), 2.66 (m, 1H), 3.95 (s, 1H), 5.48 (d, 1H), 5.52 (m, 1H), 6.37 (d, 1H) ppm.

D. [1S-(1<a,2<a,4a<b,8<b,8a<a)]-8-[[(1,1-Dimethylethyl)dimethylsilyl]oxy]-1-ethynyl-1,2,4a,5,6,7,8-,8a-octahydro-2-methylnaphthalene A −78° C. (dry ice/acetone) solution of the Part C vinyl dibromide (495 mg, 1.07 mmole) in dry THF (6 ml) was treated dropwise over 5 minutes with a 1.6M n-BuLi in hexanes solution (1.34 ml, 2.14 mmole) and the clear, colorless mixture stirred for 30 minutes under argon at −78° C. The mixture was quenched at −78° C. by addition of saturated NH₄Cl (5 ml), allowed to warm to room temperature, diluted with EtOAc, the organic phase washed with brine, dried over anhydrous Na₂SO₄ and evaporated in vacuo to give 291 mg (89.6%) of crude title acetylene as a colorless oil.

TLC hexanes $R_f$=0.43, UV+PMA

¹H NMR (CDCl₃): δ0.08 and 0.12 (2 singlets, 6H), 0.90 (s, 9H), 0.99 (m, 1H), 1.09 (d, 3H), 1.19 (m, 1H), 1.46 (m, 2H), 1.74 (m, 3H), 2.12 (d, 1H), 2.30 (m, 1H), 2.41 (m, 1H), 2.71 (m, 1H), 4.37 (m, 1H), 5.38 (d, 1H), 5.55 (m, 1H) ppm.

E. (S)-4-(Chloromethoxyphosphinyl)-3-[[(1,1-dimethylethyl)diphenylsilyl]oxy]butanoic acid, methyl ester Phosphonochloridate was prepared from the Example 25 Part B dicyclohexylamine salt by the following procedure. The free acid was regenerated by partitioning the dicyclohexyl amine salt (1.3 g, 2.05 mmole) between EtOAc and 5% KHSO₄, the organic layer was washed with 5% KHSO₄ (4 times) and brine then dried over anhydrous Na₂SO₄ and evaporated in vacuo to give the free acid as a clear viscous oil.

The phosphonic acid monomethyl ester (2.05 mmole) was taken up in dry CH₂Cl₂ (5 ml), treated with distilled N,N-diethyltrimethylsilylamine (515 μl, 4.1 mmole) and the clear, colorless solution stirred at room temperature under argon for 1 hour. Excess reagent and solvent was removed in vacuo, the residual oil chased with benzene (2×10 ml).

The crude silyl ester (∼2.05 mmole) in dry CH₂Cl₂ (5 ml) and dry DMF (1 drop) was cooled to 0° C. (ice bath) and treated dropwise with distilled oxalyl chloride (195 μl, 2.26 mmole) and the yellow mixture stirred under argon at 0° C. for 15 minutes and at room temperature for 45 minutes. The mixture was evaporated in vacuo, chased with dry benzene (2×10 ml) to give crude title phosphonochloridate as a viscous yellow oil.

F. [1S-[1<a(R*),2<a,4a<b,8<b,8a<a]]-4-[[[8-[[(1,1-dimethylethyl)dimethylsilyl]oxy]-1,2,4a,5,6,7,8-,8a-octahydro-2-methyl-1-naphthalenyl]ethynyl]methoxyphosphinyl]-3-[[(1,1-dimethylethyl)diphenylsilyl]oxy]butanoic acid, methyl ester A −78° C. solution of the Part D acetylene (356 mg, 1.17 mmole) in dry THF (5 ml) was treated dropwise with a 1.6M n-BuLi in hexanes solution (730 μl, 1.17 mmole) and the clear mixture stirred under argon at −78° C. for 30 minutes. The acetylenic anion was then transferred via cannula dropwise over 15 minutes to a −78° C. solution of the Part E phosphonochloridate in dry THF (6 ml). The yellow mixture was stirred 30 minutes at −78° C. then quenched by dropwise addition of saturated NH₄Cl (5 ml) and allowed to warm to room temperature. The mixture was partitioned between EtOAc and H₂O, the organic phase washed with brine, dried over anhydrous Na₂SO₄ and evaporated in vacuo to give 1.282 g of a pale yellow oil. The crude product was purified by flash chromatography on silica gel eluting with (7:3) hexane-EtOAc. Product fractions were evaporated to give 624 mg (72.4%) of title acetylenic phosphinate as a colorless glass.

TLC (7:3) Hexane-acetone, $R_f$=0.49, UV+PMA.

G. [1S-[1<a(R*),2<a,4a<b,8<b,8a<a]]-4-[[2-[8-[[(1,1-Dimethylethyl)dimethylsilyl]oxy]decahydro-2-methyl-1-naphthalenyl]ethyl]methoxyphosphinyl]-3-[[(1,1-dimethylethyl)diphenylsilyl]oxy]butanoic acid, methyl ester A solution of Part F acetylene phosphinate (498 mg) in CH₃OH (6 ml) was treated with 10% Pt/C (200 mg) and the black suspension shaken on a Parr apparatus under H₂ (40 psi) for 48 hours. The catalyst was removed by filtration through Celite, the reaction mixture charged with new catalyst (150 mg) and shaken on the Parr apparatus under H₂ (40 psi) for an additional 24 hours. Catalyst was removed by filtration through Celite and the filtrate evaporated in vacuo to give 448 mg of a clear glass. The crude product was purified by flash chromatography on silica gel eluting with (8:2) Hexane-EtOAc. Product fractions were evaporated in vacuo to give 334 mg (66.5%) of title compound as a colorless glass.

TLC (7:3) EtOAc-Hexane, $R_f$3 diastereomers as one spot=0.42, $R_f$ 4th diastereomer as one spot=0.49, UV+PMA.

H. [1S-[1<a(R*),2<a,4a<b,8<b,8a<a]]-4-[[2-(Decahydro-8-hydroxy-2-methyl-1-naphthalenyl)ethyl]methoxyphosphinyl]-3-[[(1,1-dimethylethyl)diphenylsilyl]oxy]butanoic acid, methyl ester A solution of Part G compound (248 mg, 0.334 mmole) in CH₃CN (4 ml) was treated with 48% HF in H₂O (36 μl, 1 mmole) and the mixture stirred for 6.5 hours under argon at room temperature. The mixture was partitioned between EtOAc and saturated NaHCO₃, the organic phase washed with brine, dried over anhydrous Na₂SO₄ and evaporated in vacuo to give 227 mg of a colorless glass. The crude product was purified by flash chromatography on silica gel eluting with (4:1) Hexane-EtOAc followed by neat EtOAc. Product fractions were evaporated in vacuo to give 159 mg (75.8%) of pure title mono alcohol as a colorless oil.

TLC (7:3) Acetane-Hexane, $R_f$=0.5 (UV (weak)+PMA.

I. [1S-[1<a(R*),2<a,4a<b,8<b,8a<a]]-3-[[(1,1--Dimethylethyl)diphenylsilyl]oxy]-4-[[2-[8-(2,2-dimethyl-1-oxobutoxy)decahydro-2-methyl-1-naphthalenyl]ethyl]methoxyphosphinyl]butanoic acid, methyl ester A solution of the Part H alcohol (147 mg, 0.234 mmole) in dry pyridine (1.5 ml) was treated with 2,2-dimethylbutyryl chloride (160 μl, 1.17 mmole, 5 eq.) followed by 4-dimethylaminopyridine (3 mg, 0.1 eq) and the pale yellow mixture heated at 100° C. under argon for 4 hours. The mixture was cooled, partitioned between 1.0N HCl and EtOAc, the organic phase washed with 1.0N HCl (2 times) and brine, dried over anhydrous $Na_2SO_4$ and evaporated to give 255 mg of a pale, yellow brown oil. The crude product was purified by flash chromatography on silica gel eluting with (55:45) Hexane-EtOAc. Product fractions were evaporated in vacuo to give 112 mg (65.9%) of desired title dimethyl butyryl ester as a colorless oil. Hexane-acetone, $R_f=0.62$, UV+PMA.

J. [1S-[1<a(R*),2<a,4a<b,8<b,8a<a]]-4-[[2-[8-(2,2-Dimethyl-1-oxobutoxy)decahydro-2-methyl-1-naphthalenyl]ethyl]methoxyphosphinyl]-3-hydroxy-butanoic acid, methyl ester A solution of the Part I silyl ester (130 mg, 0.179 mmole) in THF (2 ml) was treated successively with glacial acetic acid (HOAc) (41 μl, 0.716 mmole) and a 1.1M $(n-C_4H_9)_4NF$ solution in THF (490 μl, 0.537 mmole) and the mixture stirred overnight under argon. The mixture was partitioned between EtOAc and 5% $KHSO_4$, the organic phase washed with $H_2O$ and brine, dried over anhydrous $Na_2SO_4$ and evaporated in vacuo to give 115 mg of a colorless oil. The crude product was purified by flash chromatography on silica gel eluting with (1:1) hexane-acetone. Product fractions were evaporated in vacuo to give 72 mg (82.4%) of desired title alcohol as a colorless oil.

TLC (1:1) Hexane-acetone, $R_f=0.20$, UV+PMA.

K. [1S-[1<a(R*),2<a,4a<b,8<b,8a<a]]-4-[[2-[-(2,2-Dimethyl-1-oxobutoxy)decahydro-2-methyl-1-naphthalenyl]ethyl]hydroxyphosphinyl]-3-hydroxy-butanoic acid, dilithium salt A solution of Part J alcohol (72 mg, 0.147 mmole) in dioxane (1.5 ml) was treated with 1.0N LiOH (0.52 ml) and the mixture heated at 55° C. (oil bath) under argon for 1.5 hours. The mixture was cooled, diluted with $H_2O$, filtered and evaporated in vacuo to an oil. The crude product was chromatographed on HP-20 resin (3 cm bed, 15 mm diameter column) eluting with $H_2O$ followed by (70:30) $H_2O-CH_3OH$. Product fractions were evaporated in vacuo, dissolved in $H_2O$ (20 ml) and lyophilized to give 55 mg (74%) of desired title dilithium salt as a white solid.

TLC (8:1:1) $CH_2Cl_2-CH_2OH-CH_3COOH$, $R_f=0.05$, PMA.

Anal Calcd for $C_{23}H_{39}O_7PLi_2 + 1.78$ moles $H_2O$ (MW 504.53): C, 54.75; H, 8.50; P, 6.14. Found: C, 54.75; H, 8.64; P, 5.93.

EXAMPLE 64

(S)-4-[[[3'-(4-Fluorophenyl)spiro[cyclopentane-1,1'-[1H]indene]-2-yl]ethynyl]hydroxyphosphinyl]-3-hydroxybutanoic acid, dilithium salt A. 3-(4-Fluorophenyl)-1H-indene To a solution of solution of 4-fluorophenylmagnesium bromide (prepared from 6.43 ml of 4-fluorobromobenzene and 1.71 g of Mg in 50 ml of ether) at room temperature under argon was added dropwise over 40 minutes a solution of 1-indanone (6.61 g, 50 mmole) in dry ether (20 ml). After stirring at room temperature for 1 hour, the reaction was quenched by the dropwise addition of saturated $NH_4Cl$ solution (15 ml). The mixture was diluted with $Et_2O$, washed with saturated NaCl solution, dried ($MgSO_4$) and evaporated.

The residue was taken up in glacial acetic acid (15 ml) and refluxed under argon for 30 minutes. The acetic acid was evaporated off and chased twice with toluene. The residue (9.45 g) was purified by flash chromatography on silica gel eluting with hexane to give title compound (8.174 g, 78%) as a colorless oil which crystallized on standing, m.p. 38°-40° C. TLC (hexane) $R_f=0.21$.

B. 3'-(4-Fluorophenyl)spiro[cyclopentane-1,1'-[1H]indene]

To a solution of Part A compound (10.676 g, 50.8 mmole) in dry THF (90 ml) at 0° C. under argon was added, in portions, solid potassium t-butoxide (12.2 g, 109 mmole). After stirring at 0° C. for 30 minutes, 1,4-dibromobutane (6.50 ml, 101 mmole) was added dropwise. The resulting mixture was allowed to warm to room temperature, stirred for 2 hours, then partitioned between EtOAc-5% $KHSO_4$ (150 ml each). The organic phase was washed with saturated NaCl solution, dried ($Na_2SO_4$) and evaporated to dryness. The crude product was purified by flash chromatography on silica gel, eluting with hexane to give title compound (9.43 g, 70%) as a colorless oil. TLC ($Et_2O$-hexane; 1:9) $R_f=0.69$ ($R_f$ of Part A compound=0.63).

C. 3'-(4-Fluorophenyl)spiro[cyclopentane-1,1'-[1H]indene]-2'-carboxaldehyde

To a solution of Part B compound (9.30 g, 35.2 mmole) in dry $CH_2Cl_2$ (50 ml) at 0° C. under argon was added a 1.0M solution of $TiCl_4$ in $CH_2Cl_2$ (70 ml, 70 mmole). The resulting dark green solution was treated dropwise with 1,1-dichloromethyl methyl ether (3.50 ml, 38.7 mmole). After stirring at 0° C. for 1 hour and at room temperature for 1 hour, the mixture was poured onto cold, saturated $NaHCO_3$ solution. The organic phase was separated, dried ($Na_2SO_4$) and evaporated to dryness. The crude product was purified by flash chromatography on silica gel eluting with $Et_2O$-hexane (5:95) to give title compound (8.233 g, 80%) as a yellow oil. Crystallization of the oil from hexane gave pure title compound (6.778 g, 66%) as pale yellow crystals, 116°-117° C.

TLC ($Et_2O$-hexane; 15:85) $R_f=0.56$.

Anal Calcd for $C_{20}H_{17}OF$: C, 82.17; H, 5.86; F, 6.50. Found: C, 83.13; H, 5.82; F, 6.29.

D. 2'-Ethynyl-3'-(4-fluorophenyl)spiro[cyclopentane-1,1'-[1H]indene

To a solution of potassium t-butoxide (0.672 g, 6.00 mmol) in dry THF (8 ml) at −78° C. under argon was added dropwise a solution of dimethyl diazomethyl-phosphonate (0.960 g, 6.40 mmole, prepared as in J. Org. Chem. 36, 1379 (1971)) in THF (4 ml). After stirring at −78° C. for 5 minutes, a solution of Part C compound (1.168 g, 4.00 mmole) in THF (8 ml) was added dropwise over 10 minutes. After stirring at −78° C. for 3 hours, −45° C. for 1.5 hour and at room temperature for 1 hour, the mixture was diluted with hexane (50 ml) and washed with 5% $KHSO_4$ solution. The organic phase was washed with saturated NaCl solution, dried ($Na_2SO_4$) and concentrated to a small volume (not to dryness). The yellow solution was flash chromatgraphed on silica gel eluting with hexane. The product containing fractions were combined, treated with butylated hydroxytoluene (BHT) (0.080 g, 0.36 mmole) and concentrated to a small volume (5-10 ml) which was used immediately as a solution for the next step. TLC (Et₂O-hexane; 1:9) R_f=0.57. ¹H NMR (270 MHz, CDCl₃) using BHT as an internal standard (1.45 ppm, 18H, s) shows the presence of 3.10 mmoles (77.5% yield) of the desired acetylene (3.32 ppm, 1H, s).

E. (S)-4-(Chloromethoxyphosphinyl)-3-[[(1,1-dimethylethyl)diphenylsilyl]oxy]butanoic acid, methyl ester Title phosphonochloridate was prepared from the Example 25 Part B dicyclohexylamine salt (3.44 g, 54.4 mmole) as described in Example 29, Part J using the following quantities; trimethylsilyldiethylamine (1.36 ml, 10.85 mmole), CH₂Cl₂ (15 ml); oxalyl choride (0.50 ml, 5.73 mmole), DMF (1 drop), CH₂Cl₂ (15 ml).

F. (S)-3-[[(1,1-Dimethylethyl)diphenylsilyl]oxy]-4-[[[3'-(4-fluorophenyl)spiro[cyclopentane-1,1'-[1H]indene]-2-yl]ethynyl]methoxyphosphinyl]butanoic acid, methyl ester The hexane solution of the Part D acetylene (3.10 mmole + 0.36 mmole of BHT) was diluted with dry THF (15 ml) and cooled to −78° C. under argon. The solution was then treated with a 1.6M solution of n-BuLi in hexane (2.16 ml, 3.46 mmole) dropwise via syringe. After stirring at −78° C. for 45 minutes, the anion solution was transferred via cannula to a −78° C. solution of Part E phosphonochloridate (54.4 mmole) in dry THF (15 ml). After stirring at −78° C. for 1 hour, the reaction was quenched by the dropwise addition of saturated NH₄Cl (15 ml) and allowed to warm to room temperature. The mixture was extracted with EtOAc, the extracts washed with 5% KHSO₄, saturated NaHCO₃ and saturated NaCl solutions, dried (Na₂SO₄) and evaporated to dryness. The crude product was purified by flash chromatography on silica gel eluting with EtOAc-hexane (25:75) to give title compound (1.781 g, 80% based on Part D compound) as a pale yellow glass.

TLC (acetone-hexane; 1:1) R_f=0.46.

G. (S)-4-[[[3'-(4-Fluorophenyl)spiro[cyclopentane-1,1'-[1H]indene]-2-yl]ethynyl]methoxyphosphinyl]-3-hydroxybutanoic acid, methyl ester To a solution of Part F compound (1.00 g, 1.39 mmole) in dry THF (5 ml) at room temperature under argon was added glacial acetic acid (0.32 ml, 5.59 mmole) and a 1.1M solution of (n-C₄H₉)₄NF in THF (3.80 ml, 4.18 mmole). After stirring at room temperature for 18 hours, the mixture was diluted with EtOAc (50 ml) washed successively with 1N HCl (3×30 ml) and saturated NaCl solutions, dried (Na₂SO₄) and evaporated to dryness. The residue was taken up in Et₂O (20 ml), cooled in an ice bath and treated with excess etheral diazomethane. The residue obtained by evaporation of the ether was purified by flash chromatography on silica gel eluting with acetone-hexane (3:7) to give title compound (0.595 g, 89%) as a colorless glass. TLC (acetone-hexane; 1:1) R_f=0.29.

H. (S)-4-[[[3'-(4-Fluorophenyl)spiro[cyclopentane-1,1'-[1H]indene]-2-yl]ethynyl]hydroxyphosphinyl]-3-hydroxybutanoic acid, dilithium salt To a solution of Part G compound (0.580 g, 1.20 mmole) in dioxane (6 ml) at room temperature under argon was added 1N LiOH solution (4.2 ml, 4.2 mmole). After stirring at room temperature for 3 hours, the mixture was diluted with acetonitrile (20 ml), the white preciiptate was collected, washed with acetonitrile and dried in vacuo to give crude title product (0.670 g) as a white solid. The crude product was suspended in water (10 ml) and applied to a short pad of HP-20 (15 ml bed volume, 1 inch diameter), eluted with water (300 ml) followed by MeOH (300 ml). The product containing fractions were combined and evaporated to dryness. The solid residue was triturated with acetonitrile to give pure title product (0.550 g, 98%) as a white solid, mp 301°-303° C. (decomp).

TLC (i-C₃H₇OH-concentrated NH₄OH-H₂O; 7:2:1) R_f=0.48.

EXAMPLES 65 to 122

Following the procedures as outlined heretofore and as described in the previous working Examples, the following additional compounds may be prepared.

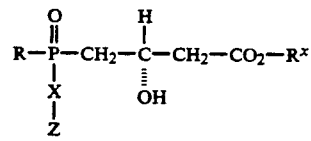

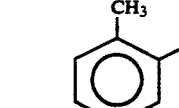

| Ex. No. | R | Z | X | Rˣ |
|---|---|---|---|---|
| 65. | OCH₃ | 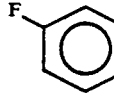 | —CH₂—CH₂— | CH₃ |
| 66. | OH | 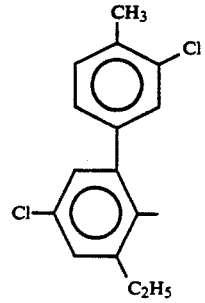 | —C≡C— | H |

-continued

| Ex. No. | R | Z | X | R$^x$ |
|---|---|---|---|---|
| 67. | OLi | 3,5-dimethylphenyl-substituted 2,3-dimethylnaphthalene | —CH$_2$CH$_2$CH$_2$— | Li |
| 68. | OH | 1-methyl-2-(4-fluorophenyl)naphthalene | —CH$_2$O— | H |
| 69. | OLi | 3-(4-fluorophenyl)-2-methyl-1-isopropylindole | —CH$_2$CH$_2$CH$_2$— | Li |
| 70. | OCH$_3$ | 3-isopropyl-2-methyl-1-(4-fluorophenyl)indole | —CH$_2$CH$_2$CH$_2$— | CH$_3$ |
| 71. | OK | 2-methylbutanoate ester of dimethyl-octahydronaphthalenol | —CH$_2$— | OK |
| 72. | ONa | benzyloxy ethyl-methyl-octahydronaphthalene | —CH$_2$— | Na |

-continued
| Ex. No. | R | Z | X | R$^x$ |
|---|---|---|---|---|
| 73. | OH | 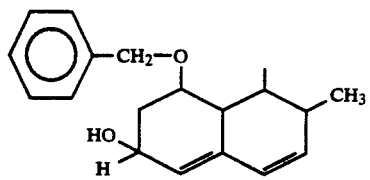 | —CH$_2$CH$_2$— | H |
| 74. | OH | 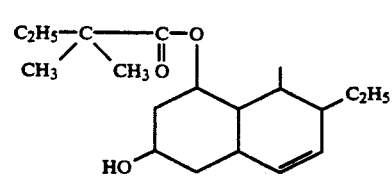 | —CH$_2$CH$_2$CH$_2$— | H |
| 75. | CH$_3$O | 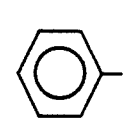 | —CH$_2$— | CH$_3$ |
| 76. | OH | 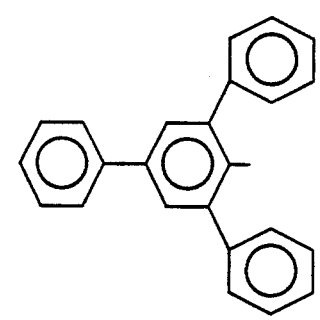 | —CH$_2$O— | H |
| 77. | OH | 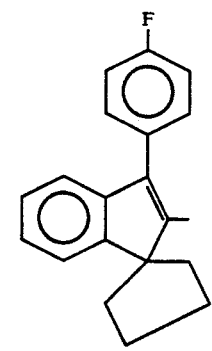 | CH$_2$CH$_2$ | H |
| 78. | OH | 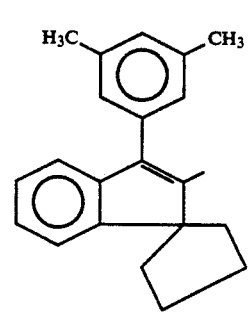 | —CH=CH— | H |

-continued

| Ex. No. | R | Z | X | R$^x$ |
|---|---|---|---|---|
| 79. | OH | (4-fluorophenyl-N, 2-methyl, 4-isopropyl, 5-phenyl pyrrole) | —CH$_2$CH$_2$— | H |
| 80. | NaO | (3-(4-fluorophenyl), 2-methyl, 1-isopropyl-N, 5-phenyl pyrrole) | —CH=CH— | Na |
| 81. | O$^-$ | (3-(4-fluorophenyl), 4-methyl, 5-isopropyl, 2-phenyl furan) | —C≡C— | Ca |
| 82. | HO | (3-(4-fluorophenyl), 4-methyl, 5-isopropyl, 2-phenyl thiophene) | —C≡C— | H |
| 83. | NaO | (3-(4-fluorophenyl), 4-methyl, 5-isopropyl, 2-isopropyl thiophene) | —C≡C— | Na |

-continued

| Ex. No. | R | Z | X | R$^x$ |
|---|---|---|---|---|
| 84. | CH$_3$O | 3,5-dimethylphenyl-thiophene-isopropyl, phenyl | —CH=CH— | H |
| 85. | CH$_3$O | 3,5-dimethylphenyl-thiophene-isopropyl, phenyl | —CH$_2$CH$_2$— | NH$_4$ |
| 86. | HO | 4-methoxyphenyl-thiophene-isopropyl, phenyl | —CH$_2$— | K |
| 87. | O$^-$ | 3-trifluoromethylphenyl-thiophene-isopropyl, phenyl | —CH$_2$CH$_2$CH$_2$— | Ca |
| 88. | CH$_3$O | biphenyl-thiophene-isopropyl, phenyl | —CH=CH— | Na |

-continued

| Ex. No. | R | Z | X | R^x |
|---|---|---|---|---|
| 89. | H | (cyclopentyl-thiophene with phenyl and CH(CH3)2 substituents) | —CH$_2$— | H |
| 90. | CH$_3$O | (diphenyl-thiophene with CH(CH3)2 substituent) | —CH=CH— | H |
| 91. | HO | (4-fluorophenyl, 4-methylphenyl-thiophene with CH(CH3)2 substituent) | —CH=CH— | H |
| 92. | CH$_3$O | (4-fluorophenyl, 4-methoxyphenyl-thiophene with CH(CH3)2 substituent) | —CH$_2$— | CH$_3$ |
| 93. | LiO | (4-fluorophenyl, 4-chlorophenyl-thiophene with CH(CH3)2 substituent) | —CH$_2$CH$_2$CH$_2$— | Li |

-continued

| Ex. No. | R | Z | X | R^x |
|---|---|---|---|---|
| 94. | KO | 4-fluorophenyl, methyl, isopropyl-substituted methylthiophene | —CH₂CH₂— | K |
| 95. | HO | 4-fluorophenyl, methyl, isopropyl-substituted thiophene with =CH—C(CH₃)₂ | —CH=CH— | H |
| 96. | HO | 4-fluorophenyl, methyl, isopropyl-substituted cyclopentylthiophene | —C≡C— | H |
| 97. | HO | isopropyl, methyl, 4-fluorophenyl, isopropyl-substituted imidazole | —C≡C— | H |
| 98. | LiO | isopropyl, methyl, 4-fluorophenyl, cyclopentyl-substituted imidazole | —C≡C— | Li |
| 99. | LiO | phenyl, 4-fluorophenyl, methyl, isopropyl-substituted pyrazole | —CH₂— | Li |

-continued
| Ex. No. | R | Z | X | $R^x$ |
|---|---|---|---|---|
| 100. | HO | 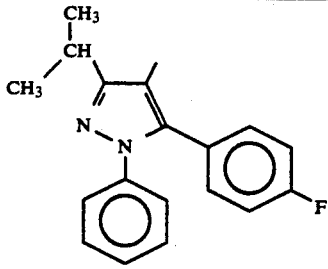 | $-CH_2-$ | H |
| 101. | HO | 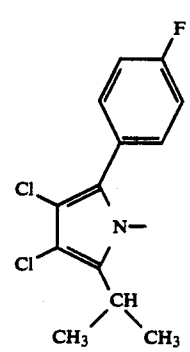 | $-CH_2CH_2-$ | H |
| 102. | NaO | 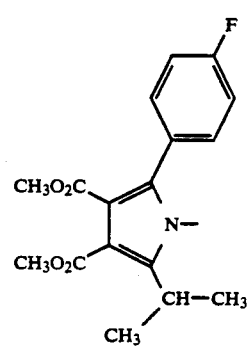 | $-CH_2-CH_2-$ | Na |
| 103. | LiO | 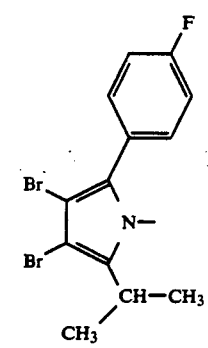 | $-CH_2CH_2-$ | Li |
| 104. | HO | 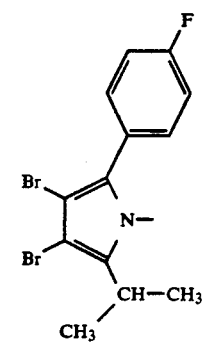 | $-CH_2-$ | H |

-continued
| Ex. No. | R | Z | X | R$^x$ |
|---|---|---|---|---|
| 105. | CH$_3$O | 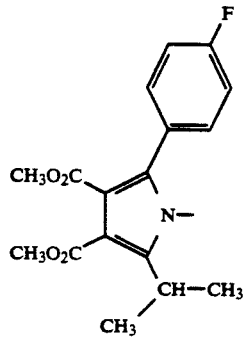 | —CH$_2$CH$_2$— | CH$_3$ |
| 106. | HO | 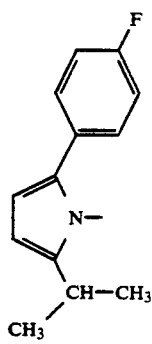 | —CH$_2$CH$_2$— | H |
| 107. | HO | 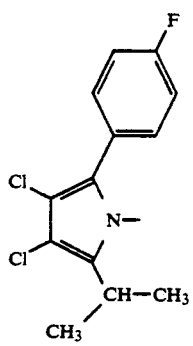 | —CH$_2$CH$_2$CH$_2$— | H |
| 108. | KO | 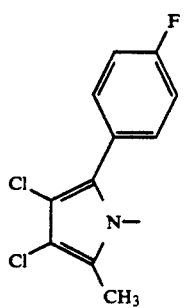 | —CH$_2$CH$_2$— | K |

| Ex. No. | R | Z | X | R$^x$ |
|---|---|---|---|---|
| 109. | HO | 2-(4-fluorophenyl)-3,4-dibromo-5-(cyclopropyl)pyrrol-1-yl | —CH$_2$CH$_2$— | H |
| 110. | LiO | 1,2-bis(4-fluorophenyl)-2-(i-C$_3$H$_7$)ethenyl | —CH=CH— | Li |
| 111. | KO | 1,2-diphenyl-2-(i-C$_3$H$_7$)ethenyl | —CH$_2$CH$_2$— | K |
| 112. | LiO | 1,2-bis(4-fluoro-3-methylphenyl)-2-(C$_2$H$_5$)ethenyl | —CH=CH— | Li |
| 113. | CH$_3$O | 1-(4-methoxyphenyl)-2-(4-methylphenyl)-2-(CH$_3$)ethenyl | —CH=CH— | CH$_3$ |
| 114. | OH | 4'-fluoro-3'-methyl-2-methylbiphenyl | —CH$_2$— | H |

-continued

| Ex. No. | R | Z | X | R$^x$ |
|---|---|---|---|---|
| 115. | LiO | 1-(4-fluoro-3-methylphenyl)-2-methyl-3-isopropylindole | —C≡C— | Li |
| 116. | LiO | 1-(4-fluoro-3-methylphenyl)-2-methyl-3-isopropylindole | —CH$_2$CH$_2$— | Li |
| 117. | LiO | 1-(3,5-dimethylphenyl)-2-methyl-3-isopropylindole | —C≡C— | Li |
| 118. | LiO | 1-(3,5-dimethylphenyl)-2-methyl-3-isopropylindole | —CH$_2$CH$_2$— | Li |
| 119. | LiO | 1-(4-fluorophenyl)-2-(4-fluorophenyl)-4-methyl-5-isopropylimidazole | —C≡C— | Li |
| 120. | LiO | 1-(4-fluorophenyl)-2-(4-fluorophenyl)-4-methyl-5-isopropylimidazole | —CH$_2$CH$_2$— | Li |

| Ex. No. | R | Z | X | R$^x$ |
|---|---|---|---|---|
| 121. | LiO | 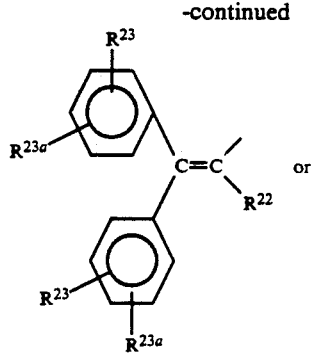 | —C≡C— | Li |
| 122. | LiO | 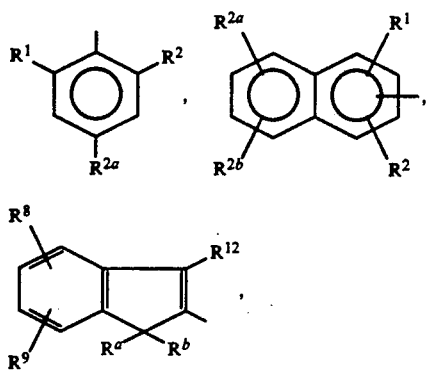 | —C≡C— | Li |

What is claimed is:

1. The compound having the formula

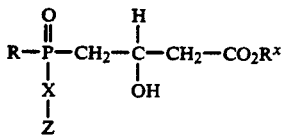

wherein R is OH or lower alkoxy;

R$^x$ is H or lower alkyl;

X is CH$_2$, —CH$_2$CH$_2$—, —CH$_2$CH$_2$CH$_2$—, —CH=CH—, —C≡C— or —CH$_2$O— (where O is linked to Z);

Z is a hydrophobic anchor which is

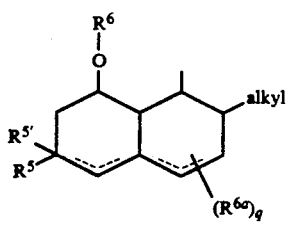

wherein R$^1$, R$^2$, R$^{2a}$ and R$^{2b}$ are the same or different and are each independently selected from H, halogen, lower alkyl, haloalkyl, phenyl, substituted phenyl or OR$^y$, wherein R$^y$ is H, alkanoyl, benzoyl, phenyl, halophenyl, phenyl-lower alkyl, lower alkyl, cinnamyl, haloalkyl, allyl, cycloalkyl-lower alkyl, adamantyllower alkyl or substituted phenyl-lower alkyl, wherein the term "substituted phenyl" by itself or as part of another group refers to phenyl substituted with 1, 2 or 3 substituents which are lower alkyl, halogen, lower alkoxy, hydroxy, phenyl, alkanoyloxy, benzoyloxy, haloalkyl, halophenyl, allyl, cycloalkylalkyl, adamantylalkyl, alkylamino, alkanoylamino, arylcarbonylamino (wherein aryl is phenyl, naphthyl or substituted phenyl or substituted naphthyl wherein the substituents are as defined for phenyl), amino, nitro, cyano, thiol and/or alkylthio;
wherein Z is

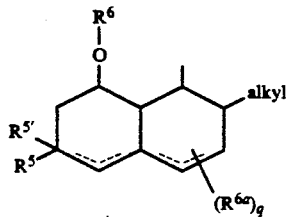

$R^5$ and $R^{5'}$ are the same or different and are H, lower alkyl or OH;
$R^6$ is lower

or arylCH$_2$—;
$R^{6a}$ is lower alkyl, hydroxy, oxo or halogen; q is 0, 1, 2 or 3, and
where Z is

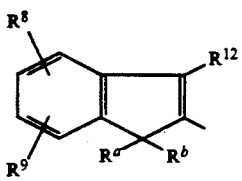

$R^a$ is H or primary or secondary 1-6C alkyl;
$R^b$ is primary or secondary 1-6C alkyl;
or $R^a + R^b$ is (CH$_2$)$_r$ or (cis)—CH$_2$—CH=CH—CH$_2$; r=2, 3, 4, 5 or 6;
$R^{12}$ is lower alkyl, cycloalkyl or

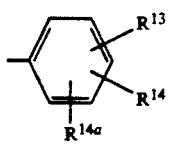

wherein $R^{13}$ is hydrogen, lower alkyl, trifluoromethyl, lower alkoxy (except t-butoxy), halogen, phenoxy or benzyloxy;
$R^{14}$ is hydrogen, lower alkyl, trifluoromethyl, lower alkoxy, halogen, phenoxy or benzyloxy;
$R^{14a}$ is hydrogen, lower alkyl, lower alkoxy, or halogen; and
with the provisos that both $R^{14}$ and $R^{14a}$ must be hydrogen when $R^{13}$ is hydrogen, $R^{14a}$ must be hydrogen when $R^{14}$ is hydrogen, not more than one of $R^{13}$ and $R^{14}$ is trifluoromethyl, not more than one of $R^{13}$ and $R^{14}$ is phenoxy and not more than one of $R^{13}$ and $R^{14}$ is benzyloxy;
$R^8$ is hydrogen, C$_{1-4}$ alkyl, C$_{3-6}$ cycloalkyl, C$_{1-4}$ alkoxy (except t-butoxy), trifluoromethyl, fluoro, chloro, phenoxy or benzyloxy;
$R^9$ is hydrogen, C$_{1-3}$ alkyl, C$_{1-3}$ alkoxy, trifluoromethyl, fluoro, chloro, phenoxy or benzyloxy, with the provisos that $R^9$ must be hydrogen when $R^8$ is hydrogen, not more than one of $R^8$ and $R^9$ is trifluoromethyl, not more than one of $R^8$ and $R^9$ is phenoxy, and not more than one of $R^8$ and $R^9$ is benzyloxy;
where Z is

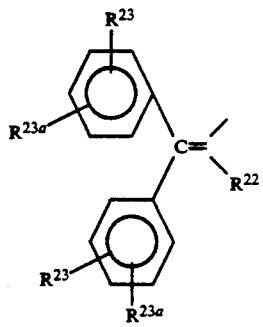

$R^{22}$ is lower alkyl, cycloalkyl, adamantyl-1 or

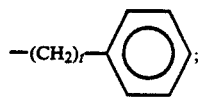

t=1, 2, 3 or 4;
$R^{23}$ and $R^{23a}$ are the same or different and are each independently selected from hydrogen, lower alkyl, lower alkoxy (except t-butoxy), halogen, phenoxy or benzyloxy; and
with the provisos that $R^{23a}$ must be hydrogen when $R^{23}$ is hydrogen, not more than one of $R^{23}$ and $R^{23a}$ is trifluoromethyl, not more than one of $R^{23}$ and $R^{23a}$ is phenoxy, and not more than one of $R^{23}$ and $R^{23a}$ is benzyloxy;
where X is —CH$_2$O— (carbon attached to P and O attached to Z), the hydrophobic anchor Z will be

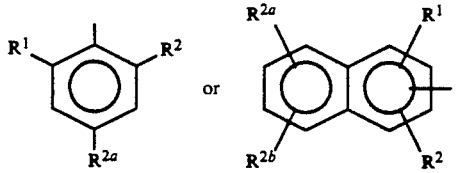

in free acid form or in the form of a physiologically-hydrolysable and -acceptable ester in salt form.

2. The compound as defined in claim 1 having the structure

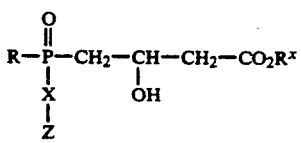

wherein R is OH or lower alkoxy and $R^x$ is H or lower alkyl, including salts thereof.

3. The compound as defined in claim 1 wherein X is —CH$_2$—CH$_2$—.

4. The compound as defined in claim 1 wherein X is —CH=CH— or —C≡C—.

5. The compound as defined in claim 1 wherein Z is

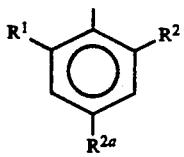

6. The compound as defined in claim 4 wherein Z is

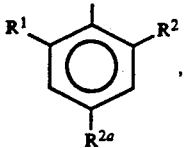

R is alkoxy, and $R^1$ is phenyl or benzyloxy, $R^2$ and $R^{2a}$ are the same or different and are halogen or lower alkyl.

7. The compound as defined in claim 1 wherein $R^1$ is 4-fluoro-3-methylphenyl and $R^2$ and $R^{2a}$ are each $CH_3$.

8. The compound as defined in claim 1 wherein X is $-CH_2-CH_2-$ and R is OH or alkoxy.

9. The compound as defined in claim 1 wherein X is $-CH=CH-$ or $-C\equiv C-$ and R is alkoxy or OH.

10. The compound as defined in claim 1 wherein X is trans $-CH=CH-$.

11. The compound as defined in claim 1 wherein X is cis $-CH=CH-$.

12. The compound as defined in claim 1 wherein Z is

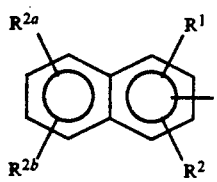

13. The compound as defined in claim 1 wherein Z is

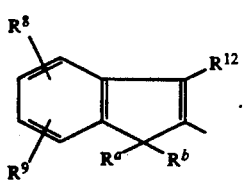

14. The compound as defined in claim 1 wherein Z is

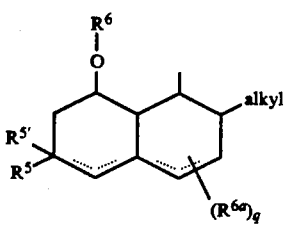

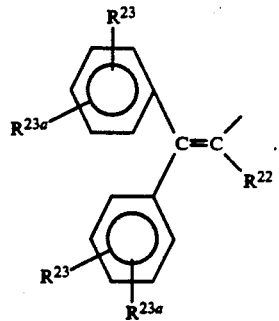

15. The compound as defined in claim 2 having the name (S)-4-[[[2-(cyclohexylmethyl)-4,6-dimethylphenyl]ethynyl]hydroxyphosphinyl]-3-hydroxybutanoic acid or its dilithium salt or methyl ester thereof;

4-[[2-[2-(cyclohexylmethyl)-4,6-dimethylphenyl]ethenyl]hydroxyphosphinyl]-3-hydroxybutanoic acid or its dilithium salt or methyl ester thereof;

(S)-4-[[2-[2-(cyclohexylmethyl)-4,6-dimethylphenyl]ethyl]hydroxyphosphinyl]-3-hydroxybutanoic acid or its dilithium salt or methyl ester thereof;

4-[[[[4'-fluoro-3,3',5-trimethyl[1,1'-biphenyl]-2-yl]oxy]methyl]hydroxyphosphinyl]-3-hydroxybutanoic acid or its dilithium salt or methyl ester thereof;

4-[[[4'-fluoro-3,3', 5-trimethyl[1,1'-biphenyl]-2-yl]methyl]hydroxyphosphinyl]-3-hydroxybutanoic acid or its dilithium salt or methyl ester thereof;

(S)-4-[[[1-(4-fluorophenyl)-3-methyl-2-naphthalenyl]ethynyl]hydroxyphosphinyl]-3-hydroxybutanoic acid or its dilithium salt or methyl ester thereof;

(E)-4-[[2-[1-(4-fluorophenyl)-3-methyl-2-naphthalenyl]ethenyl]hydroxyphosphinyl]-3-hydroxybutanoic acid or its dilithium salt or methyl ester thereof;

(S)-4-[[2-[1-(4-fluorophenyl)-3-methyl-2-naphthalenyl]ethyl]hydroxyphosphinyl]-3-hydroxybutanoic acid or its dilithium salt or methyl ester thereof;

4-[[3-[4'-fluoro-3,3', 5-trimethyl[1,1'-biphenyl]-2-yl]propyl]methoxyphosphinyl]-3-hydroxybutanoic acid, methyl ester;

4-[[3-[4'-fluoro-3,3', 5-trimethyl[1,1'-biphenyl]-2-yl]propyl]hydroxyphosphinyl]-3-hydroxybutanoic acid, dilithium salt;

[1S-[1<a(R*),2<a,4a<b,8<b,8a<a]]-4-[[2-[8-(2,2-dimethyl-1-oxobutoxy)decahydro-2-methyl-1-naphthalenyl]ethyl]methoxyphosphinyl]-3-hydroxybutanoic acid, methyl ester;

[1S-[1<a(R*),2<a,4a<b,8<b,8a<a]]-4-[[2-[8-(2,2-dimethyl-1-oxobutoxy)decahydro-2-methyl-1-naphthalenyl]ethyl]hydroxyphosphinyl]-3-hydroxybutanoic acid, dilithium salt;

(S)-4-[[[3'-(4-fluorophenyl)spiro]cyclopentane-1,1'-[1H]indene]-2-yl]ethynyl]methoxyphosphinyl]-3-hydroxybutanoic acid, methyl ester; or (S)-4-[[[3'-(4-fluorophenyl)spiro]cyclopentane-1,1'-[1H]indene]-2-yl]ethynyl]hydroxyphosphinyl]-3-hydroxybutanoic acid, dilithium salt.

16. A hypocholesterolemic or hypolipemic composition comprising a compound as defined in claim 1 and a pharmaceutically acceptable carrier therefor.

17. A method of inhibiting cholesterol biosynthesis which comprises administering to a patient in need of such treatment an effective cholesterol biosynthesis inhibiting amount of a compound as defined in claim 1.

18. The compound as defined in claim 1 having the name (S)-4-[[(E)-2-[4'-fluoro3,3',5-trimethyl[1,1'-biphenyl]-2-yl]-ethenyl]hydroxyphosphinyl]-3-hydroxybutanoic acid or its dilithium salt;

(S)-4-[[2-[4'-fluoro-3,3,'5-trimethyl[1,1'-biphenyl]-2-yl]ethyl]hydroxyphosphinyl]-3-hydroxybutanoic acid, methyl ester or mono- or di-alkali metal salts thereof;

(S)-4-[[[4'-fluoro-3,3',5-trimethyl[1,1'-biphenyl]-2-yl]ethynyl]methoxyphosphinyl]-3-hydroxybutanoic acid or the methyl ester thereof;

(5Z)-4-[[2-[4'-fluoro-3,3,',5-trimethyl[1,1'-biphenyl9 -2-yl]ethyl]hydroxyphosphinyl]-3-hydroxybutanoic acid, methyl ester thereof;

(S)-4-[[2-[[1,1'-biphenyl]-2-yl]ethyl]methoxyphosphinyl-3-hydroxybutanoic acid, methyl ester;

(S)-4-[[2-[4'-fluoro-3,3',5-trimethyl[1,1'-biphenyl]-2-yl]ethyl]hydroxyphosphinyl]-3-hydroxybutanoic acid, dilithium salt;

(S)-4-[[2-[4'-fluoro-3,3',5-trimethyl[1,1'-biphenyl]-2-yl]ethyl]hydroxyphosphinyl]-3-hydroxybutanoic acid, dilithium salt;

(SZ)-4-[[2-[4'-fluoro-3,3',5-trimethyl[1,1'-biphenyl]-2-yl]ethyl]hydroxyphosphinyl]-3-hydroxybutanoic acid, dilithium salt;

(S)-4-[[2-[(1,1'-biphenyl)-2-yl]ethyl]hydroxyphosphinyl]-3-butanoic acid, dilithium salt.

19. The compound as defined in claim 1 having the name 4-[[2-[4'-fluoro-3,3,',5-trimethyl[1,1'-biphenyl]-2-yl]ethyl]-hydroxyphosphinyl]-3-hydroxybutanoic acid or its dilithium salt or methyl ester thereof;

(E)-4-[[2-[4'-fluoro-3,3',5-trimethyl[1,1'-biphenyl]-2-yl]ethenyl]hydroxyphosphinyl]-3-hydroxybutanoic acid or its dilithium salt or methyl ester thereof;

(S)-4-[[[2,4-dimethyl-6-[(4-fluorophenyl)methoxy]-phenyl]-ethyl]hydroxyphosphinyl]-3-hydroxybutanoic acid or its dilithium salt or methyl ester thereof;

(S)-4-[[[2,4-dimethyl-6-[(4-fluorophenyl)methoxy]-phenyl]ethynyl]hydroxyphosphinyl]-3-hydroxybutanoic acid or its dilithium salt or methyl ester thereof;

(S)-4-[[2-3,5-dimethyl[1,1'-biphenyl]-2-ethyl]-hydroxyphosphinyl]-3-hydroxybutanoic acid or its dilithium salt or methyl ester thereof;

(S)-4-[[2-[4'-fluoro-3,5-dimethyl]1,1'-biphenyl]-2-yl]-ethyl]hydroxyphosphinyl]-3-hydroxybutanoic acid or its dilithium salt or methyl ester thereof;

(S)4-[[2-[[1,1'-biphenyl]-2-yl]ethynyl]hydroxyphosphinyl]-3-hydroxybutanoic acid or its dilithium salt or methyl ester thereof.

* * * * *

UNITED STATES PATENT AND TRADEMARK OFFICE
CERTIFICATE OF CORRECTION

PATENT NO. : 5,276,021

DATED : January 4, 1994

INVENTOR(S) : Donald S. Karanewsky et al

It is certified that error appears in the above-identified patent and that said Letters Patent is hereby corrected as shown below:

In Claim 1, column 168, line 63, "adamantyllower" should be --adamantyl-lower--.

In Claim 1, column 170, lines 10 to 15, " 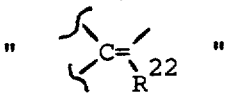 " should be --  --.

In Claim 14, column 171, line 67, at the end of the line, insert --or--.

In Claim 18, column 173, line 14, after "biphenyl", delete the number "9" and insert --]--.

In Claim 18, column 173, lines 14, 23 and 26, delete "ethyl" and insert --ethenyl--.

In Claim 19, column 174, line 4, delete "3,3,',5" and insert --3,3',5--.

In Claim 19, column 174, line 18, delete "[[2-3,5-dimethyl" and insert --[[2-[3,5-dimethyl--; and after "-2-", insert --yl]--.

Signed and Sealed this

Thirteenth Day of December, 1994

Attest:

BRUCE LEHMAN

*Attesting Officer*    *Commissioner of Patents and Trademarks*